US012799497B2

(12) United States Patent
Andersen et al.

(10) Patent No.: US 12,799,497 B2
(45) Date of Patent: Nov. 17, 2026

(54) GENETICALLY ALTERED PLANTS EXPRESSING HETEROLOGOUS RECEPTORS THAT RECOGNIZE LIPO-CHITOOLIGOSACCHARIDES

(71) Applicant: Aarhus Universitet, Aarhus (DK)

(72) Inventors: Kasper Røjkjær Andersen, Aarhus (DK); Kira Gysel, Aarhus (DK); Elena Simona Radutoiu, Aarhus (DK); Zoltan Bozsoki, Aarhus (DK); Lene Heegaard Madsen, Aarhus (DK); Simon Boje Hansen, Aarhus (DK); Jens Stougaard Jensen, Aarhus (DK)

(73) Assignee: Aarhus Universitet, Aarhus (DK)

( * ) Notice: Subject to any disclaimer, the term of this patent is extended or adjusted under 35 U.S.C. 154(b) by 432 days.

(21) Appl. No.: 17/265,793

(22) PCT Filed: Aug. 13, 2019

(86) PCT No.: PCT/EP2019/071703

§ 371 (c)(1),
(2) Date: Feb. 3, 2021

(87) PCT Pub. No.: WO2020/035486

PCT Pub. Date: Feb. 20, 2020

(65) Prior Publication Data

US 2021/0163976 A1 Jun. 3, 2021

Related U.S. Application Data

(60) Provisional application No. 62/718,186, filed on Aug. 13, 2018.

(51) Int. Cl.
*C12N 15/82* (2006.01)
*C07K 14/415* (2006.01)

(52) U.S. Cl.
CPC ........ *C12N 15/8262* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 4,407,956 | A | 10/1983 | Howell | |
| 4,536,475 | A | 8/1985 | Anderson | |
| 4,683,195 | A | 7/1987 | Mullis et al. | |
| 4,683,202 | A | 7/1987 | Mullis | |
| 4,684,611 | A | 8/1987 | Schilperoort et al. | |
| 4,800,159 | A | 1/1989 | Mullis et al. | |
| 5,633,363 | A | 5/1997 | Colbert et al. | |
| 5,679,558 | A | 10/1997 | Gobel et al. | |
| 6,140,553 | A | 10/2000 | D'Halluin | |
| 7,915,485 | B2 | 3/2011 | Jensen et al. | |
| 7,956,240 | B2 | 6/2011 | Reuzeau | |
| 8,361,462 | B2 | 1/2013 | Pandey et al. | |
| 10,167,482 | B2 | 1/2019 | Coffin | |
| 12,190,997 | B2 | 1/2025 | Anderson et al. | |
| 2006/0005275 | A1* | 1/2006 | Diehn ................ | C12N 15/8227 435/468 |
| 2006/0150283 | A1* | 7/2006 | Alexandrov et al. ........................ | C07K 14/415 536/23.6 |
| 2009/0113572 | A1* | 4/2009 | Song et al. ........ | C12N 15/8234 800/278 |
| 2012/0159672 | A1* | 6/2012 | Alexandrov et al. ........................ | C07K 14/415 536/23.6 |
| 2013/0097725 | A1 | 4/2013 | Indrasumunar et al. | |
| 2014/0090106 | A1 | 3/2014 | Wan et al. | |
| 2015/0232876 | A1 | 8/2015 | Bono et al. | |
| 2015/0368342 | A1 | 12/2015 | Wu et al. | |
| 2016/0244777 | A1* | 8/2016 | Coffin ................ | C12N 15/8274 |
| 2018/0237793 | A1 | 8/2018 | Aasen et al. | |
| 2020/0096507 | A1 | 3/2020 | Bonnet et al. | |
| 2021/0163574 | A1 | 6/2021 | Schneider et al. | |
| 2021/0163974 | A1 | 6/2021 | Batoko et al. | |
| 2021/0233608 | A1 | 7/2021 | Andersen et al. | |
| 2021/0363217 | A1 | 11/2021 | Pule et al. | |
| 2021/0366320 | A1 | 11/2021 | Radutoiu et al. | |
| 2022/0135630 | A1 | 5/2022 | Zhou et al. | |
| 2023/0078124 | A1 | 3/2023 | Coruzzi et al. | |
| 2024/0200085 | A1 | 6/2024 | Andersen et al. | |
| 2024/0344077 | A1 | 10/2024 | Radutoiu et al. | |
| 2024/0344078 | A1* | 10/2024 | Radutoiu et al. .... | C07K 14/415 |

FOREIGN PATENT DOCUMENTS

| | | | |
|---|---|---|---|
| AR | 105982 | A1 | 11/2017 |
| CN | 109136243 | A | 1/2019 |
| CN | 109734785 | A | 5/2019 |

(Continued)

OTHER PUBLICATIONS

Sun et al. (2004) Plant J 37:517-27.*
Bahr memo Feb. 22, 2018.*
Lomize et al. (2007) BMC Struct Biol 7:44.*
Rhoads et al. (1998) J Biol Chem 273(46):30750-56.*
Guo et al. (2004) Proc Natl Acad Sci USA 101:9205-10.*
Young & Udvardi (2009) Curr Opin Plant Biol 12:193-201.*
Zhang (2003) Curr Opin Plant Biol 6:430-40.*
Cao et al., (2014). "The kinase LYK5 is a major chitin receptor in *Arabidopsis* and forms a chitin-induced complex with related kinase CERK1," Elife, 3:E03766, 19 pages.
Knox et al., (2018). "The Challenges of Analysing Highly Diverse Picobirnavirus Sequence Data," Viruses, 10(685):1-13.

(Continued)

*Primary Examiner* — Russell T Boggs
(74) *Attorney, Agent, or Firm* — Morrison & Foerster LLP

(57) ABSTRACT

Aspects of the present disclosure relate to genetically modified plants comprising a nucleic acid sequence encoding a heterologous receptor polypeptide. The plants are able to recognize lipo-chitooligosaccharides (LCOs) through the heterologous receptor polypeptide. Other aspects of the present disclosure relate to methods of making such plants.

22 Claims, 34 Drawing Sheets
(15 of 34 Drawing Sheet(s) Filed in Color)

Specification includes a Sequence Listing.

(56) References Cited

FOREIGN PATENT DOCUMENTS

| | | | |
|---|---|---|---|
| CN | 112739820 | A | 4/2021 |
| CN | 108728425 | B | 12/2021 |
| EP | 67553 | A2 | 12/1982 |
| EP | 116718 | B2 | 8/1984 |
| EP | 223247 | A2 | 11/1986 |
| EP | 242246 | B1 | 10/1987 |
| EP | 270356 | B1 | 6/1988 |
| EP | 270822 | A1 | 6/1988 |
| EP | 452269 | B1 | 10/1991 |
| EP | 3837357 | | 6/2021 |
| IN | 144268 | A1 | 4/1978 |
| JP | 5229783 | B2 | 7/2013 |
| KR | 20200085159 | A | 7/2020 |
| WO | WO-1984002913 | A1 | 8/1984 |
| WO | WO-1985001856 | A1 | 5/1985 |
| WO | WO-1992009696 | A1 | 6/1992 |
| WO | WO-1996006932 | A1 | 3/1996 |
| WO | WO-1997048819 | A1 | 12/1997 |
| WO | WO-2000042207 | A2 | 7/2000 |
| WO | WO-2000071733 | A1 | 11/2000 |
| WO | WO-2002046439 | A2 | 6/2002 |
| WO | WO2005/003338 | A1 * | 1/2005 |
| WO | WO-2007076115 | A2 | 7/2007 |
| WO | WO-2009016104 | A1 | 2/2009 |
| WO | WO-2014033672 | A1 | 3/2014 |
| WO | WO-2017103582 | A1 | 6/2017 |
| WO | WO-2020035488 | A1 | 2/2020 |
| WO | WO-2020104524 | A1 | 5/2020 |
| WO | WO-2022026618 | A2 | 2/2022 |

OTHER PUBLICATIONS

Rougé et al., (2011). "Chapter 27 Docking of Chitin Oligomers and Nod Factors on Lectin Domains of the LysM-RLK Receptors in the Medicago-Rhizobium Symbiosis," The Mol. Immunol. Complex Carbohydrates—3, pp. 511-521.

UniProt, (2018). "EBI accession No. A0A2SOBYZ2: Nod-factor receptor 5," available online at <https://rest.uniprot.org/uniprotkb/A0A2S0BYZ2/txt>, 2 pages.

Waterhouse et al., (2018). "Swiss-Model: homology modelling of protein structures and complexes," Nuc. Acids Res., 46:W296-W303.

Adams et al., (2010). "Phenix: a comprehensive Python-based system for macromolecular structure solution. Acta crystallographica," Section D, Biological crystallography, 66(2):213-221.

Altschul et al., (1997). "Gapped Blast and PSI-Blast: a new generation of protein database search programs," Nucleic acids research, 25(17):3389-3402.

Altschul et al., (1990). "Basic local alignment search tool," Journal of molecular biology, 215(3):403-410.

An et al., (1996). "Strong, constitutive expression of the *Arabidopsis* ACT2/ACT8 actin subclass in vegetative tissues," The Plant Journal, 10(1):107-121.

Ardourel et al., (1994). "Rhizobium meliloti lipooligosaccharide nodulation factors: different structural requirements for bacterial entry into target root hair cells and induction of plant symbiotic developmental responses," The Plant Cell, 6(10):1357-1374.

Arrighi et al., (2006). "The Medicago truncatula Lysine Motif-Receptor-Like Kinase Gene Family Includes NFP and New Nodule-Expressed Genes," Plant Physiology, 142:265-279, 19 pages.

Bensmihen et al., (2011). "Contribution of NFP LysM Domains to the Recognition of Nod Factors during the Midicago trunculata/Sinorhizobium meliloti Symbiosis," PLOS ONE, 6:e26114, 11 pages.

Biasini et al., (2014). "Swiss-Model: modelling protein tertiary and quaternary structure using evolutionary information," Nucleic acids research, 42(W1):W252-W258.

Bozsoki et al., (2017). "Receptor-mediated chitin perception in legume roots is functionally separable from Nod factor perception," Proceedings of the National Academy of Sciences, 114(38):E8118-E8127.

Bucher et al., (2002). "The expression of an extensin-like protein correlates with cellular tip growth in tomato," Plant Physiology, 128(3):911-923.

Christensen et al., (1992). "Maize polyubiquitin genes: structure, thermal perturbation of expression and transcript splicing, and promoter activity following transfer to protoplasts by electroporation," Plant molecular biology, 18(4):675-689.

Christensen et al., (1996). "Ubiquitin promoter-based vectors for high-level expression of selectable and/or screenable marker genes in monocotyledonous plants," Transgenic research, 5(3):213-218.

Christou et al., (1990). "Soybean genetic engineering-commercial production of transgenic plants," Trends in Biotechnology, 8:145-151.

Datta et al., (1990). "Genetically engineered fertile indica-rice recovered from protoplasts," Bio/technology, 8(8):736-740.

De Framond, (1991). "A metallothionein-like gene from maize (*Zea mays*) Cloning and characterization," FEBS letters, 290(1-2):103-106.

De Lorenzo et al., (2011). "Engineering plant resistance by constructing chimeric receptors that recognize damage-associated molecular patterns (DAMPs)," FEBS Letters, 585:1521-1528.

De Pater et al., (1992). "The promoter of the rice gene GOS2 is active in various different monocot tissues and binds rice nuclear factor ASF-1," The Plant Journal, 2(6):837-844.

Delano, (2002). "Pymol: An open-source molecular graphics tool," CCP4 Newsletter on protein crystallography, 10 pages.

Depicker et al., (1982). "Nopaline synthase: transcript mapping and DNA sequence," Journal of molecular and applied genetics, 1(6):561-573.

Emsley et al., (2010). "Features and development of Coot," Acta Crystallographica Section D: Biological Crystallography, 66(4):486-501.

Engler et al., (2008). "A one pot, one step, precision cloning method with high throughput capability," PloS one, 3(11):e3647, 7 pages.

Franck et al., (1980). "Nucleotide sequence of cauliflower mosaic virus DNA," Cell, 21(1):285-294.

Franke et al., (2009). "DAMMIF, a program for rapid ab-initio shape determination in small-angle scattering," Journal of applied crystallography, 42(2):342-346.

Fromm et al., (1990). "Inheritance and expression of chimeric genes in the progeny of transgenic maize plants," Bio/technology, 8(9):833-839.

Gardner et al., (1981). "The complete nucleotide sequence of an infectious clone of cauliflower mosaic virus by M13mp7 shotgun sequencing," Nucleic acids research, 9(12):2871-2888.

GenBank Accession No. X04049, "Maize alcohol dehydrogenase 1 gene (Adh1-1S)," Nov. 14, 2006, 4 pages.

GenBank Accession No. XM 004511944, "Predicted: Cicer arietinum protein LYK5-like (LOC101515074), transcript variant X2, mRNA," Jun. 8, 2015, 2 pages.

GenBank Accession No. XM 012719006, "Predicted: Cicer arietinum protein LYK5-like (LOC101515074), transcript variant X1, mRNA," Jun. 8, 2015, 2 pages.

Gielen et al., (1984). "The complete nucleotide sequence of the TL-DNA of the Agrobacterium tumefaciens plasmid pTiAch5," The EMBO Journal, 3(4):835-846.

Gomez et al., (2009). "Medicago truncatula and Glomus intraradices gene expression in cortical cells harboring arbuscules in the arbuscular mycorrhizal symbiosis," BMC Plant Biology, 9(10):1-19.

Gordon-Kamm et al., (1990). "Transformation of Maize Cells and Regeneration of Fertile Transgenic Plants," The Plant cell, 2(7):603-618.

Gough et al., (2018). "Evolutionary History of Plant LysM Receptor Proteins Related to Root Endosymbiosis," Frontiers in Plant Science, 9:923, 9 pages.

Gust et al., (2012). "Plant LysM proteins: modules mediating symbiosis and immunity," Trends in Plant Science, 17:495-502.

Hansen et al., (1989). "Hairy roots—a short cut to transgenic root nodules," Plant Cell Reports, 8(1):12-15.

Heidstra et al., (2004). "Mosaic analyses using marked activation and deletion clones dissect *Arabidopsis* Scarecrow action in asymmetric cell division," Genes & Development, 18(16):1964-1969.

(56) References Cited

OTHER PUBLICATIONS

Hinchee et al., (1988). "Production of transgenic soybean plants using Agrobacterium-mediated DNA transfer," Bio/technology, 6.8:915-922.
Hirel et al., (1992). "Forcing expression of a soybean root glutamine synthetase gene in tobacco leaves induces a native gene encoding cytosolic enzyme," Plant molecular biology, 20(2):207-218.
Hopkins et al., (2017). "BioXTAS Raw: improvements to a free open-source program for small-angle X-ray scattering data reduction and analysis," Journal of applied crystallography, 50(5):1545-1553.
Hull et al., (1978). "Structure of the cauliflower mosaic virus genome. II. Variation in DNA structure and sequence between isolates," Virology, 86(2):482-493.
Indrasumunar et al., (2010). "Inactivation of duplicated nod factor receptor 5 (NFR5) genes in recessive loss-of-function non-nodulation mutants of allotetraploid soybean (*Glycine max* L. Merr.)," Plant and cell physiology, 51(2):201-214.
Irvine, (2016). "A Receptor for All Occasions," Cell, 164:599-600.
Kabsch, (2010). "Integration, scaling, space-group assignment and post-refinement," Acta Crystallographica Section D: Biological Crystallography, 66(2):133-144.
Karlin et al., (1990). "Methods for assessing the statistical significance of molecular sequence features by using general scoring schemes," Proceedings of the National Academy of Sciences, 87(6):2264-2268.
Karlin et al., (1993). "Applications and statistics for multiple high-scoring segments in molecular sequences," Proceedings of the National Academy of Sciences, 90(12):5873-5877.
Kay et al., (1987). "Duplication of CaMV 35S Promoter Sequences Creates a Strong Enhancer for Plant Genes," Science, 236(4806):1299-1302.
Kelly et al., (2013). "Conditional requirement for exopolysaccharide in the Mesorhizobium-Lotus symbiosis," Molecular plant-microbe interactions, 26(3):319-329.
Konarev et al., (2003). "Primus: a Windows PC-based system for small-angle scattering data analysis," Journal of applied crystallography, 36(5):1277-1282.
Last et al., (1991). "pEmu: an improved promoter for gene expression in cereal cells." TAG. Theoretical and applied genetics, 81(5):581-588.
Lerouge et al., (1990). "Symbiotic host-specificity of Rhizobium meliloti is determined by a sulphated and acylated glucosamine oligosaccharide signal," Nature, 344(6268):781-784.
Li et al., (2016). "Plant pattern-recognition receptors controlling innate immunity," Science China Life Sciences, 59:878-888.
Liu et al., (2012). "Chitin-induced dimerization activates a plant immune receptor," Science, 336(6085):1160-1164.
Madsen et al., (2003). "A receptor kinase gene of the LysM type is involved in legume perception of rhizobial signals," Nature, 425:637-640.
Maekawa et al., (2008). "Polyubiquitin promoter-based binary vectors for overexpression and gene silencing in Lotus japonicus," Molecular Plant-Microbe Interactions, 21(4):375-382.
McCoy et al., (2007). "Phaser crystallographic software," Journal of applied crystallography, 40(4):658-674.
Mulder et al., (2006). "LysM domains of Medicago truncatula NFP protein involved in Nod factor perception. Glycosylation state, molecular modeling and docking of chitooligosaccharides and Nod factors," Glycobiology, 16(9):801-809.
Murakami et al., (2018). "Epidermal LysM receptor ensures robust symbiotic signalling in Lotus japonicus," Elife, 7:e33506, 21 pages.
Nakagawa et al., (2011). From defense to symbiosis: limited alterations in the kinase domain of LysM receptor-like kinases are crucial for evolution of legume—Rhizobium symbiosis, The Plant Journal, 65(2):169-180.
Norris et al., (1993). "The intron of *Arabidopsis thaliana* polyubiquitin genes is conserved in location and is a quantitative determinant of chimeric gene expression," Plant molecular biology, 21(5):895-906.
Oldroyd et al., (2001). "Evidence for structurally specific negative feedback in the Nod factor signal transduction pathway," The Plant Journal, 28(2):191-199.
Oldroyd et al., (2011). "The rules of engagement in the legume-rhizobial symbiosis," Annual review of genetics, 45:119-144.
Radutoiu et al., (2003). "Plant recognition of symbiotic bacteria requires two LysM receptor-like kinases," Nature, 425(6958):585-592.
Radutoiu et al., (2007). "LysM domains mediate lipochitin-oligosaccharide recognition and Nfr genes extend the symbiotic host range," The EMBO Journal, 26:3923-3935.
Rasmussen et al., (2016). "Intraradical colonization by arbuscular mycorrhizal fungi triggers induction of a lipochitooligosaccharide receptor," Scientific reports, 6:29733, 12 pages.
Rodpothong et al., (2009). "Nodulation Gene Mutants of Mesorhizobium loti R7A—nodZ and noIL Mutants Have Host-Specific Phenotypes on *Lotus* spp.," Molecular plant-microbe interactions, 22(12):1546-1554.
Saiki et al., (1985). "Enzymatic amplification of beta-globin genomic sequences and restriction site analysis for diagnosis of sickle cell anemia," Science, 230(4732):1350-1354.
Samac et al., (1990). "Isolation and characterization of the genes encoding basic and acidic chitinase in *Arabidopsis thaliana*," Plant physiology, 93(3):907-914.
Schindelin et al., (2012). "Fiji: an open-source platform for biological-image analysis," Nature methods, 9(7):676-682.
Schünmann et al., (2003). "A suite of novel promoters and terminators for plant biotechnology. II. The pPlex series for use in monocots," Functional plant biology, 30(4):453-460.
Shimamoto et al., (1989). "Fertile transgenic rice plants regenerated from transformed protoplasts," Nature, 338(6212):274-276.
Smit et al., (2007). "Medicago LYK3, an entry receptor in rhizobial nodulation factor signaling," Plant physiology, 145(1):183-191.
Stougaard, (1995). "Agrobacterium rhizogenes as a vector for transforming higher plants, application in Lotus corniculatus transformation," Plant gene transfer and expression protocols, 49-61.
Svergun, (1992). "Determination of the regularization parameter in indirect-transform methods using perceptual criteria," Journal of applied crystallography, 25(4):495-503.
Svergun et al., (1995). "Crysol—a program to evaluate X-ray solution scattering of biological macromolecules from atomic coordinates," Journal of applied crystallography, 28(6):768-773.
Svergun, (1999). "Restoring low resolution structure of biological macromolecules from solution scattering using simulated annealing," Biophysical journal, 76(6):2879-2886.
Trinick, (1973). "Symbiosis between Rhizobium and the non-legume, Trema aspera," Nature, 244(5416):459-460.
Unni et al., (2011). "Web servers and services for electrostatics calculations with APBS and PDB2PQR," Journal of computational chemistry, 32(7):1488-1491, 6 pages.
Velten et al., (1984). "Isolation of a dual plant promoter fragment from the Ti plasmid of Agrobacterium tumefaciens," The EMBO Journal, 3(12):2723-2730.
Velten et al., (1985). "Selection-expression plasmid vectors for use in genetic transformation of higher plants," Nucleic Acids Research, 13(19):6981-6998.
Verdaguer et al., (1998). "Functional organization of the cassava vein mosaic virus (CsVMV) promoter," Plant molecular biology, 37(6):1055-1067.
Wang et al., (1997). "Improved vectors for Agrobacterium tumefaciens-mediated transformation of monocot plants," ISHS Acta Horticulturae 461: International Symposium on Biotechnology of Tropical and Subtropical Species Part 2, 461 (pp. 401-408).
Wang et al., (2014). "Functional analysis of chimeric lysin motif domain receptors mediating Nod factor-induced defense signaling in *Arabidopsis thaliana* and chitin-induced nodulation signaling in Lotus japonicus," The Plant Journal, 78(1):56-69.
Weber et al., (2011). "A modular cloning system for standardized assembly of multigene constructs," PloS one, 6(2):e16765, 11 pages.
Weising et al., (1988). "Foreign genes in plants: transfer, structure, expression, and applications," Annual review of genetics, 22(1):421-477.

(56) References Cited

OTHER PUBLICATIONS

Wheeler et al., (2014). "Skylign: a tool for creating informative, interactive logos representing sequence alignments and profile hidden Markov models," BMC bioinformatics, 15(7):1-9, 9 pages.
Wriggers et al., (2001). "Using Situs for the registration of protein structures with low-resolution bead models from X-ray solution scattering," Journal of applied crystallography, 34(6):773-776.
Zhang et al., (1991). "Analysis of rice Act1 5' region activity in transgenic rice plants," The Plant Cell, 3(11):1155-1165.
Zhang et al., (2007). "Molecular evolution of lysin motif-type receptor-like kinases in plants," Plant physiology, 144(2):623-636.
Zhukov et al., (2008). "The pea Sym37 receptor kinase gene controls infection-thread initiation and nodule development," Molecular Plant-Microbe Interactions, 21(12):1600-1608.
Bai et al., (2022). "Engineering Chimeras by Fusing Plant Receptor-like Kinase EMS1 and BRI1 Reveals the Two Receptors' Structural Specificity and Molecular Mechanisms," Int. J. Mol. Sci., 23:2155, 18 pages.
Bozsoki et al., (2020). "Ligand-recognizing motifs in plant LysM receptors are major determinants of specificity," Science, 369:663-670.
Brinkmann et al., (2017). "The making of bispecific antibodies," MABS, 9(2):182-212.
Chen et al., (2021). "A Promising Intracellular Protein-Degradation Strategy: TRIMbody-Away Technique Based on Nanobody Fragment," Biomolecules, 11:1512, 15 pages.
Desaki et al., (2018). "MAMP-triggered plant immunity mediated by the LysM-receptor kinase CERK1," Journal of General Plant Pathology, 85, 11 pages.
Ekerljung et al., (2012). "Generation and Evaluation of Bispecific Affibody Molecules for Simultaneous Targeting of EGFR and HER2," Bioconjugate Chemistry, 23(9):1802-1811.
Gil et al., (2020). "Optogenetic control of protein binding using light-switchable nanobodies," Nature Communications, 11:4044, 12 pages.
Hu et al., (2021). "Lysin Motif (LysM) Proteins: Interlinking Manipulation of Plant Immunity and Fungi," Int. J. Mol. Sci., 22:3114, 12 pages.
Ingram et al., (2018). "Exploiting Nanobodies' Singular Traits," Annual Review of Immunology, 36:695-715.
Keller et al., (2019). "Selection and Characterization of a Nanobody Biosensor of GTP-Bound RHO Activities," Antibodies, 8:8, 17 pages.
Liu et al., (2016). "Intracellularly expressed nanobodies against non-structural protein 4 of porcine reproductive and respiratory syndrome virus inhibit virus replication," Biotechnol Lett, 38:1081-1088.
Madsen et al., (2011). "Autophosphorylation is essential for the in vivo function of the Lotus japonicus Nod factor receptor 1 and receptor-mediated signalling in cooperation with Nod factor receptor 5," Plant Journal, 65:404-417.
Miyata et al., (2016). "Evaluation of the Role of the LysM Receptor-Like Kinase, OsNFR5/OsRLK2 for AM Symbiosis in Rice," Plant Cell Physiol, 57:2283-2290.
Mossner et al., (2020). "Multimerization strategies for efficient production and purification of highly active synthetic cytokine receptor ligands," PLoS ONE, 15(4):e0230804, 19 pages.
Muthuswamy et al., (1999). "Controlled Dimerization of ErbB Receptors Provides Evidence for Differential Signaling by Homo- and Heterodimers," Molecular and Cellular Biology, 19(10):6845-6857.
Petutschnig et al., (2010). "The lysin motif receptor-like kinase (LysM-RLK) CERK1 is a major chitin-binding protein in *Arabidopsis thaliana* and subject to chitin-induced phosphorylation," JBC, 285(37):28902-28911.
Prole et al., (2019). "A genetically encoded toolkit of functionalized nanobodies against fluorescent proteins for visualizing and manipulating intracellular signalling," BMC Biology, 17:41, 24 pages.
Rübsam et al., (2023). "Nanobody-driven signaling reveals the core receptor complex in root nodule symbiosis," Science, 379(6629):272-277.
Søgaard et al., (2023). "Transmembrane signaling by a synthetic receptor in artificial cells," Nature Communications, 14:1646, 10 pages.
Suthaus et al., (2010). "Forced Homo- and Heterodimerization of All gp 130-Type Receptor Complexes Leads to Constitutive Ligand-independent Signaling and Cytokine-independent Growth," Molecular Biology of the Cell, 21:2797-2807.
Wouters et al., (2019). "Luminescence- and Fluorescence-Based Complementation Assays to Screen for GPCR Oligomerization: Current State of the Art," International Journal of Molecular Sciences, 20:2958; 35 pages.
Yu et al., (2019). "Optogenetic activation of intracellular antibodies for direct modulation of endogenous proteins," Nature Methods, 16:1095-1100.
Zhou et al., (2019). "The juxtamembrane domains of Arabidopsis CERK1, BAK1, and FLS2 play a conserved role in chitin-induced signaling," JIPB, 62(5):556-562.
Hohmann et al., (2017). "The Structural Basis of Ligand Perception and Signal Activation by Receptor Kinases," Annu. Rev. Plant Biol., 68:109-137.
Igolkina et al., (2018). "Structural Insight Into the Role of Mutual Polymorphism and Conservatism in the Contact Zone of the NFR5-K1 Heterodimer With the Nod Factor," Frontiers in Plant Sci., 9:344, 14 pages.
GenBank Accession No. ANS10208.1, "Nod-factor receptor 5 [*Arachis hypogaea* subsp. *hypogaea*]," Apr. 26, 2017, 2 pages.
GenBank Accession No. XP_020148045.1, "serine/threonine receptor-like kinase NFP [*Aegilops tauschii* subsp. *strangulata*]," Dec. 2, 2021, 2 pages.
GenBank Accession No. XP_020399958.1, "serine/threonine receptor-like kinase NFP [*Zea mays*]," Sep. 1, 2020, 2 pages.
Gysel et al., (2021). "Kinetic proofreading of lipochitooligosaccharides determines signal activation of symbiotic plant receptors," PNAS USA, 118(44):e2111031118, 10 pages.
Tian et al., (2013). "Progress and Perspectives in Research of Chitin Triggered Immunity in Plant," Scientia Agricultura Sinica, 46(15):3115-3124. English abstract.
Wang et al., (2015). "Progress and Prospects in the Research on Wheat Receptor-like Kinases and Derivative Proteins," Chinese Bulletin of Botany, 50(2):255-262. English abstract on the last page.
Luyten et al., (2000). "Survey of genes identified in *Sinorhizobium meliloti* spp., necessary for the development of an efficient symbiosis," Eur. J. Soil Biol., 36:1-26.
Malkov et al., (2016). "Molecular basis of lipo-chitooligosaccharide recognition by the lysin motif receptor-like kinase LYR3 in legumes," Biochem. J., 473:1369-1378.
U.S. Appl. No. 18/913,825 (Andersen et al.), filed Oct. 11, 2024, titled "Genetically Altered Lysm Receptors With Altered Agonist Specificity and Affinity," (Copy not submitted herewith pursuant to the waiver of 37 C.F.R. § 1.98(a)(2)(iii)).

* cited by examiner

| Protein | A (M-1 min-1) | D (min-1) | Kd (µM) | n |
|---|---|---|---|---|
| NFP WT | 57.5 +- 0.28 | 0.00149 +- 0.0000062 | 25.98 +- 0.21 | 7 |
| **NFP L147D L154D** | 468.4 +- 8.85 | 0.022 +- 0.00012 | 47.99 +- 1.01 | 4 |

FIG. 4B

LysM1 dashed underline; LysM2 solid underline; Hydrophic patch residues bold; LysM3 *residues italicized*

Medicago NFP
>MtNFP/1-595
MSAFFLPSSSHALFLVLMLFFLTNISAQPLYISETNFTCPVDSPPSCETYVAYRAQSPNFLSLSNISDIFNLSPLRIAKASNIEAEDKKLIPDQLLLVPVTCGCTKNHSFANITYSIKQG
DNFFILSITSYQNLTNYLEFKNFNPNLSPTLLPLDTKVSVPLFCKC*PSKNQLNKGIKYLITYVWQDNDNVTLVSSKFGASQVEMLAENNHNFTASTNRSVLIPV*TSLPKLDQPSSN
GRKSSSQNLALIIGISLGSAFFILVLTLSLVYVYCLKMKRLNRSTSSSETADKLLSGVSGYVSKPTMYEIDAIMEGTTNLSDNCKIGESVYKANIDGRVLAVKKIKKDASEELKILQKV
NHGNLVKLMGVSSDNDGNCFLVYEYAENGSLEEWLFSESSKTSNSVVSLTWSQRITIAMDVAIGLQYMHEHTYPRIIHRDITTSNILLGSNFKAKIANFGMARTSTNSMMPKI
DVFAFGVVLIELLTGKKAMTTKENGEVVILWKDFWKIFDLEGNREERLRKWMDPKLESFYPIDNALSLASLAVNCTADKSLSRPTIAEIVLCLSLLNQPSSEPMLERSLTSGLDAE
ATHVVTSVIAR Lotus NFR5 (Known LCO receptor)
>LjNFR5/1-595
MAVFFLTSGSLSLFLALTLLFTNIAARSEKISGPDFSCPVDSPPSCETYVTYTAQSPNLLSLTNISDIFDISPLSIARASNIDAGKDKLVPGQVLLVPVTCGCAGNHSSANTSYQIQLG
DSYDFVATTLYENLTNWNIVQASNPGVNPYLLPERVKVVFPLFCRC*PSKNQLNKGIQYLITYVWKPNDNVSLVSAKFGASPADILTENRYGQDFTAATNLPILIPV*TQLPELTQP
SSNGRKSSIHLLVILGITLGCTLLTAVLTGTLVYVYCRRKKALNRTASSAETADKLLSGVSGYVSKPNVYEIDEIMEATKDFSDECKVGESVYKANIEGRVVAVKKIKEGGANEELKIL
QKVNHGNLVKLMGVSSGYDGNCFLVYEYAENGSLAEWLFSKSSGTPNSLTWSQRISIAVDVAVGLQYMHEHTYPRIIHRDITTSNILLDSNFKAKIANFAMARTSTNPMMPKI
DVFAFGVLLIELLTGRKAMTTKENGEVVMLWKDMWEIFDIEENREERIRKWMDPNLESFYHIDNALSLASLAVNCTADKSLSRPSMAEIVLSLSFLTQQSSNPTLERSLTSSGLD
VEDDAHIVTSITAR Pea SYM10
>Pea_SYM10/1-594 (Known LCO receptor)
MAIFFLPSSSHALFLALMFFVTNISAQPLQLSGTNFSCPVDSPPSCETYVTYFARSPNFLSLTNISDIFDMSPLSIAKASNIEDEDKKLVEGQVLLIPVTCGCTRNRYFANFTYTIKLG
DNYFIVSTTSYQNLTNYVEMENFNPNLSPNLLPPEIKVVVPLFCKC*PSKNQLSKGIKHLITYVWQANDNVTRVSSKFGASQVDMFTENNQNFTASTNVPILIPV*TKLPVIDQPSS
NGRKNSTQKPAFIIGISLGCAFFVVVLTLSLVYVYCLKMKRLNRSTSLAETADKLLSGVSGYVSKPTMYEMDAIMEATMNLSENCKIGESVYKANIDGRVLAVKKIKKDASEELKIL
QKVNHGNLVKLMGVSSDNDGNCFLVYEYAENGSLDEWLFSESSKTSNSVVSLTWSQRITVAVDVAVGLQYMHEHTYPRIIHRDITTSNILLDSNFKAKIANFSMARTSTNSM
MPKIDVFAFGVVLIELLTGKKAITTMENGEVVILWKDFWKIFDLEGNREESLRKWMDPKLENFYPIDNALSLASLAVNCTADKSLSRPSIAEIVLCLSLLNQSSSEPMLERSLTSGL
DVEATHVVTSIVAR Soybean NFR5α (Known LCO receptor)
>GmNFR5α/1-598 max
MAVFFPFLPLHSQILCLVIMLFSTNIVAQSQQDNRTNFSCPSDSPPSCETYVTYIAQSPNFLSLTNISNIFDTSPLSIARASNLEPMDDKLVKDQVLLVPVTCGCTGNRSFANISYEI
NQGDSFYFVATTSYENLTNWRAVMDLNPVLSPNKLPIGIQVVFPLFCKC*PSKNQLDKEIKYLITYVWKPGDNVSLVSDKFGASPEDIMSENNYGQNFTAANNLPVLIPV*TRLPV
LARSPSDGRKGGIRLPVIIGISLGCTLLVLVLAVLLVYVYCLKMKTLNRSASSAETADKLLSGVSGYVSKPTMYETDAIMEATMNLSEQCKIGESVYKANIEGKVLAVKRFKEDVTE
ELKILQKVNHGNLVKLMGVSSDNDGNCFVVYEYAENGSLDEWLFSKSCSDTSNSRASLTWCQRISMAVDVAMGLQYMHEHAYPRIVHRDITSSNILLDSNFKAKIANFSMAR
TFTNPMMPKIDVFAFGVVLIELLTGRKAMTTKENGEVVMLWKDIWKIFDQEENREERLKKWMDPKLESYYPIDYALSLASLAVNCTADKSLSRPTIAEIVLSLSLLTQPSPATLER
SLTSSGLDVEATQIVTSIAAR

FIG. 12A

Chickpea NFR5 (New LCO receptor)
>ChickpeaNFR5/1-557 (Cicer arietinum)
MSVFFLPSRSHVLFLALMLFLTNISAQSQHLSGTNFSCPVDSPPSCETYVTYIAQSPNFLSLTNISDLFDISPLSIARASNIDDEDKELIPGQVLLVPVTCGCTKHRSFANNTYTIKLG
DSYILVSTTSYQNLTNYLEMEDSNPGLNPNLIPPFIKVVVPIFCRC*PSKTQLNKGIKYLITYVWHANDNVSTVSSKFGASQVDILTENNYNQNFASAANLPVLIPV*TRLPILAQPSS
NGRKRSIQLPVIIDKLLSGVSGYVSKPTMYEMDVIMEATMNLSDQCKIGESVYKANIDGKVLAVKKTKKDASEELKILQKVNHGNLVKLMGVSSDNEGNCFLVYEYAENGSLD
EWLFLESSKTSDSTVSLTWSQRIGIAVDVAVGLQYMHEHTYPRIIHRDITTSNILLDANFKAKIANFSMARTSTNPMMPKIDVFAFGVVLIELLTGKKGVTTKENGEVVIMWKD
FWMIFDLEGNKEERLRKWMDPKLENFYPIDNALSLASLAVNCTADKSLSRPTIEEIVLCLNLLNQPSSEPTLERSLTFGLDVEDTQIVTSIAAR Bean NFR5 (New LCO receptor)
>BeanNFR5/1-597 (Phaseolus vulgaris)
MAVFFVSLTLGAQILYVVLMFFTCIEAQSQQTNGTNFSCPSNSPPSCETYVTYISQSPNFLSLTSVSNIFDTSPLSIARASNLQHEEDKLIPGQVLLIPVTCGCTGNRSFANISYEIN
QGDSFYFVATTLYQNLTNWHAVMDLNPGLSPFTLPIGIQVVIPLFCKC*PSKNQLDRGIKYLITHVWQPNDNVSFVSNKLGASPQDILSENNYGQNFTAASNLPVLIPV*TLLPDLI
QSPSDGRKHRIGLPVIIGISLGCTLLVVVSAILLVCVCCLKMKSLNRSASSAETADKLLSGVSGYVSKPTMYETGAILEATMNLSEQCKIGESVYKANIEGKVLAVKRFKEDVTEELK
ILQKVNHGNLVKLMGVSSDNDGNCFVVYEYAENGSLQEWLFAKSCSETLNSRTSLTWCQRISIAVDVSMGLQYMHEHAYPRIVHRDITSSNILLDSNFKAKIANFSMARTFTN
PMMSKIDVFAFGVVLIELLTGRKAMTTKENGEVVMLWTDIWKIFDQEENREERLRKWMDPKLDNYYPIDYALSLASLAMNCTADKSLSRPTIAEIVLSLSLLTQPSPATLERSLT
SSGLDVEATQIVTSISAR >PeanutNFR5/1-595 [Arachis hypogaea subsp. hypogaea]
MAFFLPSLSSSIFLAFMLFSVTSIPTQSQQVNGTDFSCPVDSPSSCGTYVTYIAKSPNFLSLSNISDIFDTSPLSIARASNIKNEGDKLVPGQVLLIPVTCGCTQNQSFANITYELRQG
DVYDIVSKTTYENLTNWRAVNNSNPDLNPVLLPIGVKVLFPLFCRC*PSKKQLQKGIEYMITYVWQNNDNVSSVAAKFGASPVDILSENNYGGNFTAATYLPVLIPV*TKLPVLTQ
PEASHGRKRSIQIPVIISISLGFTLVVAVIVISMVYAYLYQRKRTLNRGDLSAGTADKLLSGVSGYVSKPTVYEANEVIKATMNLSGQCKLGGTVYKAKIEGQVLAVKKVNQVVSE
ELNILQKVNHGNLVKLMGVSSDSDGNHFLVYEYADNGSLDGWLFSKLSLKASLTWYQRINIALDVAMGLQYLHEHTYPRIVHRDITTSNILLDSNFKAKIGNFSMVRTTTNPMI
SKIDVFAFGAVLIELLTGMKAMTTKADGEVVMLWKDIRKMFEVEDEKEKEECLRRWMDPKLECLYPVDYALSLATLAANCTADVSLSRPTMAEVVLGLSLLTQPSQAALERSL
TSSALEAEVTHVATSITAR Lotus Lys11 (New LCO receptor)
>LjLys11/1-591
MTSFFLFTNTLFLALMMFFSTTHHILAQLSHTNGTNFSCPVDSPPSCDTYVTYFAQSPNFLTLTSISDLFDTSPLSIARASNIKDENQNLVPGQLLLVPVTCACSGSNSFSNISHMI
KEGESYYYLSTTSYENLTNWETVQDSNPNYNPYLLPVGIKVVIPLFCKC*PSNYHLNKGIEYLITYVWHNNDNVSLVASKFGVSTQDIISENNFSHQNFTAATNFPILIPV*TQLPSLS
QSYSSSERKRSNHIHIIISIGISLGSTLLIALLVLVSVTCLRKRKSSENKSLLSVEIAGKKLISGVSNYVSKSILYEFRLIMEATLNLNEQCKIGESVYKAKLDGQVLAVKKVKEDVTEEVM
ILQKVNHLNLVKLMGVSSGHDGNHFLVYEFAENGSLHNWLFSNSSTGSRFLTWSQRISIAVDVAMGLQYMHEHTQPSIVHRDITSSNILLDSNFKAKIANFSVARTSINPMILK
VDVFGYGVVLLELLSGKKSLTNNEINHIREIFDLKEKREERIRRWMDPKIESLYPIDDALSLAFLAMNCTSEKPLSRPTMGEVVLSLSLLMTQHSPTTLERSWTCGLDVDVTEMQT
LIAAR

FIG. 12B

Medicago Lyr1 (New LCO receptor)
>MtLYR1/1-590
MVSSFFHTLIFFSATHILLQLPQANGKNFSCTLNSSPSCDTYVAYFANSPNFLTLTAISDIFDTSPQSIARASNIKDENMNLIHGQLLLIPITCGCNGNGNYSFANISHLIKESESYYYL
STISYQNLTNWQTVEDSNPNLNPYLLKIGTKINIPLFCRC*PSNYFAKGIEYLITYVWQPNDNLTLVASKLGASPKDIITANTNNFGQNFTVAINLPVFIPV*KNLPALSQSYYSSSERK
RINHFSIIISIGICLGCTILISLLLLFYVYCLRKRKACENKCVPSVEITDKLISEVSNYVSKPTVYEVGMIMKATMNLNEMCKIGKSVYKAKIDGLVLAVKNVKGHITVTEELMILQKV
NHANLVKLVGVSSGYDGNHFLVYEYAENGSLYNWLLSEFCTLSWSQRLSIAVDIAIGLQYLHEHTQPCIVHRNIKSSNILLDSKFKAKIANFSVARTTKNPMITKVDVLGYGMVL
MELITGKKFLSYSEHSEVNMLWKDFKCVFDTEQKREEIVRRWMDPKLGRFYNVVEALSLFTLAVNCIEEQPLLRPTMGEVVLSLSLLTQPSPTLLEVSWTYGLDVEVAEMVTPII
AR >PanNFP1/1-613
MAISLYLLLFFITHISAQSPPTLATNFSCSTNSSQPSCKTYVAYFAQPPLFMDLKSISNLFGVSPSSISEASNLVSESTKLTRGQLLLIPLSCSCNGSHYFSNVTYNITMGDSYYLVSIHS
FENLTNWPLVRDTNPTLNPNLLQIGTKVIFPLYCGC*PSKSHSKNGIKYLITYVWQPSDDIYRVSAMFNASEVDIIIENNYQDFKAAVGYPVLIPV*SRMPALSQPPYPSHSHHRSQ
LKHRWFLIAVISSAGALLILFLATFLVHSIGLYEKKKNLSHEESSLETTDLIQVKNFSKSDTLELQAKHDKLLPGVSVYLGKPIMYEIKMIMEATMNFNDQYKIGGSVYRAMINGSFL
AVKKAKENVTEELHILQKVNHGNLVKLMGISLDRDGNCFFVYEYAENGSLDKWLNPQSSTSTSSSVGILSWSQRLNIALDVANGLQYMHEHTQPSIVHKEIRTSNILLDSRFKA
KIANFSMARSAASAGMTKVDVFAFGVVLLKLLSGRKAMATRENGEIVMLWKEAKAVLEEEEKRAEKVREWIDPKLESFYPIDGALSLMTLAKACTQEKASARPSIGEVVFSLCV
LTQSFSETLEPSWTCTLEGEDVVQITSPIVA Parasponia NFP2 (Known LCO receptor)
>PanNFP2/1-582
MADSYFPFQAIFLLLLLFSTLNMAASQLNNSATDFSCSDSPPSCEAYVAYFSQPPNYMNVGNISDLFGISQALIAKSSNLVSKDSPLIPQQLLLIPLTCTCTGNHYFANITYQVEPG
DTYHYLSTLLFENLTNSQVMKKMNPEISPEYVLPYIDIIIPVFCRC*PSKSHLKSEIQQFITYVWQPNDQVSNVSAKFNTSASEIVNENKYNNFSSAVGLPVLIPV*SKLPVLARVKPP
KSVRSKKQWILIGVESLGGIVLITLFATLLVYSNRLLKKRRKILEARRLEPRIIIQDKLLSGVSEYLGRPIMYDNKMVVEGTMDFSEQCRIGGSVYRGEIYGEVFAVKKTKQDITDELN
LLQKVNHVNLVNLMGASYDTDGNRFLVYEYVENGSLERWLDLKPSSLAAASSSSSVQFLSWSQRIQIALDVANGLQYLHEHTQPNIAHWNIRTSTILLDSKFRAKIANFEVARP
VGNPAMLKVDIFAFGIVLLALVSGKKALQTIENGEVIMLWKDLAKEVFEVEEKKEDRLRKWMDPNLQSFYPIDGALSLSSLARACIREKSSARPKMAEIVFSLSVLAQSSSPGTP Barley receptor
>HvLysM-RLK1 (AK370300) (New LCO receptor)
MAAPPGRRGLAFGTAALALLAILAVARGQQQYEANAQTNCYGRNGSSVLGYVCNATAAAAPCATYVVFRSSPPYYGTAVSISYLLGSDPEAVADANGVPTVSPLADSRLVLA
PVPCGCSPRGYYQHNSSHTIELRGETYFIIANNTYQGLTTCQALLAQNPRHGSRDLVAGNNLTVPIRCAC*PTPAQAAAGVRHLLTYLVTWGDSVSAIADRFRVDAQAVFQAN*
*NLTAREIIFPFTTLLIPL*KSAPTPDMLVSPAPPPAPAPPQAQQPPASGSGKWIAVGVGVGVGVLALASLIGLMLLCVRRRRTRQGVRERGRLSKVVLDVPSSADYNALASGKHA
SSATTTSASSSALVSSDARAAVESLTVYKYSELEKATAGFSEDRRVKNASVYRAEINGDAAAVKRVAGDVSGEVGILKRVNHSSLVRLSGLCVHHGETYLVFEFAENGALSDWLH
GGGATLVWKQRVQAAFDVADGLNYLHHYTNPPCVHKNLKSSNVLLDANLRAKVSSFALARSVPTGADGGDAQLTRHVVGTQGYLAPEYLEHGLITPKLDVFAFGVILLELLS
GKEAMFNGGDKRGETLLWESAEGLVVDNEDARGKVRPFMDPRLHGDYPLDLAVAVASLAVRCVAREPRRRPSIDVVFATLSAVYNSTLDWDPSDDGNSRSSIVGR

FIG. 12C

Barley receptor
>HvLysM-RLK2 (AK357612) (New LCO receptor)
MAPLTRRRRLLATLLCLCALPAPARSQNASATPAPASVEGFNCSANGTYPCQAYALYRAGLAGVPPDLSAAGDLFGVSRFMLAHANNLSTSAAPAAGQPLLVPLQCGCPSGS
PNAYAPTQYQISSGDTFWIVSVTKLQNLTQYQAVERVNPTVVPTKLEVGDMVTFPIFCQC*PTAAQNATALVTYVMQQGDTYASIAAAFAVDAQSLVSLNGPEQGTQLFSEIL*
*VPLRRQVPKWLPPIV*TRNDASATPPSPSPPPTTTPGPSDVADNRDGVVTGLAVGLGVVGGLWLLQLLLLGCLWRRLKAKGRRGDAVASGEGGEGGRSAKTASASGGVGGE
RFLVTDISEWLDKYRVFKVEELERGTDGFDDAHLIQGSVYKANIGGEVFAVKKMKWDACEELKILQKVNHSNLVKLEGFCINTATGDCFLVYEYVENGSLDLCLLDRGRARRLD
WRTRLHIALDLAHGLQYIHEHTWPRVVHKDVKSSNVLLDARMRAKIANFGLAKTGHNAVTTHIVGTQGYIAPEYLVDGLVTTKMDVFAYGVVLLELVSGREAAGDGGDLLLA
DAEERVFRGREDRLEARAAAWMDPVLAEQTCPPGSVATVMGVARACLQRDPSKRPSMVDVAYTLSRADEYFADYSGESVSVDGSGEIAAR Barley receptor
>HvLysM-RLK3 AK372128 (New LCO receptor)
MATPTRWRGLAAVGRAALAFLVLLAVAAPWCPVARGQQEYEANAQNNCYGNNGSSVLGYTCNATAAVRPCASYVVFRSSPPYESPITISYLLNTTPAALADANAVPTVSSVA
ASRLVLAPLNCGCAPGGYYQHNASYTLQFSNETYFITANITYQGLTTCQALMAQNPNHDSRNLVVGNNLTVPIRCAC*PSPAQAASGVRHLLTYLVASGDTIADIATRFRVDAQ*
*AVLRANRLTDSENIYPFTTLLIPL*KSAPTPDMLVSPAPPPAPVPPQAQQPLPTGGSGSGKGVAIGVGVGVGVLALAGLLGLMFLCVRRRRRLRPGVGENGHPGKVVIDVPSSA
DYDPLASGKHTSSATTTSSSSSAFVSSDARAAVESLTVYKYSELEKATAGFSEDRRVKDASVYRAVINGDTAAVKRVAGDVSGEVGILKRVNHSSLVRLSGLCVHHGDTYLVFEF
AENGALSDWLHGGGATLVWKQRVQAAFDVADGLNYLHHYSTPPCVHKNLKSSNVLLDADLRAKVSSFALARSVPTGAEGGDAQLTRHVVGTQGYLAPEYLEHGLITPKLDV
FAFGVILLELLSGKEATFNGGDKRGEKLLWESAEGLVVDGEDARSKVRAFMDPQLSGDYPLDLAVAVASLALRCVAREPRGRPSMYEVFVTLSAVYNSTLDWDPSDYSNSRSSI
VGR Barley receptor
>HvLysM-RLK10 (HORVU4Hr1G066170) (New LCO receptor)
MEPRRFLCCCLVAVLAVASRRCDAQGGAGNGTGRFACVVPAPCDTFVLYRTQSPGSLDLGAISDLFGVSRAMIAAANNLSLIDEDAALLPDQPLLVPVRCGCTGNRSFVNVTY
PIHSGDTFYALALTGYENLTTPDVIQELNPQAVFNKLNVSQLVTVPLFCRC*PTPAERSAGVLQQITYMWRPVDTMSRVSKLMGSDASAIAAANNVSADFTSTTMLPMLIPVA*
RPPVLPPLRYGPSATTGDPGATKRFSGATVAASIAGSLVAVAALCVAIFGYRRYRRKKATVHSASRFASPRFCFNQNAYGIQSSSSIARMINGGDKLLTSVSQFIDKPVIFGTAEI
MEATMNLDERCRIGSSYYRAKLEGEVFAVKPAKGDVSAELRMMQMVNHANLIRLAGISIGADGDYTFLVYEFAEKGSLDKWLYQKPPSSLPSSSSSVDTLSWNQRLGIALDV
ANGLLYMHEHTQPSMVHGDVRARNILLTADFRARISNFSVATPAMADAAATSSDVFAFGLLVLELLSGRTAMEARVGAEIGMLWRDIRAVLEAGDKRDAKLRKWMDPALG
DEYYLDAALSLAGMARACTEEDAARRPKMADVVFSLSMLVQPLPVGDAFEKLWQPSSEENIRIVNEVAAR Maize receptor
>ZM1 (XP_020399958) (New LCO receptor)
MEPRHFCRALLLLLVVLLLGFRRAGAQDSTNYTVPARFACNVSSPCDTYVVYRTQSPGYLDLGSISDLFGTSQARIASANGLSSEDGVLQPGQPLLVPVRCGCTGAWSFANATY
PIRQGDTFYNLARLSYENLTEYHLIHDLNPRSEPTSLQIGQEVTVPLLCRC*PPARAVQSFITYVWQPGDTLSQVSKLMNATADEIAEANNVTSSSVSSASAAGLPMLIPV*QQRPR
LPPLLYAASAGEGRSSRSRRRALIIIGASVSGSLVALAALLVAIMAQRRYRRKKPSMRLGSPFAVNTKLSWSVNQYGHGSSNSFAHVMKGGKLLTGVSQFIDKPIIFVEEEIVEAT
MNLDERCKIGSTYYRAKLDGEVFAVKPAKGDVSAELRMMQMVNHANLIKLAGISIGADGDYAFLVYEFAEKASLDKWLYHNHQKPPSALLPSSSCTVPTTLSWGQRLSIALDV
ANGLLYMHEHTQPSMVHGDIRARNILLTADFRAKISSFSLAKPATADAAATSSDVFAFGLLLLELMSGRRAMEARIGSEIGMLWREIRAVLEAGDKREAKLRKWMDPALGSEY
QMDAALSLAGMARACTDEDAARRPNMTEVVFSLSMLAQPLSVADGFEKLWQPSSEDNIRIAGSVAAR

FIG. 12D

Maize receptor
>ZM5 (XP_008652982.1) (New LCO receptor)
MELRHFRCCASRLLLLVTLLLGFRRAGAQDSTSYTVPAQFACDVSSPCDTYVVYRTQSPGYLDLGSISDLFGTSQARIASANGLSSEDGVLQPGQPLLVPVRCGCAGAWSFANV
TYPIRQGDTFYNLAKASYENLTEYHLIQNLNPGSEPTSLQIGQEVTVPLLCRC*PARAERSRGVQSLITYMWQAGDTMSQVSKLMNATVDEIAEANNVTANTSASASFVGQPM*
*LIPV*RQRPRLPAPLYAAAAADGKSRSRRRAAVIGASVSGSLVALAALFVAILARRRYRKKPSMRLGSRFAVNTKLSWSRNQFGHDGSNSFAHVMKGGKLLTGVSQFIDKPIIFVE
EEIMEATMNLDERCKIGSTYYRAKLDGEVFAVKPAKGDVSAELKMMQMVNHANLIKLAGISIGADGDYAFLVYEFAEKGSLDKWLYEKPPSALPSSSCTVATLSWGQRLSIAL
DVANGLLYMHEHTQPSMVHDDIRARNILLTADFRAKISGFSLAKPAMVDAAATSSDVFAFGLLLLELLSGRRAMEARIGSEIGMLWREIRGVLETGDKREAKLRKWMDPALG
SEYHMDVALSLASMARACTEEDAARRPNMTEVVFSLSVLAQPLSVADGFEKLWQPSSEDNIRIAGSVAAR Apple NFP5 (New LCO receptor)
>XP_008338966.1 PREDICTED : serine/threonine receptor-like kinase NFP [Malus domestica]
MAISFLCSKPLCILLLLLFFTARILAQSTPSNSSTSFSCSVDAPPSCDTYVSYFARPQFMSLENISHLFGVSPLSIAKASNLVSEHIRLIAGQLLLVPISCGCSGNSYFSNITYEIKSGDSFY
LVSINSFENLTDWHEVLNMNPTLDPSLLQIGQKVIFPLFCKC*PSKMYTENGIKYHITYIWQPNDDISRVSSRFNVSTLDISSANNLHNDSAAVELPVVIPV*SRLPALVQPKPPQGR
NIFKQRWWLILIIILGGVLLVSSLLAIFAVYTRHQHKVKKALDGPGSSLESAEWFKMKEGKIDENFDLKFIQDKLLPGVSSYLGKPIMYEVKTIMEATMNLNEHCRIGGSVYRAIV
DGQVLAVKNTKEDVTEELNILQKVNHANLVKLMGVSSETDGSRFLVYEYAANGSLDKWLYSKSSATSSSAELLTWNQRLSIALDIANGLQYMHEHTQRSIVHMDIRTSNILLDS
KFKAKIANFSMARAAANDVTPKVDVFAFGVVLLALLSGKKGMEAKENGEAIMLWKDVRWVLEAEEEKVERLRKWMDPNLENFYPIDGALSLTALARACTQEKPSTRPSMGE
VVFNLSVLTHSSSQSTLERSWTSALEAEEVLETISPIAAR Strawberry NFR5 (New LCO receptor)
>XP_004300586.2 PREDICTED: protein LYK5-like [Fragaria vesca subsp. vesca]
MAVSFLCSSMVCILLLFFFTSQILAQPAPQSNSTTSFSCAVDAPSSCETYVAYFVESPGYMNLENISDLFGVSVSSISQASNLASSYTGQTRLVAGQLLLVPITCGCTGNRSFANITY
SIKRGDSYYVVSMYTFENLTRWPLVVEMNPALVPSLLQIGVKVIFPLFCKC*PSKMYSDLGIKYLLTYVWQTNDDIFRVSAKFNISALNISGANNFDNGSPVVGQPVLIPL*TKLPAL
SQPLPPHGKHIFKHRLMLIVIICLGVALSVASLLAIFLVHTHRLRKRQKLLNDKSLSLESAEWFRMKEGKSEEKIEMKFIQDKLLPGVSSYLGKAILYDVKTIMEATMNLNDHCGIG
GSVYRAVIDGKVLAVKKTKEDVTEELNILQKVNHANLVKLMGISSEIDGVRFLVYEYAENGSLDKWLYHKTSTNSSSGAFLTWSQRLSIALDVANGLQYLHEHTQPSIVHMDIR
TSNILLDSKYKAKIANFSMARTAANSVTPKVDVFSFGVILLSLLSGKKGMETTDNGEVIMLWKDVRGVLEAEEKKQEKLRAWMDPTLESFYPIDGALSLTALASACTQEKSSARP
SMAEVVFNLSVLTHSSSESTLERSWNSALEVEEVLQTISPIKAR

FIG. 12E

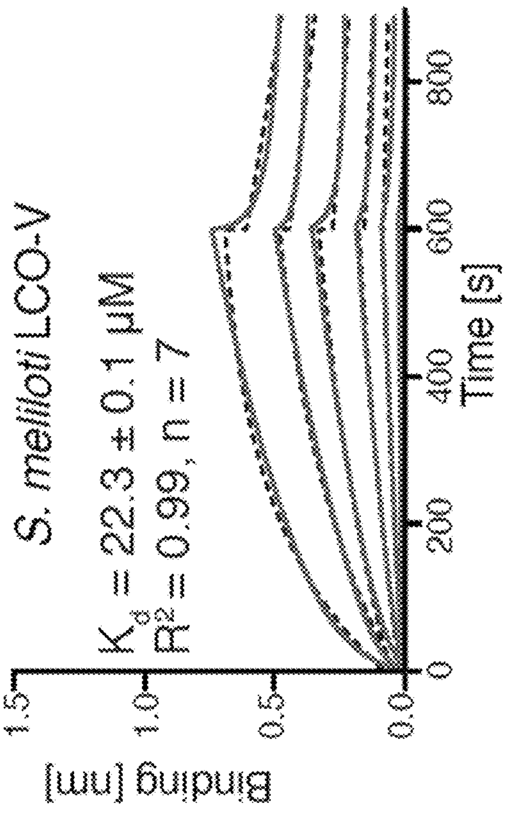
FIG. 15A
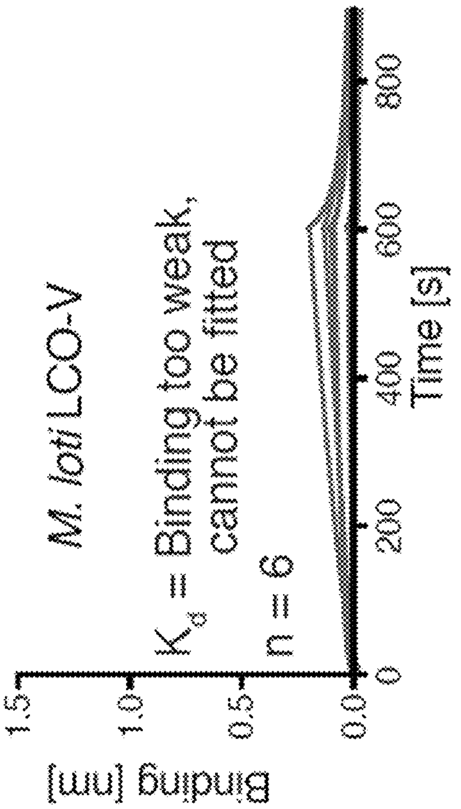
FIG. 15B
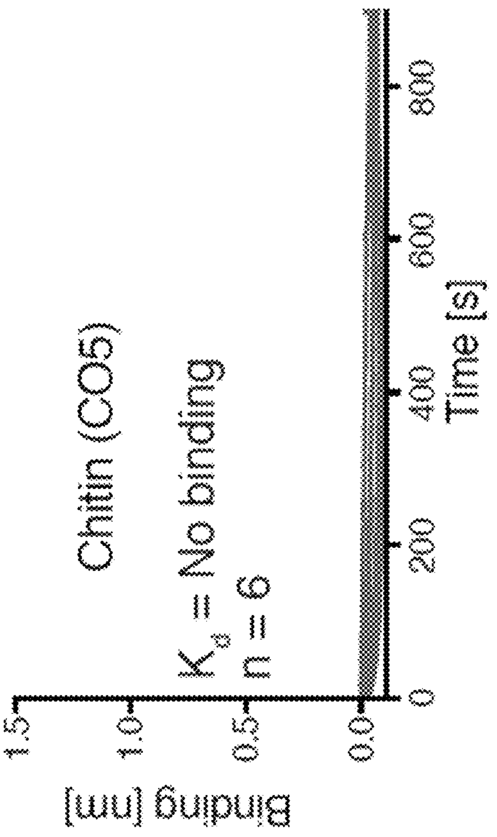
FIG. 15C
| Ligand | $K_d$ (μM) | $R^2$ | n |
|---|---|---|---|
| wt LCO-IV | 12.7 ± 0.1 | 0.99 | 7 |
| *nodL*-LCO-IV | 133.2 ± 0.3 | 0.99 | 3 |
| *nodH*-LCO-IV | 275.3 ± 1.3 | 0.99 | 4 |
| *nodFE*-LCO-IV | No binding | - | 3 |
| *nodFL*-LCO-IV | No binding | - | 3 |
FIG. 15D

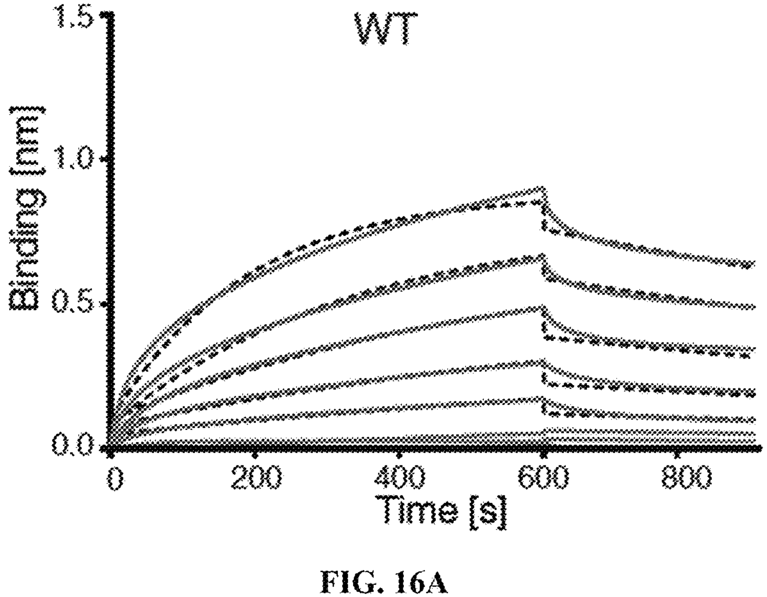
FIG. 16A
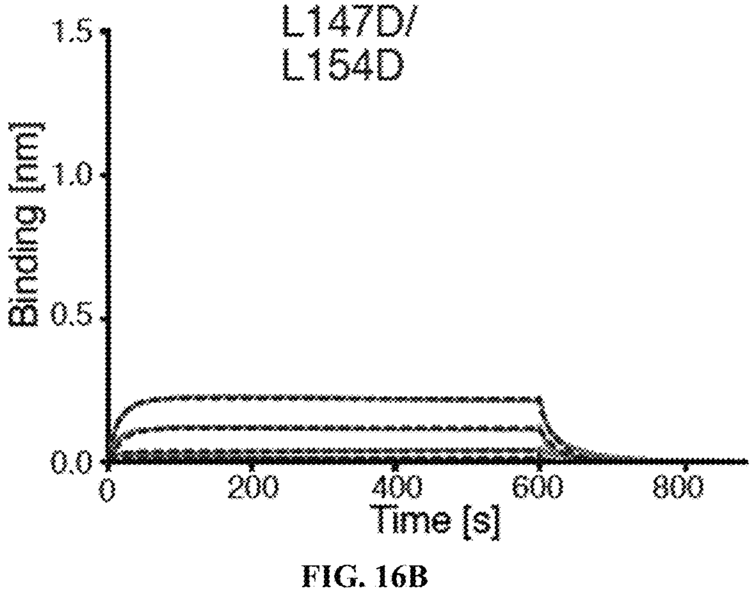
FIG. 16B
| | WT | L147D/ L154D |
|---|---|---|
| $K_d$ (μM) | 12.7 ± 0.1 | 166.7 ± 4.2 |
| $k_{on}$ ($M^{-1}s^{-1}$) | 50.3 | 227.7 |
| $k_{off}$ ($s^{-1}$) | $6.4\times10^{-4}$ | $379.9\times10^{-4}$ |
| $R^2$ | 0.99 | 0.99 |
| n | 7 | 4 |
FIG. 16C
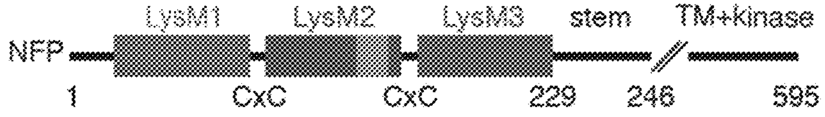
FIG. 16D

SEQUENCE LISTING

```
<160> NUMBER OF SEQ ID NOS: 59

<210> SEQ ID NO 1
<211> LENGTH: 595
<212> TYPE: PRT
<213> ORGANISM: Medicago truncatula

<400> SEQUENCE: 1

Met Ser Ala Phe Phe Leu Pro Ser Ser Ser His Ala Leu Phe Leu Val
1               5                   10                  15

Leu Met Leu Phe Phe Leu Thr Asn Ile Ser Ala Gln Pro Leu Tyr Ile
            20                  25                  30

Ser Glu Thr Asn Phe Thr Cys Pro Val Asp Ser Pro Pro Ser Cys Glu
        35                  40                  45

Thr Tyr Val Ala Tyr Arg Ala Gln Ser Pro Asn Phe Leu Ser Leu Ser
    50                  55                  60

Asn Ile Ser Asp Ile Phe Asn Leu Ser Pro Leu Arg Ile Ala Lys Ala
```

-continued

```
65                  70                  75                  80

Ser Asn Ile Glu Ala Glu Asp Lys Lys Leu Ile Pro Asp Gln Leu Leu
                85                  90                  95

Leu Val Pro Val Thr Cys Gly Cys Thr Lys Asn His Ser Phe Ala Asn
            100                 105                 110

Ile Thr Tyr Ser Ile Lys Gln Gly Asp Asn Phe Phe Ile Leu Ser Ile
        115                 120                 125

Thr Ser Tyr Gln Asn Leu Thr Asn Tyr Leu Glu Phe Lys Asn Phe Asn
    130                 135                 140

Pro Asn Leu Ser Pro Thr Leu Leu Pro Leu Asp Thr Lys Val Ser Val
145                 150                 155                 160

Pro Leu Phe Cys Lys Cys Pro Ser Lys Asn Gln Leu Asn Lys Gly Ile
                165                 170                 175

Lys Tyr Leu Ile Thr Tyr Val Trp Gln Asp Asn Asp Asn Val Thr Leu
            180                 185                 190

Val Ser Ser Lys Phe Gly Ala Ser Gln Val Glu Met Leu Ala Glu Asn
        195                 200                 205

Asn His Asn Phe Thr Ala Ser Thr Asn Arg Ser Val Leu Ile Pro Val
    210                 215                 220

Thr Ser Leu Pro Lys Leu Asp Gln Pro Ser Ser Asn Gly Arg Lys Ser
225                 230                 235                 240

Ser Ser Gln Asn Leu Ala Leu Ile Ile Gly Ile Ser Leu Gly Ser Ala
                245                 250                 255

Phe Phe Ile Leu Val Leu Thr Leu Ser Leu Val Tyr Val Tyr Cys Leu
            260                 265                 270

Lys Met Lys Arg Leu Asn Arg Ser Thr Ser Ser Ser Glu Thr Ala Asp
        275                 280                 285

Lys Leu Leu Ser Gly Val Ser Gly Tyr Val Ser Lys Pro Thr Met Tyr
    290                 295                 300

Glu Ile Asp Ala Ile Met Glu Gly Thr Thr Asn Leu Ser Asp Asn Cys
305                 310                 315                 320

Lys Ile Gly Glu Ser Val Tyr Lys Ala Asn Ile Asp Gly Arg Val Leu
                325                 330                 335

Ala Val Lys Lys Ile Lys Lys Asp Ala Ser Glu Glu Leu Lys Ile Leu
            340                 345                 350

Gln Lys Val Asn His Gly Asn Leu Val Lys Leu Met Gly Val Ser Ser
        355                 360                 365

Asp Asn Asp Gly Asn Cys Phe Leu Val Tyr Glu Tyr Ala Glu Asn Gly
    370                 375                 380

Ser Leu Glu Glu Trp Leu Phe Ser Glu Ser Ser Lys Thr Ser Asn Ser
385                 390                 395                 400

Val Val Ser Leu Thr Trp Ser Gln Arg Ile Thr Ile Ala Met Asp Val
                405                 410                 415

Ala Ile Gly Leu Gln Tyr Met His Glu His Thr Tyr Pro Arg Ile Ile
            420                 425                 430

His Arg Asp Ile Thr Thr Ser Asn Ile Leu Leu Gly Ser Asn Phe Lys
        435                 440                 445

Ala Lys Ile Ala Asn Phe Gly Met Ala Arg Thr Ser Thr Asn Ser Met
    450                 455                 460

Met Pro Lys Ile Asp Val Phe Ala Phe Gly Val Val Leu Ile Glu Leu
465                 470                 475                 480

Leu Thr Gly Lys Lys Ala Met Thr Thr Lys Glu Asn Gly Glu Val Val
                485                 490                 495
```

```
Ile Leu Trp Lys Asp Phe Trp Lys Ile Phe Asp Leu Glu Gly Asn Arg
            500                 505                 510

Glu Glu Arg Leu Arg Lys Trp Met Asp Pro Lys Leu Glu Ser Phe Tyr
        515                 520                 525

Pro Ile Asp Asn Ala Leu Ser Leu Ala Ser Leu Ala Val Asn Cys Thr
    530                 535                 540

Ala Asp Lys Ser Leu Ser Arg Pro Thr Ile Ala Glu Ile Val Leu Cys
545                 550                 555                 560

Leu Ser Leu Leu Asn Gln Pro Ser Ser Glu Pro Met Leu Glu Arg Ser
                565                 570                 575

Leu Thr Ser Gly Leu Asp Ala Glu Ala Thr His Val Val Thr Ser Val
            580                 585                 590

Ile Ala Arg
        595


<210> SEQ ID NO 2
<211> LENGTH: 595
<212> TYPE: PRT
<213> ORGANISM: Lotus japonicus

<400> SEQUENCE: 2

Met Ala Val Phe Phe Leu Thr Ser Gly Ser Leu Ser Leu Phe Leu Ala
1               5                   10                  15

Leu Thr Leu Leu Phe Thr Asn Ile Ala Ala Arg Ser Glu Lys Ile Ser
            20                  25                  30

Gly Pro Asp Phe Ser Cys Pro Val Asp Ser Pro Pro Ser Cys Glu Thr
        35                  40                  45

Tyr Val Thr Tyr Thr Ala Gln Ser Pro Asn Leu Leu Ser Leu Thr Asn
    50                  55                  60

Ile Ser Asp Ile Phe Asp Ile Ser Pro Leu Ser Ile Ala Arg Ala Ser
65                  70                  75                  80

Asn Ile Asp Ala Gly Lys Asp Lys Leu Val Pro Gly Gln Val Leu Leu
                85                  90                  95

Val Pro Val Thr Cys Gly Cys Ala Gly Asn His Ser Ser Ala Asn Thr
            100                 105                 110

Ser Tyr Gln Ile Gln Leu Gly Asp Ser Tyr Asp Phe Val Ala Thr Thr
        115                 120                 125

Leu Tyr Glu Asn Leu Thr Asn Trp Asn Ile Val Gln Ala Ser Asn Pro
    130                 135                 140

Gly Val Asn Pro Tyr Leu Leu Pro Glu Arg Val Lys Val Val Phe Pro
145                 150                 155                 160

Leu Phe Cys Arg Cys Pro Ser Lys Asn Gln Leu Asn Lys Gly Ile Gln
                165                 170                 175

Tyr Leu Ile Thr Tyr Val Trp Lys Pro Asn Asp Asn Val Ser Leu Val
            180                 185                 190

Ser Ala Lys Phe Gly Ala Ser Pro Ala Asp Ile Leu Thr Glu Asn Arg
        195                 200                 205

Tyr Gly Gln Asp Phe Thr Ala Ala Thr Asn Leu Pro Ile Leu Ile Pro
    210                 215                 220

Val Thr Gln Leu Pro Glu Leu Thr Gln Pro Ser Ser Asn Gly Arg Lys
225                 230                 235                 240

Ser Ser Ile His Leu Leu Val Ile Leu Gly Ile Thr Leu Gly Cys Thr
                245                 250                 255

Leu Leu Thr Ala Val Leu Thr Gly Thr Leu Val Tyr Val Tyr Cys Arg
```

```
            260                 265                 270

Arg Lys Lys Ala Leu Asn Arg Thr Ala Ser Ser Ala Glu Thr Ala Asp
        275                 280                 285

Lys Leu Leu Ser Gly Val Ser Gly Tyr Val Ser Lys Pro Asn Val Tyr
    290                 295                 300

Glu Ile Asp Glu Ile Met Glu Ala Thr Lys Asp Phe Ser Asp Glu Cys
305                 310                 315                 320

Lys Val Gly Glu Ser Val Tyr Lys Ala Asn Ile Glu Gly Arg Val Val
                325                 330                 335

Ala Val Lys Lys Ile Lys Glu Gly Gly Ala Asn Glu Glu Leu Lys Ile
            340                 345                 350

Leu Gln Lys Val Asn His Gly Asn Leu Val Lys Leu Met Gly Val Ser
        355                 360                 365

Ser Gly Tyr Asp Gly Asn Cys Phe Leu Val Tyr Glu Tyr Ala Glu Asn
    370                 375                 380

Gly Ser Leu Ala Glu Trp Leu Phe Ser Lys Ser Ser Gly Thr Pro Asn
385                 390                 395                 400

Ser Leu Thr Trp Ser Gln Arg Ile Ser Ile Ala Val Asp Val Ala Val
                405                 410                 415

Gly Leu Gln Tyr Met His Glu His Thr Tyr Pro Arg Ile Ile His Arg
            420                 425                 430

Asp Ile Thr Thr Ser Asn Ile Leu Leu Asp Ser Asn Phe Lys Ala Lys
        435                 440                 445

Ile Ala Asn Phe Ala Met Ala Arg Thr Ser Thr Asn Pro Met Met Pro
    450                 455                 460

Lys Ile Asp Val Phe Ala Phe Gly Val Leu Leu Ile Glu Leu Leu Thr
465                 470                 475                 480

Gly Arg Lys Ala Met Thr Thr Lys Glu Asn Gly Glu Val Val Met Leu
                485                 490                 495

Trp Lys Asp Met Trp Glu Ile Phe Asp Ile Glu Glu Asn Arg Glu Glu
            500                 505                 510

Arg Ile Arg Lys Trp Met Asp Pro Asn Leu Glu Ser Phe Tyr His Ile
        515                 520                 525

Asp Asn Ala Leu Ser Leu Ala Ser Leu Ala Val Asn Cys Thr Ala Asp
    530                 535                 540

Lys Ser Leu Ser Arg Pro Ser Met Ala Glu Ile Val Leu Ser Leu Ser
545                 550                 555                 560

Phe Leu Thr Gln Gln Ser Ser Asn Pro Thr Leu Glu Arg Ser Leu Thr
                565                 570                 575

Ser Ser Gly Leu Asp Val Glu Asp Asp Ala His Ile Val Thr Ser Ile
            580                 585                 590

Thr Ala Arg
        595


<210> SEQ ID NO 3
<211> LENGTH: 594
<212> TYPE: PRT
<213> ORGANISM: Pisum sativum

<400> SEQUENCE: 3

Met Ala Ile Phe Phe Leu Pro Ser Ser Ser His Ala Leu Phe Leu Ala
1               5                   10                  15

Leu Met Phe Phe Val Thr Asn Ile Ser Ala Gln Pro Leu Gln Leu Ser
            20                  25                  30
```

```
Gly Thr Asn Phe Ser Cys Pro Val Asp Ser Pro Pro Ser Cys Glu Thr
        35                  40                  45

Tyr Val Thr Tyr Phe Ala Arg Ser Pro Asn Phe Leu Ser Leu Thr Asn
    50                  55                  60

Ile Ser Asp Ile Phe Asp Met Ser Pro Leu Ser Ile Ala Lys Ala Ser
65                  70                  75                  80

Asn Ile Glu Asp Glu Asp Lys Lys Leu Val Glu Gly Gln Val Leu Leu
                85                  90                  95

Ile Pro Val Thr Cys Gly Cys Thr Arg Asn Arg Tyr Phe Ala Asn Phe
            100                 105                 110

Thr Tyr Thr Ile Lys Leu Gly Asp Asn Tyr Phe Ile Val Ser Thr Thr
        115                 120                 125

Ser Tyr Gln Asn Leu Thr Asn Tyr Val Glu Met Glu Asn Phe Asn Pro
    130                 135                 140

Asn Leu Ser Pro Asn Leu Leu Pro Pro Glu Ile Lys Val Val Val Pro
145                 150                 155                 160

Leu Phe Cys Lys Cys Pro Ser Lys Asn Gln Leu Ser Lys Gly Ile Lys
                165                 170                 175

His Leu Ile Thr Tyr Val Trp Gln Ala Asn Asp Asn Val Thr Arg Val
            180                 185                 190

Ser Ser Lys Phe Gly Ala Ser Gln Val Asp Met Phe Thr Glu Asn Asn
        195                 200                 205

Gln Asn Phe Thr Ala Ser Thr Asn Val Pro Ile Leu Ile Pro Val Thr
    210                 215                 220

Lys Leu Pro Val Ile Asp Gln Pro Ser Ser Asn Gly Arg Lys Asn Ser
225                 230                 235                 240

Thr Gln Lys Pro Ala Phe Ile Ile Gly Ile Ser Leu Gly Cys Ala Phe
                245                 250                 255

Phe Val Val Val Leu Thr Leu Ser Leu Val Tyr Val Tyr Cys Leu Lys
            260                 265                 270

Met Lys Arg Leu Asn Arg Ser Thr Ser Leu Ala Glu Thr Ala Asp Lys
        275                 280                 285

Leu Leu Ser Gly Val Ser Gly Tyr Val Ser Lys Pro Thr Met Tyr Glu
    290                 295                 300

Met Asp Ala Ile Met Glu Ala Thr Met Asn Leu Ser Glu Asn Cys Lys
305                 310                 315                 320

Ile Gly Glu Ser Val Tyr Lys Ala Asn Ile Asp Gly Arg Val Leu Ala
                325                 330                 335

Val Lys Lys Ile Lys Lys Asp Ala Ser Glu Glu Leu Lys Ile Leu Gln
            340                 345                 350

Lys Val Asn His Gly Asn Leu Val Lys Leu Met Gly Val Ser Ser Asp
        355                 360                 365

Asn Asp Gly Asn Cys Phe Leu Val Tyr Glu Tyr Ala Glu Asn Gly Ser
    370                 375                 380

Leu Asp Glu Trp Leu Phe Ser Glu Ser Ser Lys Thr Ser Asn Ser Val
385                 390                 395                 400

Val Ser Leu Thr Trp Ser Gln Arg Ile Thr Val Ala Val Asp Val Ala
                405                 410                 415

Val Gly Leu Gln Tyr Met His Glu His Thr Tyr Pro Arg Ile Ile His
            420                 425                 430

Arg Asp Ile Thr Thr Ser Asn Ile Leu Leu Asp Ser Asn Phe Lys Ala
        435                 440                 445

Lys Ile Ala Asn Phe Ser Met Ala Arg Thr Ser Thr Asn Ser Met Met
```

```
    450                 455                 460

Pro Lys Ile Asp Val Phe Ala Phe Gly Val Val Leu Ile Glu Leu Leu
465                 470                 475                 480

Thr Gly Lys Lys Ala Ile Thr Thr Met Glu Asn Gly Glu Val Val Ile
                485                 490                 495

Leu Trp Lys Asp Phe Trp Lys Ile Phe Asp Leu Glu Gly Asn Arg Glu
            500                 505                 510

Glu Ser Leu Arg Lys Trp Met Asp Pro Lys Leu Glu Asn Phe Tyr Pro
        515                 520                 525

Ile Asp Asn Ala Leu Ser Leu Ala Ser Leu Ala Val Asn Cys Thr Ala
    530                 535                 540

Asp Lys Ser Leu Ser Arg Pro Ser Ile Ala Glu Ile Val Leu Cys Leu
545                 550                 555                 560

Ser Leu Leu Asn Gln Ser Ser Ser Glu Pro Met Leu Glu Arg Ser Leu
                565                 570                 575

Thr Ser Gly Leu Asp Val Glu Ala Thr His Val Val Thr Ser Ile Val
            580                 585                 590

Ala Arg


<210> SEQ ID NO 4
<211> LENGTH: 598
<212> TYPE: PRT
<213> ORGANISM: Glycine max

<400> SEQUENCE: 4

Met Ala Val Phe Phe Pro Phe Leu Pro Leu His Ser Gln Ile Leu Cys
1               5                   10                  15

Leu Val Ile Met Leu Phe Ser Thr Asn Ile Val Ala Gln Ser Gln Gln
            20                  25                  30

Asp Asn Arg Thr Asn Phe Ser Cys Pro Ser Asp Ser Pro Pro Ser Cys
        35                  40                  45

Glu Thr Tyr Val Thr Tyr Ile Ala Gln Ser Pro Asn Phe Leu Ser Leu
    50                  55                  60

Thr Asn Ile Ser Asn Ile Phe Asp Thr Ser Pro Leu Ser Ile Ala Arg
65                  70                  75                  80

Ala Ser Asn Leu Glu Pro Met Asp Asp Lys Leu Val Lys Asp Gln Val
                85                  90                  95

Leu Leu Val Pro Val Thr Cys Gly Cys Thr Gly Asn Arg Ser Phe Ala
            100                 105                 110

Asn Ile Ser Tyr Glu Ile Asn Gln Gly Asp Ser Phe Tyr Phe Val Ala
        115                 120                 125

Thr Thr Ser Tyr Glu Asn Leu Thr Asn Trp Arg Ala Val Met Asp Leu
    130                 135                 140

Asn Pro Val Leu Ser Pro Asn Lys Leu Pro Ile Gly Ile Gln Val Val
145                 150                 155                 160

Phe Pro Leu Phe Cys Lys Cys Pro Ser Lys Asn Gln Leu Asp Lys Glu
                165                 170                 175

Ile Lys Tyr Leu Ile Thr Tyr Val Trp Lys Pro Gly Asp Asn Val Ser
            180                 185                 190

Leu Val Ser Asp Lys Phe Gly Ala Ser Pro Glu Asp Ile Met Ser Glu
        195                 200                 205

Asn Asn Tyr Gly Gln Asn Phe Thr Ala Ala Asn Asn Leu Pro Val Leu
    210                 215                 220

Ile Pro Val Thr Arg Leu Pro Val Leu Ala Arg Ser Pro Ser Asp Gly
```

```
225                 230                 235                 240

Arg Lys Gly Gly Ile Arg Leu Pro Val Ile Ile Gly Ile Ser Leu Gly
                245                 250                 255

Cys Thr Leu Leu Val Leu Val Leu Ala Val Leu Leu Val Tyr Val Tyr
            260                 265                 270

Cys Leu Lys Met Lys Thr Leu Asn Arg Ser Ala Ser Ser Ala Glu Thr
        275                 280                 285

Ala Asp Lys Leu Leu Ser Gly Val Ser Gly Tyr Val Ser Lys Pro Thr
    290                 295                 300

Met Tyr Glu Thr Asp Ala Ile Met Glu Ala Thr Met Asn Leu Ser Glu
305                 310                 315                 320

Gln Cys Lys Ile Gly Glu Ser Val Tyr Lys Ala Asn Ile Glu Gly Lys
                325                 330                 335

Val Leu Ala Val Lys Arg Phe Lys Glu Asp Val Thr Glu Glu Leu Lys
            340                 345                 350

Ile Leu Gln Lys Val Asn His Gly Asn Leu Val Lys Leu Met Gly Val
        355                 360                 365

Ser Ser Asp Asn Asp Gly Asn Cys Phe Val Val Tyr Glu Tyr Ala Glu
    370                 375                 380

Asn Gly Ser Leu Asp Glu Trp Leu Phe Ser Lys Ser Cys Ser Asp Thr
385                 390                 395                 400

Ser Asn Ser Arg Ala Ser Leu Thr Trp Cys Gln Arg Ile Ser Met Ala
                405                 410                 415

Val Asp Val Ala Met Gly Leu Gln Tyr Met His Glu His Ala Tyr Pro
            420                 425                 430

Arg Ile Val His Arg Asp Ile Thr Ser Ser Asn Ile Leu Leu Asp Ser
        435                 440                 445

Asn Phe Lys Ala Lys Ile Ala Asn Phe Ser Met Ala Arg Thr Phe Thr
    450                 455                 460

Asn Pro Met Met Pro Lys Ile Asp Val Phe Ala Phe Gly Val Val Leu
465                 470                 475                 480

Ile Glu Leu Leu Thr Gly Arg Lys Ala Met Thr Thr Lys Glu Asn Gly
                485                 490                 495

Glu Val Val Met Leu Trp Lys Asp Ile Trp Lys Ile Phe Asp Gln Glu
            500                 505                 510

Glu Asn Arg Glu Glu Arg Leu Lys Lys Trp Met Asp Pro Lys Leu Glu
        515                 520                 525

Ser Tyr Tyr Pro Ile Asp Tyr Ala Leu Ser Leu Ala Ser Leu Ala Val
    530                 535                 540

Asn Cys Thr Ala Asp Lys Ser Leu Ser Arg Pro Thr Ile Ala Glu Ile
545                 550                 555                 560

Val Leu Ser Leu Ser Leu Leu Thr Gln Pro Ser Pro Ala Thr Leu Glu
                565                 570                 575

Arg Ser Leu Thr Ser Ser Gly Leu Asp Val Glu Ala Thr Gln Ile Val
            580                 585                 590

Thr Ser Ile Ala Ala Arg
        595


<210> SEQ ID NO 5
<211> LENGTH: 557
<212> TYPE: PRT
<213> ORGANISM: Cicer arietinum

<400> SEQUENCE: 5
```

Met Ser Val Phe Phe Leu Pro Ser Arg Ser His Val Leu Phe Leu Ala
1 5 10 15

Leu Met Leu Phe Leu Thr Asn Ile Ser Ala Gln Ser Gln His Leu Ser
20 25 30

Gly Thr Asn Phe Ser Cys Pro Val Asp Ser Pro Pro Ser Cys Glu Thr
35 40 45

Tyr Val Thr Tyr Ile Ala Gln Ser Pro Asn Phe Leu Ser Leu Thr Asn
50 55 60

Ile Ser Asp Leu Phe Asp Ile Ser Pro Leu Ser Ile Ala Arg Ala Ser
65 70 75 80

Asn Ile Asp Asp Glu Asp Lys Glu Leu Ile Pro Gly Gln Val Leu Leu
85 90 95

Val Pro Val Thr Cys Gly Cys Thr Lys His Arg Ser Phe Ala Asn Asn
100 105 110

Thr Tyr Thr Ile Lys Leu Gly Asp Ser Tyr Ile Leu Val Ser Thr Thr
115 120 125

Ser Tyr Gln Asn Leu Thr Asn Tyr Leu Glu Met Glu Asp Ser Asn Pro
130 135 140

Gly Leu Asn Pro Asn Leu Ile Pro Pro Phe Ile Lys Val Val Val Pro
145 150 155 160

Ile Phe Cys Arg Cys Pro Ser Lys Thr Gln Leu Asn Lys Gly Ile Lys
165 170 175

Tyr Leu Ile Thr Tyr Val Trp His Ala Asn Asp Asn Val Ser Thr Val
180 185 190

Ser Ser Lys Phe Gly Ala Ser Gln Val Asp Ile Leu Thr Glu Asn Asn
195 200 205

Tyr Asn Gln Asn Phe Ala Ser Ala Ala Asn Leu Pro Val Leu Ile Pro
210 215 220

Val Thr Arg Leu Pro Ile Leu Ala Gln Pro Ser Ser Asn Gly Arg Lys
225 230 235 240

Arg Ser Ile Gln Leu Pro Val Ile Ile Asp Lys Leu Leu Ser Gly Val
245 250 255

Ser Gly Tyr Val Ser Lys Pro Thr Met Tyr Glu Met Asp Val Ile Met
260 265 270

Glu Ala Thr Met Asn Leu Ser Asp Gln Cys Lys Ile Gly Glu Ser Val
275 280 285

Tyr Lys Ala Asn Ile Asp Gly Lys Val Leu Ala Val Lys Lys Thr Lys
290 295 300

Lys Asp Ala Ser Glu Glu Leu Lys Ile Leu Gln Lys Val Asn His Gly
305 310 315 320

Asn Leu Val Lys Leu Met Gly Val Ser Ser Asp Asn Glu Gly Asn Cys
325 330 335

Phe Leu Val Tyr Glu Tyr Ala Glu Asn Gly Ser Leu Asp Glu Trp Leu
340 345 350

Phe Leu Glu Ser Ser Lys Thr Ser Asp Ser Thr Val Ser Leu Thr Trp
355 360 365

Ser Gln Arg Ile Gly Ile Ala Val Asp Val Ala Val Gly Leu Gln Tyr
370 375 380

Met His Glu His Thr Tyr Pro Arg Ile Ile His Arg Asp Ile Thr Thr
385 390 395 400

Ser Asn Ile Leu Leu Asp Ala Asn Phe Lys Ala Lys Ile Ala Asn Phe
405 410 415

Ser Met Ala Arg Thr Ser Thr Asn Pro Met Met Pro Lys Ile Asp Val

```
            420                 425                 430

Phe Ala Phe Gly Val Val Leu Ile Glu Leu Leu Thr Gly Lys Lys Gly
        435                 440                 445

Val Thr Thr Lys Glu Asn Gly Glu Val Val Ile Met Trp Lys Asp Phe
    450                 455                 460

Trp Met Ile Phe Asp Leu Glu Gly Asn Lys Glu Glu Arg Leu Arg Lys
465                 470                 475                 480

Trp Met Asp Pro Lys Leu Glu Asn Phe Tyr Pro Ile Asp Asn Ala Leu
                485                 490                 495

Ser Leu Ala Ser Leu Ala Val Asn Cys Thr Ala Asp Lys Ser Leu Ser
            500                 505                 510

Arg Pro Thr Ile Glu Glu Ile Val Leu Cys Leu Asn Leu Leu Asn Gln
        515                 520                 525

Pro Ser Ser Glu Pro Thr Leu Glu Arg Ser Leu Thr Phe Gly Leu Asp
    530                 535                 540

Val Glu Asp Thr Gln Ile Val Thr Ser Ile Ala Ala Arg
545                 550                 555


<210> SEQ ID NO 6
<211> LENGTH: 2144
<212> TYPE: DNA
<213> ORGANISM: Cicer arietinum

<400> SEQUENCE: 6

ttgaaccttc gagctcttgc atataactta ttcaatgtca ctagccaaat tactactgag     60

atttaaacat aagtaatcta ttttttata tgacaggact ttttgataga ggaagaaaat    120

gattggtatg cgaaaagata ttttattgac aacaaatgct ccatatcacc aatgctaagt    180

tcctgcatta agaaacactc ttctctcttc ccctcataat aacttccatt tcttcacaac    240

tttcacaaaa tgtctgtctt ctttcttccc tctagatctc atgttctttt tcttgcactc    300

atgttgtttc tcactaacat ctcagctcaa tcacaacacc tcagtggaac aaacttttca    360

tgccctgtgg attcacctcc ttcatgtgaa acttatgtga catacattgc tcagtctcca    420

aattttttaa gcctaacaaa catatctgat ttatttgata tcagtccttt atccatcgca    480

agagcgagta acatagacga cgaggataaa gagctgatac caggtcaagt cttattagta    540

cctgtaactt gtggctgcac taaacatcgc tctttcgcca ataacaccta cacgatcaag    600

ctcggcgaca gctacattct agtttcaacc acttcatatc agaatctcac caattatctt    660

gaaatggaag attccaaccc tggtctaaat cctaatctta ttccaccatt catcaaagtt    720

gtagtcccaa tattctgcag gtgcccttca aagactcagc tgaacaaagg aataaagtat    780

ctgataactt acgtgtggca cgctaacgac aatgtttcaa ctgtaagttc caaatttggt    840

gcatcacaag ttgatatatt gactgaaaac aattacaatc aaaactttgc ttctgcagcc    900

aaccttccag ttttgattcc tgtgacaagg ttacctattc tagctcaacc gtcttcgaat    960

ggaagaaaga gaagcattca acttcctgtt ataattggta ttagtatagg aagtgctttt   1020

ttcgttacag ttttaacagt atcacttgtg tatttatact gtctgaaaat gaagagattg   1080

aataggactg cttctttatc tgagactgca gataagttac tttcaggagt ttcgggttac   1140

gtaagcaagc caacaatgta tgaaatggat gtgatcatgg aagctacaat gaacctgagt   1200

gaccaatgta agattggtga atcagtttat aaggctaata tagatggtaa agttttagca   1260

gtgaaaaaaa ctaagaaaga tgcttctgag gagctgaaaa ttctgcagaa ggtaaatcat   1320

ggaaatctgg tgaaactaat gggtgtgtct tcggacaacg agggtaactg ttttctggtt   1380
```

```
tatgagtatg ctgaaaatgg ttctcttgat gaatggttgt tcttggaatc ttcgaaaact   1440

tcggattcga cagtctccct tacatggtct cagagaatag gcatagcagt ggatgttgca   1500

gttggtctgc aatacatgca tgaacatact tatccaagga taatccacag agacatcaca   1560

acaagtaata tccttctcga cgcgaacttt aaggccaaga tagcgaattt ttcgatggct   1620

agaacttcaa ccaacccgat gatgccgaaa atagatgttt tcgcttttgg ggtggttctg   1680

atagagttgc taaccggaaa aaaaggcgta acaacgaaag aaaatggtga ggttgttatt   1740

atgtggaagg atttttggat gatttttgat ctagaaggga ataaagaaga gaggctaaga   1800

aaatggatgg atcctaagtt agaaaacttt tatcctatag ataatgctct tagtttggct   1860

tctttggcag tgaattgcac tgctgataaa tcattgtcaa gaccaactat tgaagaaatt   1920

gttctttgtc ttaaccttct caatcaacca tcatctgaac caacattaga aagatctttg   1980

acatttgggt tagatgttga agatactcaa attgttactt ctatagcagc tcgttgatca   2040

agtgaagata atattaattc tgttttcttt catattgaag atggtacttt gtttacatga   2100

taactatatt tttatgcgtg gaagtatatg gttagtttaa ttaa                    2144
```

<210> SEQ ID NO 7
<211> LENGTH: 597
<212> TYPE: PRT
<213> ORGANISM: Phaseolus vulgaris

<400> SEQUENCE: 7

```
Met Ala Val Phe Phe Val Ser Leu Thr Leu Gly Ala Gln Ile Leu Tyr
1               5                   10                  15

Val Val Leu Met Phe Phe Thr Cys Ile Glu Ala Gln Ser Gln Gln Thr
            20                  25                  30

Asn Gly Thr Asn Phe Ser Cys Pro Ser Asn Ser Pro Pro Ser Cys Glu
        35                  40                  45

Thr Tyr Val Thr Tyr Ile Ser Gln Ser Pro Asn Phe Leu Ser Leu Thr
    50                  55                  60

Ser Val Ser Asn Ile Phe Asp Thr Ser Pro Leu Ser Ile Ala Arg Ala
65                  70                  75                  80

Ser Asn Leu Gln His Glu Glu Asp Lys Leu Ile Pro Gly Gln Val Leu
                85                  90                  95

Leu Ile Pro Val Thr Cys Gly Cys Thr Gly Asn Arg Ser Phe Ala Asn
            100                 105                 110

Ile Ser Tyr Glu Ile Asn Gln Gly Asp Ser Phe Tyr Phe Val Ala Thr
        115                 120                 125

Thr Leu Tyr Gln Asn Leu Thr Asn Trp His Ala Val Met Asp Leu Asn
    130                 135                 140

Pro Gly Leu Ser Pro Phe Thr Leu Pro Ile Gly Ile Gln Val Val Ile
145                 150                 155                 160

Pro Leu Phe Cys Lys Cys Pro Ser Lys Asn Gln Leu Asp Arg Gly Ile
                165                 170                 175

Lys Tyr Leu Ile Thr His Val Trp Gln Pro Asn Asp Asn Val Ser Phe
            180                 185                 190

Val Ser Asn Lys Leu Gly Ala Ser Pro Gln Asp Ile Leu Ser Glu Asn
        195                 200                 205

Asn Tyr Gly Gln Asn Phe Thr Ala Ala Ser Asn Leu Pro Val Leu Ile
    210                 215                 220

Pro Val Thr Leu Leu Pro Asp Leu Ile Gln Ser Pro Ser Asp Gly Arg
225                 230                 235                 240
```

-continued

```
Lys His Arg Ile Gly Leu Pro Val Ile Ile Gly Ile Ser Leu Gly Cys
                245                 250                 255

Thr Leu Leu Val Val Val Ser Ala Ile Leu Leu Val Cys Val Cys Cys
            260                 265                 270

Leu Lys Met Lys Ser Leu Asn Arg Ser Ala Ser Ser Ala Glu Thr Ala
        275                 280                 285

Asp Lys Leu Leu Ser Gly Val Ser Gly Tyr Val Ser Lys Pro Thr Met
    290                 295                 300

Tyr Glu Thr Gly Ala Ile Leu Glu Ala Thr Met Asn Leu Ser Glu Gln
305                 310                 315                 320

Cys Lys Ile Gly Glu Ser Val Tyr Lys Ala Asn Ile Glu Gly Lys Val
                325                 330                 335

Leu Ala Val Lys Arg Phe Lys Glu Asp Val Thr Glu Glu Leu Lys Ile
            340                 345                 350

Leu Gln Lys Val Asn His Gly Asn Leu Val Lys Leu Met Gly Val Ser
        355                 360                 365

Ser Asp Asn Asp Gly Asn Cys Phe Val Val Tyr Glu Tyr Ala Glu Asn
    370                 375                 380

Gly Ser Leu Gln Glu Trp Leu Phe Ala Lys Ser Cys Ser Glu Thr Leu
385                 390                 395                 400

Asn Ser Arg Thr Ser Leu Thr Trp Cys Gln Arg Ile Ser Ile Ala Val
                405                 410                 415

Asp Val Ser Met Gly Leu Gln Tyr Met His Glu His Ala Tyr Pro Arg
            420                 425                 430

Ile Val His Arg Asp Ile Thr Ser Ser Asn Ile Leu Leu Asp Ser Asn
        435                 440                 445

Phe Lys Ala Lys Ile Ala Asn Phe Ser Met Ala Arg Thr Phe Thr Asn
    450                 455                 460

Pro Met Met Ser Lys Ile Asp Val Phe Ala Phe Gly Val Val Leu Ile
465                 470                 475                 480

Glu Leu Leu Thr Gly Arg Lys Ala Met Thr Thr Lys Glu Asn Gly Glu
                485                 490                 495

Val Val Met Leu Trp Thr Asp Ile Trp Lys Ile Phe Asp Gln Glu Glu
            500                 505                 510

Asn Arg Glu Glu Arg Leu Arg Lys Trp Met Asp Pro Lys Leu Asp Asn
        515                 520                 525

Tyr Tyr Pro Ile Asp Tyr Ala Leu Ser Leu Ala Ser Leu Ala Met Asn
    530                 535                 540

Cys Thr Ala Asp Lys Ser Leu Ser Arg Pro Thr Ile Ala Glu Ile Val
545                 550                 555                 560

Leu Ser Leu Ser Leu Leu Thr Gln Pro Ser Pro Ala Thr Leu Glu Arg
                565                 570                 575

Ser Leu Thr Ser Ser Gly Leu Asp Val Glu Ala Thr Gln Ile Val Thr
            580                 585                 590

Ser Ile Ser Ala Arg
        595
```

<210> SEQ ID NO 8
<211> LENGTH: 2192
<212> TYPE: DNA
<213> ORGANISM: Phaseolus vulgaris

<400> SEQUENCE: 8

```
ggaaatttag ttaaagctaa tgacacaaac aggaccatat ttttatatta agccaaaaga     60
```

```
tatttttatt gacaaagaac tacatatcaa caacgacgat tgccagtgat agtagactgc    120

ctcataactt tcatttgttc acaacttcac atcaatggct gtcttctttg tttctcttac    180

tcttggtgct cagattcttt atgtggtact catgtttttc acttgtattg aagctcaatc    240

acaacagacc aatggaacaa acttttcatg cccttccaat tcacctcctt catgtgaaac    300

ctatgtgaca tacatatccc agtcgccaaa tttttgagt ctgaccagcg tatctaatat     360

atttgacacg agtcctttgt caattgccag agccagcaac ttacagcatg aggaagacaa    420

gttgattcca ggccaagtct tactgatacc agtaacctgt ggttgcactg gaaaccgctc    480

tttcgccaac atctcctatg agatcaacca aggtgatagc ttctactttg ttgcgaccac    540

tttataccag aatctcacaa attggcatgc agtgatggat ttaaacccag gtctaagtcc    600

atttactttg ccaataggca tccaagttgt aattccttta ttctgcaagt gtccttcaaa    660

gaaccagctg gatagaggga taaagtacct gatcactcac gtctggcagc ccaatgacaa    720

tgtttccttt gtaagtaaca agttaggtgc atcaccacag gacatattga gtgaaaacaa    780

ctatggtcaa aacttcactg ccgcaagcaa ccttccagtt ttgatcccag ttacactctt    840

gccagatctt attcaatctc cttcagatgg aagaaaacac agaattggtc ttccagttat    900

aattggtatc agcctgggat gcacactact ggttgtggtt tcagcaatat tactggtgtg    960

tgtatgttgt ctgaaaatga agagtttgaa taggagtgct tcatcagctg aaactgcaga   1020

taaactactt tctggagttt caggctatgt aagtaagcct acaatgtatg aaactggtgc   1080

aatattggaa gctactatga acctcagtga gcagtgcaag attggggaat cagtgtacaa   1140

ggctaacata gagggtaagg ttttagcagt aaaaagattc aaggaagatg tcacggagga   1200

gctgaaaatt ctgcagaagg tgaatcatgg aaatctggtg aaactaatgg gtgtctcatc   1260

agataatgat ggaaattgtt ttgtggttta tgaatatgct gaaaatgggt ctcttcaaga   1320

gtggcttttc gccaagtctt gttcagagac attaaactcg aggacctccc ttacatggtg   1380

ccagaggata agcatagcag tggatgtttc aatgggtctg cagtacatgc atgaacatgc   1440

ttatccaaga atagtccaca gggacatcac aagcagtaat atccttcttg actccaactt   1500

taaggccaag atagcaaatt tctccatggc cagaactttt accaacccca tgatgtcaaa   1560

aatagatgta tttgcttttg ggtggttct gatagaattg cttactggca ggaaagccat    1620

gacaaccaaa gaaaatggtg aggtggttat gctgtggacg gacatttgga agatctttga   1680

tcaagaagag aatagagagg agaggctcag aaaatggatg gatcctaagt tagataatta   1740

ttatcctatt gattatgctc tcagcttggc ctccttggca atgaattgca ctgcagacaa   1800

gtctttgtcc agaccaacca tagcagaaat tgtccttagt ctctcccttc tcactcaacc   1860

atctcccgcg acactggaga gatccttgac ttcttctgga ttagatgtag aagctactca   1920

aattgtcact tccatctcag ctcgttgatt gagtgaagcc aatctagttt ctcacatcca   1980

agatggtact ttttttaaa taatgattgc accttagtca ataatgatga acttggggag     2040

ttttcaacat ttagtgtttc catccctgtt gttctttatg tttgaggtag agttcgtaaa   2100

acgaatagca attgcagttc tcctcagact aaatttgctt atttctctgt acttctttta   2160

tatgacaatt gaaagtgaat caaatgatgg ag                                 2192
```

<210> SEQ ID NO 9
<211> LENGTH: 595
<212> TYPE: PRT
<213> ORGANISM: Arachis hypogaea subsp. Hypogaea

<400> SEQUENCE: 9

Met Ala Phe Phe Leu Pro Ser Leu Ser Ser Ser Ile Phe Leu Ala Phe
1               5                   10                  15

Met Leu Phe Ser Val Thr Ser Ile Pro Thr Gln Ser Gln Gln Val Asn
            20                  25                  30

Gly Thr Asp Phe Ser Cys Pro Val Asp Ser Pro Ser Ser Cys Gly Thr
        35                  40                  45

Tyr Val Thr Tyr Ile Ala Lys Ser Pro Asn Phe Leu Ser Leu Ser Asn
    50                  55                  60

Ile Ser Asp Ile Phe Asp Thr Ser Pro Leu Ser Ile Ala Arg Ala Ser
65                  70                  75                  80

Asn Ile Lys Asn Glu Gly Asp Lys Leu Val Pro Gly Gln Val Leu Leu
                85                  90                  95

Ile Pro Val Thr Cys Gly Cys Thr Gln Asn Gln Ser Phe Ala Asn Ile
            100                 105                 110

Thr Tyr Glu Leu Arg Gln Gly Asp Val Tyr Asp Ile Val Ser Lys Thr
        115                 120                 125

Thr Tyr Glu Asn Leu Thr Asn Trp Arg Ala Val Asn Asn Ser Asn Pro
    130                 135                 140

Asp Leu Asn Pro Val Leu Leu Pro Ile Gly Val Lys Val Leu Phe Pro
145                 150                 155                 160

Leu Phe Cys Arg Cys Pro Ser Lys Lys Gln Leu Gln Lys Gly Ile Glu
                165                 170                 175

Tyr Met Ile Thr Tyr Val Trp Gln Asn Asn Asp Asn Val Ser Ser Val
            180                 185                 190

Ala Ala Lys Phe Gly Ala Ser Pro Val Asp Ile Leu Ser Glu Asn Asn
        195                 200                 205

Tyr Gly Gly Asn Phe Thr Ala Ala Thr Tyr Leu Pro Val Leu Ile Pro
    210                 215                 220

Val Thr Lys Leu Pro Val Leu Thr Gln Pro Glu Ala Ser His Gly Arg
225                 230                 235                 240

Lys Arg Ser Ile Gln Ile Pro Val Ile Ile Ser Ile Ser Leu Gly Phe
                245                 250                 255

Thr Leu Val Val Ala Val Ile Val Ile Ser Met Val Tyr Ala Tyr Leu
            260                 265                 270

Tyr Gln Arg Lys Arg Thr Leu Asn Arg Gly Asp Leu Ser Ala Gly Thr
        275                 280                 285

Ala Asp Lys Leu Leu Ser Gly Val Ser Gly Tyr Val Ser Lys Pro Thr
    290                 295                 300

Val Tyr Glu Ala Asn Glu Val Ile Lys Ala Thr Met Asn Leu Ser Gly
305                 310                 315                 320

Gln Cys Lys Leu Gly Gly Thr Val Tyr Lys Ala Lys Ile Glu Gly Gln
                325                 330                 335

Val Leu Ala Val Lys Lys Val Asn Gln Val Val Ser Glu Glu Leu Asn
            340                 345                 350

Ile Leu Gln Lys Val Asn His Gly Asn Leu Val Lys Leu Met Gly Val
        355                 360                 365

Ser Ser Asp Ser Asp Gly Asn His Phe Leu Val Tyr Glu Tyr Ala Asp
    370                 375                 380

Asn Gly Ser Leu Asp Gly Trp Leu Phe Ser Lys Leu Ser Leu Lys Ala
385                 390                 395                 400

Ser Leu Thr Trp Tyr Gln Arg Ile Asn Ile Ala Leu Asp Val Ala Met
                405                 410                 415

```
Gly Leu Gln Tyr Leu His Glu His Thr Tyr Pro Arg Ile Val His Arg
            420                 425                 430

Asp Ile Thr Thr Ser Asn Ile Leu Leu Asp Ser Asn Phe Lys Ala Lys
        435                 440                 445

Ile Gly Asn Phe Ser Met Val Arg Thr Thr Thr Asn Pro Met Ile Ser
    450                 455                 460

Lys Ile Asp Val Phe Ala Phe Gly Ala Val Leu Ile Glu Leu Leu Thr
465                 470                 475                 480

Gly Met Lys Ala Met Thr Thr Lys Ala Asp Gly Glu Val Val Met Leu
                485                 490                 495

Trp Lys Asp Ile Arg Lys Met Phe Glu Val Glu Asp Glu Lys Glu Lys
            500                 505                 510

Glu Glu Cys Leu Arg Arg Trp Met Asp Pro Lys Leu Glu Cys Leu Tyr
        515                 520                 525

Pro Val Asp Tyr Ala Leu Ser Leu Ala Thr Leu Ala Ala Asn Cys Thr
    530                 535                 540

Ala Asp Val Ser Leu Ser Arg Pro Thr Met Ala Glu Val Val Leu Gly
545                 550                 555                 560

Leu Ser Leu Leu Thr Gln Pro Ser Gln Ala Ala Leu Glu Arg Ser Leu
                565                 570                 575

Thr Ser Ser Ala Leu Glu Ala Glu Val Thr His Val Ala Thr Ser Ile
            580                 585                 590

Thr Ala Arg
        595


<210> SEQ ID NO 10
<211> LENGTH: 2683
<212> TYPE: DNA
<213> ORGANISM: Arachis hypogaea subsp. Hypogaea

<400> SEQUENCE: 10

atctttctct taacagtagt agctagatta cagaatctct tattctattg ttttcgatta     60

gattagatgg aatcacgtat atgaaccgac accgtgaagc atgaaagccg cactcaaata    120

ttcaagaagg ctatttcaaa aatatgaaac cagggaaaaa atgcaagtgt aaaataatgc    180

ttatgaaaaa ttgtatgcag tgtaggtagt aattcttata aaattcatta gacccgaata    240

cttttagcac gtataaatct tgtggagaca ctacatttta aggcgtggtc tagtgataga    300

tagacatgga attggcatca gaattttctc ttatgatgtc tcaaattgga gattctttgc    360

atataagtta aaaatgacca tcctggaatc ttcattggca ttttattata ctctgctgtg    420

cgcatgaata gcatactatt gatatatgta aagtcaatgt tttccttaac atataatctt    480

agacttactt ggaaatttga tatcactgca taaataatta ggaatagata tggtaaaaca    540

gtataccaat aactcttctg ttaaaccaaa gggtatttta ttgacaaaga atcctccata    600

tcaccaaaaa tcctgagtgt ctttgacttc tgataataaa agtttccttt atgttctttc    660

cctccttctc aacttcagaa aaatggcttt ctttctaccc tctctctcaa gtagtatttt    720

tcttgtattc atgttctcca tcaccagcat cccaactcaa tcacaacagg ttaatggaac    780

agacttttca tgcccagtgg attcaccttc ttcctgtgga acatatgtga catacatcgc    840

taaatctcca aacttcttga gcctttctaa catatctgac atatttgaca ccagcccttt    900

atccattgca agagcaagta acataaagaa tgagggtgac aagctggttc caggccaagt    960

cttactgata cctgtcactt gtggttgcac tcaaaaccaa tctttcgcca atatcaccta   1020
```

```
tgagctaagg cagggtgata tgtacgactt tgtctcaaaa acaacatatg agaatctcac   1080

aaattggcgt gctgtcaacg attcaaaccc agatttgaat ccagttctgc tgccagtagg   1140

tgtgaaagta ttgttccctt tattctgcag gtgcccttct aagaagcagt tacaaaaagg   1200

gatagaatat atgatcacct atgtgtggca gaacaatgac aatgtttcct ctgtagcagc   1260

caagtttggt gcatcggcag tggacatatt gtccgaaaac aactatggtg gaaacttcac   1320

agctgcaacc tatcttccgg ttttgattcc tgtgacgaag ttgccggttc ttactcaacc   1380

cgagccttca catggaagaa agagaagcat tcaaatccct gttataatca gtattagcct   1440

ggggttcacc cttgttgttg ctgttatagt aatatcaatg gtttatgctt atctttatca   1500

gagaaagagg actttgaata ggagagactc atctgctggg acagcagata agctactctc   1560

tggagtctca ggctacgtga gtaagccaac cgtgtatgaa gccaatgagg ttatcaaagc   1620

caccatgaat ctcagcgaac agtgcaagct tgggggcaca gtttacaagg ccaaaataga   1680

agggcaggtc ttggcagtga aaaaagtgaa tcaagtagtt tctgaggagc tgaatattct   1740

gcagaaggtg aatcatggaa acctggtgaa actgatgggt gtatcttcag acagtgatgg   1800

aaaccatttc ctggtttatg agtatgctga taacgggtcc cttgatgggt ggctcttctc   1860

caagttgtct ttgaaggcct cgcttacatg gtatcagagg attaacatag cattggatgt   1920

tgccatgggt ctgcaatact tgcatgagca cacttatcca agaatagtcc atagggacat   1980

cacaacaagt aacatccttc ttgactccaa cttcaaggcc aagataggga acttctccat   2040

ggtcagaact actacaaatc ccatgatttc caagatcgat gtctttgctt tcggggttgt   2100

tctgattgag ttgcttacag gcaggaaagc catgacaaca aaggcagatg gtgaggtagt   2160

aatgctgtgg aaggatatta ggaagatgtt tgaagtggaa gatgaaaagg aaaaggagga   2220

atgtctgaga agatggatgg atcctaagct agagtgcctt taccctgtgg attatgctct   2280

cagcttggcc acgttggccg cgaattgcac ggcggatgta tcattgtcta gaccaaccat   2340

ggcagaagtt gttcttggcc tctcccttct cactcaacca tctcaagctg cactagagag   2400

atcattgact tcttctgcgt tggaagcaga ggttactcat gtggctactc ccatagcagc   2460

acgttaattg gtgacgaaag taattcagtt tctcaggttc aagagagtgt tttcttcaca   2520

tgactactgc ctataagctt tgttaataag tgtccaagtt tattgtcgct ttaaagtttc   2580

tttgtttcat cccttatatt ctttatctgt ttgtagtcga ggaatgactg cttatttctc   2640

tcaagttgac atatatgata tatataacaa aaagaatatt ttg                     2683
```

<210> SEQ ID NO 11
<211> LENGTH: 591
<212> TYPE: PRT
<213> ORGANISM: Lotus japonicus

<400> SEQUENCE: 11

```
Met Thr Ser Phe Phe Leu Phe Thr Asn Thr Leu Phe Leu Ala Leu Met
1               5                   10                  15

Met Phe Phe Ser Thr Thr His His Ile Leu Ala Gln Leu Ser His Thr
            20                  25                  30

Asn Gly Thr Asn Phe Ser Cys Pro Val Asp Ser Pro Pro Ser Cys Asp
        35                  40                  45

Thr Tyr Val Thr Tyr Phe Ala Gln Ser Pro Asn Phe Leu Thr Leu Thr
    50                  55                  60

Ser Ile Ser Asp Leu Phe Asp Thr Ser Pro Leu Ser Ile Ala Arg Ala
65                  70                  75                  80
```

```
Ser Asn Ile Lys Asp Glu Asn Gln Asn Leu Val Pro Gly Gln Leu Leu
                85                  90                  95

Leu Val Pro Val Thr Cys Ala Cys Ser Gly Ser Asn Ser Phe Ser Asn
            100                 105                 110

Ile Ser His Met Ile Lys Glu Gly Glu Ser Tyr Tyr Tyr Leu Ser Thr
        115                 120                 125

Thr Ser Tyr Glu Asn Leu Thr Asn Trp Glu Thr Val Gln Asp Ser Asn
    130                 135                 140

Pro Asn Tyr Asn Pro Tyr Leu Leu Pro Val Gly Ile Lys Val Val Ile
145                 150                 155                 160

Pro Leu Phe Cys Lys Cys Pro Ser Asn Tyr His Leu Asn Lys Gly Ile
                165                 170                 175

Glu Tyr Leu Ile Thr Tyr Val Trp His Asn Asn Asp Asn Val Ser Leu
            180                 185                 190

Val Ala Ser Lys Phe Gly Val Ser Thr Gln Asp Ile Ile Ser Glu Asn
        195                 200                 205

Asn Phe Ser His Gln Asn Phe Thr Ala Ala Thr Asn Phe Pro Ile Leu
    210                 215                 220

Ile Pro Val Thr Gln Leu Pro Ser Leu Ser Gln Ser Tyr Ser Ser Ser
225                 230                 235                 240

Glu Arg Lys Arg Ser Asn His Ile His Ile Ile Ile Ser Ile Gly Ile
                245                 250                 255

Ser Leu Gly Ser Thr Leu Leu Ile Ala Leu Leu Val Leu Val Ser Val
            260                 265                 270

Thr Cys Leu Arg Lys Arg Lys Ser Ser Glu Asn Lys Ser Leu Leu Ser
        275                 280                 285

Val Glu Ile Ala Gly Lys Lys Leu Ile Ser Gly Val Ser Asn Tyr Val
    290                 295                 300

Ser Lys Ser Ile Leu Tyr Glu Phe Arg Leu Ile Met Glu Ala Thr Leu
305                 310                 315                 320

Asn Leu Asn Glu Gln Cys Lys Ile Gly Glu Ser Val Tyr Lys Ala Lys
                325                 330                 335

Leu Asp Gly Gln Val Leu Ala Val Lys Lys Val Lys Glu Asp Val Thr
            340                 345                 350

Glu Glu Val Met Ile Leu Gln Lys Val Asn His Leu Asn Leu Val Lys
        355                 360                 365

Leu Met Gly Val Ser Ser Gly His Asp Gly Asn His Phe Leu Val Tyr
    370                 375                 380

Glu Phe Ala Glu Asn Gly Ser Leu His Asn Trp Leu Phe Ser Asn Ser
385                 390                 395                 400

Ser Thr Gly Ser Arg Phe Leu Thr Trp Ser Gln Arg Ile Ser Ile Ala
                405                 410                 415

Val Asp Val Ala Met Gly Leu Gln Tyr Met His Glu His Thr Gln Pro
            420                 425                 430

Ser Ile Val His Arg Asp Ile Thr Ser Ser Asn Ile Leu Leu Asp Ser
        435                 440                 445

Asn Phe Lys Ala Lys Ile Ala Asn Phe Ser Val Ala Arg Thr Ser Ile
    450                 455                 460

Asn Pro Met Ile Leu Lys Val Asp Val Phe Gly Tyr Gly Val Val Leu
465                 470                 475                 480

Leu Glu Leu Leu Ser Gly Lys Lys Ser Leu Thr Asn Asn Glu Ile Asn
                485                 490                 495

His Ile Arg Glu Ile Phe Asp Leu Lys Glu Lys Arg Glu Glu Arg Ile
```

```
            500                 505                 510

Arg Arg Trp Met Asp Pro Lys Ile Glu Ser Leu Tyr Pro Ile Asp Asp
        515                 520                 525

Ala Leu Ser Leu Ala Phe Leu Ala Met Asn Cys Thr Ser Glu Lys Pro
    530                 535                 540

Leu Ser Arg Pro Thr Met Gly Glu Val Val Leu Ser Leu Ser Leu Leu
545                 550                 555                 560

Met Thr Gln His Ser Pro Thr Thr Leu Glu Arg Ser Trp Thr Cys Gly
                565                 570                 575

Leu Asp Val Asp Val Thr Glu Met Gln Thr Leu Ile Ala Ala Arg
            580                 585                 590


<210> SEQ ID NO 12
<211> LENGTH: 590
<212> TYPE: PRT
<213> ORGANISM: Medicago truncatula

<400> SEQUENCE: 12

Met Val Ser Ser Phe Phe His Thr Leu Ile Phe Phe Ser Ala Thr His
1               5                   10                  15

Ile Leu Leu Gln Leu Pro Gln Ala Asn Gly Lys Asn Phe Ser Cys Thr
            20                  25                  30

Leu Asn Ser Ser Pro Ser Cys Asp Thr Tyr Val Ala Tyr Phe Ala Asn
        35                  40                  45

Ser Pro Asn Phe Leu Thr Leu Thr Ala Ile Ser Asp Ile Phe Asp Thr
    50                  55                  60

Ser Pro Gln Ser Ile Ala Arg Ala Ser Asn Ile Lys Asp Glu Asn Met
65                  70                  75                  80

Asn Leu Ile His Gly Gln Leu Leu Leu Ile Pro Ile Thr Cys Gly Cys
                85                  90                  95

Asn Gly Asn Gly Asn Tyr Ser Phe Ala Asn Ile Ser His Leu Ile Lys
            100                 105                 110

Glu Ser Glu Ser Tyr Tyr Tyr Leu Ser Thr Ile Ser Tyr Gln Asn Leu
        115                 120                 125

Thr Asn Trp Gln Thr Val Glu Asp Ser Asn Pro Asn Leu Asn Pro Tyr
    130                 135                 140

Leu Leu Lys Ile Gly Thr Lys Ile Asn Ile Pro Leu Phe Cys Arg Cys
145                 150                 155                 160

Pro Ser Asn Tyr Phe Ala Lys Gly Ile Glu Tyr Leu Ile Thr Tyr Val
                165                 170                 175

Trp Gln Pro Asn Asp Asn Leu Thr Leu Val Ala Ser Lys Leu Gly Ala
            180                 185                 190

Ser Pro Lys Asp Ile Ile Thr Ala Asn Thr Asn Asn Phe Gly Gln Asn
        195                 200                 205

Phe Thr Val Ala Ile Asn Leu Pro Val Phe Ile Pro Val Lys Asn Leu
    210                 215                 220

Pro Ala Leu Ser Gln Ser Tyr Tyr Ser Ser Ser Glu Arg Lys Arg Ile
225                 230                 235                 240

Asn His Phe Ser Ile Ile Ile Ser Ile Gly Ile Cys Leu Gly Cys Thr
                245                 250                 255

Ile Leu Ile Ser Leu Leu Leu Leu Leu Phe Tyr Val Tyr Cys Leu Arg
            260                 265                 270

Lys Arg Lys Ala Cys Glu Asn Lys Cys Val Pro Ser Val Glu Ile Thr
        275                 280                 285
```

Asp Lys Leu Ile Ser Glu Val Ser Asn Tyr Val Ser Lys Pro Thr Val
    290                 295                 300

Tyr Glu Val Gly Met Ile Met Lys Ala Thr Met Asn Leu Asn Glu Met
305                 310                 315                 320

Cys Lys Ile Gly Lys Ser Val Tyr Lys Ala Lys Ile Asp Gly Leu Val
                325                 330                 335

Leu Ala Val Lys Asn Val Lys Gly His Ile Thr Val Thr Glu Glu Leu
            340                 345                 350

Met Ile Leu Gln Lys Val Asn His Ala Asn Leu Val Lys Leu Val Gly
        355                 360                 365

Val Ser Ser Gly Tyr Asp Gly Asn His Phe Leu Val Tyr Glu Tyr Ala
    370                 375                 380

Glu Asn Gly Ser Leu Tyr Asn Trp Leu Leu Ser Glu Phe Cys Thr Leu
385                 390                 395                 400

Ser Trp Ser Gln Arg Leu Ser Ile Ala Val Asp Ile Ala Ile Gly Leu
                405                 410                 415

Gln Tyr Leu His Glu His Thr Gln Pro Cys Ile Val His Arg Asn Ile
            420                 425                 430

Lys Ser Ser Asn Ile Leu Leu Asp Ser Lys Phe Lys Ala Lys Ile Ala
        435                 440                 445

Asn Phe Ser Val Ala Arg Thr Thr Lys Asn Pro Met Ile Thr Lys Val
    450                 455                 460

Asp Val Leu Gly Tyr Gly Met Val Leu Met Glu Leu Ile Thr Gly Lys
465                 470                 475                 480

Lys Phe Leu Ser Tyr Ser Glu His Ser Glu Val Asn Met Leu Trp Lys
                485                 490                 495

Asp Phe Lys Cys Val Phe Asp Thr Glu Gln Lys Arg Glu Glu Ile Val
            500                 505                 510

Arg Arg Trp Met Asp Pro Lys Leu Gly Arg Phe Tyr Asn Val Val Glu
        515                 520                 525

Ala Leu Ser Leu Phe Thr Leu Ala Val Asn Cys Ile Glu Glu Gln Pro
    530                 535                 540

Leu Leu Arg Pro Thr Met Gly Glu Val Val Leu Ser Leu Ser Leu Leu
545                 550                 555                 560

Thr Gln Pro Ser Pro Thr Leu Leu Glu Val Ser Trp Thr Tyr Gly Leu
                565                 570                 575

Asp Val Glu Val Ala Glu Met Val Thr Pro Ile Ile Ala Arg
            580                 585                 590

<210> SEQ ID NO 13
<211> LENGTH: 613
<212> TYPE: PRT
<213> ORGANISM: Parasponia andersonii

<400> SEQUENCE: 13

Met Ala Ile Ser Leu Tyr Leu Leu Leu Phe Phe Ile Thr His Ile Ser
1               5                   10                  15

Ala Gln Ser Pro Pro Thr Leu Ala Thr Asn Phe Ser Cys Ser Thr Asn
            20                  25                  30

Ser Ser Gln Pro Ser Cys Lys Thr Tyr Val Ala Tyr Phe Ala Gln Pro
        35                  40                  45

Pro Leu Phe Met Asp Leu Lys Ser Ile Ser Asn Leu Phe Gly Val Ser
    50                  55                  60

Pro Ser Ser Ile Ser Glu Ala Ser Asn Leu Val Ser Glu Ser Thr Lys
65                  70                  75                  80

```
Leu Thr Arg Gly Gln Leu Leu Leu Ile Pro Leu Ser Cys Ser Cys Asn
                85                  90                  95

Gly Ser His Tyr Phe Ser Asn Val Thr Tyr Asn Ile Thr Met Gly Asp
            100                 105                 110

Ser Tyr Tyr Leu Val Ser Ile His Ser Phe Glu Asn Leu Thr Asn Trp
        115                 120                 125

Pro Leu Val Arg Asp Thr Asn Pro Thr Leu Asn Pro Asn Leu Leu Gln
    130                 135                 140

Ile Gly Thr Lys Val Ile Phe Pro Leu Tyr Cys Gly Cys Pro Ser Lys
145                 150                 155                 160

Ser His Ser Lys Asn Gly Ile Lys Tyr Leu Ile Thr Tyr Val Trp Gln
                165                 170                 175

Pro Ser Asp Asp Ile Tyr Arg Val Ser Ala Met Phe Asn Ala Ser Glu
            180                 185                 190

Val Asp Ile Ile Ile Glu Asn Asn Tyr Gln Asp Phe Lys Ala Ala Val
        195                 200                 205

Gly Tyr Pro Val Leu Ile Pro Val Ser Arg Met Pro Ala Leu Ser Gln
    210                 215                 220

Pro Pro Tyr Pro Ser His Ser His His Arg Ser Gln Leu Lys His Arg
225                 230                 235                 240

Trp Phe Leu Ile Ala Val Ile Ser Ser Ala Gly Ala Leu Leu Ile Leu
                245                 250                 255

Phe Leu Ala Thr Phe Leu Val His Ser Ile Gly Leu Tyr Glu Lys Lys
            260                 265                 270

Lys Asn Leu Ser His Glu Glu Ser Ser Leu Glu Thr Thr Asp Leu Ile
        275                 280                 285

Gln Val Lys Asn Phe Ser Lys Ser Asp Thr Leu Glu Leu Gln Ala Lys
    290                 295                 300

His Asp Lys Leu Leu Pro Gly Val Ser Val Tyr Leu Gly Lys Pro Ile
305                 310                 315                 320

Met Tyr Glu Ile Lys Met Ile Met Glu Ala Thr Met Asn Phe Asn Asp
                325                 330                 335

Gln Tyr Lys Ile Gly Gly Ser Val Tyr Arg Ala Met Ile Asn Gly Ser
            340                 345                 350

Phe Leu Ala Val Lys Lys Ala Lys Glu Asn Val Thr Glu Glu Leu His
        355                 360                 365

Ile Leu Gln Lys Val Asn His Gly Asn Leu Val Lys Leu Met Gly Ile
    370                 375                 380

Ser Leu Asp Arg Asp Gly Asn Cys Phe Phe Val Tyr Glu Tyr Ala Glu
385                 390                 395                 400

Asn Gly Ser Leu Asp Lys Trp Leu Asn Pro Gln Ser Ser Thr Ser Thr
                405                 410                 415

Ser Ser Ser Val Gly Ile Leu Ser Trp Ser Gln Arg Leu Asn Ile Ala
            420                 425                 430

Leu Asp Val Ala Asn Gly Leu Gln Tyr Met His Glu His Thr Gln Pro
        435                 440                 445

Ser Ile Val His Lys Glu Ile Arg Thr Ser Asn Ile Leu Leu Asp Ser
    450                 455                 460

Arg Phe Lys Ala Lys Ile Ala Asn Phe Ser Met Ala Arg Ser Ala Ala
465                 470                 475                 480

Ser Ala Gly Met Thr Lys Val Asp Val Phe Ala Phe Gly Val Val Leu
                485                 490                 495
```

Leu Lys Leu Leu Ser Gly Arg Lys Ala Met Ala Thr Arg Glu Asn Gly
500 505 510

Glu Ile Val Met Leu Trp Lys Glu Ala Lys Ala Val Leu Glu Glu Glu
515 520 525

Glu Lys Arg Ala Glu Lys Val Arg Glu Trp Ile Asp Pro Lys Leu Glu
530 535 540

Ser Phe Tyr Pro Ile Asp Gly Ala Leu Ser Leu Met Thr Leu Ala Lys
545 550 555 560

Ala Cys Thr Gln Glu Lys Ala Ser Ala Arg Pro Ser Ile Gly Glu Val
565 570 575

Val Phe Ser Leu Cys Val Leu Thr Gln Ser Phe Ser Glu Thr Leu Glu
580 585 590

Pro Ser Trp Thr Cys Thr Leu Glu Gly Glu Asp Val Val Gln Ile Thr
595 600 605

Ser Pro Ile Val Ala
610

<210> SEQ ID NO 14
<211> LENGTH: 582
<212> TYPE: PRT
<213> ORGANISM: Parasponia andersonii

<400> SEQUENCE: 14

Met Ala Asp Ser Tyr Phe Pro Phe Gln Ala Ile Phe Leu Leu Leu Leu
1 5 10 15

Leu Phe Ser Thr Leu Asn Met Ala Ala Ser Gln Leu Asn Asn Ser Ala
20 25 30

Thr Asp Phe Ser Cys Ser Asp Ser Pro Pro Ser Cys Glu Ala Tyr Val
35 40 45

Ala Tyr Phe Ser Gln Pro Pro Asn Tyr Met Asn Val Gly Asn Ile Ser
50 55 60

Asp Leu Phe Gly Ile Ser Gln Ala Leu Ile Ala Lys Ser Ser Asn Leu
65 70 75 80

Val Ser Lys Asp Ser Pro Leu Ile Pro Gln Gln Leu Leu Leu Ile Pro
85 90 95

Leu Thr Cys Thr Cys Thr Gly Asn His Tyr Phe Ala Asn Ile Thr Tyr
100 105 110

Gln Val Glu Pro Gly Asp Thr Tyr His Tyr Leu Ser Thr Leu Leu Phe
115 120 125

Glu Asn Leu Thr Asn Ser Gln Val Met Lys Lys Met Asn Pro Glu Ile
130 135 140

Ser Pro Glu Tyr Val Leu Pro Tyr Ile Asp Ile Ile Ile Pro Val Phe
145 150 155 160

Cys Arg Cys Pro Ser Lys Ser His Leu Lys Ser Glu Ile Gln Gln Phe
165 170 175

Ile Thr Tyr Val Trp Gln Pro Asn Asp Gln Val Ser Asn Val Ser Ala
180 185 190

Lys Phe Asn Thr Ser Ala Ser Glu Ile Val Asn Glu Asn Lys Tyr Asn
195 200 205

Asn Phe Ser Ser Ala Val Gly Leu Pro Val Leu Ile Pro Val Ser Lys
210 215 220

Leu Pro Val Leu Ala Arg Val Lys Pro Pro Lys Ser Val Arg Ser Lys
225 230 235 240

Lys Gln Trp Ile Leu Ile Gly Val Glu Ser Leu Gly Gly Ile Val Leu
245 250 255

```
Ile Thr Leu Phe Ala Thr Leu Leu Val Tyr Ser Asn Arg Leu Leu Lys
            260                 265                 270

Lys Arg Arg Lys Ile Leu Glu Ala Arg Arg Leu Glu Pro Arg Ile Ile
        275                 280                 285

Ile Gln Asp Lys Leu Leu Ser Gly Val Ser Glu Tyr Leu Gly Arg Pro
    290                 295                 300

Ile Met Tyr Asp Asn Lys Met Val Val Glu Gly Thr Met Asp Phe Ser
305                 310                 315                 320

Glu Gln Cys Arg Ile Gly Gly Ser Val Tyr Arg Gly Glu Ile Tyr Gly
                325                 330                 335

Glu Val Phe Ala Val Lys Lys Thr Lys Gln Asp Ile Thr Asp Glu Leu
            340                 345                 350

Asn Leu Leu Gln Lys Val Asn His Val Asn Leu Val Asn Leu Met Gly
        355                 360                 365

Ala Ser Tyr Asp Thr Asp Gly Asn Arg Phe Leu Val Tyr Glu Tyr Val
    370                 375                 380

Glu Asn Gly Ser Leu Glu Arg Trp Leu Asp Leu Lys Pro Ser Ser Leu
385                 390                 395                 400

Ala Ala Ala Ser Ser Ser Ser Ser Val Gln Phe Leu Ser Trp Ser Gln
                405                 410                 415

Arg Ile Gln Ile Ala Leu Asp Val Ala Asn Gly Leu Gln Tyr Leu His
            420                 425                 430

Glu His Thr Gln Pro Asn Ile Ala His Trp Asn Ile Arg Thr Ser Thr
        435                 440                 445

Ile Leu Leu Asp Ser Lys Phe Arg Ala Lys Ile Ala Asn Phe Glu Val
    450                 455                 460

Ala Arg Pro Val Gly Asn Pro Ala Met Leu Lys Val Asp Ile Phe Ala
465                 470                 475                 480

Phe Gly Ile Val Leu Leu Ala Leu Val Ser Gly Lys Lys Ala Leu Gln
                485                 490                 495

Thr Ile Glu Asn Gly Glu Val Ile Met Leu Trp Lys Asp Leu Ala Lys
            500                 505                 510

Glu Val Phe Glu Val Glu Glu Lys Lys Glu Asp Arg Leu Arg Lys Trp
        515                 520                 525

Met Asp Pro Asn Leu Gln Ser Phe Tyr Pro Ile Asp Gly Ala Leu Ser
    530                 535                 540

Leu Ser Ser Leu Ala Arg Ala Cys Ile Arg Glu Lys Ser Ser Ala Arg
545                 550                 555                 560

Pro Lys Met Ala Glu Ile Val Phe Ser Leu Ser Val Leu Ala Gln Ser
                565                 570                 575

Ser Ser Pro Gly Thr Pro
            580
```

<210> SEQ ID NO 15

<400> SEQUENCE: 15

000

<210> SEQ ID NO 16
<211> LENGTH: 670
<212> TYPE: PRT
<213> ORGANISM: Hordeum vulgare

<400> SEQUENCE: 16

-continued

```
Met Ala Ala Pro Pro Gly Arg Arg Gly Leu Ala Phe Gly Thr Ala Ala
1               5                   10                  15

Leu Ala Leu Leu Ala Ile Leu Ala Val Ala Arg Gly Gln Gln Gln Tyr
            20                  25                  30

Glu Ala Asn Ala Gln Thr Asn Cys Tyr Gly Arg Asn Gly Ser Ser Val
        35                  40                  45

Leu Gly Tyr Val Cys Asn Ala Thr Ala Ala Ala Ala Pro Cys Ala Thr
    50                  55                  60

Tyr Val Val Phe Arg Ser Ser Pro Pro Tyr Tyr Gly Thr Ala Val Ser
65                  70                  75                  80

Ile Ser Tyr Leu Leu Gly Ser Asp Pro Glu Ala Val Ala Asp Ala Asn
                85                  90                  95

Gly Val Pro Thr Val Ser Pro Leu Ala Asp Ser Arg Leu Val Leu Ala
            100                 105                 110

Pro Val Pro Cys Gly Cys Ser Pro Arg Gly Tyr Tyr Gln His Asn Ser
        115                 120                 125

Ser His Thr Ile Glu Leu Arg Gly Glu Thr Tyr Phe Ile Ile Ala Asn
    130                 135                 140

Asn Thr Tyr Gln Gly Leu Thr Thr Cys Gln Ala Leu Leu Ala Gln Asn
145                 150                 155                 160

Pro Arg His Gly Ser Arg Asp Leu Val Ala Gly Asn Asn Leu Thr Val
                165                 170                 175

Pro Ile Arg Cys Ala Cys Pro Thr Pro Ala Gln Ala Ala Ala Gly Val
            180                 185                 190

Arg His Leu Leu Thr Tyr Leu Val Thr Trp Gly Asp Ser Val Ser Ala
        195                 200                 205

Ile Ala Asp Arg Phe Arg Val Asp Ala Gln Ala Val Phe Gln Ala Asn
    210                 215                 220

Asn Leu Thr Ala Arg Glu Ile Ile Phe Pro Phe Thr Thr Leu Leu Ile
225                 230                 235                 240

Pro Leu Lys Ser Ala Pro Thr Pro Asp Met Leu Val Ser Pro Ala Pro
                245                 250                 255

Pro Pro Ala Pro Ala Pro Pro Gln Ala Gln Gln Pro Pro Ala Ser Gly
            260                 265                 270

Ser Gly Lys Trp Ile Ala Val Gly Val Gly Val Gly Val Gly Val Leu
        275                 280                 285

Ala Leu Ala Ser Leu Ile Gly Leu Met Leu Leu Cys Val Arg Arg Arg
    290                 295                 300

Arg Thr Arg Gln Gly Val Arg Glu Arg Gly Arg Leu Ser Lys Val Val
305                 310                 315                 320

Leu Asp Val Pro Ser Ser Ala Asp Tyr Asn Ala Leu Ala Ser Gly Lys
                325                 330                 335

His Ala Ser Ser Ala Thr Thr Thr Ser Ala Ser Ser Ser Ala Leu Val
            340                 345                 350

Ser Ser Asp Ala Arg Ala Ala Val Glu Ser Leu Thr Val Tyr Lys Tyr
        355                 360                 365

Ser Glu Leu Glu Lys Ala Thr Ala Gly Phe Ser Glu Asp Arg Arg Val
    370                 375                 380

Lys Asn Ala Ser Val Tyr Arg Ala Glu Ile Asn Gly Asp Ala Ala Ala
385                 390                 395                 400

Val Lys Arg Val Ala Gly Asp Val Ser Gly Glu Val Gly Ile Leu Lys
                405                 410                 415

Arg Val Asn His Ser Ser Leu Val Arg Leu Ser Gly Leu Cys Val His
```

```
            420                 425                 430

His Gly Glu Thr Tyr Leu Val Phe Glu Phe Ala Glu Asn Gly Ala Leu
        435                 440                 445

Ser Asp Trp Leu His Gly Gly Gly Ala Thr Leu Val Trp Lys Gln Arg
    450                 455                 460

Val Gln Ala Ala Phe Asp Val Ala Asp Gly Leu Asn Tyr Leu His His
465                 470                 475                 480

Tyr Thr Asn Pro Pro Cys Val His Lys Asn Leu Lys Ser Ser Asn Val
                485                 490                 495

Leu Leu Asp Ala Asn Leu Arg Ala Lys Val Ser Ser Phe Ala Leu Ala
            500                 505                 510

Arg Ser Val Pro Thr Gly Ala Asp Gly Gly Asp Ala Gln Leu Thr Arg
        515                 520                 525

His Val Val Gly Thr Gln Gly Tyr Leu Ala Pro Glu Tyr Leu Glu His
    530                 535                 540

Gly Leu Ile Thr Pro Lys Leu Asp Val Phe Ala Phe Gly Val Ile Leu
545                 550                 555                 560

Leu Glu Leu Leu Ser Gly Lys Glu Ala Met Phe Asn Gly Gly Asp Lys
                565                 570                 575

Arg Gly Glu Thr Leu Leu Trp Glu Ser Ala Glu Gly Leu Val Val Asp
            580                 585                 590

Asn Glu Asp Ala Arg Gly Lys Val Arg Pro Phe Met Asp Pro Arg Leu
        595                 600                 605

His Gly Asp Tyr Pro Leu Asp Leu Ala Val Ala Val Ala Ser Leu Ala
    610                 615                 620

Val Arg Cys Val Ala Arg Glu Pro Arg Arg Arg Pro Ser Ile Asp Val
625                 630                 635                 640

Val Phe Ala Thr Leu Ser Ala Val Tyr Asn Ser Thr Leu Asp Trp Asp
                645                 650                 655

Pro Ser Asp Asp Gly Asn Ser Arg Ser Ser Ile Val Gly Arg
            660                 665                 670


<210> SEQ ID NO 17
<211> LENGTH: 650
<212> TYPE: PRT
<213> ORGANISM: Hordeum vulgare

<400> SEQUENCE: 17

Met Ala Pro Leu Thr Arg Arg Arg Arg Leu Leu Ala Thr Leu Leu Cys
1               5                   10                  15

Leu Cys Ala Leu Pro Ala Pro Ala Arg Ser Gln Asn Ala Ser Ala Thr
            20                  25                  30

Pro Ala Pro Ala Ser Val Glu Gly Phe Asn Cys Ser Ala Asn Gly Thr
        35                  40                  45

Tyr Pro Cys Gln Ala Tyr Ala Leu Tyr Arg Ala Gly Leu Ala Gly Val
    50                  55                  60

Pro Pro Asp Leu Ser Ala Ala Gly Asp Leu Phe Gly Val Ser Arg Phe
65                  70                  75                  80

Met Leu Ala His Ala Asn Asn Leu Ser Thr Ser Ala Ala Pro Ala Ala
                85                  90                  95

Gly Gln Pro Leu Leu Val Pro Leu Gln Cys Gly Cys Pro Ser Gly Ser
            100                 105                 110

Pro Asn Ala Tyr Ala Pro Thr Gln Tyr Gln Ile Ser Ser Gly Asp Thr
        115                 120                 125
```

```
Phe Trp Ile Val Ser Val Thr Lys Leu Gln Asn Leu Thr Gln Tyr Gln
    130                 135                 140

Ala Val Glu Arg Val Asn Pro Thr Val Val Pro Thr Lys Leu Glu Val
145                 150                 155                 160

Gly Asp Met Val Thr Phe Pro Ile Phe Cys Gln Cys Pro Thr Ala Ala
                165                 170                 175

Gln Asn Ala Thr Ala Leu Val Thr Tyr Val Met Gln Gln Gly Asp Thr
            180                 185                 190

Tyr Ala Ser Ile Ala Ala Ala Phe Ala Val Asp Ala Gln Ser Leu Val
        195                 200                 205

Ser Leu Asn Gly Pro Glu Gln Gly Thr Gln Leu Phe Ser Glu Ile Leu
    210                 215                 220

Val Pro Leu Arg Arg Gln Val Pro Lys Trp Leu Pro Pro Ile Val Thr
225                 230                 235                 240

Arg Asn Asp Ala Ser Ala Thr Pro Pro Ser Pro Ser Pro Pro Pro Thr
                245                 250                 255

Thr Thr Pro Gly Pro Ser Asp Val Ala Asp Asn Arg Asp Gly Val Val
            260                 265                 270

Thr Gly Leu Ala Val Gly Leu Gly Val Val Gly Gly Leu Trp Leu Leu
        275                 280                 285

Gln Leu Leu Leu Leu Gly Cys Leu Trp Arg Arg Leu Lys Ala Lys Gly
    290                 295                 300

Arg Arg Gly Asp Ala Val Ala Ser Gly Glu Gly Gly Glu Gly Gly Arg
305                 310                 315                 320

Ser Ala Lys Thr Ala Ser Ala Ser Gly Gly Val Gly Gly Glu Arg Phe
                325                 330                 335

Leu Val Thr Asp Ile Ser Glu Trp Leu Asp Lys Tyr Arg Val Phe Lys
            340                 345                 350

Val Glu Glu Leu Glu Arg Gly Thr Asp Gly Phe Asp Asp Ala His Leu
        355                 360                 365

Ile Gln Gly Ser Val Tyr Lys Ala Asn Ile Gly Gly Glu Val Phe Ala
    370                 375                 380

Val Lys Lys Met Lys Trp Asp Ala Cys Glu Glu Leu Lys Ile Leu Gln
385                 390                 395                 400

Lys Val Asn His Ser Asn Leu Val Lys Leu Glu Gly Phe Cys Ile Asn
                405                 410                 415

Thr Ala Thr Gly Asp Cys Phe Leu Val Tyr Glu Tyr Val Glu Asn Gly
            420                 425                 430

Ser Leu Asp Leu Cys Leu Leu Asp Arg Gly Arg Ala Arg Arg Leu Asp
        435                 440                 445

Trp Arg Thr Arg Leu His Ile Ala Leu Asp Leu Ala His Gly Leu Gln
    450                 455                 460

Tyr Ile His Glu His Thr Trp Pro Arg Val Val His Lys Asp Val Lys
465                 470                 475                 480

Ser Ser Asn Val Leu Leu Asp Ala Arg Met Arg Ala Lys Ile Ala Asn
                485                 490                 495

Phe Gly Leu Ala Lys Thr Gly His Asn Ala Val Thr Thr His Ile Val
            500                 505                 510

Gly Thr Gln Gly Tyr Ile Ala Pro Glu Tyr Leu Val Asp Gly Leu Val
        515                 520                 525

Thr Thr Lys Met Asp Val Phe Ala Tyr Gly Val Val Leu Leu Glu Leu
    530                 535                 540

Val Ser Gly Arg Glu Ala Ala Gly Asp Gly Gly Asp Leu Leu Leu Ala
```

545 550 555 560

Asp Ala Glu Glu Arg Val Phe Arg Gly Arg Glu Asp Arg Leu Glu Ala
565 570 575

Arg Ala Ala Ala Trp Met Asp Pro Val Leu Ala Glu Gln Thr Cys Pro
580 585 590

Pro Gly Ser Val Ala Thr Val Met Gly Val Ala Arg Ala Cys Leu Gln
595 600 605

Arg Asp Pro Ser Lys Arg Pro Ser Met Val Asp Val Ala Tyr Thr Leu
610 615 620

Ser Arg Ala Asp Glu Tyr Phe Ala Asp Tyr Ser Gly Glu Ser Val Ser
625 630 635 640

Val Asp Gly Ser Gly Glu Ile Ala Ala Arg
645 650

<210> SEQ ID NO 18
<211> LENGTH: 681
<212> TYPE: PRT
<213> ORGANISM: Hordeum vulgare

<400> SEQUENCE: 18

Met Ala Thr Pro Thr Arg Trp Arg Gly Leu Ala Ala Val Gly Arg Ala
1 5 10 15

Ala Leu Ala Phe Leu Val Leu Leu Ala Val Ala Ala Pro Trp Cys Pro
20 25 30

Val Ala Arg Gly Gln Gln Glu Tyr Glu Ala Asn Ala Gln Asn Asn Cys
35 40 45

Tyr Gly Asn Asn Gly Ser Ser Val Leu Gly Tyr Thr Cys Asn Ala Thr
50 55 60

Ala Ala Val Arg Pro Cys Ala Ser Tyr Val Val Phe Arg Ser Ser Pro
65 70 75 80

Pro Tyr Glu Ser Pro Ile Thr Ile Ser Tyr Leu Leu Asn Thr Thr Pro
85 90 95

Ala Ala Leu Ala Asp Ala Asn Ala Val Pro Thr Val Ser Ser Val Ala
100 105 110

Ala Ser Arg Leu Val Leu Ala Pro Leu Asn Cys Gly Cys Ala Pro Gly
115 120 125

Gly Tyr Tyr Gln His Asn Ala Ser Tyr Thr Leu Gln Phe Ser Asn Glu
130 135 140

Thr Tyr Phe Ile Thr Ala Asn Ile Thr Tyr Gln Gly Leu Thr Thr Cys
145 150 155 160

Gln Ala Leu Met Ala Gln Asn Pro Asn His Asp Ser Arg Asn Leu Val
165 170 175

Val Gly Asn Asn Leu Thr Val Pro Ile Arg Cys Ala Cys Pro Ser Pro
180 185 190

Ala Gln Ala Ala Ser Gly Val Arg His Leu Leu Thr Tyr Leu Val Ala
195 200 205

Ser Gly Asp Thr Ile Ala Asp Ile Ala Thr Arg Phe Arg Val Asp Ala
210 215 220

Gln Ala Val Leu Arg Ala Asn Arg Leu Thr Asp Ser Glu Asn Ile Tyr
225 230 235 240

Pro Phe Thr Thr Leu Leu Ile Pro Leu Lys Ser Ala Pro Thr Pro Asp
245 250 255

Met Leu Val Ser Pro Ala Pro Pro Pro Ala Pro Val Pro Pro Gln Ala
260 265 270

```
Gln Gln Pro Leu Pro Thr Gly Gly Ser Gly Ser Gly Lys Gly Val Ala
        275                 280                 285

Ile Gly Val Gly Val Gly Val Gly Val Leu Ala Leu Ala Gly Leu Leu
    290                 295                 300

Gly Leu Met Phe Leu Cys Val Arg Arg Arg Arg Arg Leu Arg Pro Gly
305                 310                 315                 320

Val Gly Glu Asn Gly His Pro Gly Lys Val Val Ile Asp Val Pro Ser
                325                 330                 335

Ser Ala Asp Tyr Asp Pro Leu Ala Ser Gly Lys His Thr Ser Ser Ala
            340                 345                 350

Thr Thr Thr Ser Ser Ser Ser Ser Ala Phe Val Ser Ser Asp Ala Arg
        355                 360                 365

Ala Ala Val Glu Ser Leu Thr Val Tyr Lys Tyr Ser Glu Leu Glu Lys
    370                 375                 380

Ala Thr Ala Gly Phe Ser Glu Asp Arg Arg Val Lys Asp Ala Ser Val
385                 390                 395                 400

Tyr Arg Ala Val Ile Asn Gly Asp Thr Ala Ala Val Lys Arg Val Ala
                405                 410                 415

Gly Asp Val Ser Gly Glu Val Gly Ile Leu Lys Arg Val Asn His Ser
            420                 425                 430

Ser Leu Val Arg Leu Ser Gly Leu Cys Val His His Gly Asp Thr Tyr
        435                 440                 445

Leu Val Phe Glu Phe Ala Glu Asn Gly Ala Leu Ser Asp Trp Leu His
    450                 455                 460

Gly Gly Gly Ala Thr Leu Val Trp Lys Gln Arg Val Gln Ala Ala Phe
465                 470                 475                 480

Asp Val Ala Asp Gly Leu Asn Tyr Leu His His Tyr Ser Thr Pro Pro
                485                 490                 495

Cys Val His Lys Asn Leu Lys Ser Ser Asn Val Leu Leu Asp Ala Asp
            500                 505                 510

Leu Arg Ala Lys Val Ser Ser Phe Ala Leu Ala Arg Ser Val Pro Thr
        515                 520                 525

Gly Ala Glu Gly Gly Asp Ala Gln Leu Thr Arg His Val Val Gly Thr
    530                 535                 540

Gln Gly Tyr Leu Ala Pro Glu Tyr Leu Glu His Gly Leu Ile Thr Pro
545                 550                 555                 560

Lys Leu Asp Val Phe Ala Phe Gly Val Ile Leu Leu Glu Leu Leu Ser
                565                 570                 575

Gly Lys Glu Ala Thr Phe Asn Gly Gly Asp Lys Arg Gly Glu Lys Leu
            580                 585                 590

Leu Trp Glu Ser Ala Glu Gly Leu Val Val Asp Gly Glu Asp Ala Arg
        595                 600                 605

Ser Lys Val Arg Ala Phe Met Asp Pro Gln Leu Ser Gly Asp Tyr Pro
    610                 615                 620

Leu Asp Leu Ala Val Ala Val Ala Ser Leu Ala Leu Arg Cys Val Ala
625                 630                 635                 640

Arg Glu Pro Arg Gly Arg Pro Ser Met Tyr Glu Val Phe Val Thr Leu
                645                 650                 655

Ser Ala Val Tyr Asn Ser Thr Leu Asp Trp Asp Pro Ser Asp Tyr Ser
            660                 665                 670

Asn Ser Arg Ser Ser Ile Val Gly Arg
        675                 680
```

<210> SEQ ID NO 19
<211> LENGTH: 633
<212> TYPE: PRT
<213> ORGANISM: Hordeum vulgare

<400> SEQUENCE: 19

```
Met Glu Pro Arg Arg Phe Leu Cys Cys Cys Leu Val Ala Val Leu Ala
1               5                   10                  15

Val Ala Ser Arg Arg Cys Asp Ala Gln Gly Gly Ala Gly Asn Gly Thr
            20                  25                  30

Gly Arg Phe Ala Cys Val Val Pro Ala Pro Cys Asp Thr Phe Val Leu
        35                  40                  45

Tyr Arg Thr Gln Ser Pro Gly Ser Leu Asp Leu Gly Ala Ile Ser Asp
    50                  55                  60

Leu Phe Gly Val Ser Arg Ala Met Ile Ala Ala Ala Asn Asn Leu Ser
65                  70                  75                  80

Leu Ile Asp Glu Asp Ala Ala Leu Leu Pro Asp Gln Pro Leu Leu Val
                85                  90                  95

Pro Val Arg Cys Gly Cys Thr Gly Asn Arg Ser Phe Val Asn Val Thr
            100                 105                 110

Tyr Pro Ile His Ser Gly Asp Thr Phe Tyr Ala Leu Ala Leu Thr Gly
        115                 120                 125

Tyr Glu Asn Leu Thr Thr Pro Asp Val Ile Gln Glu Leu Asn Pro Gln
    130                 135                 140

Ala Val Phe Asn Lys Leu Asn Val Ser Gln Leu Val Thr Val Pro Leu
145                 150                 155                 160

Phe Cys Arg Cys Pro Thr Pro Ala Glu Arg Ser Ala Gly Val Leu Gln
                165                 170                 175

Gln Ile Thr Tyr Met Trp Arg Pro Val Asp Thr Met Ser Arg Val Ser
            180                 185                 190

Lys Leu Met Gly Ser Asp Ala Ser Ala Ile Ala Ala Ala Asn Asn Val
        195                 200                 205

Ser Ala Asp Phe Thr Ser Thr Thr Met Leu Pro Met Leu Ile Pro Val
    210                 215                 220

Ala Arg Pro Pro Val Leu Pro Pro Leu Arg Tyr Gly Pro Ser Ala Thr
225                 230                 235                 240

Thr Gly Asp Pro Gly Ala Thr Lys Arg Phe Ser Gly Ala Thr Val Ala
                245                 250                 255

Ala Ser Ile Ala Gly Ser Leu Val Ala Val Ala Ala Leu Cys Val Ala
            260                 265                 270

Ile Phe Gly Tyr Arg Arg Tyr Arg Arg Lys Lys Ala Thr Val His Ser
        275                 280                 285

Ala Ser Arg Phe Ala Ser Pro Arg Phe Cys Phe Asn Gln Asn Ala Tyr
    290                 295                 300

Gly Ile Gln Ser Ser Ser Ser Ile Ala Arg Met Ile Asn Gly Gly Asp
305                 310                 315                 320

Lys Leu Leu Thr Ser Val Ser Gln Phe Ile Asp Lys Pro Val Ile Phe
                325                 330                 335

Gly Thr Ala Glu Ile Met Glu Ala Thr Met Asn Leu Asp Glu Arg Cys
            340                 345                 350

Arg Ile Gly Ser Ser Tyr Tyr Arg Ala Lys Leu Glu Gly Glu Val Phe
        355                 360                 365

Ala Val Lys Pro Ala Lys Gly Asp Val Ser Ala Glu Leu Arg Met Met
    370                 375                 380
```

```
Gln Met Val Asn His Ala Asn Leu Ile Arg Leu Ala Gly Ile Ser Ile
385                 390                 395                 400

Gly Ala Asp Gly Asp Tyr Thr Phe Leu Val Tyr Glu Phe Ala Glu Lys
                405                 410                 415

Gly Ser Leu Asp Lys Trp Leu Tyr Gln Lys Pro Pro Ser Ser Leu Pro
            420                 425                 430

Ser Ser Ser Ser Ser Val Asp Thr Leu Ser Trp Asn Gln Arg Leu Gly
        435                 440                 445

Ile Ala Leu Asp Val Ala Asn Gly Leu Leu Tyr Met His Glu His Thr
    450                 455                 460

Gln Pro Ser Met Val His Gly Asp Val Arg Ala Arg Asn Ile Leu Leu
465                 470                 475                 480

Thr Ala Asp Phe Arg Ala Arg Ile Ser Asn Phe Ser Val Ala Thr Pro
                485                 490                 495

Ala Met Ala Asp Ala Ala Ala Thr Ser Ser Asp Val Phe Ala Phe Gly
            500                 505                 510

Leu Leu Val Leu Glu Leu Leu Ser Gly Arg Thr Ala Met Glu Ala Arg
        515                 520                 525

Val Gly Ala Glu Ile Gly Met Leu Trp Arg Asp Ile Arg Ala Val Leu
    530                 535                 540

Glu Ala Gly Asp Lys Arg Asp Ala Lys Leu Arg Lys Trp Met Asp Pro
545                 550                 555                 560

Ala Leu Gly Asp Glu Tyr Tyr Leu Asp Ala Ala Leu Ser Leu Ala Gly
                565                 570                 575

Met Ala Arg Ala Cys Thr Glu Glu Asp Ala Ala Arg Arg Pro Lys Met
            580                 585                 590

Ala Asp Val Val Phe Ser Leu Ser Met Leu Val Gln Pro Leu Pro Val
        595                 600                 605

Gly Asp Ala Phe Glu Lys Leu Trp Gln Pro Ser Ser Glu Glu Asn Ile
    610                 615                 620

Arg Ile Val Asn Glu Val Ala Ala Arg
625                 630
```

<210> SEQ ID NO 20
<211> LENGTH: 638
<212> TYPE: PRT
<213> ORGANISM: Zea mays

<400> SEQUENCE: 20

```
Met Glu Pro Arg His Phe Cys Arg Ala Leu Leu Leu Leu Leu Val Val
1               5                   10                  15

Leu Leu Leu Gly Phe Arg Arg Ala Gly Ala Gln Asp Ser Thr Asn Tyr
            20                  25                  30

Thr Val Pro Ala Arg Phe Ala Cys Asn Val Ser Ser Pro Cys Asp Thr
        35                  40                  45

Tyr Val Val Tyr Arg Thr Gln Ser Pro Gly Tyr Leu Asp Leu Gly Ser
    50                  55                  60

Ile Ser Asp Leu Phe Gly Thr Ser Gln Ala Arg Ile Ala Ser Ala Asn
65                  70                  75                  80

Gly Leu Ser Ser Glu Asp Gly Val Leu Gln Pro Gly Gln Pro Leu Leu
                85                  90                  95

Val Pro Val Arg Cys Gly Cys Thr Gly Ala Trp Ser Phe Ala Asn Ala
            100                 105                 110

Thr Tyr Pro Ile Arg Gln Gly Asp Thr Phe Tyr Asn Leu Ala Arg Leu
        115                 120                 125
```

-continued

```
Ser Tyr Glu Asn Leu Thr Glu Tyr His Leu Ile His Asp Leu Asn Pro
    130                 135                 140

Arg Ser Glu Pro Thr Ser Leu Gln Ile Gly Gln Glu Val Thr Val Pro
145                 150                 155                 160

Leu Leu Cys Arg Cys Pro Pro Ala Arg Ala Val Gln Ser Phe Ile Thr
                165                 170                 175

Tyr Val Trp Gln Pro Gly Asp Thr Leu Ser Gln Val Ser Lys Leu Met
            180                 185                 190

Asn Ala Thr Ala Asp Glu Ile Ala Glu Ala Asn Asn Val Thr Ser Ser
        195                 200                 205

Ser Val Ser Ser Ala Ser Ala Ala Gly Leu Pro Met Leu Ile Pro Val
    210                 215                 220

Gln Gln Arg Pro Arg Leu Pro Pro Leu Leu Tyr Ala Ala Ser Ala Gly
225                 230                 235                 240

Glu Gly Arg Ser Ser Arg Ser Arg Arg Arg Ala Leu Ile Ile Ile Gly
                245                 250                 255

Ala Ser Val Ser Gly Ser Leu Val Ala Leu Ala Ala Leu Leu Val Ala
            260                 265                 270

Ile Met Ala Gln Arg Arg Tyr Arg Arg Lys Lys Pro Ser Met Arg Leu
        275                 280                 285

Gly Ser Pro Phe Ala Val Asn Thr Lys Leu Ser Trp Ser Val Asn Gln
    290                 295                 300

Tyr Gly His Gly Ser Ser Asn Ser Phe Ala His Val Met Lys Gly Gly
305                 310                 315                 320

Lys Leu Leu Thr Gly Val Ser Gln Phe Ile Asp Lys Pro Ile Ile Phe
                325                 330                 335

Val Glu Glu Glu Ile Val Glu Ala Thr Met Asn Leu Asp Glu Arg Cys
            340                 345                 350

Lys Ile Gly Ser Thr Tyr Tyr Arg Ala Lys Leu Asp Gly Glu Val Phe
        355                 360                 365

Ala Val Lys Pro Ala Lys Gly Asp Val Ser Ala Glu Leu Arg Met Met
    370                 375                 380

Gln Met Val Asn His Ala Asn Leu Ile Lys Leu Ala Gly Ile Ser Ile
385                 390                 395                 400

Gly Ala Asp Gly Asp Tyr Ala Phe Leu Val Tyr Glu Phe Ala Glu Lys
                405                 410                 415

Ala Ser Leu Asp Lys Trp Leu Tyr His Asn His Gln Lys Pro Pro Ser
            420                 425                 430

Ala Leu Leu Pro Ser Ser Ser Cys Thr Val Pro Thr Thr Leu Ser Trp
        435                 440                 445

Gly Gln Arg Leu Ser Ile Ala Leu Asp Val Ala Asn Gly Leu Leu Tyr
    450                 455                 460

Met His Glu His Thr Gln Pro Ser Met Val His Gly Asp Ile Arg Ala
465                 470                 475                 480

Arg Asn Ile Leu Leu Thr Ala Asp Phe Arg Ala Lys Ile Ser Ser Phe
                485                 490                 495

Ser Leu Ala Lys Pro Ala Thr Ala Asp Ala Ala Ala Thr Ser Ser Asp
            500                 505                 510

Val Phe Ala Phe Gly Leu Leu Leu Leu Glu Leu Met Ser Gly Arg Arg
        515                 520                 525

Ala Met Glu Ala Arg Ile Gly Ser Glu Ile Gly Met Leu Trp Arg Glu
    530                 535                 540
```

Ile Arg Ala Val Leu Glu Ala Gly Asp Lys Arg Glu Ala Lys Leu Arg
545 550 555 560

Lys Trp Met Asp Pro Ala Leu Gly Ser Glu Tyr Gln Met Asp Ala Ala
565 570 575

Leu Ser Leu Ala Gly Met Ala Arg Ala Cys Thr Asp Glu Asp Ala Ala
580 585 590

Arg Arg Pro Asn Met Thr Glu Val Val Phe Ser Leu Ser Met Leu Ala
595 600 605

Gln Pro Leu Ser Val Ala Asp Gly Phe Glu Lys Leu Trp Gln Pro Ser
610 615 620

Ser Glu Asp Asn Ile Arg Ile Ala Gly Ser Val Ala Ala Arg
625 630 635

<210> SEQ ID NO 21
<211> LENGTH: 636
<212> TYPE: PRT
<213> ORGANISM: Zea mays

<400> SEQUENCE: 21

Met Glu Leu Arg His Phe Arg Cys Cys Ala Ser Arg Leu Leu Leu Leu
1 5 10 15

Val Thr Leu Leu Leu Gly Phe Arg Arg Ala Gly Ala Gln Asp Ser Thr
20 25 30

Ser Tyr Thr Val Pro Ala Gln Phe Ala Cys Asp Val Ser Ser Pro Cys
35 40 45

Asp Thr Tyr Val Val Tyr Arg Thr Gln Ser Pro Gly Tyr Leu Asp Leu
50 55 60

Gly Ser Ile Ser Asp Leu Phe Gly Thr Ser Gln Ala Arg Ile Ala Ser
65 70 75 80

Ala Asn Gly Leu Ser Ser Glu Asp Gly Val Leu Gln Pro Gly Gln Pro
85 90 95

Leu Leu Val Pro Val Arg Cys Gly Cys Ala Gly Ala Trp Ser Phe Ala
100 105 110

Asn Val Thr Tyr Pro Ile Arg Gln Gly Asp Thr Phe Tyr Asn Leu Ala
115 120 125

Lys Ala Ser Tyr Glu Asn Leu Thr Glu Tyr His Leu Ile Gln Asn Leu
130 135 140

Asn Pro Gly Ser Glu Pro Thr Ser Leu Gln Ile Gly Gln Glu Val Thr
145 150 155 160

Val Pro Leu Leu Cys Arg Cys Pro Ala Arg Ala Glu Arg Ser Arg Gly
165 170 175

Val Gln Ser Leu Ile Thr Tyr Met Trp Gln Ala Gly Asp Thr Met Ser
180 185 190

Gln Val Ser Lys Leu Met Asn Ala Thr Val Asp Glu Ile Ala Glu Ala
195 200 205

Asn Asn Val Thr Ala Asn Thr Ser Ala Ser Ala Ser Phe Val Gly Gln
210 215 220

Pro Met Leu Ile Pro Val Arg Gln Arg Pro Arg Leu Pro Ala Pro Leu
225 230 235 240

Tyr Ala Ala Ala Ala Ala Asp Gly Lys Ser Arg Ser Arg Arg Arg Ala
245 250 255

Ala Val Ile Gly Ala Ser Val Ser Gly Ser Leu Val Ala Leu Ala Ala
260 265 270

Leu Phe Val Ala Ile Leu Ala Arg Arg Arg Tyr Arg Lys Lys Pro Ser
275 280 285

Met Arg Leu Gly Ser Arg Phe Ala Val Asn Thr Lys Leu Ser Trp Ser
290 295 300

Arg Asn Gln Phe Gly His Asp Gly Ser Asn Ser Phe Ala His Val Met
305 310 315 320

Lys Gly Gly Lys Leu Leu Thr Gly Val Ser Gln Phe Ile Asp Lys Pro
325 330 335

Ile Ile Phe Val Glu Glu Glu Ile Met Glu Ala Thr Met Asn Leu Asp
340 345 350

Glu Arg Cys Lys Ile Gly Ser Thr Tyr Tyr Arg Ala Lys Leu Asp Gly
355 360 365

Glu Val Phe Ala Val Lys Pro Ala Lys Gly Asp Val Ser Ala Glu Leu
370 375 380

Lys Met Met Gln Met Val Asn His Ala Asn Leu Ile Lys Leu Ala Gly
385 390 395 400

Ile Ser Ile Gly Ala Asp Gly Asp Tyr Ala Phe Leu Val Tyr Glu Phe
405 410 415

Ala Glu Lys Gly Ser Leu Asp Lys Trp Leu Tyr Glu Lys Pro Pro Ser
420 425 430

Ala Leu Pro Ser Ser Ser Cys Thr Val Ala Thr Leu Ser Trp Gly Gln
435 440 445

Arg Leu Ser Ile Ala Leu Asp Val Ala Asn Gly Leu Leu Tyr Met His
450 455 460

Glu His Thr Gln Pro Ser Met Val His Asp Asp Ile Arg Ala Arg Asn
465 470 475 480

Ile Leu Leu Thr Ala Asp Phe Arg Ala Lys Ile Ser Gly Phe Ser Leu
485 490 495

Ala Lys Pro Ala Met Val Asp Ala Ala Ala Thr Ser Ser Asp Val Phe
500 505 510

Ala Phe Gly Leu Leu Leu Leu Glu Leu Leu Ser Gly Arg Arg Ala Met
515 520 525

Glu Ala Arg Ile Gly Ser Glu Ile Gly Met Leu Trp Arg Glu Ile Arg
530 535 540

Gly Val Leu Glu Thr Gly Asp Lys Arg Glu Ala Lys Leu Arg Lys Trp
545 550 555 560

Met Asp Pro Ala Leu Gly Ser Glu Tyr His Met Asp Val Ala Leu Ser
565 570 575

Leu Ala Ser Met Ala Arg Ala Cys Thr Glu Glu Asp Ala Ala Arg Arg
580 585 590

Pro Asn Met Thr Glu Val Val Phe Ser Leu Ser Val Leu Ala Gln Pro
595 600 605

Leu Ser Val Ala Asp Gly Phe Glu Lys Leu Trp Gln Pro Ser Ser Glu
610 615 620

Asp Asn Ile Arg Ile Ala Gly Ser Val Ala Ala Arg
625 630 635

<210> SEQ ID NO 22
<211> LENGTH: 620
<212> TYPE: PRT
<213> ORGANISM: Malus domestica

<400> SEQUENCE: 22

Met Ala Ile Ser Phe Leu Cys Ser Lys Pro Leu Cys Ile Leu Leu Leu
1 5 10 15

Leu Leu Phe Phe Thr Ala Arg Ile Leu Ala Gln Ser Thr Pro Ser Asn

```
            20                  25                  30

Ser Ser Thr Ser Phe Ser Cys Ser Val Asp Ala Pro Pro Ser Cys Asp
        35                  40                  45

Thr Tyr Val Ser Tyr Phe Ala Arg Pro Gln Phe Met Ser Leu Glu Asn
    50                  55                  60

Ile Ser His Leu Phe Gly Val Ser Pro Leu Ser Ile Ala Lys Ala Ser
65                  70                  75                  80

Asn Leu Val Ser Glu His Ile Arg Leu Ile Ala Gly Gln Leu Leu Leu
                85                  90                  95

Val Pro Ile Ser Cys Gly Cys Ser Gly Asn Ser Tyr Phe Ser Asn Ile
            100                 105                 110

Thr Tyr Glu Ile Lys Ser Gly Asp Ser Phe Tyr Leu Val Ser Ile Asn
        115                 120                 125

Ser Phe Glu Asn Leu Thr Asp Trp His Glu Val Leu Asn Met Asn Pro
    130                 135                 140

Thr Leu Asp Pro Ser Leu Leu Gln Ile Gly Gln Lys Val Ile Phe Pro
145                 150                 155                 160

Leu Phe Cys Lys Cys Pro Ser Lys Met Tyr Thr Glu Asn Gly Ile Lys
                165                 170                 175

Tyr His Ile Thr Tyr Ile Trp Gln Pro Asn Asp Asp Ile Ser Arg Val
            180                 185                 190

Ser Ser Arg Phe Asn Val Ser Thr Leu Asp Ile Ser Ser Ala Asn Asn
        195                 200                 205

Leu His Asn Asp Ser Ala Ala Val Glu Leu Pro Val Val Ile Pro Val
    210                 215                 220

Ser Arg Leu Pro Ala Leu Val Gln Pro Lys Pro Pro Gln Gly Arg Asn
225                 230                 235                 240

Ile Phe Lys Gln Arg Trp Trp Leu Ile Leu Ile Ile Ile Leu Gly Gly
                245                 250                 255

Val Leu Leu Val Ser Ser Leu Leu Ala Ile Phe Ala Val Tyr Thr Arg
            260                 265                 270

His Gln His Lys Val Lys Lys Ala Leu Asp Gly Pro Gly Ser Ser Leu
        275                 280                 285

Glu Ser Ala Glu Trp Phe Lys Met Lys Glu Gly Lys Ile Asp Glu Asn
    290                 295                 300

Phe Asp Leu Lys Phe Ile Gln Asp Lys Leu Leu Pro Gly Val Ser Ser
305                 310                 315                 320

Tyr Leu Gly Lys Pro Ile Met Tyr Glu Val Lys Thr Ile Met Glu Ala
                325                 330                 335

Thr Met Asn Leu Asn Glu His Cys Arg Ile Gly Gly Ser Val Tyr Arg
            340                 345                 350

Ala Ile Val Asp Gly Gln Val Leu Ala Val Lys Asn Thr Lys Glu Asp
        355                 360                 365

Val Thr Glu Glu Leu Asn Ile Leu Gln Lys Val Asn His Ala Asn Leu
    370                 375                 380

Val Lys Leu Met Gly Val Ser Ser Glu Thr Asp Gly Ser Arg Phe Leu
385                 390                 395                 400

Val Tyr Glu Tyr Ala Ala Asn Gly Ser Leu Asp Lys Trp Leu Tyr Ser
                405                 410                 415

Lys Ser Ser Ala Thr Ser Ser Ser Ala Glu Leu Leu Thr Trp Asn Gln
            420                 425                 430

Arg Leu Ser Ile Ala Leu Asp Ile Ala Asn Gly Leu Gln Tyr Met His
        435                 440                 445
```

Glu His Thr Gln Arg Ser Ile Val His Met Asp Ile Arg Thr Ser Asn
    450                 455                 460

Ile Leu Leu Asp Ser Lys Phe Lys Ala Lys Ile Ala Asn Phe Ser Met
465                 470                 475                 480

Ala Arg Ala Ala Ala Asn Asp Val Thr Pro Lys Val Asp Val Phe Ala
                485                 490                 495

Phe Gly Val Val Leu Leu Ala Leu Leu Ser Gly Lys Lys Gly Met Glu
            500                 505                 510

Ala Lys Glu Asn Gly Glu Ala Ile Met Leu Trp Lys Asp Val Arg Trp
        515                 520                 525

Val Leu Glu Ala Glu Glu Glu Lys Val Glu Arg Leu Arg Lys Trp Met
    530                 535                 540

Asp Pro Asn Leu Glu Asn Phe Tyr Pro Ile Asp Gly Ala Leu Ser Leu
545                 550                 555                 560

Thr Ala Leu Ala Arg Ala Cys Thr Gln Glu Lys Pro Ser Thr Arg Pro
                565                 570                 575

Ser Met Gly Glu Val Val Phe Asn Leu Ser Val Leu Thr His Ser Ser
            580                 585                 590

Ser Gln Ser Thr Leu Glu Arg Ser Trp Thr Ser Ala Leu Glu Ala Glu
        595                 600                 605

Glu Val Leu Glu Thr Ile Ser Pro Ile Ala Ala Arg
    610                 615                 620

<210> SEQ ID NO 23
<211> LENGTH: 624
<212> TYPE: PRT
<213> ORGANISM: Fragaria vesca subsp. Vesca

<400> SEQUENCE: 23

Met Ala Val Ser Phe Leu Cys Ser Ser Met Val Cys Ile Leu Leu Leu
1               5                   10                  15

Phe Phe Phe Thr Ser Gln Ile Leu Ala Gln Pro Ala Pro Gln Ser Asn
            20                  25                  30

Ser Thr Thr Ser Phe Ser Cys Ala Val Asp Ala Pro Ser Ser Cys Glu
        35                  40                  45

Thr Tyr Val Ala Tyr Phe Val Glu Ser Pro Gly Tyr Met Asn Leu Glu
    50                  55                  60

Asn Ile Ser Asp Leu Phe Gly Val Ser Val Ser Ser Ile Ser Gln Ala
65                  70                  75                  80

Ser Asn Leu Ala Ser Ser Tyr Thr Gly Gln Thr Arg Leu Val Ala Gly
                85                  90                  95

Gln Leu Leu Leu Val Pro Ile Thr Cys Gly Cys Thr Gly Asn Arg Ser
            100                 105                 110

Phe Ala Asn Ile Thr Tyr Ser Ile Lys Arg Gly Asp Ser Tyr Tyr Val
        115                 120                 125

Val Ser Met Tyr Thr Phe Glu Asn Leu Thr Arg Trp Pro Leu Val Val
    130                 135                 140

Glu Met Asn Pro Ala Leu Val Pro Ser Leu Leu Gln Ile Gly Val Lys
145                 150                 155                 160

Val Ile Phe Pro Leu Phe Cys Lys Cys Pro Ser Lys Met Tyr Ser Asp
                165                 170                 175

Leu Gly Ile Lys Tyr Leu Leu Thr Tyr Val Trp Gln Thr Asn Asp Asp
            180                 185                 190

Ile Phe Arg Val Ser Ala Lys Phe Asn Ile Ser Ala Leu Asn Ile Ser

```
        195                 200                 205

Gly Ala Asn Asn Phe Asp Asn Gly Ser Pro Val Val Gly Gln Pro Val
    210                 215                 220

Leu Ile Pro Leu Thr Lys Leu Pro Ala Leu Ser Gln Pro Leu Pro Pro
225                 230                 235                 240

His Gly Lys His Ile Phe Lys His Arg Leu Met Leu Ile Val Ile Ile
                245                 250                 255

Cys Leu Gly Val Ala Leu Ser Val Ala Ser Leu Leu Ala Ile Phe Leu
            260                 265                 270

Val His Thr His Arg Leu Arg Lys Arg Gln Lys Leu Leu Asn Asp Lys
        275                 280                 285

Ser Leu Ser Leu Glu Ser Ala Glu Trp Phe Arg Met Lys Glu Gly Lys
    290                 295                 300

Ser Glu Glu Lys Ile Glu Met Lys Phe Ile Gln Asp Lys Leu Leu Pro
305                 310                 315                 320

Gly Val Ser Ser Tyr Leu Gly Lys Ala Ile Leu Tyr Asp Val Lys Thr
                325                 330                 335

Ile Met Glu Ala Thr Met Asn Leu Asn Asp His Cys Gly Ile Gly Gly
            340                 345                 350

Ser Val Tyr Arg Ala Val Ile Asp Gly Lys Val Leu Ala Val Lys Lys
        355                 360                 365

Thr Lys Glu Asp Val Thr Glu Glu Leu Asn Ile Leu Gln Lys Val Asn
    370                 375                 380

His Ala Asn Leu Val Lys Leu Met Gly Ile Ser Ser Glu Ile Asp Gly
385                 390                 395                 400

Val Arg Phe Leu Val Tyr Glu Tyr Ala Glu Asn Gly Ser Leu Asp Lys
                405                 410                 415

Trp Leu Tyr His Lys Thr Ser Thr Asn Ser Ser Ser Gly Ala Phe Leu
            420                 425                 430

Thr Trp Ser Gln Arg Leu Ser Ile Ala Leu Asp Val Ala Asn Gly Leu
        435                 440                 445

Gln Tyr Leu His Glu His Thr Gln Pro Ser Ile Val His Met Asp Ile
    450                 455                 460

Arg Thr Ser Asn Ile Leu Leu Asp Ser Lys Tyr Lys Ala Lys Ile Ala
465                 470                 475                 480

Asn Phe Ser Met Ala Arg Thr Ala Ala Asn Ser Val Thr Pro Lys Val
                485                 490                 495

Asp Val Phe Ser Phe Gly Val Ile Leu Leu Ser Leu Leu Ser Gly Lys
            500                 505                 510

Lys Gly Met Glu Thr Thr Asp Asn Gly Glu Val Ile Met Leu Trp Lys
        515                 520                 525

Asp Val Arg Gly Val Leu Glu Ala Glu Glu Lys Lys Gln Glu Lys Leu
    530                 535                 540

Arg Ala Trp Met Asp Pro Thr Leu Glu Ser Phe Tyr Pro Ile Asp Gly
545                 550                 555                 560

Ala Leu Ser Leu Thr Ala Leu Ala Ser Ala Cys Thr Gln Glu Lys Ser
                565                 570                 575

Ser Ala Arg Pro Ser Met Ala Glu Val Val Phe Asn Leu Ser Val Leu
            580                 585                 590

Thr His Ser Ser Ser Glu Ser Thr Leu Glu Arg Ser Trp Asn Ser Ala
        595                 600                 605

Leu Glu Val Glu Glu Val Leu Gln Thr Ile Ser Pro Ile Lys Ala Arg
    610                 615                 620
```

<210> SEQ ID NO 24
<211> LENGTH: 1317
<212> TYPE: DNA
<213> ORGANISM: Lotus japonicus

<400> SEQUENCE: 24
ggacatgaga ttgaagctcc aaaattagct cttttttctg atgaatactt aatgctttgt 60
tgtattcact tgattaagtg ctagaaatca tctttgcatg atcatagatt aaatgaattt 120
ccagttggtg tgtggagagc tattttgtta tgctgacatc tgcaatttgc agggcatcta 180
atgattgtca tttcttaaat tattattggt tgtttccgtt tctttaatta tctgttttaa 240
tcttgcaggt catacaaatt aaaatactag ccaccaccca agacatacta aatggggtag 300
tagagggaag ggtaaggtcg ataaggatga ctttttattc tataaaattt aggagaattt 360
gagcttaagt ggcaaggcaa acgacattac tatacgaatt ggctttgtac cagaaacagg 420
gaacaaataa tattttacaa ataagctatt atcatgtcag ctcatttgtt caactttgat 480
ttgattaaaa attaaatgaa gttgaatttg ttgagctgct ttattatata tgccactgga 540
tgtttccgca ttctaagtgc atgtttgaaa acatttctac aattgattac gaaggaaaaa 600
ttaatcatgg agagaagctt atgtgcgtag cttctgtatt tctgaattga ttctatctgt 660
acagtagcat ttagataatg aatgatcttg gttctcgcta agcatcaaac caatctctac 720
ccttttaaaa ttgcaagaat tataagtcat gcattgaccc aaatccttct gtggttatgc 780
cccttaaaaa tccggcaaga catcaagtta gttggtcatt agggttccac cagctagctg 840
acaccttgta caacaactgg ccgtcctaaa gttgggtaag cattacaata ctaaatgcca 900
ttttattata ttttgcgcat ggttatatac ctaagtagga tttgtccaca gtttctttga 960
ttcggaaagg aaaaaatatt tagttgacac tgacagaagc agattttata tacatatatt 1020
atgaaatgac tcctacatga gatacacgaa tctcatcccc atgagttgca gtttgacaga 1080
gtacacactt atcaacttgc tggaatatag gaaagtctaa ccaatgatgt cgatccgtat 1140
tgccttaatt ttggtaaatt tagtattaca tgatcattat tgatatacta aaccacagga 1200
tattttattg acaatgtgaa tgttccatat tttcaacaat gctgattccc tctgataaag 1260
aacaagttcc ttttctcttt ccctgttaac tatcatttgt tccccacttc acaaaca 1317

<210> SEQ ID NO 25
<211> LENGTH: 1317
<212> TYPE: DNA
<213> ORGANISM: Lotus japonicus

<400> SEQUENCE: 25
ggacatgaga ttgaagctcc aaaattagct cttttttctg atgaatactt aatgctttgt 60
tgtattcact tgattaagtg ctagaaatca tctttgcatg atcatagatt aaatgaattt 120
ccagttggtg tgtggagagc tattttgtta tgctgacatc tgcaatttgc agggcatcta 180
atgattgtca tttcttaaat tattattggt tgtttccgtt tctttaatta tctgttttaa 240
tcttgcaggt catacaaatt aaaatactag ccaccaccca agacatacta aatggggtag 300
tagagggaag ggtaaggtcg ataaggatga ctttttattc tataaaattt aggagaattt 360
gagcttaagt ggcaaggcaa acgacattac tatacgaatt ggctttgtac cagaaacagg 420
gaacaaataa tattttacaa ataagctatt atcatgtcag ctcatttgtt caactttgat 480
ttgattaaaa attaaatgaa gttgaatttg ttgagctgct ttattatata tgccactgga 540

```
tgtttccgca ttctaagtgc atgtttgaaa acatttctac aattgattac gaaggaaaaa    600

ttaatcatgg agagaagctt atgtgcgtag cttctgtatt tctgaattga ttctatctgt    660

acagtagcat ttagataatg aatgatcttg gttctcgcta agcatcaaac caatctctac    720

ccttttaaaa ttgcaagaat tataagtcat gcattgaccc aaatccttct gtggttatgc    780

cccttaaaaa tccggcaaga catcaagtta gttggtcatt agggttccac cagctagctg    840

acaccttgta caacaactgg ccgtcctaaa gttgggtaag cattacaata ctaaatgcca    900

ttttattata ttttgcgcat ggttatatac ctaagtagga tttgtccaca gtttctttga    960

ttcggaaagg aaaaaatatt tagttgacac tgacagaagc agattttata tacatatatt   1020

atgaaatgac tcctacatga gatacacgaa tctcatcccc atgagttgca gtttgacaga   1080

gtacacactt atcaacttgc tggaatatag gaaagtctaa ccaatgatgt cgatccgtat   1140

tgccttaatt ttggtaaatt tagtattaca tgatcattat tgatatacta aaccacagga   1200

tattttattg acaatgtgaa tgttccatat tttcaacaat gctgattccc tctgataaag   1260

aacaagttcc ttttctcttt ccctgttaac tatcatttgt tccccacttc acaaaca      1317


<210> SEQ ID NO 26
<211> LENGTH: 61
<212> TYPE: PRT
<213> ORGANISM: Medicago truncatula

<400> SEQUENCE: 26

Cys Thr Lys Asn His Ser Phe Ala Asn Ile Thr Tyr Ser Ile Lys Gln
1               5                   10                  15

Gly Asp Asn Phe Phe Ile Leu Ser Ile Thr Ser Tyr Gln Asn Leu Thr
            20                  25                  30

Asn Tyr Leu Glu Phe Lys Asn Phe Asn Pro Asn Leu Ser Pro Thr Leu
        35                  40                  45

Leu Pro Leu Asp Thr Lys Val Ser Val Pro Leu Phe Cys
    50                  55                  60


<210> SEQ ID NO 27
<211> LENGTH: 61
<212> TYPE: PRT
<213> ORGANISM: Lotus japonicus

<400> SEQUENCE: 27

Cys Ala Gly Asn His Ser Ser Ala Asn Thr Ser Tyr Gln Ile Gln Leu
1               5                   10                  15

Gly Asp Ser Tyr Asp Phe Val Ala Thr Thr Leu Tyr Glu Asn Leu Thr
            20                  25                  30

Asn Trp Asn Ile Val Gln Ala Ser Asn Pro Gly Val Asn Pro Tyr Leu
        35                  40                  45

Leu Pro Glu Arg Val Lys Val Val Phe Pro Leu Phe Cys
    50                  55                  60


<210> SEQ ID NO 28
<211> LENGTH: 233
<212> TYPE: PRT
<213> ORGANISM: Artificial Sequence
<220> FEATURE:
<223> OTHER INFORMATION: Synthetic Construct

<400> SEQUENCE: 28

Met Val Ser Ala Ile Val Leu Tyr Val Leu Leu Ala Ala Ala Ala His
1               5                   10                  15
```

Ser Ala Phe Ala Gln Gly Gly Ala Gly Asn Gly Thr Gly Arg Phe Ala
20 25 30

Cys Val Val Pro Ala Pro Cys Asp Thr Phe Val Leu Tyr Arg Thr Gln
35 40 45

Ser Pro Gly Ser Leu Asp Leu Gly Ala Ile Ser Asp Leu Phe Gly Val
50 55 60

Ser Arg Ala Met Ile Ala Ala Ala Asn Asn Leu Ser Leu Ile Asp Glu
65 70 75 80

Asp Ala Ala Leu Leu Pro Asp Gln Pro Leu Leu Val Pro Val Arg Cys
85 90 95

Gly Cys Thr Gly Asn Arg Ser Phe Val Asn Val Thr Tyr Pro Ile His
100 105 110

Ser Gly Asp Thr Phe Tyr Ala Leu Ala Leu Thr Gly Tyr Glu Asn Leu
115 120 125

Thr Thr Pro Asp Val Ile Gln Glu Leu Asn Pro Gln Ala Val Phe Asn
130 135 140

Lys Leu Asn Val Ser Gln Leu Val Thr Val Pro Leu Phe Cys Arg Cys
145 150 155 160

Pro Thr Pro Ala Glu Arg Ser Ala Gly Val Leu Gln Gln Ile Thr Tyr
165 170 175

Met Trp Arg Pro Val Asp Thr Met Ser Arg Val Ser Lys Leu Met Gly
180 185 190

Ser Asp Ala Ser Ala Ile Ala Ala Ala Asn Asn Val Ser Ala Asp Phe
195 200 205

Thr Ser Thr Thr Met Leu Pro Met Leu Ile Pro Val Ala Arg Pro Pro
210 215 220

Val Leu Pro His His His His His His
225 230

<210> SEQ ID NO 29
<211> LENGTH: 207
<212> TYPE: PRT
<213> ORGANISM: Artificial Sequence
<220> FEATURE:
<223> OTHER INFORMATION: Synthetic Construct

<400> SEQUENCE: 29

Gln Gly Gly Ala Gly Asn Gly Thr Gly Arg Phe Ala Cys Val Val Pro
1 5 10 15

Ala Pro Cys Asp Thr Phe Val Leu Tyr Arg Thr Gln Ser Pro Gly Ser
20 25 30

Leu Asp Leu Gly Ala Ile Ser Asp Leu Phe Gly Val Ser Arg Ala Met
35 40 45

Ile Ala Ala Ala Asn Asn Leu Ser Leu Ile Asp Glu Asp Ala Ala Leu
50 55 60

Leu Pro Asp Gln Pro Leu Leu Val Pro Val Arg Cys Gly Cys Thr Gly
65 70 75 80

Asn Arg Ser Phe Val Asn Val Thr Tyr Pro Ile His Ser Gly Asp Thr
85 90 95

Phe Tyr Ala Leu Ala Leu Thr Gly Tyr Glu Asn Leu Thr Thr Pro Asp
100 105 110

Val Ile Gln Glu Leu Asn Pro Gln Ala Val Phe Asn Lys Leu Asn Val
115 120 125

Ser Gln Leu Val Thr Val Pro Leu Phe Cys Arg Cys Pro Thr Pro Ala
130 135 140

Glu Arg Ser Ala Gly Val Leu Gln Gln Ile Thr Tyr Met Trp Arg Pro
145 150 155 160

Val Asp Thr Met Ser Arg Val Ser Lys Leu Met Gly Ser Asp Ala Ser
165 170 175

Ala Ile Ala Ala Ala Asn Asn Val Ser Ala Asp Phe Thr Ser Thr Thr
180 185 190

Met Leu Pro Met Leu Ile Pro Val Ala Arg Pro Pro Val Leu Pro
195 200 205

<210> SEQ ID NO 30
<211> LENGTH: 622
<212> TYPE: PRT
<213> ORGANISM: Lotus japonicus

<400> SEQUENCE: 30

Met Glu His Pro Arg Leu Gly Phe Pro Ile Thr Leu Leu Leu Phe Ser
1 5 10 15

Phe Ile Leu Leu Pro Ser Thr Ser Gln Ser Lys Cys Thr His Gly Cys
20 25 30

Ala Leu Ala Gln Ala Ser Tyr Tyr Leu Leu Asn Gly Ser Asn Leu Thr
35 40 45

Tyr Ile Ser Glu Ile Met Gln Ser Ser Leu Leu Thr Lys Pro Glu Asp
50 55 60

Ile Val Ser Tyr Asn Gln Asp Thr Ile Ala Ser Lys Asp Ser Val Gln
65 70 75 80

Ala Gly Gln Arg Ile Asn Val Pro Phe Pro Cys Asp Cys Ile Glu Gly
85 90 95

Glu Phe Leu Gly His Thr Phe Gln Tyr Asp Val Gln Lys Gly Asp Arg
100 105 110

Tyr Asp Thr Ile Ala Gly Thr Asn Tyr Ala Asn Leu Thr Thr Val Glu
115 120 125

Trp Leu Arg Arg Phe Asn Ser Tyr Pro Pro Asp Asn Ile Pro Asp Thr
130 135 140

Gly Thr Leu Asn Val Thr Val Asn Cys Ser Cys Gly Asp Ser Gly Val
145 150 155 160

Gly Asp Tyr Gly Leu Phe Val Thr Tyr Pro Leu Arg Pro Gly Glu Thr
165 170 175

Leu Gly Ser Val Ala Ser Asn Val Lys Leu Asp Ser Ala Leu Leu Gln
180 185 190

Lys Tyr Asn Pro Asn Val Asn Phe Asn Gln Gly Ser Gly Ile Val Tyr
195 200 205

Ile Pro Ala Lys Asp Gln Asn Gly Ser Tyr Val Leu Leu Gly Ser Ser
210 215 220

Ser Gly Gly Leu Ala Gly Gly Ala Ile Ala Gly Ile Ala Ala Gly Val
225 230 235 240

Ala Val Cys Leu Leu Leu Leu Ala Gly Phe Ile Tyr Val Gly Tyr Phe
245 250 255

Arg Lys Lys Arg Ile Gln Lys Glu Glu Leu Leu Ser Gln Glu Thr Arg
260 265 270

Ala Ile Phe Pro Gln Asp Gly Lys Asp Glu Asn Pro Arg Ser Thr Val
275 280 285

Asn Glu Thr Pro Gly Pro Gly Gly Pro Ala Ala Met Ala Gly Ile Thr
290 295 300

Val Asp Lys Ser Val Glu Phe Ser Tyr Asp Glu Leu Ala Thr Ala Thr
305 310 315 320

```
Asp Asn Phe Ser Leu Ala Asn Lys Ile Gly Gln Gly Gly Phe Gly Ser
                325                 330                 335

Val Tyr Tyr Ala Glu Leu Arg Gly Glu Arg Ala Ala Ile Lys Lys Met
            340                 345                 350

Asp Met Gln Ala Ser Lys Glu Phe Leu Ala Glu Leu Lys Val Leu Thr
        355                 360                 365

Arg Val His His Leu Asn Leu Val Arg Leu Ile Gly Tyr Ser Ile Glu
    370                 375                 380

Gly Ser Leu Phe Leu Val Tyr Glu Phe Ile Glu Asn Gly Asn Leu Ser
385                 390                 395                 400

Gln His Leu Arg Gly Ser Gly Arg Asp Pro Leu Pro Trp Ala Thr Arg
                405                 410                 415

Val Gln Ile Ala Leu Asp Ser Ala Arg Gly Leu Glu Tyr Ile His Glu
            420                 425                 430

His Thr Val Pro Val Tyr Ile His Arg Asp Ile Lys Ser Ala Asn Ile
        435                 440                 445

Leu Ile Asp Lys Asn Tyr Arg Gly Lys Val Ala Asp Phe Gly Leu Thr
    450                 455                 460

Lys Leu Thr Glu Val Gly Ser Ser Ser Leu Pro Thr Gly Arg Leu Val
465                 470                 475                 480

Gly Thr Phe Gly Tyr Met Pro Pro Glu Tyr Ala Gln Tyr Gly Asp Val
                485                 490                 495

Ser Pro Lys Val Asp Val Tyr Ala Phe Gly Val Val Leu Tyr Glu Leu
            500                 505                 510

Ile Ser Ala Lys Asp Ala Ile Val Lys Thr Ser Glu Ser Ile Thr Asp
        515                 520                 525

Ser Lys Gly Leu Val Ala Leu Phe Glu Gly Val Leu Ser Gln Pro Asp
    530                 535                 540

Pro Thr Glu Asp Leu Arg Lys Leu Val Asp Gln Arg Leu Gly Asp Asn
545                 550                 555                 560

Tyr Pro Val Asp Ser Val Arg Lys Met Ala Gln Leu Ala Lys Ala Cys
                565                 570                 575

Thr Gln Asp Asn Pro Gln Leu Arg Pro Ser Met Arg Ser Ile Val Val
            580                 585                 590

Ala Leu Met Thr Leu Ser Ser Thr Thr Asp Asp Trp Asp Val Gly Ser
        595                 600                 605

Phe Tyr Glu Asn Gln Asn Leu Val Asn Leu Met Ser Gly Arg
    610                 615                 620
```

<210> SEQ ID NO 31
<211> LENGTH: 621
<212> TYPE: PRT
<213> ORGANISM: Medicago truncatula

<400> SEQUENCE: 31

```
Met Glu His Gln Pro Arg Phe Thr Ser Phe Ile Ser Leu Pro Leu Phe
1               5                   10                  15

Ser Ile Phe Leu Ala Ser Ile Pro Phe Ile Thr Glu Ser Lys Cys Thr
            20                  25                  30

Lys Gly Cys Ser Leu Ala Leu Ala Asn Phe Tyr Val Ser Gln Gly Ser
        35                  40                  45

Asn Leu Thr Tyr Ile Ser Ser Ile Met Arg Ser Asn Ile Gln Thr Arg
    50                  55                  60

Pro Glu Asp Ile Val Glu Tyr Ser Arg Glu Ile Ile Pro Ser Lys Asp
```

```
65                  70                  75                  80

Ser Val Gln Ala Gly Gln Arg Leu Asn Val Pro Phe Pro Cys Asp Cys
                85                  90                  95

Ile Asp Gly Gln Phe Leu Gly His Lys Phe Ser Tyr Asp Val Glu Thr
            100                 105                 110

Gly Asp Thr Tyr Glu Thr Val Ala Thr Asn Asn Tyr Ala Asn Leu Thr
        115                 120                 125

Asn Val Glu Trp Leu Arg Arg Phe Asn Thr Tyr Pro Pro Asn Asp Ile
    130                 135                 140

Pro Asp Thr Gly Thr Leu Asn Val Thr Val Asn Cys Ser Cys Gly Asp
145                 150                 155                 160

Ala Asp Val Gly Asn Tyr Ala Leu Phe Val Thr Tyr Pro Leu Arg Pro
                165                 170                 175

Gly Glu Thr Leu Val Ser Val Ala Asn Ser Ser Lys Val Asp Ser Ser
            180                 185                 190

Leu Leu Gln Arg Tyr Asn Pro Gly Val Asn Phe Asn Gln Gly Ser Gly
        195                 200                 205

Ile Val Phe Val Pro Gly Lys Asp Gln Asn Gly Ser Phe Val Phe Leu
    210                 215                 220

Gly Ser Ser Ser Gly Leu Gly Gly Gly Ala Ile Gly Gly Ile Ala Val
225                 230                 235                 240

Gly Ile Val Val Val Leu Leu Leu Val Ala Ala Ala Ile Tyr Phe Gly
                245                 250                 255

Tyr Phe Arg Lys Lys Lys Ile Gln Lys Glu Glu Leu Phe Ser Arg Asp
            260                 265                 270

Ser Thr Ala Leu Phe Ser Gln Asp Gly Lys Asp Glu Asn Ser His Gly
        275                 280                 285

Ala Ala Asn Val Thr Gln Arg Pro Gly Val Met Thr Gly Ile Thr Val
    290                 295                 300

Asp Lys Ser Val Glu Phe Ser Tyr Asp Glu Leu Ala Ala Ala Ser Asp
305                 310                 315                 320

Asn Phe Ser Met Ala Asn Lys Ile Gly Gln Gly Gly Phe Gly Ser Val
                325                 330                 335

Tyr Tyr Ala Glu Leu Arg Gly Glu Lys Ala Ala Ile Lys Lys Met Asp
            340                 345                 350

Met Gln Ala Thr Lys Glu Phe Leu Ala Glu Leu Lys Val Leu Thr Arg
        355                 360                 365

Val His His Leu Asn Leu Val Arg Leu Ile Gly Tyr Ser Ile Glu Gly
    370                 375                 380

Ser Leu Phe Leu Val Tyr Glu Tyr Ile Glu Asn Gly Asn Leu Ser Gln
385                 390                 395                 400

His Leu Arg Gly Ser Gly Arg Asp Pro Leu Pro Trp Ala Thr Arg Val
                405                 410                 415

Gln Ile Ala Leu Asp Ser Ala Arg Gly Leu Glu Tyr Ile His Glu His
            420                 425                 430

Thr Val Pro Val Tyr Ile His Arg Asp Ile Lys Pro Ala Asn Ile Leu
        435                 440                 445

Ile Asp Lys Asn Phe Arg Gly Lys Val Ala Asp Phe Gly Leu Thr Lys
    450                 455                 460

Leu Thr Glu Val Gly Ser Ser Ser Leu Pro Thr Gly Arg Leu Val Gly
465                 470                 475                 480

Thr Phe Gly Tyr Met Pro Pro Glu Tyr Ala Gln Tyr Gly Asp Val Ser
                485                 490                 495
```

Pro Lys Val Asp Val Tyr Ala Phe Gly Val Val Leu Tyr Glu Leu Ile
500 505 510

Ser Ala Lys Glu Ala Ile Val Lys Ser Ser Glu Ser Val Ala Asp Ser
515 520 525

Lys Gly Leu Val Gly Leu Phe Glu Gly Val Leu Ser Gln Pro Asp Pro
530 535 540

Thr Glu Asp Leu Arg Lys Ile Val Asp Pro Arg Leu Gly Asp Asn Tyr
545 550 555 560

Pro Ala Asp Ser Val Arg Lys Met Ala Gln Leu Ala Lys Ala Cys Thr
565 570 575

Gln Glu Asn Pro Gln Leu Arg Pro Ser Met Arg Ser Ile Val Val Ala
580 585 590

Leu Met Thr Leu Ser Ser Thr Thr Asp Asp Trp Asp Val Gly Ser Phe
595 600 605

Tyr Glu Asn Gln Asn Leu Val Asn Leu Met Ser Gly Arg
610 615 620

<210> SEQ ID NO 32
<211> LENGTH: 623
<212> TYPE: PRT
<213> ORGANISM: Lotus japonicus

<400> SEQUENCE: 32

Met Lys Leu Lys Thr Gly Leu Leu Leu Phe Phe Ile Leu Leu Leu Gly
1 5 10 15

His Val Cys Phe His Val Glu Ser Asn Cys Leu Lys Gly Cys Asp Leu
20 25 30

Ala Leu Ala Ser Tyr Tyr Ile Leu Pro Gly Val Phe Ile Leu Gln Asn
35 40 45

Ile Thr Thr Phe Met Gln Ser Glu Ile Val Ser Ser Asn Asp Ala Ile
50 55 60

Thr Ser Tyr Asn Lys Asp Lys Ile Leu Asn Asp Ile Asn Ile Gln Ser
65 70 75 80

Phe Gln Arg Leu Asn Ile Pro Phe Pro Cys Asp Cys Ile Gly Gly Glu
85 90 95

Phe Leu Gly His Val Phe Glu Tyr Ser Ala Ser Lys Gly Asp Thr Tyr
100 105 110

Glu Thr Ile Ala Asn Leu Tyr Tyr Ala Asn Leu Thr Thr Val Asp Leu
115 120 125

Leu Lys Arg Phe Asn Ser Tyr Asp Pro Lys Asn Ile Pro Val Asn Ala
130 135 140

Lys Val Asn Val Thr Val Asn Cys Ser Cys Gly Asn Ser Gln Val Ser
145 150 155 160

Lys Asp Tyr Gly Leu Phe Ile Thr Tyr Pro Ile Arg Pro Gly Asp Thr
165 170 175

Leu Gln Asp Ile Ala Asn Gln Ser Ser Leu Asp Ala Gly Leu Ile Gln
180 185 190

Ser Phe Asn Pro Ser Val Asn Phe Ser Lys Asp Ser Gly Ile Ala Phe
195 200 205

Ile Pro Gly Arg Tyr Lys Asn Gly Val Tyr Val Pro Leu Tyr His Arg
210 215 220

Thr Ala Gly Leu Ala Ser Gly Ala Ala Val Gly Ile Ser Ile Ala Gly
225 230 235 240

Thr Phe Val Leu Leu Leu Leu Ala Phe Cys Met Tyr Val Arg Tyr Gln

```
                245                 250                 255

Lys Lys Glu Glu Glu Lys Ala Lys Leu Pro Thr Asp Ile Ser Met Ala
            260                 265                 270

Leu Ser Thr Gln Asp Gly Asn Ala Ser Ser Ser Ala Glu Tyr Glu Thr
        275                 280                 285

Ser Gly Ser Ser Gly Pro Gly Thr Ala Ser Ala Thr Gly Leu Thr Ser
    290                 295                 300

Ile Met Val Ala Lys Ser Met Glu Phe Ser Tyr Gln Glu Leu Ala Lys
305                 310                 315                 320

Ala Thr Asn Asn Phe Ser Leu Asp Asn Lys Ile Gly Gln Gly Gly Phe
                325                 330                 335

Gly Ala Val Tyr Tyr Ala Glu Leu Arg Gly Lys Lys Thr Ala Ile Lys
            340                 345                 350

Lys Met Asp Val Gln Ala Ser Thr Glu Phe Leu Cys Glu Leu Lys Val
        355                 360                 365

Leu Thr His Val His His Leu Asn Leu Val Arg Leu Ile Gly Tyr Cys
    370                 375                 380

Val Glu Gly Ser Leu Phe Leu Val Tyr Glu His Ile Asp Asn Gly Asn
385                 390                 395                 400

Leu Gly Gln Tyr Leu His Gly Ser Gly Lys Glu Pro Leu Pro Trp Ser
                405                 410                 415

Ser Arg Val Gln Ile Ala Leu Asp Ala Ala Arg Gly Leu Glu Tyr Ile
            420                 425                 430

His Glu His Thr Val Pro Val Tyr Ile His Arg Asp Val Lys Ser Ala
        435                 440                 445

Asn Ile Leu Ile Asp Lys Asn Leu Arg Gly Lys Val Ala Asp Phe Gly
    450                 455                 460

Leu Thr Lys Leu Ile Glu Val Gly Asn Ser Thr Leu Gln Thr Arg Leu
465                 470                 475                 480

Val Gly Thr Phe Gly Tyr Met Pro Pro Glu Tyr Ala Gln Tyr Gly Asp
                485                 490                 495

Ile Ser Pro Lys Ile Asp Val Tyr Ala Phe Gly Val Val Leu Phe Glu
            500                 505                 510

Leu Ile Ser Ala Lys Asn Ala Val Leu Lys Thr Gly Glu Leu Val Ala
        515                 520                 525

Glu Ser Lys Gly Leu Val Ala Leu Phe Glu Glu Ala Leu Asn Lys Ser
    530                 535                 540

Asp Pro Cys Asp Ala Leu Arg Lys Leu Val Asp Pro Arg Leu Gly Glu
545                 550                 555                 560

Asn Tyr Pro Ile Asp Ser Val Leu Lys Ile Ala Gln Leu Gly Arg Ala
                565                 570                 575

Cys Thr Arg Asp Asn Pro Leu Leu Arg Pro Ser Met Arg Ser Leu Val
            580                 585                 590

Val Ala Leu Met Thr Leu Ser Ser Leu Thr Glu Asp Cys Asp Asp Glu
        595                 600                 605

Ser Ser Tyr Glu Ser Gln Thr Leu Ile Asn Leu Leu Ser Val Arg
    610                 615                 620
```

<210> SEQ ID NO 33
<211> LENGTH: 620
<212> TYPE: PRT
<213> ORGANISM: Medicago truncatula

<400> SEQUENCE: 33

-continued

```
Met Asn Leu Lys Asn Gly Leu Leu Leu Phe Ile Leu Phe Leu Asp Cys
1               5                   10                  15

Val Phe Phe Lys Val Glu Ser Lys Cys Val Lys Gly Cys Asp Val Ala
            20                  25                  30

Leu Ala Ser Tyr Tyr Ile Ile Pro Ser Ile Gln Leu Arg Asn Ile Ser
        35                  40                  45

Asn Phe Met Gln Ser Lys Ile Val Leu Thr Asn Ser Phe Asp Val Ile
    50                  55                  60

Met Ser Tyr Asn Arg Asp Val Val Phe Asp Lys Ser Gly Leu Ile Ser
65                  70                  75                  80

Tyr Thr Arg Ile Asn Val Pro Phe Pro Cys Glu Cys Ile Gly Gly Glu
                85                  90                  95

Phe Leu Gly His Val Phe Glu Tyr Thr Thr Lys Glu Gly Asp Asp Tyr
            100                 105                 110

Asp Leu Ile Ala Asn Thr Tyr Tyr Ala Ser Leu Thr Thr Val Glu Leu
        115                 120                 125

Leu Lys Lys Phe Asn Ser Tyr Asp Pro Asn His Ile Pro Val Lys Ala
    130                 135                 140

Lys Ile Asn Val Thr Val Ile Cys Ser Cys Gly Asn Ser Gln Ile Ser
145                 150                 155                 160

Lys Asp Tyr Gly Leu Phe Val Thr Tyr Pro Leu Arg Ser Asp Asp Thr
                165                 170                 175

Leu Ala Lys Ile Ala Thr Lys Ala Gly Leu Asp Glu Gly Leu Ile Gln
            180                 185                 190

Asn Phe Asn Gln Asp Ala Asn Phe Ser Ile Gly Ser Gly Ile Val Phe
        195                 200                 205

Ile Pro Gly Arg Asp Gln Asn Gly His Phe Phe Pro Leu Tyr Ser Arg
    210                 215                 220

Thr Gly Ile Ala Lys Gly Ser Ala Val Gly Ile Ala Met Ala Gly Ile
225                 230                 235                 240

Phe Gly Leu Leu Leu Phe Val Ile Tyr Ile Tyr Ala Lys Tyr Phe Gln
                245                 250                 255

Lys Lys Glu Glu Glu Lys Thr Lys Leu Pro Gln Thr Ser Arg Ala Phe
            260                 265                 270

Ser Thr Gln Asp Ala Ser Gly Ser Ala Glu Tyr Glu Thr Ser Gly Ser
        275                 280                 285

Ser Gly His Ala Thr Gly Ser Ala Ala Gly Leu Thr Gly Ile Met Val
    290                 295                 300

Ala Lys Ser Thr Glu Phe Thr Tyr Gln Glu Leu Ala Lys Ala Thr Asn
305                 310                 315                 320

Asn Phe Ser Leu Asp Asn Lys Ile Gly Gln Gly Gly Phe Gly Ala Val
                325                 330                 335

Tyr Tyr Ala Glu Leu Arg Gly Glu Lys Thr Ala Ile Lys Lys Met Asp
            340                 345                 350

Val Gln Ala Ser Ser Glu Phe Leu Cys Glu Leu Lys Val Leu Thr His
        355                 360                 365

Val His His Leu Asn Leu Val Arg Leu Ile Gly Tyr Cys Val Glu Gly
    370                 375                 380

Ser Leu Phe Leu Val Tyr Glu His Ile Asp Asn Gly Asn Leu Gly Gln
385                 390                 395                 400

Tyr Leu His Gly Ile Gly Thr Glu Pro Leu Pro Trp Ser Ser Arg Val
                405                 410                 415

Gln Ile Ala Leu Asp Ser Ala Arg Gly Leu Glu Tyr Ile His Glu His
```

```
            420                 425                 430

Thr Val Pro Val Tyr Ile His Arg Asp Val Lys Ser Ala Asn Ile Leu
        435                 440                 445

Ile Asp Lys Asn Leu Arg Gly Lys Val Ala Asp Phe Gly Leu Thr Lys
    450                 455                 460

Leu Ile Glu Val Gly Asn Ser Thr Leu His Thr Arg Leu Val Gly Thr
465                 470                 475                 480

Phe Gly Tyr Met Pro Pro Glu Tyr Ala Gln Tyr Gly Asp Val Ser Pro
                485                 490                 495

Lys Ile Asp Val Tyr Ala Phe Gly Val Val Leu Tyr Glu Leu Ile Thr
            500                 505                 510

Ala Lys Asn Ala Val Leu Lys Thr Gly Glu Ser Val Ala Glu Ser Lys
        515                 520                 525

Gly Leu Val Gln Leu Phe Glu Glu Ala Leu His Arg Met Asp Pro Leu
    530                 535                 540

Glu Gly Leu Arg Lys Leu Val Asp Pro Arg Leu Lys Glu Asn Tyr Pro
545                 550                 555                 560

Ile Asp Ser Val Leu Lys Met Ala Gln Leu Gly Arg Ala Cys Thr Arg
                565                 570                 575

Asp Asn Pro Leu Leu Arg Pro Ser Met Arg Ser Ile Val Val Ala Leu
            580                 585                 590

Met Thr Leu Ser Ser Pro Thr Glu Asp Cys Asp Asp Asp Ser Ser Tyr
        595                 600                 605

Glu Asn Gln Ser Leu Ile Asn Leu Leu Ser Thr Arg
    610                 615                 620


<210> SEQ ID NO 34
<211> LENGTH: 617
<212> TYPE: PRT
<213> ORGANISM: Zea mays

<400> SEQUENCE: 34

Met Ala Arg Ile Leu Met Arg Leu Leu Leu Leu Ala Ala Ala Ala Ala
1               5                   10                  15

Val Ala Ala Gly Asp Gly Cys Leu Asn Ser Gly Cys Val Ala Leu Gly
            20                  25                  30

Ser Tyr Leu Val Ala Arg Asn Gln Asn Leu Thr Tyr Ile Ala Ser Leu
        35                  40                  45

Phe Gly Ile Gly Asp Tyr His Ala Leu Ala Arg Tyr Asn Pro Gly Thr
    50                  55                  60

Thr Asn Leu Asp Tyr Ile Gln Ala Gly Gln Ser Val Asn Ile Ser Phe
65                  70                  75                  80

Thr Cys Gly Cys His Thr Phe Pro Asn Ser Asp Ala Thr Tyr Leu Gly
                85                  90                  95

Gly Ser Phe Pro His Lys Val Val Thr Gly Asp Thr Tyr Gly Gly Ile
            100                 105                 110

Ala Gln Asn Tyr Asn Asn Leu Thr Ser Ala Ala Trp Leu Ala Val Thr
        115                 120                 125

Asn Pro Tyr Pro Thr Asn Asn Ile Pro Asp Thr Asn Thr Val Val Asn
    130                 135                 140

Val Thr Val Asn Cys Thr Cys Gly Asp Pro Lys Ile Ser Ser Asp Tyr
145                 150                 155                 160

Gly Phe Phe Leu Thr Tyr Pro Leu Met Gly Gln Thr Leu Ala Ala Val
                165                 170                 175
```

```
Ala Ala Asn Tyr Ser Phe Asn Ser Ser Ser Gln Leu Asp Leu Leu Arg
            180                 185                 190

Lys Tyr Asn Pro Gly Met Asp Thr Ala Thr Ser Gly Leu Val Phe Ile
        195                 200                 205

Pro Val Lys Asp Gly Asn Gly Ser Tyr His Pro Leu Lys Pro Pro Gly
    210                 215                 220

Asn Gly Gly Ser Ile Gly Ala Ile Val Gly Gly Val Val Gly Gly Val
225                 230                 235                 240

Ala Ile Leu Val Leu Gly Val Leu Leu Tyr Ile Met Phe Tyr Arg Arg
                245                 250                 255

Lys Lys Ala Asn Lys Ala Ala Leu Leu Pro Ser Ser Glu Asp Ser Thr
            260                 265                 270

Gln Leu Ala Thr Thr Ser Met Asp Lys Ser Ala Leu Ser Thr Ser Gln
        275                 280                 285

Ala Asp Ser Ser Ser Gly Val Pro Gly Ile Thr Val Asp Lys Ser Val
    290                 295                 300

Glu Phe Ser Tyr Glu Glu Leu Phe Asn Ala Thr Glu Gly Phe Ser Met
305                 310                 315                 320

Ser Asn Lys Ile Gly Gln Gly Gly Phe Gly Ala Val Tyr Tyr Ala Glu
                325                 330                 335

Leu Arg Gly Glu Lys Ala Ala Ile Lys Lys Met Asp Met Gln Ala Ser
            340                 345                 350

His Glu Phe Leu Ala Glu Leu Lys Val Leu Thr His Val His His Leu
        355                 360                 365

Asn Leu Val Arg Leu Ile Gly Phe Cys Thr Glu Ser Ser Leu Phe Leu
    370                 375                 380

Val Tyr Glu Phe Ile Glu Asn Gly Asn Leu Ser Gln His Leu Arg Gly
385                 390                 395                 400

Thr Gly Tyr Glu Pro Leu Ser Trp Ala Ala Arg Val Gln Ile Ala Leu
                405                 410                 415

Asp Ser Ala Arg Gly Leu Glu Tyr Ile His Glu His Thr Val Pro Val
            420                 425                 430

Tyr Ile His Arg Asp Ile Lys Ser Ala Asn Ile Leu Ile Asp Lys Asn
        435                 440                 445

Tyr Arg Ala Lys Val Ala Asp Phe Gly Leu Thr Lys Leu Thr Glu Val
    450                 455                 460

Gly Asn Thr Ser Leu Pro Thr Arg Gly Ile Val Gly Thr Phe Gly Tyr
465                 470                 475                 480

Met Pro Pro Glu Tyr Ala Arg Tyr Gly Asp Val Ser Pro Lys Val Asp
                485                 490                 495

Val Tyr Ala Phe Gly Val Val Leu Tyr Glu Leu Ile Ser Ala Lys Asp
            500                 505                 510

Ala Ile Val Arg Ser Thr Glu Ser Ser Ser Asp Ser Lys Gly Leu Val
        515                 520                 525

Tyr Leu Phe Glu Glu Ala Leu Asn Thr Pro Asp Pro Lys Glu Gly Leu
    530                 535                 540

Gln Arg Leu Ile Asp Pro Ala Leu Gly Glu Asp Tyr Pro Ile Asp Ser
545                 550                 555                 560

Ile Leu Lys Met Thr Val Leu Ala Arg Ala Cys Thr Gln Glu Asp Pro
                565                 570                 575

Lys Ala Arg Pro Thr Met Arg Ser Ile Val Val Ala Leu Met Thr Leu
            580                 585                 590

Ser Ser Thr Ser Glu Phe Trp Asp Met Asn Ala Ile Gln Glu Asn Gln
```

```
        595                 600                 605

Gly Val Val Asn Leu Met Ser Gly Arg
    610                 615


<210> SEQ ID NO 35
<211> LENGTH: 626
<212> TYPE: PRT
<213> ORGANISM: Hordeum vulgare

<400> SEQUENCE: 35

Met Glu Ala Pro Leu His Ser Leu Leu Leu Leu Leu Leu Leu Ala Ala
1               5                   10                  15

Ala Ala Gly Pro Lys Thr Ala Ala Ala Val Gly Asp Gly Cys Ser Arg
            20                  25                  30

Gly Cys Asp Leu Ala Leu Ala Ser Tyr Tyr Ile Ala Pro Asn Gln Asn
        35                  40                  45

Val Thr Tyr Ile Ala Ser Leu Phe Gly Phe Ser Glu Tyr Arg Val Leu
    50                  55                  60

Gly Gln Tyr Asn Pro Gly Val Asn Asn Leu Asp Tyr Val Val Ala Gly
65                  70                  75                  80

Asp Arg Leu Asn Val Ser Leu Thr Cys Lys Cys Leu Ala Ser Leu Ser
                85                  90                  95

Ala Pro Ala Ser Thr Phe Leu Ala Ala Ser Ile Pro Tyr Lys Val Ala
            100                 105                 110

Thr Gly Glu Thr Tyr Leu Arg Ile Ala Asp Asn Tyr Asn Asn Leu Thr
        115                 120                 125

Thr Ala Asp Trp Leu Val Ala Thr Asn Thr Tyr Pro Ala Asn Asn Ile
    130                 135                 140

Pro Asp Val Ala Thr Val Asn Ala Thr Val Asn Cys Ser Cys Gly Asp
145                 150                 155                 160

Ala Gly Ile Ser Thr Asp Tyr Gly Leu Phe Leu Thr Tyr Pro Leu Arg
                165                 170                 175

Asp Arg Glu Thr Leu Ala Ser Val Ala Ala Asn His Gly Phe Ser Ser
            180                 185                 190

Pro Glu Lys Met Asp Leu Leu Lys Lys Tyr Asn Pro Gly Met Asp Gly
        195                 200                 205

Val Thr Gly Ser Gly Ile Val Tyr Ile Pro Ala Lys Asp Pro Asn Gly
    210                 215                 220

Ser Tyr Arg Pro Leu Glu Ser Pro Gly Lys Lys Ser Ser Ala Gly Ala
225                 230                 235                 240

Ile Ala Gly Gly Val Val Ala Gly Val Val Ala Leu Val Leu Gly Val
                245                 250                 255

Val Leu Phe Leu Phe Tyr Arg Arg Arg Lys Ala Lys Lys Asp Ala Leu
            260                 265                 270

Leu Pro Ser Ser Glu Glu Ser Thr Arg Leu Ala Ser Ala Ile Ser Met
        275                 280                 285

Gln Lys Val Thr Pro Ser Thr Ser Gln Ala Asp Gly Ala Ser Pro Ala
    290                 295                 300

Ala Gly Ile Thr Val Asp Lys Ser Val Glu Phe Ser Tyr Glu Glu Leu
305                 310                 315                 320

Phe Asn Ala Thr Glu Gly Phe Asn Ile Ile His Lys Ile Gly Gln Gly
                325                 330                 335

Gly Phe Gly Ala Val Tyr Tyr Ala Glu Leu Arg Gly Glu Lys Ala Ala
            340                 345                 350
```

```
Ile Lys Lys Met Asp Met Gln Ala Thr Gln Glu Phe Leu Ala Glu Leu
        355                 360                 365

Lys Val Leu Thr His Val His His Leu Asn Leu Val Arg Leu Ile Gly
    370                 375                 380

Tyr Cys Thr Glu Ser Ser Leu Phe Leu Val Tyr Glu Phe Ile Glu Asn
385                 390                 395                 400

Gly Asn Leu Ser Gln His Leu Arg Gly Thr Gly Tyr Glu Pro Leu Ser
                405                 410                 415

Trp Val Glu Arg Val Gln Ile Ala Leu Asp Ser Ala Arg Gly Leu Glu
            420                 425                 430

Tyr Ile His Glu His Thr Val Pro Val Tyr Ile His Arg Asp Ile Lys
        435                 440                 445

Ser Ala Asn Ile Leu Ile Asp Lys Asn Thr Arg Ala Lys Val Ala Asp
    450                 455                 460

Phe Gly Leu Thr Lys Leu Thr Glu Val Gly Gly Gly Thr Ser Leu Gln
465                 470                 475                 480

Thr Arg Val Val Gly Thr Phe Gly Tyr Met Pro Pro Glu Tyr Ala Arg
                485                 490                 495

Tyr Gly Asp Val Ser Pro Lys Val Asp Val Tyr Ala Phe Gly Val Val
            500                 505                 510

Leu Tyr Glu Leu Ile Ser Ala Lys Asp Ala Ile Val Arg Ser Ala Glu
        515                 520                 525

Ser Thr Ser Asp Ser Lys Gly Leu Val Tyr Leu Phe Glu Glu Ala Leu
    530                 535                 540

Ser Ala Pro Asp Pro Lys Glu Gly Ile Arg Arg Leu Met Asp Pro Lys
545                 550                 555                 560

Leu Gly Asp Asp Tyr Pro Ile Asp Ala Ile Leu Lys Met Thr His Leu
                565                 570                 575

Ala Asn Ala Cys Thr Gln Glu Asp Pro Lys Leu Arg Pro Thr Met Arg
            580                 585                 590

Ser Val Val Val Ala Leu Met Thr Leu Ser Ser Thr Ser Glu Phe Trp
        595                 600                 605

Asp Met Asn Ala Leu Tyr Glu Asn Pro Gly Leu Val Asn Leu Met Ser
    610                 615                 620

Gly Arg
625
```

<210> SEQ ID NO 36
<211> LENGTH: 613
<212> TYPE: PRT
<213> ORGANISM: Oryza sativa Japonica Group

<400> SEQUENCE: 36

```
Met Phe Ser Leu Pro Ala Leu Leu Ile Gly Ala Cys Ala Phe Ala Ala
1               5                   10                  15

Ala Ala Val Ala Ala Ser Gly Asp Gly Cys Arg Ala Gly Cys Ser Leu
            20                  25                  30

Ala Ile Ala Ala Tyr Tyr Phe Ser Glu Gly Ser Asn Leu Thr Phe Ile
        35                  40                  45

Ala Thr Ile Phe Ala Ile Gly Gly Gly Gly Tyr Gln Ala Leu Leu Pro
    50                  55                  60

Tyr Asn Pro Ala Ile Thr Asn Pro Asp Tyr Val Val Thr Gly Asp Arg
65                  70                  75                  80

Val Leu Val Pro Phe Pro Cys Ser Cys Leu Gly Leu Pro Ala Ala Pro
                85                  90                  95
```

```
Ala Ser Thr Phe Leu Ala Gly Ala Ile Pro Tyr Pro Leu Pro Leu Pro
            100                 105                 110

Arg Gly Gly Gly Asp Thr Tyr Asp Ala Val Ala Ala Asn Tyr Ala Asp
        115                 120                 125

Leu Thr Thr Ala Ala Trp Leu Glu Ala Thr Asn Ala Tyr Pro Pro Gly
    130                 135                 140

Arg Ile Pro Gly Gly Asp Gly Arg Val Asn Val Thr Ile Asn Cys Ser
145                 150                 155                 160

Cys Gly Asp Glu Arg Val Ser Pro Arg Tyr Gly Leu Phe Leu Thr Tyr
                165                 170                 175

Pro Leu Trp Asp Gly Glu Thr Leu Glu Ser Val Ala Ala Gln Tyr Gly
            180                 185                 190

Phe Ser Ser Pro Ala Glu Met Glu Leu Ile Arg Arg Tyr Asn Pro Gly
        195                 200                 205

Met Gly Gly Val Ser Gly Lys Gly Ile Val Phe Ile Pro Val Lys Asp
    210                 215                 220

Pro Asn Gly Ser Tyr His Pro Leu Lys Ser Gly Val Gly Ile Val Leu
225                 230                 235                 240

Leu Phe Cys Gly Met Gly Asn Ser Leu Ser Gly Gly Ala Ile Ala Gly
                245                 250                 255

Ile Val Ile Ala Cys Ile Ala Ile Phe Ile Val Ala Ile Trp Leu Ile
            260                 265                 270

Ile Met Phe Tyr Arg Trp Gln Lys Phe Arg Lys Ala Thr Ser Arg Pro
        275                 280                 285

Ser Pro Glu Glu Thr Ser His Leu Asp Asp Ala Ser Gln Ala Glu Gly
    290                 295                 300

Ile Lys Val Glu Arg Ser Ile Glu Phe Ser Tyr Glu Glu Ile Phe Asn
305                 310                 315                 320

Ala Thr Gln Gly Phe Ser Met Glu His Lys Ile Gly Gln Gly Gly Phe
                325                 330                 335

Gly Ser Val Tyr Tyr Ala Glu Leu Arg Gly Glu Lys Thr Ala Ile Lys
            340                 345                 350

Lys Met Gly Met Gln Ala Thr Gln Glu Phe Leu Ala Glu Leu Lys Val
        355                 360                 365

Leu Thr His Val His His Leu Asn Leu Val Arg Leu Ile Gly Tyr Cys
    370                 375                 380

Val Glu Asn Cys Leu Phe Leu Val Tyr Glu Phe Ile Asp Asn Gly Asn
385                 390                 395                 400

Leu Ser Gln His Leu Gln Arg Thr Gly Tyr Ala Pro Leu Ser Trp Ala
                405                 410                 415

Thr Arg Val Gln Ile Ala Leu Asp Ser Ala Arg Gly Leu Glu Tyr Leu
            420                 425                 430

His Glu His Val Val Pro Val Tyr Val His Arg Asp Ile Lys Ser Ala
        435                 440                 445

Asn Ile Leu Leu Asp Lys Asp Phe Arg Ala Lys Ile Ala Asp Phe Gly
    450                 455                 460

Leu Ala Lys Leu Thr Glu Val Gly Ser Met Ser Gln Ser Leu Ser Thr
465                 470                 475                 480

Arg Val Ala Gly Thr Phe Gly Tyr Met Pro Pro Glu Ala Arg Tyr Gly
                485                 490                 495

Glu Val Ser Pro Lys Val Asp Val Tyr Ala Phe Gly Val Val Leu Tyr
            500                 505                 510
```

```
Glu Leu Leu Ser Ala Lys Gln Ala Ile Val Arg Ser Ser Glu Ser Val
        515                 520                 525

Ser Glu Ser Lys Gly Leu Val Phe Leu Phe Glu Glu Ala Leu Ser Ala
    530                 535                 540

Pro Asn Pro Thr Glu Ala Leu Asp Glu Leu Ile Asp Pro Ser Leu Gln
545                 550                 555                 560

Gly Asp Tyr Pro Val Asp Ser Ala Leu Lys Ile Ala Ser Leu Ala Lys
                565                 570                 575

Ser Cys Thr His Glu Glu Pro Gly Met Arg Pro Thr Met Arg Ser Val
            580                 585                 590

Val Val Ala Leu Met Ala Leu Thr Ala Asn Thr Asp Leu Arg Asp Met
        595                 600                 605

Asp Tyr His Pro Phe
    610


<210> SEQ ID NO 37
<211> LENGTH: 617
<212> TYPE: PRT
<213> ORGANISM: Arabidopsis thaliana

<400> SEQUENCE: 37

Met Lys Leu Lys Ile Ser Leu Ile Ala Pro Ile Leu Leu Leu Phe Ser
1               5                   10                  15

Phe Phe Phe Ala Val Glu Ser Lys Cys Arg Thr Ser Cys Pro Leu Ala
            20                  25                  30

Leu Ala Ser Tyr Tyr Leu Glu Asn Gly Thr Thr Leu Ser Val Ile Asn
        35                  40                  45

Gln Asn Leu Asn Ser Ser Ile Ala Pro Tyr Asp Gln Ile Asn Phe Asp
    50                  55                  60

Pro Ile Leu Arg Tyr Asn Ser Asn Ile Lys Asp Lys Asp Arg Ile Gln
65                  70                  75                  80

Met Gly Ser Arg Val Leu Val Pro Phe Pro Cys Glu Cys Gln Pro Gly
                85                  90                  95

Asp Phe Leu Gly His Asn Phe Ser Tyr Ser Val Arg Gln Glu Asp Thr
            100                 105                 110

Tyr Glu Arg Val Ala Ile Ser Asn Tyr Ala Asn Leu Thr Thr Met Glu
        115                 120                 125

Ser Leu Gln Ala Arg Asn Pro Phe Pro Ala Thr Asn Ile Pro Leu Ser
    130                 135                 140

Ala Thr Leu Asn Val Leu Val Asn Cys Ser Cys Gly Asp Glu Ser Val
145                 150                 155                 160

Ser Lys Asp Phe Gly Leu Phe Val Thr Tyr Pro Leu Arg Pro Glu Asp
                165                 170                 175

Ser Leu Ser Ser Ile Ala Arg Ser Ser Gly Val Ser Ala Asp Ile Leu
            180                 185                 190

Gln Arg Tyr Asn Pro Gly Val Asn Phe Asn Ser Gly Asn Gly Ile Val
        195                 200                 205

Tyr Val Pro Gly Arg Asp Pro Asn Gly Ala Phe Pro Pro Phe Lys Ser
    210                 215                 220

Ser Lys Gln Asp Gly Val Gly Ala Gly Val Ile Ala Gly Ile Val Ile
225                 230                 235                 240

Gly Val Ile Val Ala Leu Leu Leu Ile Leu Phe Ile Val Tyr Tyr Ala
                245                 250                 255

Tyr Arg Lys Asn Lys Ser Lys Gly Asp Ser Phe Ser Ser Ser Ile Pro
            260                 265                 270
```

Leu Ser Thr Lys Ala Asp His Ala Ser Ser Thr Ser Leu Gln Ser Gly
275 280 285

Gly Leu Gly Gly Ala Gly Val Ser Pro Gly Ile Ala Ala Ile Ser Val
290 295 300

Asp Lys Ser Val Glu Phe Ser Leu Glu Glu Leu Ala Lys Ala Thr Asp
305 310 315 320

Asn Phe Asn Leu Ser Phe Lys Ile Gly Gln Gly Gly Phe Gly Ala Val
325 330 335

Tyr Tyr Ala Glu Leu Arg Gly Glu Lys Ala Ala Ile Lys Lys Met Asp
340 345 350

Met Glu Ala Ser Lys Gln Phe Leu Ala Glu Leu Lys Val Leu Thr Arg
355 360 365

Val His His Val Asn Leu Val Arg Leu Ile Gly Tyr Cys Val Glu Gly
370 375 380

Ser Leu Phe Leu Val Tyr Glu Tyr Val Glu Asn Gly Asn Leu Gly Gln
385 390 395 400

His Leu His Gly Ser Gly Arg Glu Pro Leu Pro Trp Thr Lys Arg Val
405 410 415

Gln Ile Ala Leu Asp Ser Ala Arg Gly Leu Glu Tyr Ile His Glu His
420 425 430

Thr Val Pro Val Tyr Val His Arg Asp Ile Lys Ser Ala Asn Ile Leu
435 440 445

Ile Asp Gln Lys Phe Arg Ala Lys Val Ala Asp Phe Gly Leu Thr Lys
450 455 460

Leu Thr Glu Val Gly Gly Ser Ala Thr Arg Gly Ala Met Gly Thr Phe
465 470 475 480

Gly Tyr Met Ala Pro Glu Thr Val Tyr Gly Glu Val Ser Ala Lys Val
485 490 495

Asp Val Tyr Ala Phe Gly Val Val Leu Tyr Glu Leu Ile Ser Ala Lys
500 505 510

Gly Ala Val Val Lys Met Thr Glu Ala Val Gly Glu Phe Arg Gly Leu
515 520 525

Val Gly Val Phe Glu Glu Ser Phe Lys Glu Thr Asp Lys Glu Glu Ala
530 535 540

Leu Arg Lys Ile Ile Asp Pro Arg Leu Gly Asp Ser Tyr Pro Phe Asp
545 550 555 560

Ser Val Tyr Lys Met Ala Glu Leu Gly Lys Ala Cys Thr Gln Glu Asn
565 570 575

Ala Gln Leu Arg Pro Ser Met Arg Tyr Ile Val Val Ala Leu Ser Thr
580 585 590

Leu Phe Ser Ser Thr Gly Asn Trp Asp Val Gly Asn Phe Gln Asn Glu
595 600 605

Asp Leu Val Ser Leu Met Ser Gly Arg
610 615

<210> SEQ ID NO 38
<211> LENGTH: 620
<212> TYPE: PRT
<213> ORGANISM: Lotus japonicus

<400> SEQUENCE: 38

Met Phe Tyr Asp Phe Thr Thr Met Ala Ser Leu Thr His Pro Leu Cys
1 5 10 15

Val Leu Leu Thr Leu Met Ala Ala Ala Ser Phe Ala Ser Val Phe Ser

```
            20                  25                  30

Leu Glu Val Ser Ser Lys Thr Thr Tyr Met Glu Pro Phe Asn Cys Ser
        35                  40                  45

Thr Lys Ile Arg Thr Cys Asn Ser Leu Leu Tyr His Ile Ser Ile Gly
    50                  55                  60

Leu Lys Val Glu Glu Ile Ala Arg Phe Tyr Ser Val Asn Leu Ser Arg
65                  70                  75                  80

Ile Lys Pro Ile Thr Arg Gly Thr Lys Gln Asp Tyr Leu Val Ser Val
                85                  90                  95

Pro Cys Thr Cys Arg Asn Thr Asn Gly Leu Asn Gly Tyr Phe Tyr His
            100                 105                 110

Thr Ser Tyr Lys Val Lys Val Asn Asp Ser Phe Val Asp Ile Gln Asn
        115                 120                 125

Leu Phe Tyr Ser Gly Gln Ala Trp Pro Val Asn Glu Asp Leu Val Val
    130                 135                 140

Pro Asn Glu Thr Met Thr Ile His Ile Pro Cys Gly Cys Ser Glu Ser
145                 150                 155                 160

Gly Ser Gln Ile Val Val Thr Tyr Thr Val Gln Arg Asn Asp Thr Pro
                165                 170                 175

Leu Ser Ile Ala Leu Leu Leu Asn Ala Thr Val Glu Gly Met Val Ser
            180                 185                 190

Val Asn Ser Val Met Ala Pro Asn Pro Thr Phe Ile Asp Val Gly Trp
        195                 200                 205

Val Leu Tyr Val Pro Lys Glu Leu Asn Pro Ile Ser His Gly Lys Glu
    210                 215                 220

Asn Lys His Lys Leu Glu Lys Ile Ile Gly Ile Leu Ala Gly Val Ile
225                 230                 235                 240

Leu Leu Ser Ile Ile Thr Leu Ile Ile Leu Ile Val Arg Arg Asn Arg
                245                 250                 255

Ser Tyr Glu Thr Cys Lys Asp Asp Pro Arg Ala Ile Ser Lys Arg Ser
            260                 265                 270

Ile Gly Lys Arg Thr Ser Ser Leu Met Asn Arg Asp Phe His Lys Glu
        275                 280                 285

Tyr Met Glu Asp Ala Thr Ser Phe Asp Ser Glu Arg Pro Val Ile Tyr
    290                 295                 300

Thr Leu Glu Glu Ile Glu Gln Ala Thr Asn Asp Phe Asp Glu Thr Arg
305                 310                 315                 320

Arg Ile Gly Val Gly Gly Tyr Gly Thr Val Tyr Phe Gly Val Leu Gly
                325                 330                 335

Glu Lys Glu Val Ala Ile Lys Lys Met Lys Ser Asn Lys Ser Lys Glu
            340                 345                 350

Phe Tyr Ala Glu Leu Lys Ala Leu Cys Lys Ile His His Ile Asn Ile
        355                 360                 365

Val Glu Leu Leu Gly Tyr Ala Ser Gly Asp Asp His Leu Tyr Leu Val
    370                 375                 380

Tyr Glu Tyr Val Pro Asn Gly Ser Leu Ser Glu His Leu His Asp Pro
385                 390                 395                 400

Leu Leu Lys Gly His Gln Pro Leu Ser Trp Cys Ala Arg Ile Gln Ile
                405                 410                 415

Ala Leu Asp Ser Ala Lys Gly Ile Glu Tyr Ile His Asp Tyr Thr Lys
            420                 425                 430

Ala Gln Tyr Val His Arg Asp Ile Lys Thr Ser Asn Ile Leu Leu Asp
        435                 440                 445
```

```
Glu Lys Leu Arg Ala Lys Val Ala Asp Phe Gly Leu Ala Lys Leu Val
    450                 455                 460

Glu Arg Thr Asn Asp Glu Glu Phe Ile Ala Thr Arg Leu Val Gly Thr
465                 470                 475                 480

Pro Gly Tyr Leu Pro Pro Glu Ser Leu Lys Glu Leu Gln Val Thr Val
                485                 490                 495

Lys Thr Asp Val Phe Ala Phe Gly Val Val Met Leu Glu Leu Ile Thr
            500                 505                 510

Gly Lys Arg Ala Leu Phe Arg Asp Asn Gln Glu Ala Asn Asn Met Arg
        515                 520                 525

Ser Leu Val Ala Val Val Asn Gln Ile Phe Gln Glu Asp Asn Pro Glu
    530                 535                 540

Thr Ala Leu Glu Val Thr Val Asp Gly Asn Leu Gln Arg Ser Tyr Pro
545                 550                 555                 560

Met Glu Asp Val Tyr Asn Met Ala Glu Leu Ser His Trp Cys Leu Arg
                565                 570                 575

Glu Asn Pro Val Asp Arg Pro Glu Met Ser Glu Ile Val Val Lys Leu
            580                 585                 590

Ser Lys Ile Ile Met Ser Ser Ile Glu Trp Glu Ala Ser Leu Gly Gly
        595                 600                 605

Asp Ser Gln Val Phe Ser Gly Val Phe Asp Gly Arg
    610                 615                 620
```

<210> SEQ ID NO 39
<211> LENGTH: 613
<212> TYPE: PRT
<213> ORGANISM: Medicago truncatula

<400> SEQUENCE: 39

```
Met Ala Ser Leu Ile Gln Leu Leu Ser Ile Phe Leu Pro Leu Leu Ala
1               5                   10                  15

Ser Ser Leu Pro Thr Ile Phe Ser Ile Glu Val Ser Met Lys Lys Ala
            20                  25                  30

Tyr Met Glu Pro Tyr Lys Cys Ser Thr Lys Met Arg Thr Cys Asn Ala
        35                  40                  45

Ser Leu Tyr His Ile Asn Tyr Asn His Asn Ile Glu Gln Ile Ala Asn
    50                  55                  60

Phe Tyr Ser Ile Asp Pro Ser Gln Ile Lys Pro Ile Ile Arg Ser Thr
65                  70                  75                  80

Lys Gln Asp Tyr Leu Val Lys Val Pro Cys Ser Cys Lys Asn Ile Lys
                85                  90                  95

Asp Leu Ser Gly Tyr Phe Tyr Glu Thr Thr Tyr Lys Val Ser Pro Asn
            100                 105                 110

Glu Thr Ser Val Asp Ile Met Asn Leu Ile Tyr Ser Gly Gln Ala Trp
        115                 120                 125

Gln Val Asn Glu Asp Leu Val Ala Asn Glu Asn Val Thr Ile His Ile
    130                 135                 140

Pro Cys Gly Cys Ser Glu Phe Glu Ser Gln Ile Val Val Thr Tyr Thr
145                 150                 155                 160

Val Gln Gln Ser Asp Thr Pro Thr Ser Ile Ser Leu Leu Leu Asn Ala
                165                 170                 175

Thr Ile Asp Gly Met Val Arg Ile Asn Gln Ile Leu Gly Pro Asn Pro
            180                 185                 190

Thr Phe Ile Asp Ile Gly Trp Val Leu Tyr Val Pro Lys Glu Leu Lys
```

```
        195                 200                 205

Gly Ser Pro Leu Tyr His Gly Lys Glu Lys Lys His Lys Trp Val Ile
    210                 215                 220

Ile Ile Gly Ile Leu Val Ser Val Thr Leu Leu Ser Val Ile Thr Leu
225                 230                 235                 240

Ile Ile Phe Ile Leu Arg Arg Asn Lys Ala Tyr Glu Thr Ser Lys Tyr
                245                 250                 255

Asp Pro Lys Thr Val Ser Lys Arg Ser Phe Gly Asn Arg Thr Ile Ser
            260                 265                 270

Leu Arg Asn His Glu Phe His Lys Glu Tyr Met Glu Asp Ala Thr Gln
        275                 280                 285

Phe Asp Ser Glu Arg Pro Val Ile Tyr Asp Phe Glu Glu Ile Glu His
    290                 295                 300

Ala Thr Asn Asn Phe Asp Glu Thr Arg Arg Ile Gly Val Gly Gly Tyr
305                 310                 315                 320

Gly Thr Val Tyr Phe Gly Met Leu Glu Glu Lys Glu Val Ala Val Lys
                325                 330                 335

Lys Met Lys Ser Asn Lys Ser Lys Glu Phe Tyr Ala Glu Leu Lys Ala
            340                 345                 350

Leu Cys Lys Ile His His Ile Asn Ile Val Glu Leu Leu Gly Tyr Ala
        355                 360                 365

Ser Gly Asp Asp His Leu Tyr Leu Val Tyr Glu Tyr Val Pro Asn Gly
    370                 375                 380

Ser Leu Ser Glu His Leu His Asp Pro Leu Leu Lys Gly His Gln Pro
385                 390                 395                 400

Leu Ser Trp Cys Ala Arg Thr Gln Ile Ala Leu Asp Ser Ala Lys Gly
                405                 410                 415

Ile Glu Tyr Ile His Asp Tyr Thr Lys Ala Arg Tyr Val His Arg Asp
            420                 425                 430

Ile Lys Thr Ser Asn Ile Leu Leu Asp Glu Lys Leu Arg Ala Lys Val
        435                 440                 445

Ala Asp Phe Gly Leu Ala Lys Leu Val Glu Arg Thr Asn Asp Glu Glu
    450                 455                 460

Phe Leu Ala Thr Arg Leu Val Gly Thr Pro Gly Tyr Leu Pro Pro Glu
465                 470                 475                 480

Ser Val Lys Glu Leu Gln Val Thr Ile Lys Thr Asp Val Phe Ala Phe
                485                 490                 495

Gly Val Val Ile Ser Glu Leu Ile Thr Gly Lys Arg Ala Leu Phe Arg
            500                 505                 510

Asp Asn Lys Glu Ala Asn Asn Met Lys Ser Leu Ile Ala Val Val Asn
        515                 520                 525

Lys Ile Phe Gln Asp Glu Asp Pro Val Ala Ala Leu Glu Ala Val Val
    530                 535                 540

Asp Gly Asn Leu Leu Arg Asn Tyr Pro Ile Glu Gly Val Tyr Lys Met
545                 550                 555                 560

Ala Glu Leu Ser His Trp Cys Leu Ser Glu Glu Pro Val Asp Arg Pro
                565                 570                 575

Glu Met Lys Glu Ile Val Val Ala Val Ser Lys Ile Val Met Ser Ser
            580                 585                 590

Ile Glu Trp Glu Ala Ser Leu Gly Gly Asp Ser Gln Val Phe Ser Gly
        595                 600                 605

Val Phe Asp Gly Arg
    610
```

<210> SEQ ID NO 40
<211> LENGTH: 595
<212> TYPE: PRT
<213> ORGANISM: Lotus japonicus

<400> SEQUENCE: 40

Met Ala Val Phe Phe Leu Thr Ser Gly Ser Leu Ser Leu Phe Leu Ala
1               5                   10                  15

Leu Thr Leu Leu Phe Thr Asn Ile Ala Ala Arg Ser Glu Lys Ile Ser
            20                  25                  30

Gly Pro Asp Phe Ser Cys Pro Val Asp Ser Pro Pro Ser Cys Glu Thr
        35                  40                  45

Tyr Val Thr Tyr Thr Ala Gln Ser Pro Asn Leu Leu Ser Leu Thr Asn
    50                  55                  60

Ile Ser Asp Ile Phe Asp Ile Ser Pro Leu Ser Ile Ala Arg Ala Ser
65                  70                  75                  80

Asn Ile Asp Ala Gly Lys Asp Lys Leu Val Pro Gly Gln Val Leu Leu
                85                  90                  95

Val Pro Val Thr Cys Gly Cys Ala Gly Asn His Ser Ser Ala Asn Thr
            100                 105                 110

Ser Tyr Gln Ile Gln Leu Gly Asp Ser Tyr Asp Phe Val Ala Thr Thr
        115                 120                 125

Leu Tyr Glu Asn Leu Thr Asn Trp Asn Ile Val Gln Ala Ser Asn Pro
    130                 135                 140

Gly Val Asn Pro Tyr Leu Leu Pro Glu Arg Val Lys Val Val Phe Pro
145                 150                 155                 160

Leu Phe Cys Arg Cys Pro Ser Lys Asn Gln Leu Asn Lys Gly Ile Gln
                165                 170                 175

Tyr Leu Ile Thr Tyr Val Trp Lys Pro Asn Asp Asn Val Ser Leu Val
            180                 185                 190

Ser Ala Lys Phe Gly Ala Ser Pro Ala Asp Ile Leu Thr Glu Asn Arg
        195                 200                 205

Tyr Gly Gln Asp Phe Thr Ala Ala Thr Asn Leu Pro Ile Leu Ile Pro
    210                 215                 220

Val Thr Gln Leu Pro Glu Leu Thr Gln Pro Ser Ser Asn Gly Arg Lys
225                 230                 235                 240

Ser Ser Ile His Leu Leu Val Ile Leu Gly Ile Thr Leu Gly Cys Thr
                245                 250                 255

Leu Leu Thr Ala Val Leu Thr Gly Thr Leu Val Tyr Val Tyr Cys Arg
            260                 265                 270

Arg Lys Lys Ala Leu Asn Arg Thr Ala Ser Ser Ala Glu Thr Ala Asp
        275                 280                 285

Lys Leu Leu Ser Gly Val Ser Gly Tyr Val Ser Lys Pro Asn Val Tyr
    290                 295                 300

Glu Ile Asp Glu Ile Met Glu Ala Thr Lys Asp Phe Ser Asp Glu Cys
305                 310                 315                 320

Lys Val Gly Glu Ser Val Tyr Lys Ala Asn Ile Glu Gly Arg Val Val
                325                 330                 335

Ala Val Lys Lys Ile Lys Glu Gly Gly Ala Asn Glu Glu Leu Lys Ile
            340                 345                 350

Leu Gln Lys Val Asn His Gly Asn Leu Val Lys Leu Met Gly Val Ser
        355                 360                 365

Ser Gly Tyr Asp Gly Asn Cys Phe Leu Val Tyr Glu Tyr Ala Glu Asn

```
    370                 375                 380

Gly Ser Leu Ala Glu Trp Leu Phe Ser Lys Ser Ser Gly Thr Pro Asn
385                 390                 395                 400

Ser Leu Thr Trp Ser Gln Arg Ile Ser Ile Ala Val Asp Val Ala Val
                405                 410                 415

Gly Leu Gln Tyr Met His Glu His Thr Tyr Pro Arg Ile Ile His Arg
            420                 425                 430

Asp Ile Thr Thr Ser Asn Ile Leu Leu Asp Ser Asn Phe Lys Ala Lys
        435                 440                 445

Ile Ala Asn Phe Ala Met Ala Arg Thr Ser Thr Asn Pro Met Met Pro
    450                 455                 460

Lys Ile Asp Val Phe Ala Phe Gly Val Leu Leu Ile Glu Leu Leu Thr
465                 470                 475                 480

Gly Arg Lys Ala Met Thr Thr Lys Glu Asn Gly Glu Val Val Met Leu
                485                 490                 495

Trp Lys Asp Met Trp Glu Ile Phe Asp Ile Glu Glu Asn Arg Glu Glu
            500                 505                 510

Arg Ile Arg Lys Trp Met Asp Pro Asn Leu Glu Ser Phe Tyr His Ile
        515                 520                 525

Asp Asn Ala Leu Ser Leu Ala Ser Leu Ala Val Asn Cys Thr Ala Asp
    530                 535                 540

Lys Ser Leu Ser Arg Pro Ser Met Ala Glu Ile Val Leu Ser Leu Ser
545                 550                 555                 560

Phe Leu Thr Gln Gln Ser Ser Asn Pro Thr Leu Glu Arg Ser Leu Thr
                565                 570                 575

Ser Ser Gly Leu Asp Val Glu Asp Asp Ala His Ile Val Thr Ser Ile
            580                 585                 590

Thr Ala Arg
        595


<210> SEQ ID NO 41
<211> LENGTH: 632
<212> TYPE: PRT
<213> ORGANISM: Medicago truncatula

<400> SEQUENCE: 41

Met Lys Thr Leu Lys Pro His His His Gln Leu Ser Thr Phe Ile Phe
1               5                   10                  15

Ile Leu Leu Phe Pro Phe Leu Lys Ser Gln Thr Ala Arg Gln Gln Asn
            20                  25                  30

Asn Thr Gly Tyr Thr Cys Pro Asn Asn Asn Asn Asn Asn Asn Asn Thr
        35                  40                  45

Tyr Pro Cys Gln Thr Tyr Val Tyr Tyr Lys Ala Thr Pro Pro Asn Tyr
    50                  55                  60

Leu Asp Leu Ala Thr Ile Ser Asp Leu Phe Gln Leu Ser Arg Leu Met
65                  70                  75                  80

Ile Ser Lys Pro Ser Asn Ile Ser Ser Pro Ser Ser Pro Leu Leu Pro
                85                  90                  95

Asn Gln Pro Leu Leu Ile Pro Leu Thr Cys Ser Cys Asn Phe Ile Asn
            100                 105                 110

Thr Thr Phe Gly Ser Ile Ser Tyr Ser Asn Ile Thr Tyr Thr Ile Lys
        115                 120                 125

Pro Asn Asp Thr Phe Phe Leu Val Ser Thr Ile Asn Phe Gln Asn Leu
    130                 135                 140
```

```
Thr Thr Tyr Pro Ser Val Gln Val Val Asn Pro Asn Leu Val Ala Thr
145                 150                 155                 160

Asn Leu Ser Ile Gly Asp Asn Ala Val Phe Pro Ile Phe Cys Lys Cys
                165                 170                 175

Pro Asp Lys Thr Lys Thr Asn Ser Ser Phe Met Ile Ser Tyr Val Val
            180                 185                 190

Gln Pro His Asp Asn Val Ser Ser Ile Ala Ser Met Phe Gly Thr Ser
        195                 200                 205

Glu Lys Ser Ile Val Asp Val Asn Gly Glu Arg Leu Tyr Asp Tyr Asp
    210                 215                 220

Thr Ile Phe Val Pro Val Thr Glu Leu Pro Val Leu Lys Gln Pro Ser
225                 230                 235                 240

Thr Ile Val Pro Ser Pro Ala Pro Arg Gly Asn Ser Asp Asp Gly Asp
                245                 250                 255

Asp Asp Asp Asp Lys Ser Gly Ile Val Lys Gly Leu Ala Ile Gly Leu
            260                 265                 270

Gly Ile Leu Gly Phe Leu Leu Ile Leu Val Ile Val Phe Trp Phe Tyr
        275                 280                 285

Arg Glu Val Leu Phe Lys Lys Glu Lys Lys Gly Lys Gly Leu Tyr Phe
    290                 295                 300

Gly Asp Lys Gly Tyr Lys Gly Asn Asp Glu Lys Lys Lys Lys Met Asp
305                 310                 315                 320

Val Asn Phe Met Ala Asn Val Ser Asp Cys Leu Asp Lys Tyr Arg Val
                325                 330                 335

Phe Gly Phe Asp Glu Leu Val Glu Ala Thr Asp Gly Phe Asp Glu Arg
            340                 345                 350

Phe Leu Ile Gln Gly Ser Val Tyr Lys Gly Glu Ile Asp Gly Gln Val
        355                 360                 365

Tyr Ala Ile Lys Lys Met Lys Trp Asn Ala Tyr Glu Glu Leu Lys Ile
    370                 375                 380

Leu Gln Lys Val Asn His Gly Asn Leu Val Lys Leu Glu Gly Phe Cys
385                 390                 395                 400

Ile Glu Pro Glu Glu Ser Asn Cys Tyr Leu Val Tyr Glu Tyr Val Glu
                405                 410                 415

Asn Gly Ser Leu Tyr Ser Trp Leu His Glu Asp Lys Asn Glu Lys Leu
            420                 425                 430

Asn Trp Val Thr Arg Leu Arg Ile Ala Val Asp Ile Ala Asn Gly Leu
        435                 440                 445

Leu Tyr Ile His Glu His Thr Arg Pro Lys Val Val His Lys Asp Ile
    450                 455                 460

Lys Ser Ser Asn Ile Leu Leu Asp Ser Asn Met Arg Ala Lys Ile Ala
465                 470                 475                 480

Asn Phe Gly Leu Ala Lys Ser Gly Ile Asn Ala Ile Thr Met His Ile
                485                 490                 495

Val Gly Thr Gln Gly Tyr Ile Ser Pro Glu Tyr Leu Ala Asp Gly Ile
            500                 505                 510

Val Ser Thr Lys Met Asp Val Phe Ser Phe Gly Ile Val Leu Leu Glu
        515                 520                 525

Leu Ile Ser Gly Lys Glu Val Ile Asp Glu Glu Gly Asn Val Leu Trp
    530                 535                 540

Ala Ser Ala Ile Lys Thr Phe Glu Val Lys Asn Glu Gln Glu Lys Ala
545                 550                 555                 560

Arg Arg Leu Lys Glu Trp Leu Asp Arg Thr Met Leu Lys Glu Thr Cys
```

```
                565                 570                 575

Ser Met Glu Ser Leu Met Gly Val Leu His Val Ala Ile Ala Cys Leu
            580                 585                 590

Asn Arg Asp Pro Ser Lys Arg Pro Ser Ile Ile Asp Ile Val Tyr Ser
        595                 600                 605

Leu Ser Lys Cys Glu Glu Ala Gly Phe Glu Leu Ser Asp Asp Gly Phe
    610                 615                 620

Gly Ser Glu Arg Leu Val Ala Arg
625                 630


<210> SEQ ID NO 42
<211> LENGTH: 423
<212> TYPE: PRT
<213> ORGANISM: Arabidopsis thaliana

<400> SEQUENCE: 42

Met Lys Asn Pro Glu Lys Pro Leu Leu Leu Phe Leu Ile Leu Ala Ser
1               5                   10                  15

Ser Leu Ala Ser Met Ala Thr Ala Lys Ser Thr Ile Glu Pro Cys Ser
            20                  25                  30

Ser Lys Asp Thr Cys Asn Ser Leu Leu Gly Tyr Thr Leu Tyr Thr Asp
        35                  40                  45

Leu Lys Val Thr Glu Val Ala Ser Leu Phe Gln Val Asp Pro Val Ser
    50                  55                  60

Met Leu Leu Ser Asn Ser Ile Asp Ile Ser Tyr Pro Asp Val Glu Asn
65                  70                  75                  80

His Val Leu Pro Ala Lys Leu Phe Leu Lys Ile Pro Ile Thr Cys Ser
                85                  90                  95

Cys Val Asp Gly Ile Arg Lys Ser Leu Ser Thr His Tyr Lys Thr Arg
            100                 105                 110

Thr Ser Asp Thr Leu Gly Ser Ile Ala Asp Ser Val Tyr Gly Gly Leu
        115                 120                 125

Val Ser Pro Glu Gln Ile Gln Val Ala Asn Ser Glu Thr Asp Leu Ser
    130                 135                 140

Val Leu Asp Val Gly Thr Lys Leu Val Ile Pro Leu Pro Cys Ala Cys
145                 150                 155                 160

Phe Asn Gly Thr Asp Glu Ser Leu Pro Ala Leu Tyr Leu Ser Tyr Val
                165                 170                 175

Val Arg Gly Ile Asp Thr Met Ala Gly Ile Ala Lys Arg Phe Ser Thr
            180                 185                 190

Ser Val Thr Asp Leu Thr Asn Val Asn Ala Met Gly Ala Pro Asp Ile
        195                 200                 205

Asn Pro Gly Asp Ile Leu Ala Val Pro Leu Leu Ala Cys Ser Ser Asn
    210                 215                 220

Phe Pro Lys Tyr Ala Thr Asp Tyr Gly Leu Ile Ile Pro Asn Gly Ser
225                 230                 235                 240

Tyr Ala Leu Thr Ala Gly His Cys Val Gln Cys Ser Cys Val Leu Gly
                245                 250                 255

Ser Arg Ser Met Tyr Cys Glu Pro Ala Ser Ile Ser Val Ser Cys Ser
            260                 265                 270

Ser Met Arg Cys Arg Asn Ser Asn Phe Met Leu Gly Asn Ile Thr Ser
        275                 280                 285

Gln Gln Ser Ser Ser Gly Cys Lys Leu Thr Thr Cys Ser Tyr Asn Gly
    290                 295                 300
```

Phe Ala Ser Gly Thr Ile Leu Thr Thr Leu Ser Met Ser Leu Gln Pro
305 310 315 320

Arg Cys Pro Gly Pro Gln Gln Leu Ala Pro Leu Ile Ala Pro Pro Asp
325 330 335

Asn Val Pro Lys Glu Leu Met Tyr Leu Pro Ser Pro Ser Pro Ser Pro
340 345 350

Ser Pro Glu Phe Asp Asp Ile Ala Gly Gly Gly Ser Ser Ile Ala Ala
355 360 365

Val Pro Ala Ala Ser Pro Gly Gly Ala Thr Val Ser Ser Ser Asn Ser
370 375 380

Ile Pro Gly Asn Pro Ala Asn Gly Pro Gly Gly Ser Ile Ser Ile Ala
385 390 395 400

Ser Cys Pro Leu Ser Tyr Tyr Ser Phe Ile Ala Leu Leu Ile Pro Ile
405 410 415

Gly Ser Cys Phe Phe Val Phe
420

<210> SEQ ID NO 43
<211> LENGTH: 382
<212> TYPE: PRT
<213> ORGANISM: Oryza sativa Japonica Group

<400> SEQUENCE: 43

Pro Ala Pro Val Ser Thr Arg Gln Ser Asn Lys His Gln Ala Ser His
1 5 10 15

Ser His Leu Ser Arg Arg Ala Phe Pro Thr Met Ala Ser Leu Thr Ala
20 25 30

Ala Leu Ala Thr Pro Ala Ala Ala Ala Leu Leu Leu Leu Val Leu Leu
35 40 45

Ala Ala Pro Ala Ser Ala Ala Asn Phe Thr Cys Ala Val Ala Ser Gly
50 55 60

Thr Thr Cys Lys Ser Ala Ile Leu Tyr Thr Ser Pro Asn Ala Thr Thr
65 70 75 80

Tyr Gly Asn Leu Val Ala Arg Phe Asn Thr Thr Thr Leu Pro Asp Leu
85 90 95

Leu Gly Ala Asn Gly Leu Pro Asp Gly Thr Leu Ser Ser Ala Pro Val
100 105 110

Ala Ala Asn Ser Thr Val Lys Ile Pro Phe Arg Cys Arg Cys Asn Gly
115 120 125

Asp Val Gly Gln Ser Asp Arg Leu Pro Ile Tyr Val Val Gln Pro Gln
130 135 140

Asp Gly Leu Asp Ala Ile Ala Arg Asn Val Phe Asn Ala Phe Val Thr
145 150 155 160

Tyr Gln Glu Ile Ala Ala Ala Asn Asn Ile Pro Asp Pro Asn Lys Ile
165 170 175

Asn Val Ser Gln Thr Leu Trp Ile Pro Leu Pro Cys Ser Cys Asp Lys
180 185 190

Glu Glu Gly Ser Asn Val Met His Leu Ala Tyr Ser Val Gly Lys Gly
195 200 205

Glu Asn Thr Ser Ala Ile Ala Ala Lys Tyr Gly Val Thr Glu Ser Thr
210 215 220

Leu Leu Thr Arg Asn Lys Ile Asp Asp Pro Thr Lys Leu Gln Met Gly
225 230 235 240

Gln Ile Leu Asp Val Pro Leu Pro Val Cys Arg Ser Ser Ile Ser Asp
245 250 255

```
Thr Ser Ala Asp His Asn Leu Met Leu Leu Pro Asp Gly Thr Tyr Gly
            260                 265                 270

Phe Thr Ala Gly Asn Cys Ile Arg Cys Ser Cys Ser Ser Thr Thr Tyr
        275                 280                 285

Gln Leu Asn Cys Thr Ala Val Gln Asn Lys Gly Cys Pro Ser Val Pro
    290                 295                 300

Leu Cys Asn Gly Thr Leu Lys Leu Gly Glu Thr Asn Gly Thr Gly Cys
305                 310                 315                 320

Gly Ser Thr Thr Cys Ala Tyr Ser Gly Tyr Ser Asn Ser Ser Ser Leu
                325                 330                 335

Ile Ile Gln Thr Ser Leu Ala Thr Asn Gln Thr Thr Ala Cys Gln Arg
            340                 345                 350

Gly Gly Ser Gly Arg Ser Gln Phe Ala Arg Ser Met Trp Ser Met Ser
        355                 360                 365

Val Ile Ser Phe His Met Val Leu Ile Ile Ile Cys Phe Leu
    370                 375                 380


<210> SEQ ID NO 44
<211> LENGTH: 350
<212> TYPE: PRT
<213> ORGANISM: Arabidopsis thaliana

<400> SEQUENCE: 44

Met Glu Thr Ser Cys Phe Thr Leu Leu Gly Leu Leu Val Ser Leu Ser
1               5                   10                  15

Phe Phe Leu Thr Leu Ser Ala Gln Met Thr Gly Asn Phe Asn Cys Ser
            20                  25                  30

Gly Ser Thr Ser Thr Cys Gln Ser Leu Val Gly Tyr Ser Ser Lys Asn
        35                  40                  45

Ala Thr Thr Leu Arg Asn Ile Gln Thr Leu Phe Ala Val Lys Asn Leu
    50                  55                  60

Arg Ser Ile Leu Gly Ala Asn Asn Leu Pro Leu Asn Thr Ser Arg Asp
65                  70                  75                  80

Gln Arg Val Asn Pro Asn Gln Val Val Arg Val Pro Ile His Cys Ser
                85                  90                  95

Cys Ser Asn Gly Thr Gly Val Ser Asn Arg Asp Ile Glu Tyr Thr Ile
            100                 105                 110

Lys Lys Asp Asp Ile Leu Ser Phe Val Ala Thr Glu Ile Phe Gly Gly
        115                 120                 125

Leu Val Thr Tyr Glu Lys Ile Ser Glu Val Asn Lys Ile Pro Asp Pro
    130                 135                 140

Asn Lys Ile Glu Ile Gly Gln Lys Phe Trp Ile Pro Leu Pro Cys Ser
145                 150                 155                 160

Cys Asp Lys Leu Asn Gly Glu Asp Val Val His Tyr Ala His Val Val
                165                 170                 175

Lys Leu Gly Ser Ser Leu Gly Glu Ile Ala Ala Gln Phe Gly Thr Asp
            180                 185                 190

Asn Thr Thr Leu Ala Gln Leu Asn Gly Ile Ile Gly Asp Ser Gln Leu
        195                 200                 205

Leu Ala Asp Lys Pro Leu Asp Val Pro Leu Lys Ala Cys Ser Ser Ser
    210                 215                 220

Val Arg Lys Asp Ser Leu Asp Ala Pro Leu Leu Leu Ser Asn Asn Ser
225                 230                 235                 240

Tyr Val Phe Thr Ala Asn Asn Cys Val Lys Cys Thr Cys Asp Ala Leu
```

```
                245                 250                 255

Lys Asn Trp Thr Leu Ser Cys Gln Ser Ser Ser Glu Ile Lys Pro Ser
            260                 265                 270

Asn Trp Gln Thr Cys Pro Pro Phe Ser Gln Cys Asp Gly Ala Leu Leu
        275                 280                 285

Asn Ala Ser Cys Arg Gln Pro Arg Asp Cys Val Tyr Ala Gly Tyr Ser
    290                 295                 300

Asn Gln Thr Ile Phe Thr Thr Ala Ser Pro Ala Cys Pro Asp Ser Ala
305                 310                 315                 320

Gly Pro Asp Asn Tyr Ala Ser Thr Leu Ser Ser Ser Phe Asn Phe Val
                325                 330                 335

Ile Val Leu Ile Gln Cys Ala Leu Leu Cys Leu Cys Leu Leu
            340                 345                 350


<210> SEQ ID NO 45
<211> LENGTH: 632
<212> TYPE: PRT
<213> ORGANISM: Medicago truncatula

<400> SEQUENCE: 45

Met Lys Thr Leu Lys Pro His His His Gln Leu Ser Thr Phe Ile Phe
1               5                   10                  15

Ile Leu Leu Phe Pro Phe Leu Lys Ser Gln Thr Ala Arg Gln Gln Asn
            20                  25                  30

Asn Thr Gly Tyr Thr Cys Pro Asn Asn Asn Asn Asn Asn Asn Asn Thr
        35                  40                  45

Tyr Pro Cys Gln Thr Tyr Val Tyr Tyr Lys Ala Thr Pro Pro Asn Tyr
    50                  55                  60

Leu Asp Leu Ala Thr Ile Ser Asp Leu Phe Gln Leu Ser Arg Leu Met
65                  70                  75                  80

Ile Ser Lys Pro Ser Asn Ile Ser Ser Pro Ser Ser Pro Leu Leu Pro
                85                  90                  95

Asn Gln Pro Leu Leu Ile Pro Leu Thr Cys Ser Cys Asn Phe Ile Asn
            100                 105                 110

Thr Thr Phe Gly Ser Ile Ser Tyr Ser Asn Ile Thr Tyr Thr Ile Lys
        115                 120                 125

Pro Asn Asp Thr Phe Phe Leu Val Ser Thr Ile Asn Phe Gln Asn Leu
    130                 135                 140

Thr Thr Tyr Pro Ser Val Gln Val Val Asn Pro Asn Leu Val Ala Thr
145                 150                 155                 160

Asn Leu Ser Ile Gly Asp Asn Ala Val Phe Pro Ile Phe Cys Lys Cys
                165                 170                 175

Pro Asp Lys Thr Lys Thr Asn Ser Ser Phe Met Ile Ser Tyr Val Val
            180                 185                 190

Gln Pro His Asp Asn Val Ser Ser Ile Ala Ser Met Phe Gly Thr Ser
        195                 200                 205

Glu Lys Ser Ile Val Asp Val Asn Gly Glu Arg Leu Tyr Asp Tyr Asp
    210                 215                 220

Thr Ile Phe Val Pro Val Thr Glu Leu Pro Val Leu Lys Gln Pro Ser
225                 230                 235                 240

Thr Ile Val Pro Ser Pro Ala Pro Arg Gly Asn Ser Asp Asp Gly Asp
                245                 250                 255

Asp Asp Asp Asp Lys Ser Gly Ile Val Lys Gly Leu Ala Ile Gly Leu
            260                 265                 270
```

```
Gly Ile Leu Gly Phe Leu Leu Ile Leu Val Ile Val Phe Trp Phe Tyr
        275                 280                 285

Arg Glu Val Leu Phe Lys Lys Glu Lys Lys Gly Lys Gly Leu Tyr Phe
    290                 295                 300

Gly Asp Lys Gly Tyr Lys Gly Asn Asp Glu Lys Lys Lys Lys Met Asp
305                 310                 315                 320

Val Asn Phe Met Ala Asn Val Ser Asp Cys Leu Asp Lys Tyr Arg Val
                325                 330                 335

Phe Gly Phe Asp Glu Leu Val Glu Ala Thr Asp Gly Phe Asp Glu Arg
            340                 345                 350

Phe Leu Ile Gln Gly Ser Val Tyr Lys Gly Glu Ile Asp Gly Gln Val
        355                 360                 365

Tyr Ala Ile Lys Lys Met Lys Trp Asn Ala Tyr Glu Glu Leu Lys Ile
    370                 375                 380

Leu Gln Lys Val Asn His Gly Asn Leu Val Lys Leu Glu Gly Phe Cys
385                 390                 395                 400

Ile Glu Pro Glu Glu Ser Asn Cys Tyr Leu Val Tyr Glu Tyr Val Glu
                405                 410                 415

Asn Gly Ser Leu Tyr Ser Trp Leu His Glu Asp Lys Asn Glu Lys Leu
            420                 425                 430

Asn Trp Val Thr Arg Leu Arg Ile Ala Val Asp Ile Ala Asn Gly Leu
        435                 440                 445

Leu Tyr Ile His Glu His Thr Arg Pro Lys Val Val His Lys Asp Ile
    450                 455                 460

Lys Ser Ser Asn Ile Leu Leu Asp Ser Asn Met Arg Ala Lys Ile Ala
465                 470                 475                 480

Asn Phe Gly Leu Ala Lys Ser Gly Ile Asn Ala Ile Thr Met His Ile
                485                 490                 495

Val Gly Thr Gln Gly Tyr Ile Ser Pro Glu Tyr Leu Ala Asp Gly Ile
            500                 505                 510

Val Ser Thr Lys Met Asp Val Phe Ser Phe Gly Ile Val Leu Leu Glu
        515                 520                 525

Leu Ile Ser Gly Lys Glu Val Ile Asp Glu Glu Gly Asn Val Leu Trp
    530                 535                 540

Ala Ser Ala Ile Lys Thr Phe Glu Val Lys Asn Glu Gln Glu Lys Ala
545                 550                 555                 560

Arg Arg Leu Lys Glu Trp Leu Asp Arg Thr Met Leu Lys Glu Thr Cys
                565                 570                 575

Ser Met Glu Ser Leu Met Gly Val Leu His Val Ala Ile Ala Cys Leu
            580                 585                 590

Asn Arg Asp Pro Ser Lys Arg Pro Ser Ile Ile Asp Ile Val Tyr Ser
        595                 600                 605

Leu Ser Lys Cys Glu Glu Ala Gly Phe Glu Leu Ser Asp Asp Gly Phe
    610                 615                 620

Gly Ser Glu Arg Leu Val Ala Arg
625                 630
```

```
<210> SEQ ID NO 46
<211> LENGTH: 647
<212> TYPE: PRT
<213> ORGANISM: Zea mays

<400> SEQUENCE: 46

Met Arg Pro Pro Ala Leu Arg Leu Ser Ala Leu Leu Leu Phe Leu Cys
1               5                   10                  15
```

```
Leu Tyr Ala Ala Pro Ala Arg Ser Gln Asn Ala Thr Thr Val Thr Ala
            20                  25                  30

Ala Pro Ala Ser Val Glu Gly Phe Asn Cys Ser Val Asn Arg Thr Tyr
        35                  40                  45

Pro Cys Gln Ala Tyr Ala Leu Tyr Arg Ala Gly Phe Ala Gly Val Pro
    50                  55                  60

Leu Asn Leu Ala Ala Ile Gly Asp Leu Phe Ala Ala Ser Arg Phe Met
65                  70                  75                  80

Val Ala His Ala Asn Asn Leu Ser Thr Ala Ala Ala Pro Ala Thr Gly
                85                  90                  95

Gln Pro Leu Leu Val Pro Leu Gln Cys Gly Cys Pro Ser Gly Ser Pro
            100                 105                 110

Asn Ser Tyr Ala Pro Met Gln Tyr Gln Ile Ala Ser Gly Asp Thr Tyr
        115                 120                 125

Trp Ile Ile Ser Thr Thr Lys Leu Gln Asn Leu Thr Gln Tyr Gln Ala
    130                 135                 140

Val Glu Arg Val Asn Pro Thr Leu Val Pro Thr Asn Leu Asp Val Gly
145                 150                 155                 160

Thr Met Val Thr Phe Pro Ile Phe Cys Gln Cys Pro Ala Ala Ala Asp
                165                 170                 175

Asn Ala Thr Ala Leu Val Thr Tyr Val Met Gln Pro Gly Asp Thr Tyr
            180                 185                 190

Ser Thr Ile Ala Ala Ala Phe Ser Val Asp Ala Gln Ser Leu Val Ser
        195                 200                 205

Leu Asn Gly Pro Glu Pro Arg Thr Gln Gln Phe Ala Glu Ile Leu Val
    210                 215                 220

Pro Leu Arg Arg Gln Val Pro Gly Trp Leu Pro Pro Ile Val Leu Arg
225                 230                 235                 240

Asn Asn Ala Ser Ala Thr Pro Ala Ala Pro Pro Pro Ser Ala Ser Pro
                245                 250                 255

Asn Ala Thr Val Val Arg Asn Asp Arg Asn Gly Val Val Thr Gly Leu
            260                 265                 270

Ala Val Gly Leu Gly Val Val Gly Ala Leu Trp Leu Leu Gln Met Leu
        275                 280                 285

Leu Leu Ala Cys Leu Cys Arg Arg Leu Arg Ala Asn Gly Arg Arg Gly
    290                 295                 300

Asp Ala Val Leu Ser Gly Asp Gly Val Glu Gly Gly Val Phe Ala Lys
305                 310                 315                 320

Gly Ser Ser Ala Ala Ala Ala Gly Gly Gly Glu Arg Phe Leu Val Ser
                325                 330                 335

Asp Met Ser Glu Trp Leu Asp Lys Tyr Arg Val Phe Thr Val Glu Glu
            340                 345                 350

Leu Glu Arg Gly Thr Gly Gly Phe Asp Asp Ala His Leu Val Asn Gly
        355                 360                 365

Ser Val Tyr Lys Ala Asn Ile Asp Gly Leu Val Phe Ala Val Lys Lys
    370                 375                 380

Met Lys Trp Asp Ala Cys Glu Glu Leu Lys Ile Leu Gln Lys Val Asn
385                 390                 395                 400

His Ser Asn Leu Val Lys Leu Glu Gly Phe Cys Ile Asp Ser Ala Thr
                405                 410                 415

Gly Asp Cys Tyr Leu Val Tyr Glu Tyr Val Glu Asn Gly Ser Leu Asp
            420                 425                 430
```

```
Leu Trp Leu Leu Asp Arg Asp His Ala Arg Arg Leu Asn Trp Arg Ala
        435                 440                 445

Arg Leu His Ile Ala Leu Asp Leu Ala His Gly Leu Gln Tyr Ile His
    450                 455                 460

Glu His Thr Trp Pro Arg Val Val His Lys Asp Met Lys Ser Ser Asn
465                 470                 475                 480

Val Leu Leu Asp Ala Arg Met Arg Ala Lys Ile Ala Asn Phe Gly Leu
                485                 490                 495

Ala Lys Thr Gly His Asn Ala Ile Thr Thr His Ile Val Gly Thr Gln
            500                 505                 510

Gly Tyr Ile Ala Pro Glu Tyr Leu Ala Asp Gly Leu Val Thr Thr Lys
        515                 520                 525

Ile Asp Val Phe Ala Tyr Gly Val Val Leu Leu Glu Leu Val Ser Gly
    530                 535                 540

Arg Glu Ala Ala Asp Glu Ser Gly Glu Pro Leu Trp Ala Asp Ala Glu
545                 550                 555                 560

Asp Arg Val Phe Arg Gly Arg Asp Glu Arg Leu Glu Ala Arg Val Ala
                565                 570                 575

Ala Trp Met Asp Pro Ala Leu Ala Glu Gln Thr Cys Pro Leu Gly Ser
            580                 585                 590

Val Ala Thr Val Val Ser Val Ala Arg Ala Cys Leu His Lys Asp Pro
        595                 600                 605

Ser Lys Arg Pro Ser Met Val Asp Val Ala Tyr Thr Leu Ser Lys Ala
    610                 615                 620

Asp Glu His Phe Ala Asp Tyr Ser Gly Glu Ser Val Ser Val Asp Gly
625                 630                 635                 640

Ser Gly Glu Ile Ala Ala Arg
                645


<210> SEQ ID NO 47
<211> LENGTH: 680
<212> TYPE: PRT
<213> ORGANISM: Zea mays

<400> SEQUENCE: 47

Met Ala Pro Pro Pro Gln Pro Glu Leu Pro Ala Ala Ala Leu Ala Leu
1               5                   10                  15

Leu Val Leu Leu Leu Ala Ala Ala Val Pro Ala Arg Ala Gln Gln Glu
            20                  25                  30

Tyr Glu Ala Asn Lys Gln Asn Ala Cys Tyr Ala Thr Asn Ala Ser Ser
        35                  40                  45

Val Leu Gly Tyr Thr Cys Asn Ala Thr Ala Ala Ser Thr Pro Ala Cys
    50                  55                  60

Glu Ser Tyr Leu Ile Phe Arg Ser Ser Pro Ser Tyr Tyr Asn Thr Pro
65                  70                  75                  80

Val Ser Ile Ser Tyr Leu Leu Asn Ser Ser Pro Ala Thr Val Ala Ala
                85                  90                  95

Ala Asn Ala Val Pro Thr Val Ser Pro Leu Ala Ala Ser Ser Leu Val
            100                 105                 110

Leu Val Pro Val Pro Cys Ala Cys Thr Pro Gly Gly Tyr Tyr Gln His
        115                 120                 125

Asn Ser Ser Tyr Thr Ile Glu Phe Gln Ser Glu Thr Tyr Phe Ile Ile
    130                 135                 140

Ala Asn Ile Thr Tyr Gln Gly Leu Thr Thr Cys Gln Ala Leu Ile Ala
145                 150                 155                 160
```

```
Gln Asn Pro Leu His Asp Ser Arg Gly Leu Val Ala Gly Asn Asn Leu
                165                 170                 175

Thr Val Pro Leu Arg Cys Ala Cys Pro Ser Pro Ala Gln Ala Ala Lys
            180                 185                 190

Gly Phe Arg Tyr Leu Leu Ser Tyr Leu Val Met Trp Gly Asp Gly Val
        195                 200                 205

Pro Ser Ile Ala Ala Arg Phe Arg Val Asp Pro Gln Ala Val Leu Asp
    210                 215                 220

Ala Asn Ser Leu Thr Ala Asp Asp Ile Ile Phe Pro Phe Thr Thr Leu
225                 230                 235                 240

Leu Ile Pro Leu Lys Ala Ala Pro Thr Pro Asp Met Leu Ala Ser Pro
                245                 250                 255

Ala Pro Pro Pro Ser Pro Thr Pro Pro Gln Pro Thr Pro Ala Pro Ser
            260                 265                 270

Gly Gly Ser Gly Ser Gly Lys Trp Val Gly Val Gly Val Gly Leu Gly
        275                 280                 285

Cys Gly Ala Leu Ala Leu Ala Ala Ile Leu Gly Leu Leu Phe Leu Arg
    290                 295                 300

Thr Arg Arg Arg Arg Gly Gln Arg Phe Ala Asp Gly Glu Ser Val Arg
305                 310                 315                 320

Gln Gly Ser Lys Val Val Ile Asp Val Ser Ser Ser Ala Glu Tyr Gly
                325                 330                 335

Ala Leu Ala Ser Gly Lys Gln Thr Ser Asn Thr Thr Thr Ser Thr Thr
            340                 345                 350

Ser Ser Ala Thr Arg Ser Leu Val Ala Ser Asp Val Arg Gly Ala Val
        355                 360                 365

Glu Ser Leu Thr Val Tyr Lys Tyr Ser Glu Leu Glu Lys Ala Thr Ala
    370                 375                 380

Gly Phe Ala Glu Glu Arg Gln Val Pro Gly Thr Ser Val Phe Arg Ala
385                 390                 395                 400

Val Ile Asn Gly Asp Ala Ala Ala Val Lys Leu Val Ala Gly Asp Val
                405                 410                 415

Arg Asp Glu Val Ser Ile Leu Met Arg Val Asn His Ser Cys Leu Val
            420                 425                 430

Arg Leu Ser Gly Leu Cys Val His Arg Gly Asp Thr Tyr Leu Val Phe
        435                 440                 445

Glu Phe Ala Glu Asn Gly Ala Leu Ser Asp Trp Ile His Gly Gly Gly
    450                 455                 460

Gly Ser Thr Leu Arg Trp Arg Gln Arg Val Gln Val Ala Phe Asp Val
465                 470                 475                 480

Ala Asp Gly Leu Asn Tyr Leu His His Tyr Thr Asn Pro Pro Cys Val
                485                 490                 495

His Lys Asn Leu Lys Ser Ser Asn Val Leu Leu Asp Ala Asp Leu Arg
            500                 505                 510

Ala Lys Val Ser Ser Phe Gly Leu Ala Arg Thr Val Ala Ala Ser Asp
        515                 520                 525

Gly Gly Ala Gln Leu Thr Arg His Val Ala Gly Thr Gln Gly Tyr Leu
    530                 535                 540

Ala Pro Glu Tyr Leu Glu Asp Gly Leu Ile Thr Pro Lys Leu Asp Val
545                 550                 555                 560

Phe Ala Phe Gly Val Val Leu Leu Glu Leu Leu Ser Gly Lys Glu Ala
                565                 570                 575
```

Ala Phe Ala Asp Ala Gly Thr Gly Glu Glu Thr Leu Leu Trp Glu Ala
580 585 590

Ala Glu Glu Ala Leu Val Ala Asp Gly Gly Glu Asp Val Asp Arg Ala
595 600 605

Lys Val Arg Ala Phe Met Asp Pro Arg Leu His Gly Asp Phe Pro Ile
610 615 620

Asp Leu Ala Leu Ala Met Ala Ala Leu Ala Leu Arg Cys Val Ala Thr
625 630 635 640

Glu Pro Arg Ala Arg Pro Ala Met Asp Glu Val Phe Val Ser Leu Thr
645 650 655

Ala Val His Asn Ser Thr Leu Asp Trp Asp Pro Ser Asp Tyr Gly Thr
660 665 670

Ser Gly Ser Ser Met Val Gly Arg
675 680

<210> SEQ ID NO 48
<211> LENGTH: 684
<212> TYPE: PRT
<213> ORGANISM: Zea mays

<400> SEQUENCE: 48

Met Met Ala Ser Pro Pro Gln Thr Glu Leu Gln Ala Val Ala Leu Ala
1 5 10 15

Leu Leu Val Leu Leu Leu Ala Gly Ala Ala Pro Ala Arg Ala Gln Gln
20 25 30

Glu Tyr Glu Ala Asn Lys Gln Asn Ala Cys Tyr Ala Thr Asn Ala Ser
35 40 45

Ser Val Leu Gly Tyr Thr Cys Asn Ala Thr Thr Ala Ser Thr Pro Ala
50 55 60

Cys Asp Ser Tyr Leu Ile Phe Arg Ser Ser Pro Thr Tyr Tyr Asn Thr
65 70 75 80

Pro Val Ser Ile Ser Tyr Leu Leu Asn Ser Ser Val Ser Ala Thr Ala
85 90 95

Ala Ala Asn Ala Val Pro Ser Val Ser Pro Leu Ala Pro Ser Ser Leu
100 105 110

Val Leu Val Pro Val Pro Cys Ala Cys Thr Pro Gly Gly Tyr Tyr Gln
115 120 125

His Asn Ser Ser Tyr Thr Ile Gln Phe Arg Gly Glu Thr Tyr Phe Ile
130 135 140

Ile Ala Asn Ile Thr Tyr Gln Gly Leu Thr Thr Cys Gln Ala Leu Ile
145 150 155 160

Ala His Asn Pro Leu His Asp Ser Arg Gly Leu Val Ala Gly Asn Asn
165 170 175

Leu Thr Val Pro Leu Arg Cys Ala Cys Pro Ser Pro Ala Gln Ala Ala
180 185 190

Lys Gly Phe Lys Tyr Leu Leu Ser Tyr Leu Ile Met Trp Gly Asp Asp
195 200 205

Val Thr Ser Ile Ala Ala Arg Phe Arg Ala Asp Pro Gln Ala Val Leu
210 215 220

Asp Ala Asn Ser Leu Thr Ala Asp Asp Ile Ile Phe Pro Phe Thr Thr
225 230 235 240

Leu Leu Ile Pro Leu Lys Thr Ala Pro Thr Leu Asp Met Leu Ala Ser
245 250 255

Thr Ala Pro Pro Pro Ala Pro Thr Pro Pro Gln Pro Ala Pro Ala Pro
260 265 270

```
Ser Gly Arg Ser Gly Ser Gly Lys Leu Val Gly Phe Gly Val Gly Leu
        275                 280                 285

Gly Cys Gly Ala Leu Ala Leu Ala Gly Ile Leu Gly Leu Leu Phe Leu
    290                 295                 300

Arg Ala Arg Arg Arg Gln Arg Leu Pro Val Gly Glu Ser Val Arg Gln
305                 310                 315                 320

Gly Ser Lys Val Val Ile Asp Val Ser Ser Ser Ala Asp Tyr Gly Ala
                325                 330                 335

Leu Ala Ser Gly Lys Lys Ile Thr Asn Thr Thr Thr Ser Ser Met Ser
            340                 345                 350

Ser Ala Ala Trp Ser Leu Val Ala Ser Asp Val Arg Gly Ala Val Glu
        355                 360                 365

Ser Leu Thr Val Tyr Lys Tyr Ser Glu Leu Glu Lys Ala Thr Ala Gly
    370                 375                 380

Phe Ala Glu Glu His Gln Val Pro Gly Thr Ser Val Tyr Arg Ala Val
385                 390                 395                 400

Ile Asn Gly Asp Ala Ala Ala Val Lys Arg Leu Ala Gly Asp Val Ser
                405                 410                 415

Gly Glu Val Gly Ile Leu Met Arg Val Asn His Ser Cys Leu Val Arg
            420                 425                 430

Leu Ser Gly Leu Cys Val His Arg Gly Asp Thr Tyr Leu Val Phe Glu
        435                 440                 445

Phe Ala Glu Asn Gly Ala Leu Ser Asp Trp Ile His Gly Gly Ser Gly
    450                 455                 460

Ser Cys Ser Gly Ser Asn Thr Leu Arg Trp Arg Gln Arg Val Gln Val
465                 470                 475                 480

Ala Phe Asp Ile Ala Asp Gly Leu Asn Tyr Leu His His Tyr Thr Asn
                485                 490                 495

Pro Pro Cys Val His Lys Asn Leu Lys Ser Ser Asn Val Leu Leu Asp
            500                 505                 510

Ala Asp Leu Arg Ala Lys Val Ser Gly Phe Gly Leu Ala Arg Ala Val
        515                 520                 525

Thr Ala Ala His Gly Gly Ala Gln Leu Thr Gly His Val Val Gly Thr
    530                 535                 540

Gln Gly Tyr Leu Ala Pro Glu Tyr Leu Glu Asp Gly Leu Ile Thr Pro
545                 550                 555                 560

Lys Leu Asp Val Phe Ala Phe Gly Val Val Leu Leu Glu Leu Leu Ser
                565                 570                 575

Gly Lys Glu Ala Gly Phe Ala Asp Ala Gly Thr Gly Glu Glu Ile Leu
            580                 585                 590

Leu Cys Glu Ser Ala Glu Glu Ala Leu Val Ala Asp Gly Gly Glu Asp
        595                 600                 605

Met Asp Arg Ala Lys Val Arg Ala Phe Met Asp Pro Arg Leu His Gly
    610                 615                 620

Asp Phe Pro Met Asp Leu Ala Leu Ser Met Ala Ala Leu Ala Leu Arg
625                 630                 635                 640

Cys Val Ala Met Glu Pro Arg Ala Arg Pro Ala Met Asp Glu Val Phe
                645                 650                 655

Ile Ser Leu Ser Ala Val Tyr Asn Ser Thr Met Asp Cys Asp Pro Ser
            660                 665                 670

Asp Tyr Gly Thr Ser Gly Ser Ser Met Ile Gly Arg
        675                 680
```

<210> SEQ ID NO 49
<211> LENGTH: 723
<212> TYPE: PRT
<213> ORGANISM: Zea mays

<400> SEQUENCE: 49

Met Asn Phe Ser Thr Trp Lys Thr Lys Glu Val Gln Val Arg Ser Phe
1 5 10 15

Thr Thr Arg Lys Pro Thr Pro Gln Ala Ala Cys Ala Met Ala Ser Phe
20 25 30

His Asp Leu Thr Ala Thr Ala Val Leu Leu Leu Leu Phe Ser Ile Leu
35 40 45

Ser Gly Gly Leu Ala Pro Leu Gln Val Gln Ala Gln Gln Pro Tyr Gly
50 55 60

Ser Gln Ile Ala Asp Cys Thr Asn Gln His Asn Ser Ser Ser Leu Leu
65 70 75 80

Gly Tyr Phe Cys Gly Ala Ala Gly Ser Ala Pro Ser Cys Pro Thr Phe
85 90 95

Leu Thr Phe Thr Ala Arg Ala Gln Tyr Ser Ser Leu Ala Thr Ile Gly
100 105 110

Ala Leu Leu Gly Ala Asp Pro Ala Ser Val Leu Ala Pro Asn Glu Ala
115 120 125

Thr Gly Ala Asp Ala Pro Leu Pro Ala Gly Thr Arg Val Leu Val Pro
130 135 140

Ala Thr Cys Ala Cys Thr Ala Thr Pro Gly Gly Arg Phe Tyr Gln Arg
145 150 155 160

Asn Ala Thr Tyr Val Ala Val Ala Gly Asp Thr Leu Leu Ile Ile Ala
165 170 175

Asn Asn Thr Phe Gln Gly Leu Thr Ser Cys Gln Ala Leu Glu Ala Gln
180 185 190

Ala Leu Arg Gly Ala Pro Pro Gln Ser Leu Asp Val Gly Gln Ser Leu
195 200 205

Pro Val Pro Leu Arg Cys Ala Cys Pro Ser Ala Ala Gln Ala Ala Ala
210 215 220

Gly Ala Arg Tyr Leu Val Ser Tyr Leu Val Asp Val Phe Asp Asp Leu
225 230 235 240

Thr Thr Val Ala Ala Arg Phe Gly Val Asp Met Gly Thr Val Ala Ala
245 250 255

Ser Asn Gln Leu Gln Pro Pro Phe Thr Ile Asp Pro Tyr Thr Thr Leu
260 265 270

Leu Ile Pro Val Ser Ala Gln Pro Asn Val Ser Arg Ile Gln Thr Pro
275 280 285

Pro Ser Pro Pro Pro Pro Pro Pro Val Val Ala Arg Ala Pro Ala Pro
290 295 300

Gly Lys Lys Ser Ser Asn His Val Gly Val Tyr Ile Gly Val Ala Val
305 310 315 320

Ala Val Val Val Val Ala Ala Ile Val Ser Ala Gly Ala Phe Leu Ala
325 330 335

Val Arg Ala Arg Arg Arg Arg Ala Gly Ala Val Leu Ala Thr Gly Glu
340 345 350

Val Ala Lys Lys Glu Ser Lys Ala Gly Asn Asp Arg Ala Ala Thr Ser
355 360 365

Ser Gly Phe Thr Gly Gly Glu Phe Ser Leu Ser Thr Ser Glu Ala Phe
370 375 380

```
Ser Ser Ile Ser Val Thr Asp Ile Lys Ser Ser Leu Lys Val Tyr Thr
385                 390                 395                 400

Tyr Ala Glu Leu Lys Ala Ala Thr Asp Asp Phe Ser Pro Glu His Arg
                405                 410                 415

Ile Gly Gly Ser Val Tyr Arg Ala Ala Phe Asn Gly Asp Ala Ala Ala
            420                 425                 430

Val Glu Val Val Asp Arg Asn Val Ser Thr Glu Val Glu Ile Met Arg
        435                 440                 445

Lys Ile Asn His Leu Asn Leu Ile Arg Leu Ile Gly Leu Cys His His
    450                 455                 460

Arg Gly Arg Trp Tyr Leu Val Thr Glu Tyr Ala Glu His Gly Ala Leu
465                 470                 475                 480

Arg Asp Arg Leu Leu Ala Ser Ala Thr Gly Thr Ala Ala Pro Leu Thr
                485                 490                 495

Trp Ala Gln Arg Val His Ile Ala Leu Asp Val Ala Glu Gly Leu Arg
            500                 505                 510

Tyr Leu His Glu Tyr Ala Arg Pro Ala Trp Val His Met Asp Val Ser
        515                 520                 525

Ser Gly Ser Val Leu Leu Ala Gly Asp Gly Pro Arg Ala Lys Leu Arg
    530                 535                 540

Gly Phe Gly Ala Ala Arg Ala Ile Thr Gly Ala Thr Ala Gly Val Asp
545                 550                 555                 560

Gly Glu Glu Gly Ala Glu Glu Ala Leu Phe Thr Met Thr Ser Arg Ile
                565                 570                 575

Ala Gly Thr Arg Gly Tyr Ile Ala Pro Glu Tyr Leu Glu His Gly Val
            580                 585                 590

Val Ser Pro Lys Ala Asp Val Tyr Ser Leu Gly Val Val Leu Leu Glu
        595                 600                 605

Leu Val Thr Gly Arg Asp Ala Glu Glu Leu Val Gly Asp Gly Val Gly
    610                 615                 620

Asp Pro Phe Val Ala Leu Arg Glu Leu Ala Glu Glu Leu Asp Gly Gly
625                 630                 635                 640

Gly Asp Ala Val Leu Gln Arg Leu Glu Glu Leu Val Asp Pro Ala Leu
                645                 650                 655

Pro Ala Gly Ser Cys Pro Gln Asp Ala Val Val Met Val Val Arg Leu
            660                 665                 670

Ile Glu Arg Cys Val Arg Gln Asp Pro Ala Arg Arg Pro Thr Thr Gly
        675                 680                 685

Glu Val Ala Gln Arg Leu Leu Lys Leu Ser Gly Val Ser Val Val Ser
    690                 695                 700

Trp Arg Asn Ser Pro Glu Ser Pro Arg Ser Ser Gly Ser Gly Lys Gly
705                 710                 715                 720

Leu Met Tyr


<210> SEQ ID NO 50
<211> LENGTH: 587
<212> TYPE: PRT
<213> ORGANISM: Zea mays

<400> SEQUENCE: 50

Met Thr Lys His Gly Leu Leu Phe Phe Leu Ala Ile Ala Leu Leu Leu
1               5                   10                  15

His Arg His Tyr Thr Ser Ala Ser Ser Thr Gly Gln Pro Thr Arg Ser
            20                  25                  30
```

-continued

```
Ser Ser Thr Ala Ser Arg Ser Thr Ala Glu Trp Gln Pro Leu His Cys
        35                  40                  45

Ser Pro Val Ser Ser Cys Gly Ser Phe Leu Tyr Val Thr Pro Gly Gly
    50                  55                  60

Arg Asn Leu Ser Glu Ile Ala Ser Val Phe Asn Gly Asn Ala Ser Leu
65                  70                  75                  80

Ile Gln Pro Val Lys Arg Leu Ser Gly Ser Glu Asp Leu Leu Met Ala
                85                  90                  95

Val Ala Cys Glu Cys Gln Ala Ile Ser Asn Thr Thr Thr Ala Ala Ala
            100                 105                 110

Phe Leu His Asp Thr Gln Tyr Lys Val Glu Pro Asp Ala Ile Pro Asp
        115                 120                 125

Asp Val Lys Ser Asn Thr Phe Ser Gly Leu Ala Met Asp Val Gly Asp
    130                 135                 140

Gly Phe Pro Leu Thr Pro Gly Ala Thr Val Thr Val Arg Leu Pro Cys
145                 150                 155                 160

Gly Cys Ser Ser Ser Thr Ala Ser Lys Gly Val Leu Ser Tyr Ser Val
                165                 170                 175

Gln Glu Glu Asp Thr Leu Ser Thr Ile Ala Ser Leu Phe Ser Ser Ser
            180                 185                 190

Pro Glu Ala Ile Leu Asn Leu Asn Pro Ser Val Lys Asn Pro Asp Phe
        195                 200                 205

Ile Lys Pro Gly Trp Ile Leu Phe Val Pro Met Gly Val Ala Gly Ser
    210                 215                 220

Ser Lys Lys Lys Arg Val Gly Ser Thr Thr Ile Thr Ile Ala Ala Ser
225                 230                 235                 240

Val Ser Ala Ile Ile Leu Ser Val Cys Val Leu Thr Val Ile Leu Arg
                245                 250                 255

Leu Arg Arg Arg Pro Ser Gln Gln Asn Ala Glu Ala Pro Glu Ile Lys
            260                 265                 270

Met Glu Arg Ala Pro Asn Ile Asp Pro Phe Gln Thr Glu Arg Pro Val
        275                 280                 285

Ile Phe Ser Leu Lys Val Val Gly Asp Ala Thr Ala Asn Phe Asp Glu
    290                 295                 300

Lys Arg Lys Ile Gly Glu Gly Gly Tyr Gly Ser Val Tyr Leu Gly Phe
305                 310                 315                 320

Ile Gly Thr His Glu Ile Ala Val Lys Lys Met Arg Ala Ser Lys Ser
                325                 330                 335

Lys Glu Phe Phe Ala Glu Leu Lys Ala Leu Cys Lys Val His His Ile
            340                 345                 350

Asn Val Val Glu Leu Ile Gly Tyr Ala Ala Gly Asp Asp His Leu Tyr
        355                 360                 365

Leu Val Tyr Glu Tyr Val Gln Asn Gly Ser Leu Ser Glu His Leu His
    370                 375                 380

Asp Pro Leu Leu Lys Gly His Gln Pro Leu Ser Trp Thr Ala Arg Thr
385                 390                 395                 400

Gln Ile Ala Leu Asp Ala Ala Arg Gly Ile Glu Tyr Ile His Asp His
                405                 410                 415

Thr Lys Ala Cys Tyr Val Ala Asp Phe Gly Leu Val Lys Leu Val Glu
            420                 425                 430

Arg Ser Asp Glu Glu Glu Trp Val Ala Thr Arg Leu Val Gly Thr Pro
        435                 440                 445
```

Gly Tyr Leu Pro Pro Glu Ser Val Leu Glu Leu His Met Thr Thr Lys
    450                 455                 460

Ser Asp Val Tyr Ala Phe Gly Val Val Leu Ala Glu Leu Ile Thr Gly
465                 470                 475                 480

Leu Arg Ala Leu Ile Arg Asp Asn Lys Glu Val Asn Lys Thr Lys Ser
                485                 490                 495

Ile Ile Ser Ile Met Arg Lys Ala Phe Asp Ser Glu Asp Leu Glu Arg
            500                 505                 510

Ser Leu Glu Thr Ile Ile Asp Pro Asn Leu Lys Asp Ser Tyr Pro Ile
        515                 520                 525

Glu Glu Val Cys Lys Met Ala Asn Val Ser Met Trp Cys Leu Ser Glu
    530                 535                 540

Asp Pro Leu Asn Arg Pro Glu Met Arg Asp Thr Met Pro Ala Leu Cys
545                 550                 555                 560

Gln Ile His Leu Ala Ser Ile Glu Trp Glu Ala Ser Leu Gly Gly Asp
                565                 570                 575

Gly Glu Val Phe Ser Gly Val Ser Tyr Gly Arg
            580                 585

<210> SEQ ID NO 51
<211> LENGTH: 629
<212> TYPE: PRT
<213> ORGANISM: Zea mays

<400> SEQUENCE: 51

Met Leu Tyr Pro His Ser Ala Gln Gln Thr Arg Thr Ala Trp Thr Thr
1               5                   10                  15

Arg Ser Arg Ser Arg Met Asp Thr Ala Cys His His Tyr Thr Ser Ala
            20                  25                  30

Ser Phe Thr Asp Gln Pro Ser Ser Ile Ala Ser Ala Ala Glu Trp Gln
        35                  40                  45

Pro Leu Thr Cys Asn Ala Ala Val Ser Asn Asn Pro Ser Cys Gly Ser
    50                  55                  60

Phe Leu Tyr Val Thr Pro Arg Gly Arg Thr Leu Ser Glu Val Val Ser
65                  70                  75                  80

Val Phe Asn Gly Asn Ala Ser Leu Ile Gln Pro Ile Lys Arg Leu Ser
                85                  90                  95

Gly Ser Glu Asp Leu Leu Val Gly Val Ala Cys Lys Cys Glu Ala Ile
            100                 105                 110

Asn Asp Thr Met Thr Ala Phe Phe His Asp Thr Gln Tyr Glu Val Glu
        115                 120                 125

Pro Gly Asp Thr Pro Asp Asn Val Lys Ser Asn Asn Phe Ser Gly Leu
    130                 135                 140

Ala Met Asn Val Gly Asp Gly Arg Thr Leu Ile Ala Gly Thr Thr Ile
145                 150                 155                 160

Ala Val His Leu Pro Cys Gly Cys Ser Ser Thr Ala Pro Glu Gly Val
                165                 170                 175

Leu Ser Tyr Ser Val Gln Glu Glu Asp Thr Leu Ser Thr Ile Ala Ser
            180                 185                 190

Leu Phe Ser Ser Arg Gln Gln Asp Ile Leu Asn Leu Asn Pro Ile Leu
        195                 200                 205

Arg Asn Ala Asp Phe Ile Arg Thr Gly Trp Ile Leu Phe Ile Pro Met
    210                 215                 220

Gly Val Ala Gly Ser Ser Lys Lys Gly Ile Gly Ser Met Arg Ile Ile
225                 230                 235                 240

```
Ile Ala Ala Ser Val Ser Ala Ala Val Leu Leu Phe Cys Val Leu Ala
                245                 250                 255

Val Ile Leu Arg Arg Arg Arg Arg Ser Ser Gln His Asn Val Glu Ala
            260                 265                 270

Pro Glu Ile Lys Met Glu Arg Ala Pro Ser Asn Thr Ser Ile Ala Ala
        275                 280                 285

Leu Glu Ser Arg Phe Phe Pro Thr Met Arg Thr Asn Asp Thr Asp Pro
    290                 295                 300

Phe Gln Thr Glu Arg Pro Val Ile Phe Ser Leu Lys Gln Val Gly Asp
305                 310                 315                 320

Ala Thr Ala Asp Phe Ser Glu Lys Arg Lys Ile Gly Glu Gly Gly Tyr
                325                 330                 335

Gly Ser Val Tyr Leu Gly Phe Ile Gly Ala His Glu Ile Ala Ile Lys
            340                 345                 350

Lys Met Lys Ala Ser Lys Ser Lys Glu Phe Phe Ala Glu Leu Lys Ala
        355                 360                 365

Leu Cys Lys Val His His Ile Asn Val Val Glu Leu Ile Gly Tyr Ala
    370                 375                 380

Ala Gly Asp Asp His Leu Tyr Leu Val Tyr Glu Tyr Val Gln Asn Gly
385                 390                 395                 400

Ser Leu Thr Asp His Leu His Asp Pro Leu Leu Lys Gly His Gln Pro
                405                 410                 415

Leu Ser Trp Thr Ala Arg Thr Gln Ile Ala Leu Asp Ala Ala Arg Gly
            420                 425                 430

Ile Glu Tyr Ile His Asp His Thr Lys Ala Cys Tyr Val His Arg Asp
        435                 440                 445

Ile Lys Thr Ser Asn Ile Leu Leu Asp Asn Gly Leu Arg Ala Lys Val
    450                 455                 460

Ala Asp Phe Gly Leu Val Lys Leu Val Glu Arg Ser Asp Glu Glu Glu
465                 470                 475                 480

Phe Val Ala Thr Arg Leu Val Gly Thr Pro Gly Tyr Leu Pro Pro Glu
                485                 490                 495

Ser Val Leu Glu Leu His Met Thr Thr Lys Ser Asp Val Tyr Ala Phe
            500                 505                 510

Gly Val Val Leu Ala Glu Leu Ile Thr Gly Leu Arg Ala Leu Ile Arg
        515                 520                 525

Asp Asn Lys Glu Val Asn Lys Thr Lys Ser Ile Thr Ser Ile Met Arg
    530                 535                 540

Glu Val Phe Lys Ser Glu Asp Leu Glu Arg Ser Leu Glu Thr Ile Ile
545                 550                 555                 560

Asp Pro Asn Leu Lys Asp Ser Tyr Pro Ile Glu Glu Val Cys Lys Met
                565                 570                 575

Ala Asn Val Ser Met Trp Cys Leu Ser Glu Asp Pro Leu Asn Arg Pro
            580                 585                 590

Glu Thr Arg Asp Ile Met Ser Thr Leu Gly Gln Ile His Leu Ala Ser
        595                 600                 605

Ile Glu Trp Glu Ala Ser Leu Cys Gly Asp Gly Glu Val Phe Ser Gly
    610                 615                 620

Val Ser Tyr Gly Arg
625
```

<210> SEQ ID NO 52
<211> LENGTH: 612

<212> TYPE: PRT
<213> ORGANISM: Hordeum vulgare

<400> SEQUENCE: 52

```
Met Ala Arg His Ser Leu Phe Phe Phe Phe Leu Ala Leu Ser Leu Gln
1               5                   10                  15

His Leu His Ile Ser Val Gly Leu Pro Gly Arg Ser Leu Ala Thr Ala
            20                  25                  30

Thr Glu Gln Trp Gln Pro Met Gln Cys Asp Ala Ala Ser Leu Asn Ala
        35                  40                  45

Ser Cys Ser Ser Tyr Leu Tyr Val Thr Pro Gln Gly Arg Ser Leu Ser
    50                  55                  60

Glu Ile Ala Ser Leu Phe Asn Gly Ser Ala Ser Arg Thr Gln Pro Ile
65                  70                  75                  80

Lys Arg Leu Ser Gly Ser Glu Asp Leu Leu Val Pro Val Pro Cys Met
                85                  90                  95

Cys Asp Ala Ile Asn Asp Asn Met Ser Gly Leu Phe His Asp Thr Ala
            100                 105                 110

Tyr Lys Val Asn Leu Asn Asp Thr Ala Asp Asn Ile Asn Ser Ile Phe
        115                 120                 125

Ser Gly Leu Ala Trp Asn Ile Thr Ala Thr Ala Asn Thr Thr Ile Thr
    130                 135                 140

Val His Leu Leu Cys Gly Cys Ser Ser Thr Ala Pro Glu Gly Val Ile
145                 150                 155                 160

Ser Tyr Met Val Gln Ala Arg Asp Thr Leu Ser Asn Ile Ala Thr Leu
                165                 170                 175

Phe Arg Ser Gly Ser Ser Glu Ile Leu Ser Leu Asn Ala Gly Val Thr
            180                 185                 190

Asp Pro Asp Phe Leu Gln Pro Gly Trp Ile Leu Phe Ile Pro Met Gly
        195                 200                 205

Val Ala Ser Ser Ser Lys Arg Lys Phe Gly Gly Leu Pro Ile Ile Ile
    210                 215                 220

Ala Val Ser Ile Ser Ala Ala Ile Met Leu Leu Cys Thr Leu Thr Ile
225                 230                 235                 240

Val Leu Arg Leu Arg Arg Arg Ser Leu Val Pro Asn Ala Glu Val Pro
                245                 250                 255

Lys Lys Glu Met Glu Arg Val Pro Ser Asn Thr Ser Ile Ala Ile Leu
            260                 265                 270

Glu Ser Arg Tyr Phe Pro Ser Lys Arg Ile Asp Asp Ile Asp Pro Phe
        275                 280                 285

Gln Thr Glu Arg Pro Val Ile Phe Ser Leu Lys Ala Val Gly Glu Ala
    290                 295                 300

Thr Ala Asn Phe Asp Glu Lys Arg Lys Ile Gly Glu Gly Gly Tyr Gly
305                 310                 315                 320

Met Val Tyr Leu Gly Phe Ile Gly Thr His Glu Ile Ala Val Lys Met
                325                 330                 335

Met Lys Asp Ser Lys Ser Lys Glu Phe Phe Ala Glu Leu Lys Val Leu
            340                 345                 350

Cys Lys Val His His Ile Asn Val Val Glu Leu Ile Gly Tyr Ala Ser
        355                 360                 365

Gly Glu Asp His Leu Tyr Leu Val Tyr Glu Tyr Val Gln Asn Gly Ser
    370                 375                 380

Leu Ser Glu His Leu His Asp Pro Leu Leu Lys Gly His Gln Pro Leu
385                 390                 395                 400
```

Ser Trp Thr Ala Arg Thr Gln Ile Ala Thr Asp Ala Ala Arg Gly Ile
405 410 415

Glu Tyr Ile His Asp His Thr Lys Ala Cys Tyr Val His Arg Asp Ile
420 425 430

Lys Thr Ser Asn Ile Leu Leu Asp Asp Gly Leu Arg Ala Lys Val Ala
435 440 445

Asp Phe Gly Leu Val Lys Leu Val Glu Arg Ser Asp Glu Glu Asp Cys
450 455 460

Leu Ala Thr Arg Leu Val Gly Thr Pro Gly Tyr Leu Pro Pro Glu Ser
465 470 475 480

Val Arg Glu Leu His Met Thr Thr Lys Ser Asp Val Tyr Ala Phe Gly
485 490 495

Val Val Leu Ala Glu Leu Ile Thr Gly Leu Arg Ala Leu Val Arg Asp
500 505 510

Asn Lys Glu Ala Asn Lys Thr Lys Ser Leu Ile Ser Thr Met Arg Lys
515 520 525

Ala Phe Lys Ser Glu Asp Val Glu Ser Ser Leu Glu Asn Ile Ile Asp
530 535 540

Pro Ser Leu Lys Asp Asn Tyr Pro Ile Glu Glu Val Cys Lys Leu Ala
545 550 555 560

Asn Ile Ser Met Trp Cys Leu Ser Glu Asp Pro Leu Asp Arg Pro Glu
565 570 575

Met Arg Glu Ile Met Pro Met Leu Ser Arg Ile His Leu Thr Ser Ile
580 585 590

Glu Trp Glu Ala Ser Leu Gly Gly Asp His Glu Val Phe Ser Gly Val
595 600 605

Phe Asn Gly Arg
610

<210> SEQ ID NO 53
<211> LENGTH: 673
<212> TYPE: PRT
<213> ORGANISM: Zea mays

<400> SEQUENCE: 53

Met Pro Pro His Arg Leu Leu Pro Leu Leu Leu Leu Leu Leu Pro Leu
1 5 10 15

Gly Val Ser Gly Ala Ala Ala Ala Gly Gly Asn Ala Thr Ser Ala Pro
20 25 30

Leu Pro Cys Ser Glu Leu Ser Arg Val Cys Thr Ala Phe Ile Ala Phe
35 40 45

Pro Thr Ala Gly Ala Gly Pro Ala Asn Ala Thr Val Leu Glu Ser Met
50 55 60

Phe Asp Ala Ala Pro Gly Asp Leu Thr Ala Asp Ala Ala Ala Ser Pro
65 70 75 80

Arg Tyr Ala Phe Val Arg Lys Asn Cys Ser Cys Leu Pro Ser Arg Thr
85 90 95

Tyr Leu Ala Asn Thr Thr Tyr Thr Ile Pro Ser Ser Ala Thr Thr Ser
100 105 110

Phe Pro Asn Thr Thr Ala Ala Asp Val Ala Ala Ala Ala Tyr Ser Gly
115 120 125

Leu Ala Val Pro Pro Pro Gly Gly Ala Ala Gln Arg Pro Pro Arg Pro
130 135 140

Gly Ala Val Val Ala Leu His Leu Leu Cys Gly Cys Ser Ser Gly Pro

```
145                 150                 155                 160

Trp Asn Tyr Leu Leu Thr Tyr Val Gly Val Glu Gly Asp Thr Val Glu
                165                 170                 175

Ser Leu Ser Ser Arg Phe Gly Ala Ser Met Asp Ala Ile Glu Thr Ala
            180                 185                 190

Asn Ala Met Ala Gly Pro Asp Pro Ile Thr Ala Gly Lys Val Tyr Tyr
        195                 200                 205

Ile Pro Leu Asn Ser Val Pro Gly Gln Ala Tyr Val Thr Leu Pro Ala
    210                 215                 220

Pro Pro Ala Pro Ala Pro Ala Pro Thr Asp Tyr Thr Leu Ser Gly Thr
225                 230                 235                 240

Pro Asp Tyr His Ser Ser Lys Phe Pro Tyr Gly Trp Val Ile Gly Ser
                245                 250                 255

Met Gly Val Ala Leu Ala Leu Ile Val Ile Ala Val Leu Ala Leu Val
            260                 265                 270

Leu Trp Lys Phe Phe Gly Tyr Lys Pro Gln Asp Arg Asn Gly Gln Arg
        275                 280                 285

Lys Ser Pro Asp Arg His Lys Phe Gln Leu Leu Lys Ser Gly Ser Phe
    290                 295                 300

Cys Tyr Gly Ser Gly Arg Tyr Leu Cys Cys Gln Phe Gly Asn Ala Lys
305                 310                 315                 320

Pro Thr Arg Ala Asp Gly Gly Glu His His Ile Asn Val Pro Lys Gly
                325                 330                 335

Val Ala Ala Asp Val Phe Asp Arg Glu Lys Pro Ile Val Phe Thr His
            340                 345                 350

Glu Glu Ile Leu Ile Ser Thr Asp Ser Phe Ser Asp Ala Asn Leu Leu
        355                 360                 365

Gly His Gly Thr Tyr Gly Ser Val Tyr Tyr Gly Val Leu Arg Glu Gln
    370                 375                 380

Glu Val Ala Ile Lys Arg Met Met Ala Thr Lys Thr Lys Glu Phe Ile
385                 390                 395                 400

Val Glu Met Lys Val Leu Cys Lys Val His His Ala Ser Leu Val Glu
                405                 410                 415

Leu Ile Gly Tyr Ala Ala Gly Lys Asp Glu Leu Phe Leu Val Tyr Glu
            420                 425                 430

Tyr Ser Gln Asn Gly Ser Leu Lys Asn His Leu His Asp Pro Glu Arg
        435                 440                 445

Lys Gly Cys Ser Ser Leu Ser Trp Ile Phe Arg Val Gln Ile Ala Leu
    450                 455                 460

Asp Ala Ala Arg Gly Leu Glu Tyr Ile His Glu His Thr Lys Asp His
465                 470                 475                 480

Tyr Val His Arg Asp Ile Lys Ser Ser Asn Ile Leu Leu Asp Gly Ser
                485                 490                 495

Phe Arg Ala Lys Ile Ser Asp Phe Gly Leu Ala Lys Leu Val Val Lys
            500                 505                 510

Ser Asn Asp Ala Glu Ala Ser Val Thr Lys Val Val Gly Thr Phe Gly
        515                 520                 525

Tyr Leu Ala Pro Glu Tyr Leu Arg Asp Gly Leu Ala Thr Thr Lys Ser
    530                 535                 540

Asp Val Tyr Ala Phe Gly Val Val Leu Phe Glu Leu Ile Ser Gly Lys
545                 550                 555                 560

Glu Ala Ile Thr Arg Ala Glu Gly Met Gly Ala Ser Ser Asn Ser Glu
                565                 570                 575
```

```
Arg Cys Ser Leu Ala Ser Val Met Leu Ala Ala Val Arg Lys Cys Pro
            580                 585                 590

Asn Ser Thr Tyr Met Gly Asn Leu Lys Asp Cys Ile Asp His Asn Leu
        595                 600                 605

Arg Asp Leu Tyr Pro Tyr Asp Cys Ala Tyr Lys Met Ala Met Leu Ala
    610                 615                 620

Lys Gln Cys Val Asp Glu Asp Pro Val Leu Arg Pro Asp Met Lys Gln
625                 630                 635                 640

Val Val Ile Thr Leu Ser Gln Ile Leu Leu Ser Ser Ile Glu Trp Glu
                645                 650                 655

Ala Thr Gln Ala Gly Asn Ser Gln Val Phe Ser Gly Leu Val Ala Gly
            660                 665                 670

Arg


<210> SEQ ID NO 54
<211> LENGTH: 722
<212> TYPE: PRT
<213> ORGANISM: Hordeum vulgare

<400> SEQUENCE: 54

Met Pro Pro Arg Arg Arg Leu Leu Leu Leu Leu Leu Ala Leu Ala Cys
1               5                   10                  15

Ser Gly Gly Gly Ala Ala Val Asp Thr Ala Pro Gly Asn Gly Thr Ser
            20                  25                  30

Ser Pro Leu Ala Cys Ser Glu Leu Ser Arg Val Cys Thr Ala Phe Leu
        35                  40                  45

Ala Phe Pro Ala Ala Gly Asn Ala Ser Val Leu Gln Ser Met Phe Asp
    50                  55                  60

Ala Ser Pro Gly Asp Leu Thr Ser Asp Pro Ala Ala Ser Pro Gly Tyr
65                  70                  75                  80

Ala Phe Val Arg Lys Asn Cys Ser Cys Leu Ala Ser Arg Thr Tyr Leu
                85                  90                  95

Ala Asn Thr Thr Tyr Thr Ile Pro Ser Thr Val Pro Leu Asn Ala Thr
            100                 105                 110

Ala Ala Gln Val Ala Ala Ala Ala Tyr Gly Gly Leu Ala Val Pro Pro
        115                 120                 125

Pro Gly Gly Ala Leu Gln Arg Pro Pro Arg Pro Gly Ala Val Val Ala
    130                 135                 140

Leu His Leu Ile Cys Gly Cys Ser Ser Gly Pro Trp Asn Tyr Leu Leu
145                 150                 155                 160

Ser Tyr Val Gly Ser Asp Gly Asp Thr Val Glu Ser Leu Ser Ser Arg
                165                 170                 175

Phe Gly Ala Ser Met Asp Ala Ile Glu Ala Ala Asn Gly Met Pro Gly
            180                 185                 190

Pro Asp Pro Ile Thr Thr Gly Lys Val Tyr Tyr Ile Pro Leu Asn Ser
        195                 200                 205

Val Pro Gly Gln Pro Tyr Val Ala Met Ser Ser Ala Pro Val Pro Ala
    210                 215                 220

Pro Ala Pro Thr Gln Asn Thr Leu Ser Glu Ile Ser Asp His His Ser
225                 230                 235                 240

Ala Lys Phe Pro Tyr Gly Trp Val Ile Gly Gly Met Gly Val Ala Leu
                245                 250                 255

Ala Leu Ile Ala Ile Ala Leu Leu Ala Leu Leu Met Cys Lys Ser Phe
            260                 265                 270
```

```
Gln Tyr Asn His Gln Gly Ser Asn Asn Gln Gly Lys Ser Pro Asp Gln
        275                 280                 285

Pro Met Pro His Asn Phe Gln Leu Leu Lys Ser Gly Ser Phe Cys Tyr
    290                 295                 300

Gly Ser Gly Arg Tyr Phe Cys Cys Gln Phe Gly Asn Ala Lys Gln Ser
305                 310                 315                 320

Arg Lys Gly Gly Glu Asp His His Ile Asn Val Pro Lys Gly Met Val
                325                 330                 335

Val Asp Val Phe Asp Arg Glu Lys Pro Ile Val Phe Thr Tyr Glu Glu
            340                 345                 350

Ile Leu Ala Ser Thr Asp Leu Phe Ser Asp Ala Asn Leu Leu Gly His
        355                 360                 365

Gly Thr Tyr Gly Ser Val Tyr Tyr Gly Val Leu Arg Asp Gln Glu Val
    370                 375                 380

Ala Ile Lys Arg Met Thr Ser Thr Asn Thr Lys Glu Phe Ile Val Glu
385                 390                 395                 400

Met Lys Val Leu Cys Lys Val His His Ala Ser Leu Val Glu Leu Ile
                405                 410                 415

Gly Tyr Ala Ala Ser Lys Asp Glu Leu Phe Leu Val Tyr Glu Tyr Ser
            420                 425                 430

Gln Lys Gly Ser Leu Arg Asn His Leu His Asp Pro Gln Ser Lys Gly
        435                 440                 445

Tyr Thr Ser Leu Ser Trp Ile Tyr Arg Val Gln Ile Ala Leu Asp Ala
    450                 455                 460

Ala Arg Gly Leu Glu Tyr Ile His Glu His Thr Lys Asp His Tyr Val
465                 470                 475                 480

His Arg Asp Ile Lys Ser Ser Asn Ile Leu Leu Asp Gly Ser Phe Arg
                485                 490                 495

Ala Lys Ile Ser Asp Phe Gly Leu Ala Lys Leu Gly Leu Arg Ser Asn
            500                 505                 510

Asp Ala Glu Ala Ser Val Thr Lys Val Val Gly Thr Phe Gly Tyr Leu
        515                 520                 525

Ala Pro Glu Tyr Leu Arg Asp Gly Leu Ala Thr Ala Lys Cys Asp Val
    530                 535                 540

Tyr Ala Phe Gly Val Val Leu Phe Glu Leu Ile Ser Gly Lys Glu Ala
545                 550                 555                 560

Ile Thr Lys Ala Asp Ala Val Gly Ala Ser Ser Asn Ser Glu Arg Arg
                565                 570                 575

Ser Leu Ala Ser Val Val Ser Phe Leu Thr Cys Thr Gln Ala Val Ile
            580                 585                 590

Gln Ser Thr Ala Cys Val Phe Ala Val Ile Ser Leu Pro Lys Val Tyr
        595                 600                 605

Ile Gly Ile Ser Ser Thr Ser Phe Tyr Thr Ser Asn Leu Lys Asp Leu
    610                 615                 620

Ser Arg Phe Gly Leu Thr Gly Gln Met Leu Thr Ala Leu Arg Asn Cys
625                 630                 635                 640

His Asp Pro Thr Cys Val Gly Ser Leu Lys Asp Cys Ile Asp Pro Asn
                645                 650                 655

Leu Met Asp Leu Tyr Pro His Asp Cys Ile Tyr Gln Met Ala Met Leu
            660                 665                 670

Ala Lys Gln Cys Ala Asp Glu Asp Pro Val Leu Arg Pro Asp Met Lys
        675                 680                 685
```

Gln Ala Val Ile Thr Leu Ser Gln Ile Leu Leu Ser Ser Ile Glu Trp
690 695 700

Glu Ala Thr Leu Gly Gly Asn Ser Gln Val Phe Ser Gly Leu Val Ala
705 710 715 720

Gly Arg

<210> SEQ ID NO 55
<211> LENGTH: 613
<212> TYPE: PRT
<213> ORGANISM: Hordeum vulgare

<400> SEQUENCE: 55

Met Pro Pro Pro Pro Ala Tyr His His Leu Leu Leu Leu Leu Leu Leu
1 5 10 15

Leu Leu Arg Leu His Gly Ala Ile Ala Ser Ala Thr Gly Phe Thr Cys
20 25 30

Thr Lys Pro Ser Thr Cys Gln Ser Ala Val Ile Gly Tyr Val Val Pro
35 40 45

Asn Thr Ile Thr Tyr Lys Glu Leu Ile Ser Gln Phe Ser Pro Thr Thr
50 55 60

Leu His Asp Val Val Ala Ala Asn Gln Leu Pro Phe Asn Thr Ala Thr
65 70 75 80

Lys Gln Val Ile Pro Pro Lys Thr Thr Leu Thr Ile Pro Phe Arg Cys
85 90 95

Arg Cys Thr Gly Asn Gly Ile Gly Gln Ser Gly Leu Tyr Ile Ala Gln
100 105 110

Asn Lys Leu Asp Asp Gly Leu Ala Thr Tyr Gln Pro Glu Ile Val Ser
115 120 125

Ser Lys Ser Ile Ala Asp Asn Ala Ala Asn Trp Lys Gly Trp Ile Pro
130 135 140

Leu Pro Cys Ser Cys Asp Gly Ala Asp Val Thr His Phe Pro Tyr Ile
145 150 155 160

Val Arg Ser Gly Asp Ser Ala Leu Ala Ile Ala Ala Lys Tyr Gly Val
165 170 175

Leu Leu Ser Val Leu Leu Glu Ile Asn Asn Ile Thr Asn His Ala Ser
180 185 190

Leu Tyr Gln Gly Gln Val Leu Asp Ile Pro Leu Gln Gly Lys Val Gly
195 200 205

Glu Glu Leu Ser Ser Met Gly Arg Trp Ser Arg Val Tyr Tyr Ile Ser
210 215 220

Gly Tyr Arg Lys Arg Arg Leu Gly Trp Phe Asn Ser Ala Ala Ala Glu
225 230 235 240

Gln Ser Ala His Ala Ala Ala Glu Ala Val Ala Ala Thr Lys Glu Ala
245 250 255

Ala Glu Asn Ser His Tyr Ser Pro Glu Ala Ala Asp Thr Val Val Lys
260 265 270

Arg Val Leu Val Leu Leu Leu Ile Ile Ile Ile Leu Ser Leu Leu Tyr
275 280 285

Phe Thr Phe Tyr Tyr Trp Lys Ser Ala Cys Glu Ser Leu Ser Ser Arg
290 295 300

Thr Asn Gly Val Ile Gln Phe Tyr Tyr Ser Asp Leu Ala Arg Ala Thr
305 310 315 320

His Arg Phe Ser Lys Glu Ser Lys Ile Gly Glu Gly Gln Tyr Gly Thr
325 330 335

```
Val Tyr Lys Ala Thr Ile Lys Gly His Glu Met Ala Val Lys Lys Leu
            340                 345                 350

Lys Ala Glu Gly Glu Thr Lys Glu Leu His Arg Glu Leu Gln Thr Ile
        355                 360                 365

Ser Asn Thr Lys His Thr Asn Leu Val Ser Leu Lys Gly Trp Cys Gly
    370                 375                 380

Arg Leu Arg Leu Ile Asp Gly Lys Ser Cys Trp Lys Arg Gln Ile Lys
385                 390                 395                 400

Val Glu Leu Leu Leu Val Phe Glu Trp Ile Pro Asn Gly Asn Leu Ala
                405                 410                 415

Asp His Leu His Asn Arg Glu Gln Val Leu Ser Trp Glu Lys Arg Tyr
            420                 425                 430

Lys Ile Val Lys Gly Ile Gly Ser Ala Leu Arg Tyr Leu His His Glu
        435                 440                 445

Cys Lys Pro Ser Ile Leu His Arg Asp Ile Lys Pro Asp Asn Ile Leu
    450                 455                 460

Leu Asp Tyr His Phe Asn Ala Lys Leu Ala Asp Phe Gly Leu Ser Met
465                 470                 475                 480

Ile Thr Asp Gln Asn Gly Ala Thr Val Phe Thr Ile Ala Ile Gly Pro
                485                 490                 495

Arg Arg Tyr Met Asp Pro Gln Leu Met Lys Glu Gly Glu Phe Arg Phe
            500                 505                 510

Asn His Lys Ser Asp Ile Tyr Ser Phe Gly Ile Val Leu Leu Glu Ile
        515                 520                 525

Ala Cys Thr Gly Lys Ser Arg Glu Asn Ile Leu His Ile Leu Gly Gly
    530                 535                 540

Gly Ser Gly Gln His Val Gln Val Asp Gly Leu Ala Asp His Arg Leu
545                 550                 555                 560

Ser Ile Phe Asp Arg Thr Glu Met Ala Arg Val Val Val Leu Gly Leu
                565                 570                 575

Gln Cys Ser His Pro Asp Glu Arg Gln Arg Pro Ser Met Tyr Met Ala
            580                 585                 590

Met Arg Phe Leu Glu Glu Gly Ile Glu Leu Pro Ile Ala Ser His Asn
        595                 600                 605

Arg Arg Glu Arg Leu
    610


<210> SEQ ID NO 56
<211> LENGTH: 416
<212> TYPE: PRT
<213> ORGANISM: Arabidopsis thaliana

<400> SEQUENCE: 56

Met Lys Ile Pro Glu Lys Pro Ile Phe Leu Ile Phe Val Ser Leu Ile
1               5                   10                  15

Leu Ala Ser Ser Leu Thr Phe Thr Ala Thr Ala Lys Ser Thr Ile Glu
            20                  25                  30

Pro Cys Ser Ser Asn Asp Thr Cys Asn Ala Leu Leu Gly Tyr Thr Leu
        35                  40                  45

Tyr Thr Asp Leu Lys Val Ser Glu Val Ala Ser Leu Phe Gln Val Asp
    50                  55                  60

Pro Ile Ser Ile Leu Leu Ala Asn Ala Ile Asp Ile Ser Tyr Pro Asp
65                  70                  75                  80

Val Glu Asn His Ile Leu Pro Ser Lys Leu Phe Leu Lys Ile Pro Ile
                85                  90                  95
```

```
Thr Cys Ser Cys Val Asp Gly Ile Arg Lys Ser Val Ser Thr His Tyr
            100                 105                 110

Lys Thr Arg Pro Ser Asp Asn Leu Gly Ser Ile Ala Asp Ser Val Tyr
        115                 120                 125

Gly Gly Leu Val Ser Ala Glu Gln Ile Gln Glu Ala Asn Ser Val Asn
    130                 135                 140

Asp Pro Ser Leu Leu Asp Val Gly Thr Ser Leu Val Ile Pro Leu Pro
145                 150                 155                 160

Cys Ala Cys Phe Asn Gly Thr Asp Asn Ser Leu Pro Ala Val Tyr Leu
                165                 170                 175

Ser Tyr Val Val Lys Glu Ile Asp Thr Leu Val Gly Ile Ala Arg Arg
            180                 185                 190

Tyr Ser Thr Thr Ile Thr Asp Leu Met Asn Val Asn Ala Met Gly Ala
        195                 200                 205

Pro Asp Val Ser Ser Gly Asp Ile Leu Ala Val Pro Leu Ser Ala Cys
    210                 215                 220

Ala Ser Lys Phe Pro Arg Tyr Ala Ser Asp Phe Gly Leu Ile Val Pro
225                 230                 235                 240

Asn Gly Ser Tyr Ala Leu Ala Ala Gly His Cys Val Gln Cys Ser Cys
                245                 250                 255

Ala Leu Gly Ser Arg Asn Leu Tyr Cys Glu Pro Ala Ser Leu Ala Val
            260                 265                 270

Ser Cys Ser Ser Met Gln Cys Arg Asn Ser Asn Leu Met Leu Gly Asn
        275                 280                 285

Ile Thr Val Gln Gln Thr Ser Ala Gly Cys Asn Val Thr Thr Cys Asp
    290                 295                 300

Tyr Asn Gly Ile Ala Asn Gly Thr Ile Leu Thr Met Leu Thr Arg Ser
305                 310                 315                 320

Leu Gln Pro Arg Cys Pro Gly Pro Gln Gln Phe Ala Pro Leu Leu Ala
                325                 330                 335

Pro Pro Asp Thr Val Pro Arg Asp Val Met Tyr Ala Pro Ala Pro Ser
            340                 345                 350

Pro Asp Phe Asp Gly Pro Gly Ser Ile Ala Ser Ser Pro Arg Ser Ser
        355                 360                 365

Met Leu Pro Gly Gly Gly Ile Leu Pro Gly Asn Pro Ala Asn Gly Pro
    370                 375                 380

Ala Gly Ser Ile Ser Thr Ala Ser Ala Ser Ser Val Ser Tyr Phe Phe
385                 390                 395                 400

Ile Thr Phe Leu Ile Ser Ile Ala Ser Phe Ser Leu Ala Leu Ser Ser
                405                 410                 415
```

<210> SEQ ID NO 57
<211> LENGTH: 415
<212> TYPE: PRT
<213> ORGANISM: Lotus japonicus

<400> SEQUENCE: 57

```
Met Arg Met Gln Gln Gln Gln Ser Thr Leu Leu Phe Leu Val Val Leu
1               5                   10                  15

Leu Phe His Ser Leu Thr Thr Thr Thr Cys Lys Ser Thr Ile Glu Pro
            20                  25                  30

Cys Thr Asn Ser Asp Ser Cys Asn Ala Leu Leu Gly Tyr Thr Leu Tyr
        35                  40                  45

Thr Asp Leu Lys Val Ser Glu Val Ala Ser Leu Phe Gly Ile Asp Pro
```

```
    50                  55                  60

Ile Ser Leu Leu Thr Ala Asn Ala Ile Asp Ile Ser Tyr Pro Asp Ala
65                  70                  75                  80

Glu His His Ile Leu Pro Pro Lys Leu Phe Leu Lys Ile Pro Ile Ser
                85                  90                  95

Cys Ser Cys Val Asp Gly Ile Arg Lys Ser Val Ser Thr Ser Tyr Lys
            100                 105                 110

Thr Arg Pro Ser Asp Thr Leu Ser Ser Ile Ala Asp Ser Val Tyr Gly
        115                 120                 125

Gly Leu Val Ser Ala Asp Gln Leu Thr Asp Pro Ser Val Leu Asp Val
    130                 135                 140

Gly Gln Ser Leu Val Val Pro Leu Pro Cys Thr Cys Phe Asn Gly Ser
145                 150                 155                 160

Asp Asn Ser Leu Pro Ala Ile Tyr Leu Ser Tyr Val Val Gln Pro Val
                165                 170                 175

Asp Ser Leu Ala Ala Ile Ala Ala Arg Tyr Leu Thr Thr Leu Thr Asp
            180                 185                 190

Leu Met Asn Val Asn Ala Met Gly Ser Thr Ala Ile Ser Asp Gly Asp
        195                 200                 205

Ile Leu Ala Val Pro Ile Pro Ala Cys Ala Ser Asn Phe Pro Lys Ser
    210                 215                 220

Ala Ser Asp Phe Gly Leu Leu Val Pro Asn Gly Ser Tyr Ala Ile Thr
225                 230                 235                 240

Ala Gly His Cys Val Gln Cys Ser Cys Gly Pro Arg Asn Leu Asn Leu
                245                 250                 255

Tyr Cys Met Pro Thr Ser Leu Ser Ala Ser Cys Ser Ser Met Gln Cys
            260                 265                 270

Lys Asn Ser Asn Leu Met Leu Gly Asn Val Thr Ala Gln Gln Ser Ser
        275                 280                 285

Ala Gly Cys Asn Val Ser Ser Cys Ser Tyr Asp Gly Leu Val Asn Gly
    290                 295                 300

Thr Ile Ala Thr Thr Leu Ser Ala Ser Leu Gln Pro Arg Cys Pro Gly
305                 310                 315                 320

Leu Gln Glu Phe Pro Pro Leu Val Ala Pro Pro Thr Ser Val Glu Lys
                325                 330                 335

Asp Pro Thr Phe Ala Ser Gly Pro Ala Pro Ser Pro Ser Pro Gln Ser
            340                 345                 350

His Gly Ser Gly Leu Pro Ser Pro Lys Ser Ser Gly Met Pro Gly Leu
        355                 360                 365

Pro Gly Phe Ser Pro Ala Asn Gly Pro Val Ser Gly Ile Ser Ser Gly
    370                 375                 380

Ala Ser Ala Ala Cys Ser Leu Val Lys Pro Ser Pro Thr Leu Thr Ser
385                 390                 395                 400

Ala Leu Val Leu Leu Leu Ala Met Leu Val Ile Pro Val Ala Leu
                405                 410                 415


<210> SEQ ID NO 58
<211> LENGTH: 394
<212> TYPE: PRT
<213> ORGANISM: Lotus japonicus

<400> SEQUENCE: 58

Met Arg Asn His Leu Gln Phe Leu Trp Arg His Ile Leu Val Phe Leu
1               5                   10                  15
```

```
Leu Leu Ser Val Ser Tyr Gln Val Glu Ala Lys Ser Thr Ile Glu Pro
            20                  25                  30

Cys Ser Ser Gly Phe Pro Cys Pro Ser Leu Leu Ser Tyr Ile Leu Pro
        35                  40                  45

Trp Asp Ser Lys Leu Ser Glu Ile Ala Thr Arg Phe Ser Val Asn Val
    50                  55                  60

Ser Asn Ile Leu Ala Ala Asn Ser Val Phe Pro Ile Thr Pro Ser Ser
65                  70                  75                  80

Gly His Gln Ile Leu Ser Ala Lys Ser Ile Val Lys Ile Pro Phe Ser
                85                  90                  95

Cys Pro Cys Val Asp Gly Ile Arg Arg Ser Ile Ser Thr Ile Tyr Asn
            100                 105                 110

Val Glu Ala Ser Asp Thr Leu Ala Ser Ile Ser Glu Gly Tyr Gly Gly
        115                 120                 125

Leu Val Ser Ala Glu Gln Ile Lys Thr Met Asn Ser Ile Asn Glu Thr
    130                 135                 140

Asn Pro Leu Thr Tyr Gly Ser Ser Ile Val Ile Pro Leu Pro Cys Lys
145                 150                 155                 160

Cys Leu Asn Asn Val Asn Asn Gly Asp Thr Thr Val Tyr Met Ser Tyr
                165                 170                 175

Val Val Gln Lys Gly Gln Ser Leu Gly Ser Ile Ala Thr Met Tyr Gly
            180                 185                 190

Thr Thr Val Ser Asp Leu Glu Ser Val Asn Gly Leu Gly Gln Asn Ala
        195                 200                 205

Val Asp Pro Gly Asp Ile Leu Ser Val Pro Val Ala Ala Cys Ser Ser
    210                 215                 220

Ala Thr Leu Asn Trp Tyr Ser Glu Asn Leu Ile Val Pro Asn Gly Ser
225                 230                 235                 240

Tyr Ile Leu Thr Ala Ser Asn Cys Ile Gln Cys Thr Cys Thr Pro Arg
                245                 250                 255

Asp Leu Lys Met Glu Cys Leu Pro Ser Gly Met Asp Val Pro Cys Tyr
            260                 265                 270

Asn Leu His Cys Lys Gly Ser Asn Leu Ile Ile Gly Asn Glu Tyr Val
        275                 280                 285

Glu His Ser Gln Thr Ser Cys Asn Val Ser Gln Cys Val Tyr Arg Gly
    290                 295                 300

His Arg Gly Gly Lys Ile Leu Ser Ser Ile Ile Asn Ser Ser Tyr Leu
305                 310                 315                 320

Gln Cys Pro Asp Asn Gln Ser Tyr Ser Gly Pro Ser Arg Trp Pro Ser
                325                 330                 335

Leu Thr Pro Tyr Ala Ala Glu Tyr Pro Phe Asp Ile Ser Pro Ser Pro
            340                 345                 350

Ser Ser Pro Pro Leu Pro Val Ser Glu Ala Ala Leu Arg Thr Arg Ala
        355                 360                 365

Ser Gly Gly Trp Gln Gly Gln Ser Leu Ile Asn Val Met Gln Leu Phe
    370                 375                 380

Leu Ile Lys Leu Ile Leu Tyr Phe Ile Met
385                 390
```

<210> SEQ ID NO 59
<211> LENGTH: 370
<212> TYPE: PRT
<213> ORGANISM: Lotus japonicus

<400> SEQUENCE: 59

```
Met Gly Thr Val Trp Leu Ser Lys Leu Val Ala Thr Thr Met Leu Val
1               5                   10                  15

Ala Val Leu Gly Leu Leu Ala Glu Ala Gln Ile Glu Ala Lys Phe Lys
            20                  25                  30

Cys Ile Ser Glu Asn Ala Pro Cys His Ala Leu Ala Asp Tyr Ser His
        35                  40                  45

Pro Asn Gly Thr Thr Leu Arg Arg Ile Gln Thr Leu Phe Thr Val Lys
    50                  55                  60

Tyr Leu Pro Asp Ile Leu Gly Ala Asn Asn Leu Pro Ala Asn Thr Thr
65                  70                  75                  80

Arg Val Ala Pro Asp Gln Val Ile Lys Val Pro Phe Pro Cys Arg Cys
                85                  90                  95

Ser Asn Gly Thr Gly Leu Ser Asn Lys Val Pro Arg Tyr Lys Ile Lys
            100                 105                 110

Lys Gly Asp Thr Leu Tyr Asp Ile Ala Thr Thr Val Phe Ala Gly Leu
        115                 120                 125

Val Lys Tyr Pro Gln Ile Gln Val Ala Asn Glu Ile Pro Asp Ala Asn
    130                 135                 140

Asn Ile Thr Ala Gly Asp Thr Ile Trp Ile Pro Leu Pro Cys Ser Cys
145                 150                 155                 160

Asp Ala Val Ala Gly Ser Ser Val Val His Tyr Ala His Leu Val Gln
                165                 170                 175

Asp Gly Ser Ser Val Glu Ser Ile Ala Gln Glu Tyr Gly Ser Thr Gln
            180                 185                 190

Gln Ile Leu Leu Ser Leu Asn Gly Ile Ser Asp Pro Lys Leu Leu Gln
        195                 200                 205

Ala Arg Gln Leu Leu Asp Val Pro Leu Gln Ala Cys Ser Ser Ser Val
    210                 215                 220

Lys Asn Asp Ser Pro Asp Tyr Pro Leu Leu Val Pro Asn Ala Thr Tyr
225                 230                 235                 240

Val Tyr Thr Ala Lys Glu Cys Val Lys Cys Lys Cys Asp Ser Ser Asn
                245                 250                 255

Asn Phe Arg Leu Gln Cys Glu Pro Ser Gln His Lys Pro Ile Asn Asp
            260                 265                 270

Trp Ser Val Cys Pro Ser Met Glu Cys Ser Lys Asn Val Leu Ile Gly
        275                 280                 285

Asn Thr Thr Ser Thr Asp Ser Cys Asn Arg Thr Ile Cys Asp Tyr Ala
    290                 295                 300

Gly Tyr Ser Asn Ser Lys Ile Ser Thr Ile Leu Ala Thr Gln Asn Thr
305                 310                 315                 320

Cys Ala Val Pro Pro Ser Gly Ser Gly Thr Ser Ser Gly Ser Gly Ser
                325                 330                 335

Gly Asp Ser Gly Ser Gly Ala Ser Arg Ser Asn Leu His Gly Trp Val
            340                 345                 350

Trp Ser Ser Pro Leu Ile Val Ile His Phe Leu Leu Phe Val Val Phe
        355                 360                 365

Leu Leu
    370
```

GENETICALLY ALTERED PLANTS EXPRESSING HETEROLOGOUS RECEPTORS THAT RECOGNIZE LIPO-CHITOOLIGOSACCHARIDES

CROSS-REFERENCE TO RELATED APPLICATIONS

This application is a national stage application under 35 U.S.C. § 371 of International Application No. PCT/EP2019/071703, filed Aug. 13, 2019, which claims the benefit of U.S. Provisional Application No. 62/718,186, filed Aug. 13, 2018, which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 794542000300SEQLIST.TXT, date recorded: Jan. 25, 2021, size: 253 KB).

TECHNICAL FIELD

The present disclosure relates to genetically altered plants. In particular, the present disclosure relates to genetically altered plants containing a nucleic acid sequence encoding a heterologous receptor polypeptide. The plants are able to recognize lipo-chitooligosaccharides (LCOs) through the heterologous receptor polypeptide.

BACKGROUND

Plants are exposed to a wide variety of microbes in their environment, both benign and pathogenic. To protect against the pathogenic microbes, plants have the ability to recognize specific molecular signals of the microbes through an array of receptors and, depending upon the pattern of the signals, can initiate an appropriate immune response. The molecular signals are derived from secreted materials, cell-wall components, and even cytosolic proteins of the microbes. Chitooligosaccharides (COs) are an important fungal molecular signal that plants recognize through the chitin receptors CEBiP and CERK1 found on the plasma membrane. These receptors are in the LysM class of receptors and recognize the size and the acetylation of COs from fungi. Lipo-chitooligosaccharides (LCOs) are another important molecular signal produced by both bacteria and fungi that are recognized by other LysM receptors.

In addition to benign and pathogenic microbes, some microbes can be beneficial to plants through association or symbiosis. Plants that enter into symbiotic relationships with certain nitrogen fixing bacteria and fungi need to be able to recognize the specific bacterial or fungal species to initiate the symbiosis while still being able to activate their immune systems to respond to other bacteria and fungi. One important mechanism that allows plants to recognize these specific bacteria or fungi is through specialized LysM receptors that have high affinity and high selectivity for the form of LCOs produced by the specific bacteria or fungi while LCOs from other bacteria and fungi are not recognized by these specialized LysM receptors.

Functional studies using mutant plants and phenotypic outputs have been used to identify these specialized LysM receptors. At present, however, only a few high affinity and high selectivity LysM receptors from a limited number of plant species and able to recognize a limited number of potential symbionts have been experimentally identified. As these receptors are required for recognizing symbiotic bacterial and fungal species, and for initiating symbiosis, it will be important for more receptors to be available that can be used to engineer recognition of additional symbiotic bacterial and fungal species. A broader range of receptors is needed both for engineering symbiosis in plants not currently able to form symbiotic relationships and for optimizing symbiosis in plants able to form symbiotic relationships.

BRIEF SUMMARY

There exists a clear need for additional specialized LysM receptors in order to engineer plant-microbial symbiotic relationships. Accordingly, the present disclosure provides multiple new high affinity and high selectivity LysM receptors that allow plants to recognize lipo-chitooligosaccharides (LCOs) produced by bacterial or fungal species.

Certain aspects of the present disclosure relate to a genetically altered plant or plant part containing a nucleic acid sequence encoding a heterologous receptor polypeptide, wherein the heterologous receptor polypeptide is selected from the group of a first polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:5 [chickpea/*Cicer arietinum* NFR5], a second polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:7 [bean/*Phaseolus vulgaris* NFR5], a third polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:9 [peanut/*Arachis* NFR5], a fourth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:11 [*Lotus* LYS11], a fifth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:12 [*Medicago* LYR1], a sixth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:13 [*Parasponia* NFP1], a seventh polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:16 [barley HvLysM-RLK1 (AK370300)], an eighth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:17 [barley HvLysM-RLK2 (AK357612)], a ninth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:18 [barley HvLysM-RLK3 AK372128], a tenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:19 [barley HvLysM-RLK10 (HORVU4Hr1 G066170)], an eleventh polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:20 [maize ZM1 (XP 020399958)], a twelfth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:21 [maize ZM5 (XP 008652982.1)], a thirteenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:22 [apple NFP5 XP 008338966.1], or a fourteenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:23 [strawberry NFR5 XP 004300586.2]. In some embodiments, the heterologous receptor polypeptide is selected from the group of SEQ ID NO:5 [chickpea/*Cicer arietinum* NFR5], SEQ ID NO:7 [bean/*Phaseolus vulgaris* NFR5], SEQ ID NO:9 [peanut/*Arachis* NFR5], SEQ ID NO:11 [*Lotus* LYS11], SEQ ID NO:12 [*Medicago* LYR1], SEQ ID NO:13 [*Parasponia* NFP1], SEQ ID NO:16 [barley HvLysM-RLK1 (AK370300)], SEQ ID NO:17 [barley HvLysM-RLK2 (AK357612)], SEQ ID NO:18 [barley HvLysM-RLK3 AK372128], SEQ ID NO:19 [barley HvLysM-RLK10 (HORVU4Hr1G066170)], SEQ ID NO:20 [maize ZM1 (XP 020399958)], SEQ ID NO:21 [maize ZM5 (XP 008652982.1)], SEQ ID NO:22 [apple NFP5 XP 008338966.1], and SEQ ID NO:23 [strawberry NFR5 XP 004300586.2]. In some embodiments, the expression of the heterologous receptor polypeptide allows the plant or part thereof to recognize lipo-chitooligosaccharides (LCOs) through the heterologous receptor polypeptide. In some embodiments, the LCOs are produced by nitrogen-fixing bacteria or by mycorrhizal fungi. In some embodiments, the LCOs are produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli, Burkholderiales* optionally symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizobium* spp., *Azorhizobium* spp. *Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division *Glomeromycota*, or any combination thereof. In some embodiments, the heterologous polypeptide is localized to a plant cell plasma membrane. In some embodiments, the plant cell is a root cell. In some embodiments, the root cell is a root epidermal cell or a root cortex cell. In some embodiments, the heterologous polypeptide is expressed in a developing plant root system. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the plant is selected from the group of corn (e.g., maize, *Zea mays*), rice (e.g., *Oryza sativa, Oryza glaberrima, Zizania* spp.), barley (e.g., *Hordeum vulgare*), wheat (e.g., common wheat, spelt, durum, *Triticum aestivum, Triticum spelta, Triticum durum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa*), apple (e.g., *Malus pumila*), pear (e.g., *Pyrus communis, Pyrus*×bretschneideri, *Pyrus pyrifolia, Pyrus sinkiangensis, Pyrus pashia, Pyrus* spp.), plum (e.g., prune, damson, bullaces, *Prunus domestica, Prunus* salicina), apricot (e.g., *Prunus armeniaca, Prunus brigantina, Prunus mandshurica, Prunus mume, Prunus sibirica*), peach (e.g., nectarine, *Prunus persica*), almond (e.g., *Prunus dulcis, Prunus amygdalus*), walnut (e.g., Persian walnut, English walnut, black walnut, *Juglans regia, Juglans nigra, Juglans cinerea, Juglans californica*), strawberry (e.g., *Fragaria*×

*ananassa, Fragaria chiloensis, Fragaria virginiana, Fragaria vesca*), raspberry (e.g., European red raspberry, black raspberry, *Rubus idaeus, Rubus occidentalis, Rubus strigosus*), blackberry (e.g., evergreen blackberry, Himalayan blackberry, *Rubus fruticosus, Rubus ursinus, Rubus laciniatus, Rubus argutus, Rubus armeniacus, Rubus plicatus, Rubus ulmifolius, Rubus allegheniensis*), red currant (e.g., *Ribes rubrum, Ribes spicatum, Ribesbes alpinum, Ribes schlechtendalii, Ribes multiflorum, Ribes petraeum, Ribes triste*), black currant (e.g., *Ribes nigrum*), melon (e.g., watermelon, winter melon, casabas, cantaloupe, honeydew, muskmelon, *Citrullus lanatus, Benincasa hispida, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vinifera, Vitis amurensis, Vitis labrusca, Vitis mustangensis, Vitis riparia, Vitis rotundifolia*), or hemp (e.g., *cannabis, Cannabis sativa*).

In some embodiments of any of the above embodiments, the plant part is a leaf, a stem, a root, a root primordia, a flower, a seed, a fruit, a kernel, a grain, a cell, or a portion thereof. In some embodiments, the part is a fruit, a kernel, or a grain.

In some aspects, the present disclosure relates to a pollen grain or an ovule of the genetically altered plant of any of the above embodiments.

In some aspects, the present disclosure relates to a protoplast produced from the plant of any of the above embodiments.

In some aspects, the present disclosure relates to a tissue culture produced from protoplasts or cells from the plant of any of the above embodiments, wherein the cells or protoplasts are produced from a plant part selected from the group consisting of leaf, anther, pistil, stem, petiole, root, root primordia, root tip, fruit, seed, flower, cotyledon, hypocotyl, embryo, and meristematic cell.

Certain aspects of the present disclosure relate to a method of producing the genetically altered plant of any of the above embodiments, comprising introducing a genetic alteration to the plant comprising the nucleic acid sequence. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the nucleic acid sequence is inserted into the genome of the plant so that the nucleic acid sequence is operably linked to an endogenous promoter. In some embodiments, the endogenous promoter is a root specific promoter.

In some aspects, the present disclosure relates to a genetically altered plant seed containing a nucleic acid sequence encoding a heterologous receptor polypeptide, wherein the heterologous receptor polypeptide is selected from the group of a first polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:5 [chickpea/*Cicer arietinum* NFR5], a second polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:7 [bean/*Phaseolus vulgaris* NFR5], a third polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:9 [peanut/*Arachis* NFR5], a fourth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:11 [*Lotus* LYS11], a fifth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:12 [*Medicago* LYR1], a sixth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:13 [*Parasponia* NFP1], a seventh polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:16 [barley HvLysM-RLK1 (AK370300)], an eighth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:17 [barley HvLysM-RLK2 (AK357612)], a ninth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:18 [barley HvLysM-RLK3 AK372128], a tenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:19

[barley HvLysM-RLK10 (HORVU4Hr1 G066170)], an eleventh polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:20 [maize ZM1 (XP 020399958)], a twelfth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:21 [maize ZM5 (XP 008652982.1)], a thirteenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:22 [apple NFP5 XP_008338966.1], or a fourteenth polypeptide with at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to SEQ ID NO:23 [strawberry NFR5 XP_004300586.2]. In some embodiments, the heterologous receptor polypeptide is selected from the group of SEQ ID NO:5 [chickpea/*Cicer arietinum* NFR5], SEQ ID NO:7 [bean/*Phaseolus vulgaris* NFR5], SEQ ID NO:9 [peanut/*Arachis* NFR5], SEQ ID NO:11 [*Lotus* LYS11], SEQ ID NO:12 [*Medicago* LYR1], SEQ ID NO:13 [*Parasponia* NFP1], SEQ ID NO:16 [barley HvLysM-RLK1 (AK370300)], SEQ ID NO:17 [barley HvLysM-RLK2 (AK357612)], SEQ ID NO:18 [barley HvLysM-RLK3 AK372128], SEQ ID NO:19 [barley HvLysM-RLK10 (HORVU4Hr1G066170)], SEQ ID NO:20 [maize ZM1 (XP_020399958)], SEQ ID NO:21 [maize ZM5 (XP_008652982.1)], SEQ ID NO:22 [apple NFP5 XP_008338966.1], or SEQ ID NO:23 [strawberry NFR5 XP_004300586.2]. In some embodiments, the expression of the heterologous receptor polypeptide allows the plant or part thereof to recognize lipo-chitooligosaccharides (LCOs) through the heterologous receptor polypeptide. In some embodiments, the LCOs are produced by nitrogen-fixing bacteria or by mycorrhizal fungi. In some embodiments, the LCOs are produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli, Burkholderiales* optionally symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizobium* spp., *Azorhizobium* spp. *Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon* pyriformis, *Paraglomus* spp., other species in the division *Glomeromycota*, or any combination thereof. In some embodiments, the heterologous polypeptide is localized to a plant cell plasma membrane when the seed is grown into a plant. In some embodiments, the plant cell is a root cell. In some embodiments, the root cell is a root epidermal cell or a root cortex cell. In some embodiments, the heterologous polypeptide is expressed in a developing plant root system when the seed is grown into a plant. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the plant is selected from the group of corn (e.g., maize, *Zea mays*), rice (e.g., *Oryza sativa, Oryza glaberrima, Zizania* spp.), barley (e.g., *Hordeum vulgare*), wheat (e.g., common wheat, spelt, durum, *Triticum aestivum, Triticum spelta, Triticum durum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa*), apple (e.g., *Malus pumila*), pear (e.g., *Pyrus communis, Pyrus xbretschneideri, Pyrus pyrifolia, Pyrus sinkiangensis, Pyrus pashia, Pyrus* spp.), plum (e.g., prune, damson, bullaces, *Prunus domestica, Prunus salicina*), apricot (e.g., *Prunus armeniaca, Prunus brigantina, Prunus mandshurica, Prunus mume, Prunus sibirica*), peach (e.g., nectarine, *Prunus persica*), almond (e.g., *Prunus dulcis, Prunus amygdalus*), walnut (e.g., Persian walnut, English walnut, black walnut, *Juglans regia, Juglans nigra, Juglans cinerea, Juglans californica*), strawberry (e.g., *Fragaria*× *ananassa, Fragaria chiloensis, Fragaria virginiana, Fragaria vesca*), raspberry (e.g., European red raspberry, black raspberry, *Rubus idaeus, Rubus occidentalis, Rubus strigosus*), blackberry (e.g., evergreen blackberry, Himalayan blackberry, *Rubus fruticosus, Rubus ursinus, Rubus laciniatus, Rubus argutus, Rubus armeniacus, Rubus plicatus, Rubus ulmifolius, Rubus allegheniensis*), red currant (e.g., *Ribes rubrum, Ribes spicatum*, Rib esbes *alpinum, Ribes schlechtendalii, Ribes multiflorum, Ribes petraeum, Ribes triste*), black currant (e.g., *Ribes nigrum*), melon (e.g., watermelon, winter melon, casabas, cantaloupe, honeydew, muskmelon, *Citrullus lanatus, Benincasa hispida, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vinifera, Vitis amurensis, Vitis labrusca, Vitis mustangensis, Vitis riparia, Vitis rotundifolia*), or hemp (e.g., *cannabis, Cannabis sativa*).

In some aspects, the present disclosure relates to a plant produced from the genetically altered plant seed of any one of the above embodiments, wherein the plant the plant expresses the heterologous polypeptide, and wherein the expression of the heterologous polypeptide allows the plant to recognize lipo-chitooligosaccharides (LCOs) through the heterologous receptor polypeptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a NFP-ECD with the three LysM domains labeled and colored in blue (LysM1), green (LysM2), and red (LysM3). Motifs within the LysM domains are also labeled: LysM1 motifs=α1, α2, β1, and β2; LysM2 motifs=α3, α4, β3, and β4; and LysM3 motifs=α5, α6, β5, and β6. Glycosylations (di-GlcNAc cores) are shown (projecting from α1 at upper; additional cores visible at center adjacent to β2 and β1 as well as at bottom left behind α4), and disulfide bridges are indicated with arrows and labeled with the residue numbers (C47-C166; C39-C104; and C102-C164). FIG. 1B shows SAXS envelope of NFP-ECD showing a rigid stalk region of the receptor. The overall dimensions are shown in angstrom (Å).

FIG. 2A shows NFP binds *S. meliloti* LCO-IV (*S. meliloti* Nod-LCO-IV) with an average $K_D$ of 26±0.2 μM, and that NFP binds *S. meliloti* LCO-V (*S. meliloti* Nod-LCO-V) with an average $K_D$ of 32±0.2 μM. The results shown in FIG. 2A are from seven replicates. FIG. 2B shows NFP does not bind *M. loti* LCO-V (*M. loti* Nod-LCO-V) and *M. loti* C06. The results shown in FIG. 2B are from six replicates.

FIG. 3A shows a schematic of *S. meliloti* LCO-IV mutants with arrows indicating the locations that are affected in LCO-IV by each of the four mutations NodL, NodH, NodFE, and NodFL. FIG. 3B shows binding assays performed using three LCO-IV mutants and *S. meliloti* LCO-IV as a control. The results shown for LCO-IV are from seven replicates, the results shown for NodH (*S. meliloti* ΔH) are from four replicates, the results shown for NodFE (*S. meliloti* ΔFE) are from three replicates, and the results shown for NodFL (*S. meliloti* ΔFL) are from three replicates.

FIGS. 4A-4B show the hydrophobic patch in the *Medicago* NFP LysM2 domain, and binding assay measurements using mutants of important residues within the hydrophobic patch. FIG. 4A shows molecular docking of CO4 (designated as "Ligand") onto *Medicago* NFP colored with electrostatic surface potential (negative=red; hydrophobic=white; positive=blue). The hydrophobic patch is circled by a dashed black line, and the locations of important residues L147 and L154 are shown using arrows. The position of the LCO fatty-acid is depicted with a dashed orange line. FIG. 4B shows binding assay measurements comparing a wild type (WT) NFP ("NFP WT"; in green) with an NFP mutated at residues 147 and 154 ("NFP L147D L154D"; in black). The results shown for NFP WT are from seven replicates and the results shown for NFP L147D L154D are from four replicates.

FIG. 6A shows complementation tested by inoculation with *S. meliloti* strain 2011; columns represent the mean nodule numbers after 49 dpi. FIG. 6B shows complementation tested by inoculation with *S. medicae*; columns represent the mean nodule numbers after 28 dpi. For FIGS. 6A-6B, circles represent the individual counts; empty circles=*Medicago* Jemalong wild type background (WT); filled circles=*Medicago* nfp mutant background (nfp); EVC=empty vector control; WT=wild type NFP control; error bars show the SEM; different letters indicate significant differences among the samples (ANOVA, Tukey, $P<0.05$); and number of plants assayed indicated at labels on x-axis in parentheses.

FIG. 7A shows homology modelling of other characterized LCO receptors: *Lotus* NFR5, pea (*Pisum sativum*) SYM10, and soybean (*Glycine max*) NFR5a. FIG. 7B shows homology modelling of the previously uncharacterized LCO receptor homologues in chickpea (*Cicer arietinum*) NFR5, bean (*Phaseolus vulgaris*) NFR5, and peanut (*Arachis hypogaea*) NFR5, which have a hydrophobic patch. FIG. 7C-7E show homology modelling of more distantly related receptors including (FIG. 7C) LYS receptors: LYS11, LYS12, LYS13, LYS14, LYS15, LYS16, LYS17, and LYS18; (FIG. 7D) LYR receptors: LYR1, LYR2, LYR3, and LYR4, and (FIG. 7E) NFP receptors: *Parasponia* NFP1 and *Parasponia* NFP2. FIG. 7F shows models of *Medicago* LYR3 and *Lotus* LYS12 receptors that have no hydrophobic patch (models viewed from the LysM3 domain and with docked ligand (chitin). FIG. 7G shows a comparison of the *Lotus* LYS11 model (LYS11-model; left; also in FIG. 7C) with the crystal structure of *Lotus* LYS11 (LYS11-crystal structure; right).

FIG. 8A shows the first two portions of the alignment including all of the LysM1 domain and part of the LysM2 domain. FIG. 8B shows the third and fourth portions of the alignment including the rest of the LysM2 domain and all of the LysM3 domain. FIG. 8C shows the fifth portion of the alignment.

FIG. 9A shows the first and second portions of the alignment including all of the LysM1 domain and part of the LysM2 domain. FIG. 9B shows the third and fourth portions of the alignment including the rest of the LysM2 domain and all of the LysM3 domain.

FIG. 10A shows the first, second, and third portions of the alignment including all of the LysM1 domain and all of the LysM2 domain. FIG. 10B shows the fourth, fifth, and sixth portions of the alignment including all of the LysM3 domain.

FIG. 11A shows the first, second, third, and fourth portions of the alignment including all of the LysM1 domain, all of the LysM2 domain, and all of the LysM3 domain. FIG. 11B shows the fifth, sixth, and seventh portions of the alignment.

FIGS. 12A-12E show annotated amino acid sequences of previously known LCO receptors and newly identified LCO receptors. FIG. 12A shows the annotation key; the LysM1 domain is shown with a dashed underline, the LysM2 domain is shown with a solid underline, the hydrophobic patch residues are shown in bold, and the LysM3 domain is shown with residues italicized. *Medicago* NFP (MtNFP/1-595; SEQ ID NO: 1), *Lotus* NFR5 (a known LCO receptor; LjNFR5/1-595; SEQ ID NO: 2), Pea SYM10 (a known LCO receptor; Pea SYM10/1-594; SEQ ID NO: 3), and Soybean NFR5a (a known LCO receptor; GmNFR5a/1-598 max; SEQ ID NO: 4) are shown. FIG. 12B shows Chickpea NFR5 (a new LCO receptor; ChickpeaNFR5/1-557 (*Cicer arietinum*); SEQ ID NO: 5), Bean NFR5 (a new LCO receptor; BeanNFR5/1-597 (*Phaseolus vulgaris*); SEQ ID NO: 7), Peanut NFR5 (a new LCO receptor; PeanutNFR5/1-595 [*Arachis hypogaea* subsp. *hypogaea*]; SEQ ID NO: 9), and *Lotus* Lys11 (a new LCO receptor; LjLys11/1-591; SEQ ID NO: 11). FIG. 12C shows *Medicago* LYR1 (a new LCO receptor; MtLYR1/1-590; SEQ ID NO: 12), *Parasponia* NFP1 (a new LCO receptor; PanNFP1/1-613; SEQ ID NO: 13), *Parasponia* NFP2 (a known LCO receptor; PanNFP2/1-582; SEQ ID NO: 14), and Barley receptor HvLysM-RLK1 (a new LCO receptor; HvLysM-RLK1 (AK370300); SEQ ID NO: 16). FIG. 12D shows Barley receptor HvLysM-RLK2 (a new LCO receptor; HvLysM-RLK2 (AK357612); SEQ ID NO: 17), Barley receptor HvLysM-RLK3 AK372128 (a new LCO receptor; HvLysM-RLK3 AK372128; SEQ ID NO: 18), Barley receptor HvLysM-RLK10 (a new LCO receptor; HvLysM-RLK10 (HORVU4Hr1 G066170); SEQ ID NO: 19), and Maize receptor ZM1 (a new LCO receptor; ZM1 (XP_020399958); SEQ ID NO: 20). FIG. 12E shows Maize receptor ZM5 (a new LCO receptor; ZM5 (XP_008652982.1); SEQ ID NO: 21), Apple NFP5 (a new LCO receptor; XP_008338966.1 PREDICTED: serine/threonine receptor-like kinase NFP [*Malus domestica*]; SEQ ID NO: 22), and Strawberry NFR5 (a new LCO receptor; XP_004300586.2 PREDICTED: protein LYK5-like [*Fragaria vesca* subsp. *vesca*]; SEQ ID NO: 23).

FIG. 13A shows a schematic of the purified HvRLK10 ectodomain at the top (N-terminus=N'; LysM1=M1; LysM2=M2; LysM3=M3; 6×HIS tag used for purification=6×HIS; C-terminus=C') and the results of binding assays of HvRLK10 ectodomain with C05 at the bottom. FIG. 13B shows homology modelling of the barley receptor RLK10 (HvRLK10) ectodomain with surface representation shaded according to its electrostatic potential. The hydrophobic patch is circled by a dashed black line, and a CO ligand is shown at the top of the hydrophobic patch. FIG. 13C shows the results of binding assays of HvRLK10 ectodomain with *M. loti* LCO. FIG. 13D shows the results of binding assays of HvRLK10 ectodomain with *S. meliloti* LCO. For FIGS.

13A, and 13C-13D, binding in nm is shown on the y-axes, time in seconds (s) is shown on the x-axes, and the tested molecules are shown in the titles of the graphs (C05, *M. loti* LCO, and *S. meliloti* LCO).

Figure 14A:
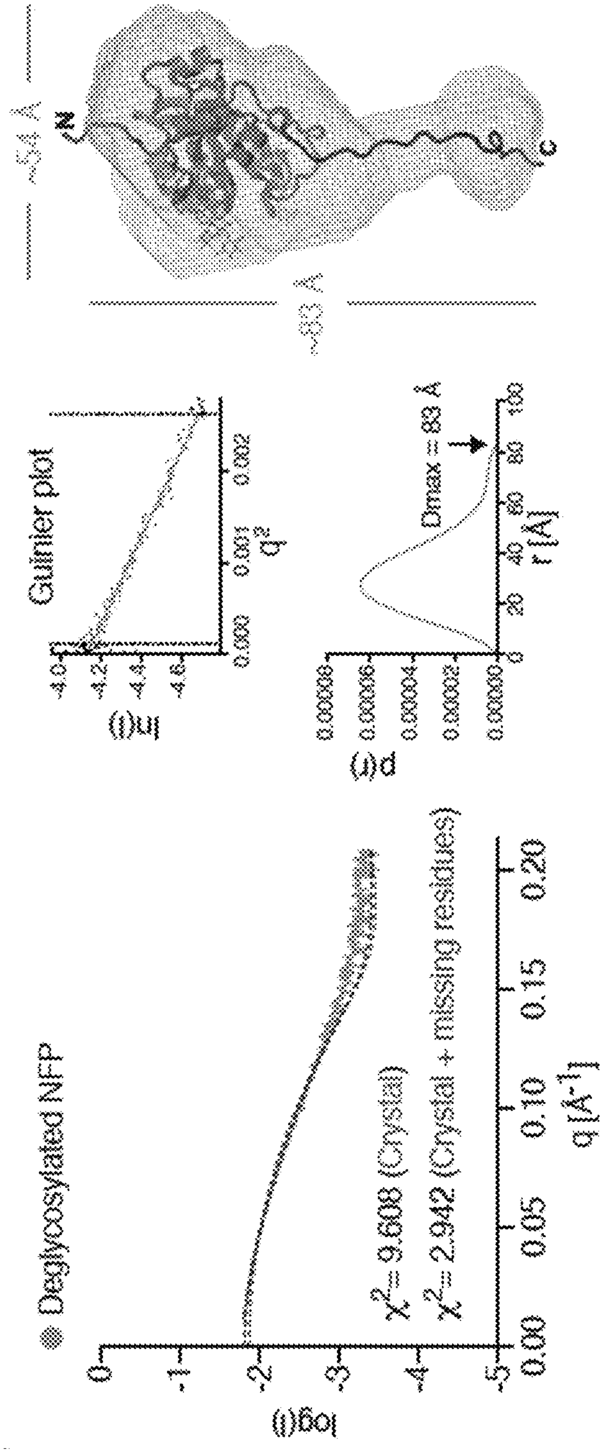
Figure 14B:
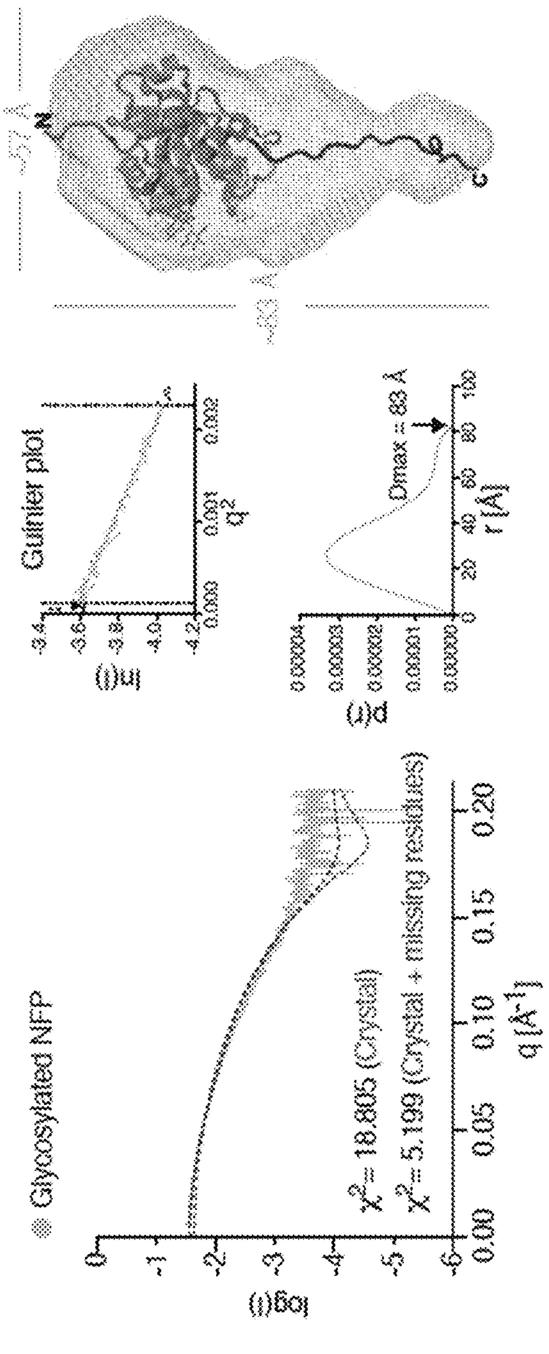
Figure 14C:
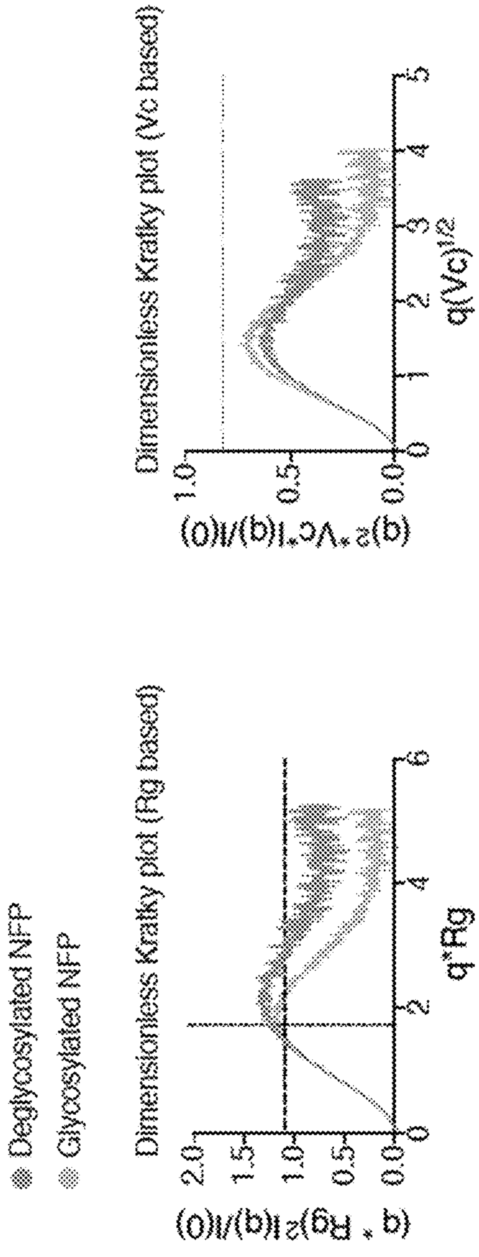

FIGS. 14A-14C show SAXS analyses of deglycosylated NFP-ECD and of glycosylated NFP-ECD, and dimensionless Kratky plots for deglycosylated NFP-ECD and glycosylated NFP-ECD. FIG. 14A shows SAXS analysis showing scattering curves with model fit (c2; left graph), Guinier plot (top middle graph), and P(r) distance distribution plot with Dmax indicated (bottom middle graph) for deglycosylated NFP-ECD, as well as the NFP-ECD crystal structure docked into the SAXS envelope for deglycosylated NFP-ECD (shows an extended stem-like structure; overall dimensions are shown in angstrom (Å)). FIG. 14B shows SAXS analysis showing scattering curves with model fit (c2; left graph), Guinier plot (top middle graph), and P(r) distance distribution plot with Dmax indicated (bottom middle graph) for glycosylated NFP-ECD, as well as the NFP-ECD crystal structure docked into the SAXS envelope for glycosylated NFP-ECD (shows an extended stem-like structure; overall dimensions are shown in angstrom (Å)). FIG. 14C shows the dimensionless Kratky plot (Rg based, Guinier and Vc based) for deglycosylated NFP-ECD (grey) and glycosylated NFP-ECD (light grey).

Figure 15E:
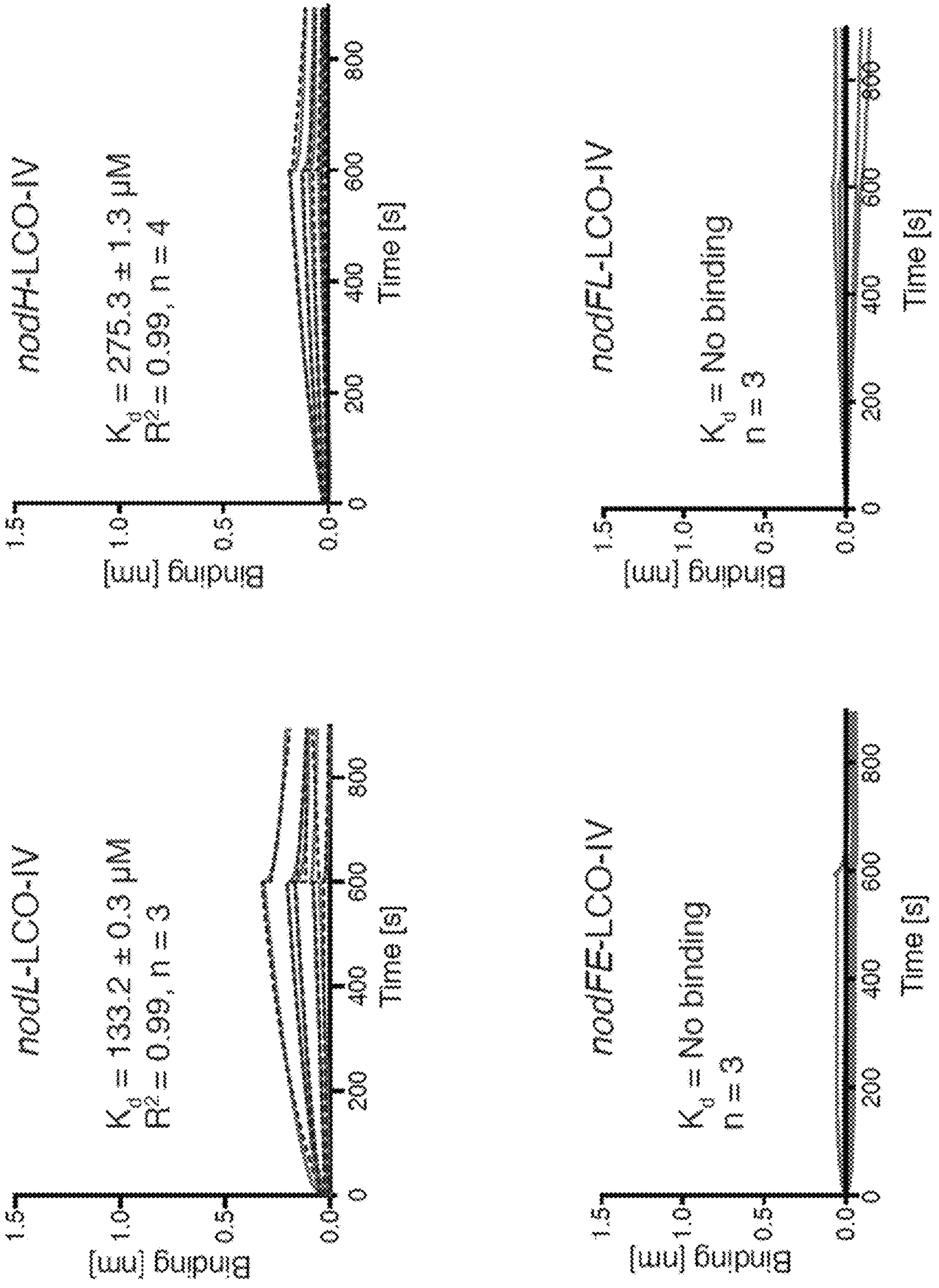

FIGS. 15A-15E show BLI binding curves for NFP-ECD binding to *S. meliloti* LCO-V, *M. loti* LCO-V and Chitin (chitopentaose; C05). FIG. 15A shows NFP-ECD binds *S. meliloti* LCO-V with an average $K_d$ of 22.3±0.1 μM (goodness of fit is described by the global fit $R^2$ on the mean value of each point=0.99; n=7). FIG. 15B shows NFP-ECD binds *M. loti* LCO-V with a $K_d$ that cannot be fitted because binding is too weak (n=6). FIG. 15C shows NFP-ECD does not bind chitin (n=6). FIG. 15D shows a table of BLI binding curve results for NFP-ECD binding to *S. meliloti* LCO-IV and LCO-IV variants. FIG. 15E shows BLI binding curve results for NFP-ECD binding to *S. meliloti* LCO-IV and LCO-IV variants. For FIGS. 15A-15C and 15E, seven 2-fold dilution series of analyte (1.56-100 μM) were used for each experiment; experimental binding curves are represented in solid lines, fitting curves in dashed lines; and number of replicates performed using independent protein preparations (n) are indicated. For FIGS. 15D-15E, LCO-IV variants shown in FIG. 3A and goodness of fit described by the global fit $R^2$ on the mean value of each point.

FIGS. 16A-16D show BLI binding curves for WT NFP-ECD and hydrophobic patch mutant NFP-ECD (L147D/L154D) binding to *S. meliloti* LCO-IV and a schematic of the NFP receptor. FIG. 16A shows WT NFP-ECD binding to *S. meliloti* LCO-IV. FIG. 16B shows L147D/L154D NFP-ECD binding to *S. meliloti* LCO-IV. For FIGS. 16A-16B, seven 2-fold dilution series of analyte (1.56-100 μM) were used for each experiment; and experimental binding curves are represented in solid lines, fitting curves in dashed lines. FIG. 16C shows a table summarizing the kinetic parameters of FIGS. 16A-16B, with goodness of fit described by the global fit $R^2$ on the mean value of each point, and number of replicates performed using independent protein preparations (n) indicated. FIG. 16D shows a schematic of the NFP receptor with LysM1, LysM2, LysM3, stem, and transmembrane (TM) and kinase domains labeled, and the location of the hydrophobic patch in LysM2 indicated by a grey bar. Numbers below the schematic provide the corresponding amino acid residues, and the locations of the CxC motifs flanking the LysM domains are shown.

Figure 17B:
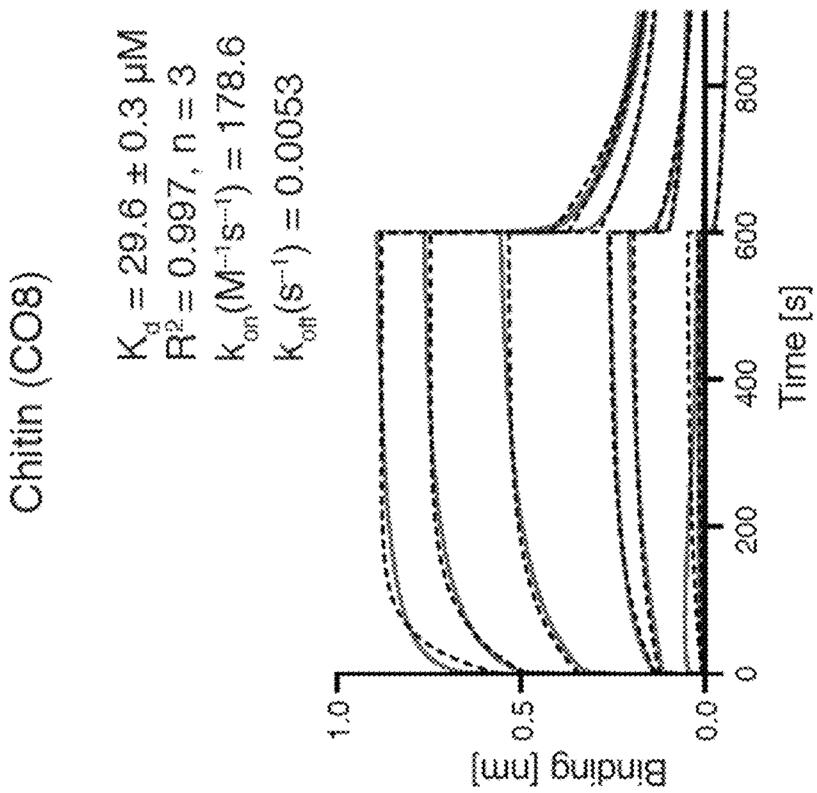
Figure 17A:
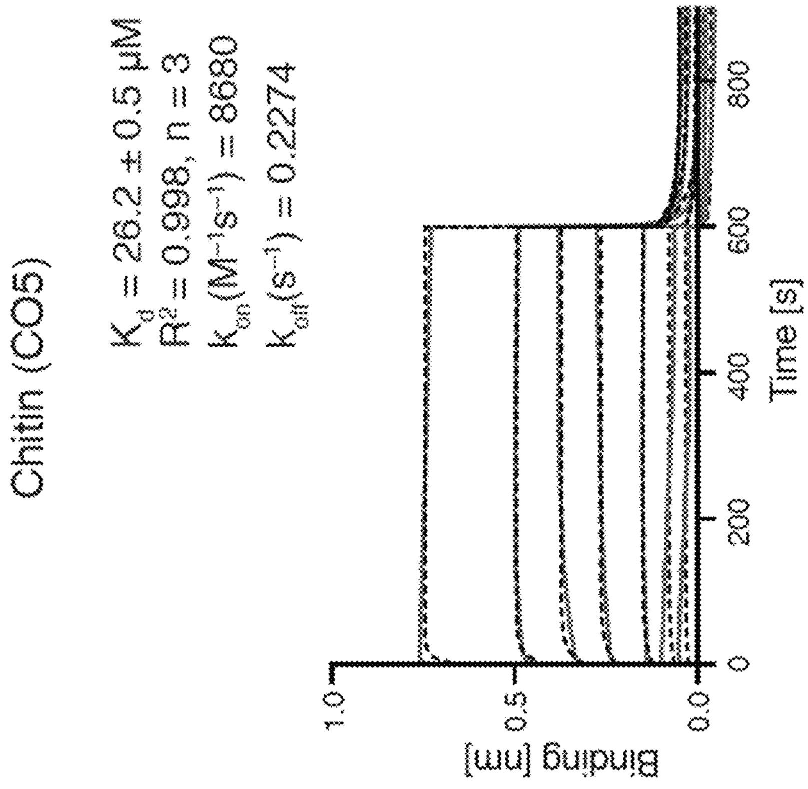

FIGS. 17A-17B show BLI binding curves for *A. thaliana* CERK1 (AtCERK1) binding to chitopentaose (C05) and chitooctaose (C08). FIG. 17A shows AtCERK1 binding to chitopentaose (Chitin (C05)). FIG. 17B shows AtCERK1 binding to chitooctaose (Chitin (CO8)). For FIGS. 17A-17B, seven 2-fold dilution series of analyte (1.56-100 μM) were used for each experiment; experimental binding curves are represented in solid lines, fitting curves in dashed lines; goodness of fit is described by the global fit $R^2$ on the mean value of each point; number of replicates performed using independent protein preparations (n) indicated; and kinetic parameters ($k_{on}$ and $k_{off}$) are shown.

DETAILED DESCRIPTION

The following description sets forth exemplary methods, parameters, and the like. It should be recognized, however, that such description is not intended as a limitation on the scope of the present disclosure but is instead provided as a description of exemplary embodiments.

Genetically Altered Plants and Seeds

Certain aspects of the present disclosure relate to a genetically altered plant or plant part containing a nucleic acid sequence encoding a heterologous receptor polypeptide, wherein the heterologous receptor polypeptide is selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:5 (i.e., chickpea, *Cicer arietinum* NFR5), a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:7 (i.e., bean, *Phaseolus vulgaris* NFR5), a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:9 (i.e., peanut, *Arachis* NFR5), a fourth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:11 (i.e., *Lotus* LYS11), a fifth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:12 (i.e., *Medicago* LYR1), a sixth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:13 (i.e., *Parasponia* NFP1), a seventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:16 (i.e., barley HvLysM-RLK1 (AK370300)), an eighth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:17 (i.e., barley HvLysM-RLK2 (AK357612)), a ninth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:18 (i.e., barley HvLysM-RLK3 AK372128), a tenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:19 (i.e., barley HvLysM-RLK10 (HORVU4Hr1 G066170)), an eleventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:20 (i.e., maize ZM1 (XP_020399958)), a twelfth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:21 (i.e., maize ZM5 (XP_008652982.1)), a thirteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:22 (i.e., apple NFP5 XP_008338966.1), or a fourteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:23 (i.e., strawberry NFR5 XP_004300586.2). In some embodiments, the heterologous receptor polypeptide is selected from the group of SEQ ID NO:5 (i.e., chickpea, *Cicer arietinum* NFR5), SEQ ID NO:7 (i.e., bean, *Phaseolus vulgaris* NFR5), SEQ ID NO:9 (i.e., peanut, *Arachis* NFR5), SEQ ID NO:11 (i.e., *Lotus* LYS11), SEQ ID NO:12 (i.e., *Medicago* LYR1), SEQ ID NO:13 (i.e., *Parasponia* NFP1), SEQ ID NO:16 (i.e., barley HvLysM-RLK1 (AK370300)), SEQ ID NO:17 (i.e., barley HvLysM-RLK2 (AK357612)), SEQ ID NO:18 (i.e., barley HvLysM-RLK3 AK372128), SEQ ID NO:19 (i.e., barley HvLysM-RLK10 (HORVU4Hr1 G066170)), SEQ ID NO:20 (i.e., maize ZM1 (XP_020399958)), SEQ ID NO:21 (i.e., maize ZM5 (XP_008652982.1)), SEQ ID NO:22 (i.e., apple NFP5 XP_008338966.1), and SEQ ID NO:23 (i.e., strawberry NFR5 XP_004300586.2). In some embodiments, the expression of the heterologous receptor polypeptide allows the plant or part thereof to recognize lipo-chitooligosaccharides (LCOs) through the heterologous receptor polypeptide. In some embodiments, the LCOs are produced by nitrogen-fixing bacteria or by mycorrhizal fungi. In some embodiments, the LCOs are produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli, Burkholderiales* optionally symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizobium* spp., *Azorhizobium* spp. *Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division *Glomeromycota*, or any combination thereof. In some embodiments, the heterologous polypeptide is localized to a plant cell plasma membrane. In some embodiments, the plant cell is a root cell. In some embodiments, the root cell is a root epidermal cell or a root cortex cell. In some embodiments, the heterologous polypeptide is expressed in a developing plant root system. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the plant is selected from the group of corn (e.g., maize, *Zea mays*), rice (e.g., *Oryza sativa, Oryza glaberrima, Zizania* spp.), barley (e.g., *Hordeum vulgare*), wheat (e.g., common wheat, spelt, durum, *Triticum aestivum, Triticum spelta, Triticum durum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa*), apple (e.g., *Malus pumila*), pear (e.g., *Pyrus communis, Pyrus xbretschneideri, Pyrus pyrifolia, Pyrus sinkiangensis, Pyrus pashia, Pyrus* spp.), plum (e.g., prune, damson, bullaces, *Prunus domestica, Prunus* salicina), apricot (e.g., *Prunus armeniaca, Prunus brigantina, Prunus mandshurica, Prunus mume, Prunus sibirica*), peach (e.g., nectarine, *Prunus persica*), almond (e.g., *Prunus dulcis, Prunus amygdalus*), walnut (e.g., Persian walnut, English walnut, black walnut, *Juglans regia, Juglans nigra, Juglans cinerea, Juglans californica*), strawberry (e.g., *Fragaria× ananassa, Fragaria chiloensis, Fragaria virginiana, Fragaria vesca*), raspberry (e.g., European red raspberry, black raspberry, *Rubus idaeus, Rubus occidentalis, Rubus strigosus*), blackberry (e.g., evergreen blackberry, Himalayan blackberry, *Rubus fruticosus, Rubus ursinus, Rubus laciniatus, Rubus* argutus, *Rubus armeniacus, Rubus plicatus, Rubus ulmifolius, Rubus allegheniensis*), red currant (e.g., *Ribes rubrum, Ribes spicatum, Ribesbes alpinum, Ribes schlechtendalii, Ribes multiflorum, Ribes petraeum, Ribes triste*), black currant (e.g., *Ribes nigrum*), melon (e.g., watermelon, winter melon, casabas, cantaloupe, honeydew, muskmelon, *Citrullus lanatus, Benincasa hispida, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vin-*

*ifera, Vitis amurensis, Vitis labrusca, Vitis mustangensis, Vitis riparia, Vitis rotundifolia*), or hemp (e.g., *cannabis, Cannabis sativa*).

In some embodiments of any of the above embodiments, the plant part is a leaf, a stem, a root, a root primordia, a flower, a seed, a fruit, a kernel, a grain, a cell, or a portion thereof. In some embodiments, the part is a fruit, a kernel, or a grain.

In some aspects, the present disclosure relates to a pollen grain or an ovule of the genetically altered plant of any of the above embodiments.

In some aspects, the present disclosure relates to a protoplast produced from the plant of any of the above embodiments.

In some aspects, the present disclosure relates to a tissue culture produced from protoplasts or cells from the plant of any of the above embodiments, wherein the cells or protoplasts are produced from a plant part selected from the group consisting of leaf, anther, pistil, stem, petiole, root, root primordia, root tip, fruit, seed, flower, cotyledon, hypocotyl, embryo, and meristematic cell.

In some aspects, the present disclosure relates to a genetically altered plant seed containing a nucleic acid sequence encoding a heterologous receptor polypeptide, wherein the heterologous receptor polypeptide is selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:5 (i.e., chickpea, *Cicer arietinum* NFR5), a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:7 (i.e., bean, *Phaseolus vulgaris* NFR5), a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:9 (i.e., peanut, *Arachis* NFR5), a fourth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:11 (i.e., *Lotus* LYS11), a fifth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:12 (i.e., *Medicago* LYR1), a sixth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:13 (i.e., *Parasponia* NFP1), a seventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:16 (i.e., barley HvLysM-RLK1 (AK370300)), an eighth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:17 (i.e., barley HvLysM-RLK2 (AK357612)), a ninth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:18 (i.e., barley HvLysM-RLK3 AK372128), a tenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:19 (i.e., barley HvLysM-RLK10 (HORVU4Hr1 G066170)), an eleventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:20 (i.e., maize ZM1 (XP_020399958)), a twelfth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:21 (i.e., maize ZM5 (XP_008652982.1)), a thirteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:22 (i.e., apple NFP5 XP_008338966.1), or a fourteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:23 (i.e., strawberry NFR5 XP_004300586.2). In some embodiments, the heterologous receptor polypeptide is selected from the group of SEQ ID NO:5 (i.e., chickpea, *Cicer arietinum* NFR5), SEQ ID NO:7 (i.e., bean, *Phaseolus vulgaris* NFR5), SEQ ID NO:9 (i.e., peanut, *Arachis* NFR5), SEQ ID NO:11 (i.e., *Lotus* LYS11), SEQ ID NO:12 (i.e., *Medicago* LYR1), SEQ ID NO:13 (i.e., *Parasponia* NFP1), SEQ ID NO:16 (i.e., barley HvLysM-RLK1 (AK370300)), SEQ ID NO:17 (i.e., barley HvLysM-RLK2 (AK357612)), SEQ ID NO:18 (i.e., barley HvLysM-RLK3 AK372128), SEQ ID NO:19 (i.e., barley HvLysM-RLK10 (HORVU4Hr1G066170)), SEQ ID NO:20 (i.e., maize ZM1 (XP_020399958)), SEQ ID NO:21 (i.e., maize ZM5 (XP_008652982.1)), SEQ ID NO:22 (i.e., apple NFP5 XP_008338966.1), and SEQ ID NO:23 (i.e., strawberry NFR5 XP_004300586.2). In some embodiments, the expression of the heterologous receptor polypeptide allows the plant or part thereof to recognize lipo-chitooligosaccharides (LCOs) through the heterologous receptor polypeptide. In some embodiments, the LCOs are produced by nitrogen-fixing bacteria or by mycorrhizal fungi. In some embodiments, the LCOs are produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli, Burkholderiales* optionally symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizo-*

*bium* spp., *Azorhizobium* spp. *Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division *Glomeromycota*, or any combination thereof. In some embodiments, the heterologous polypeptide is localized to a plant cell plasma membrane when the seed is grown into a plant. In some embodiments, the plant cell is a root cell. In some embodiments, the root cell is a root epidermal cell or a root cortex cell. In some embodiments, the heterologous polypeptide is expressed in a developing plant root system when the seed is grown into a plant. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the plant is selected from the group of corn (e.g., maize, *Zea mays*), rice (e.g., *Oryza sativa, Oryza glaberrima, Zizania* spp.), barley (e.g., *Hordeum vulgare*), wheat (e.g., common wheat, spelt, durum, *Triticum aestivum, Triticum spelta, Triticum durum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa*), apple (e.g., *Malus pumila*), pear (e.g., *Pyrus communis, Pyrus xbretschneideri, Pyrus pyrifolia, Pyrus sinkiangensis, Pyrus pashia, Pyrus* spp.), plum (e.g., prune, damson, bullaces, *Prunus domestica, Prunus salicina*), apricot (e.g., *Prunus armeniaca, Prunus brigantina, Prunus mandshurica, Prunus mume, Prunus sibirica*), peach (e.g., nectarine, *Prunus persica*), almond (e.g., *Prunus dulcis, Prunus amygdalus*), walnut (e.g., Persian walnut, English walnut, black walnut, *Juglans regia, Juglans nigra, Juglans cinerea, Juglans californica*), strawberry (e.g., *Fragaria× ananassa, Fragaria chiloensis, Fragaria virginiana, Fragaria vesca*), raspberry (e.g., European red raspberry, black raspberry, *Rubus idaeus, Rubus occidentalis, Rubus strigosus*), blackberry (e.g., evergreen blackberry, Himalayan blackberry, *Rubus fruticosus, Rubus ursinus, Rubus laciniatus, Rubus argutus, Rubus armeniacus, Rubus plicatus, Rubus ulmifolius, Rubus alleghenïensis*), red currant (e.g., *Ribes rubrum, Ribes spicatum, Rib esbes alpinum, Ribes schlechtendalii, Ribes multiflorum, Ribes petraeum, Ribes triste*), black currant (e.g., *Ribes nigrum*), melon (e.g., watermelon, winter melon, casabas, cantaloupe, honeydew, muskmelon, *Citrullus lanatus, Benincasa hispida, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vinifera, Vitis amurensis, Vitis labrusca, Vitis mustangensis, Vitis riparia, Vitis rotundifolia*), or hemp (e.g., *cannabis, Cannabis sativa*).

In some aspects, the present disclosure relates to a plant produced from the genetically altered plant seed of any one of the above embodiments, wherein the plant the plant expresses the heterologous polypeptide, and wherein the expression of the heterologous polypeptide allows the plant to recognize lipo-chitooligosaccharides (LCOs) through the heterologous receptor polypeptide.

In some aspects, the present disclosure related to a plant or part thereof able to recognize LCOs containing at least one modified nucleic acid sequence containing at least one coding sequence of a high affinity and/or high selectivity LCO receptor in the plant or part thereof, wherein the LCO receptor is expressed in the plant or part thereof; wherein the expression of the LCO receptor allows the plant to recognize LCOs. In some embodiments, the present disclosure related to a plant or part thereof able to recognize LCOs with high affinity and/or high selectivity containing at least one modified nucleic acid sequence containing at least one coding sequence of a high affinity and/or high selectivity LCO receptor in the plant or part thereof, wherein the high affinity and/or high selectivity LCO receptor is expressed in the plant or part thereof; wherein the expression of the high affinity and/or high selectivity LCO receptor allows the plant to recognize LCOs with high affinity and/or high selectivity. In some embodiments, the LCO receptor is from a legume.

Figure 8A:
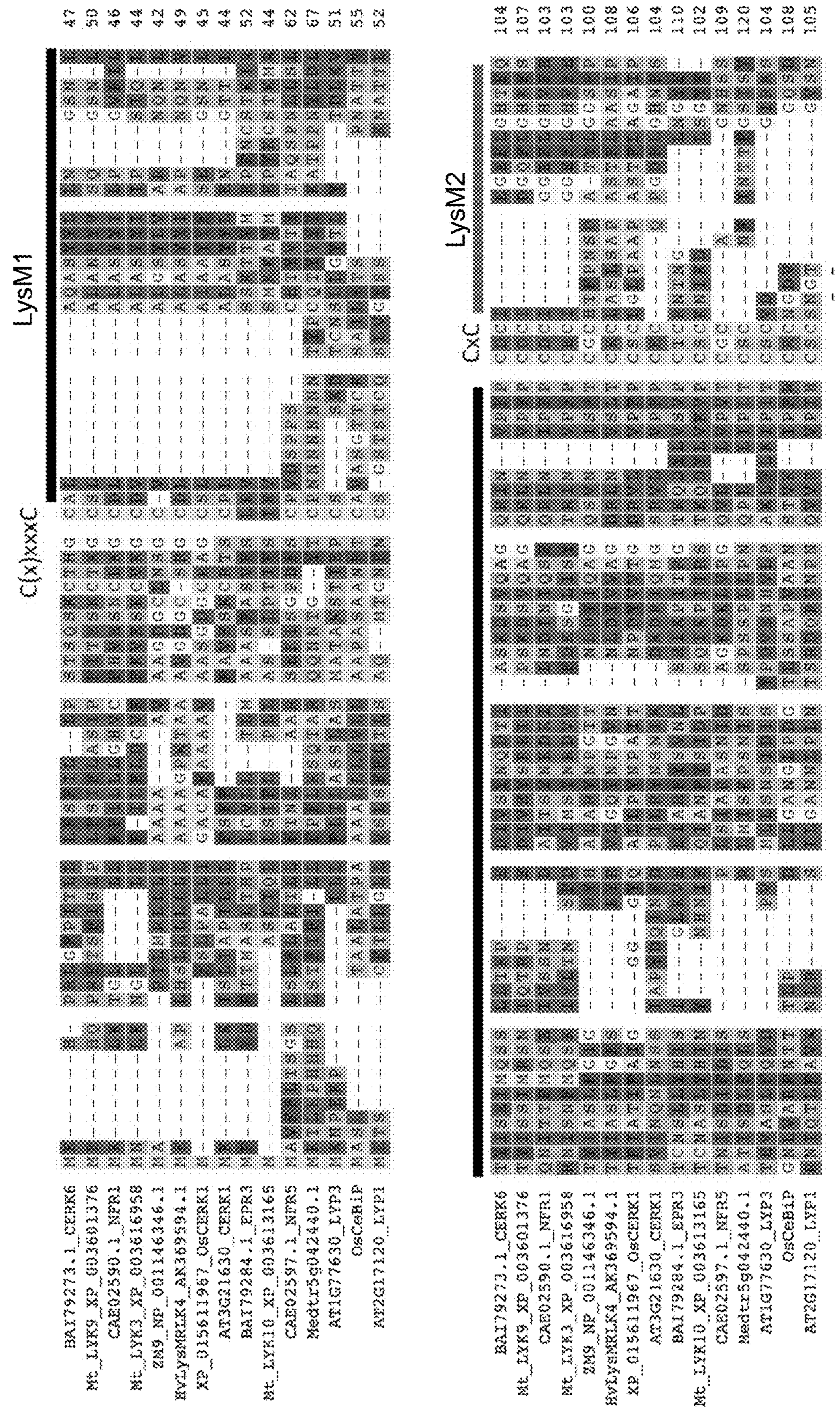
FIGS. 8A-8C show an alignment of selected LysM receptors from *Arabidopsis thaliana* (At; AT3G21630_CERK1 (SEQ ID NO: 37), AT1G77630_LYP3 (SEQ ID NO: 42), AT2G17120 LYP1 (SEQ ID NO: 44)), *Zea mays* (Zm; ZM9_NP_001146346.1 (SEQ ID NO: 34)), *Hordeum vulgare* (Hv; HvLysMRLK4_AK369594.1 (SEQ ID NO: 35)), *Medicago truncatula* (Mt or Medtr; Mt_LYK9_XP_003601376 (SEQ ID NO: 31), Mt_LYK3_XP_003616958 (SEQ ID NO: 33), Mt_LYK10_XP_003613165 (SEQ ID NO: 39), Medtr5g042440.1 (SEQ ID NO: 41)), *Oryza sativa* (Os; XP_015611967_OsCERK1 (SEQ ID NO: 36), OsCeBiP (SEQ ID NO: 43)) and *Lotus japonicus* (Lj; BAI79273.1_CERK6 (SEQ ID NO: 30), CAE02590.1_NFR1 (SEQ ID NO: 32), BAI79284.1_EPR3 (SEQ ID NO: 38), CAE02597.1 NFR5 (SEQ ID NO: 40)). NFR1 and NFR5 are Nod factor receptors, EPR3 is an exopolysaccharide receptor, AtLYP1 and AtLYP3 are peptidoglycan receptors, AtCERK1, OsCERK1, OsCeBIP, CERK6 are chitooligosaccharide receptors. C(x)XXXC and CxC motifs flanking the three LysM domains are shown. LysM1 (black line), LysM2 (green line) and LysM3 (brown line) are shown.
Figure 8B:
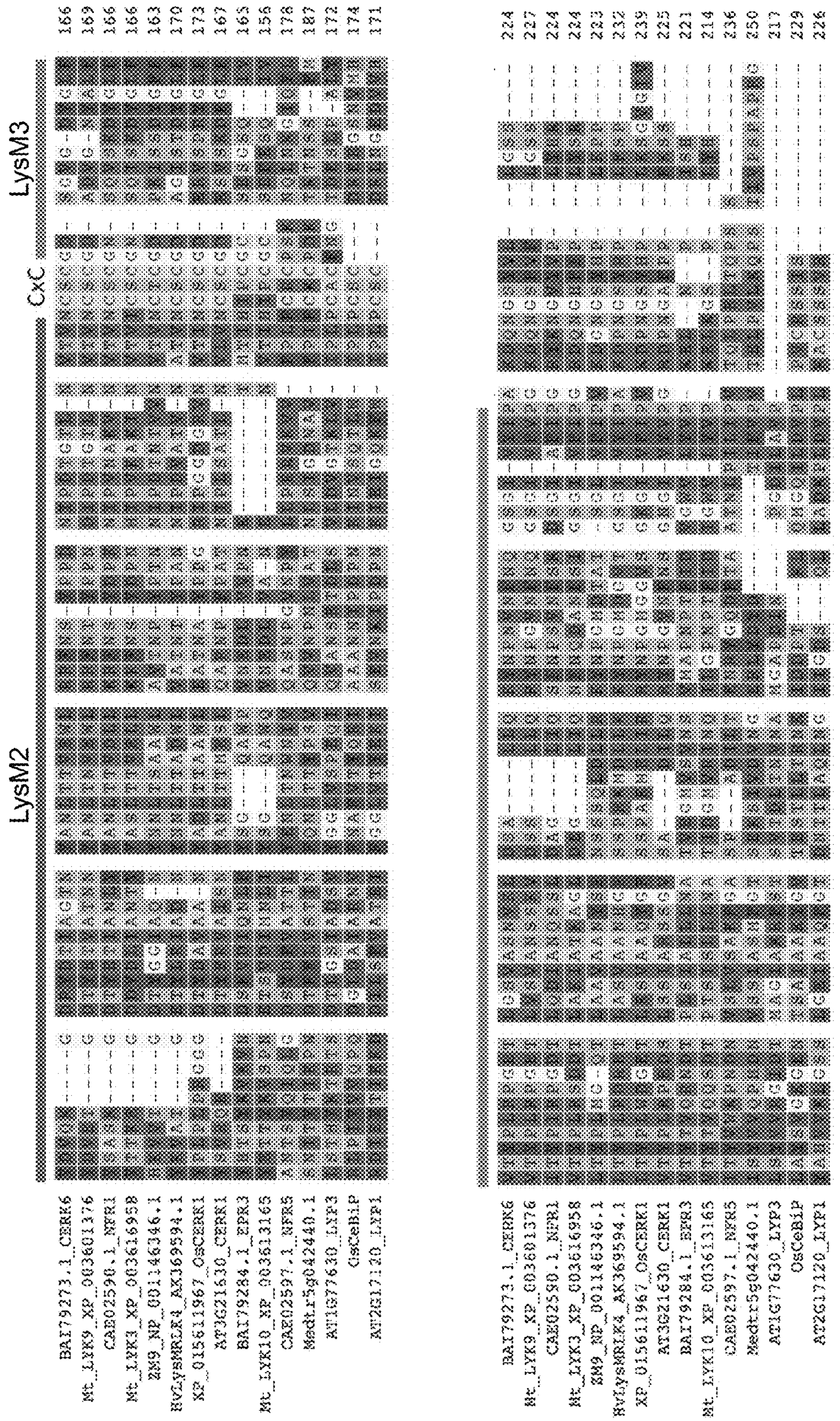
Figure 8C:
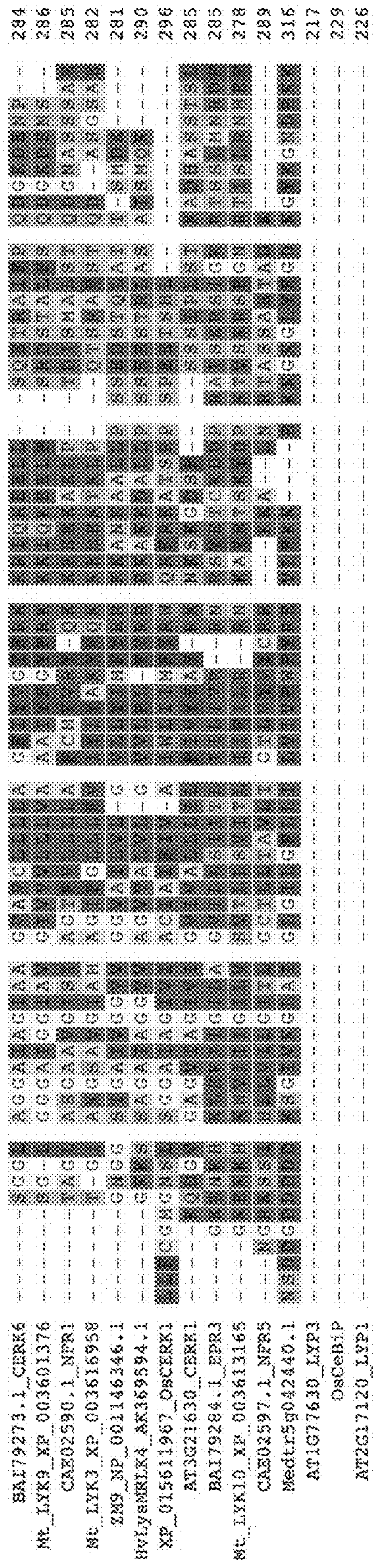
Figure 9A:
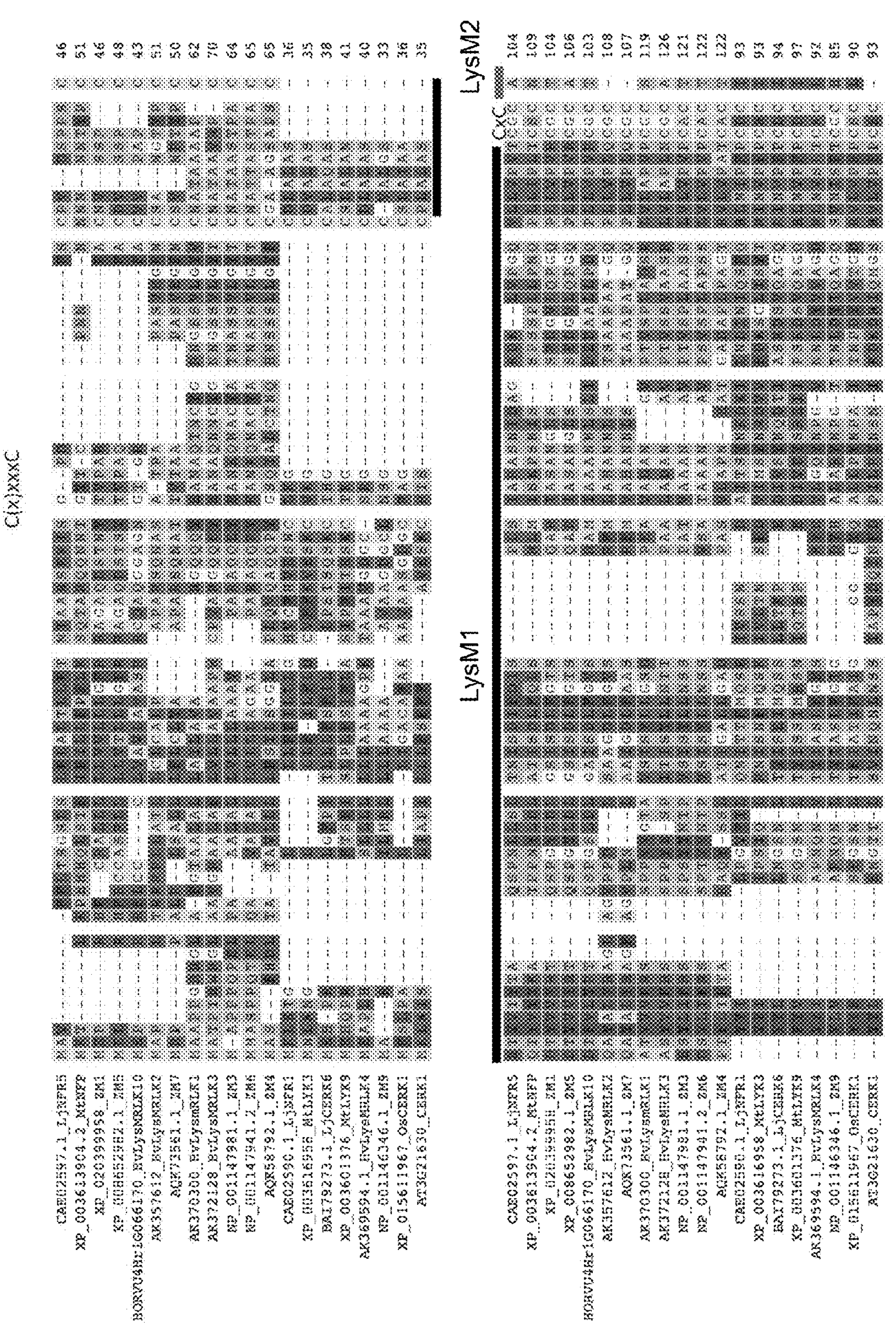
FIGS. 9A-9B show an alignment of selected LysM receptors from *Arabidopsis thaliana* (At; AT3G21630_CERK1 (SEQ ID NO: 37)), *Zea mays* (Zm; XP 020399958 ZM1 (SEQ ID NO: 20), XP_008652982.1_ZM5 (SEQ ID NO: 21), AQK73561.1_ZM7 (SEQ ID NO: 46), NP_001147981.1_ZM3 (SEQ ID NO: 47), NP_001147941.2_ZM6 (SEQ ID NO: 48), AQK58792.1_ZM4 (SEQ ID NO: 49), ZM9_NP_001146346.1 (SEQ ID NO: 34)), *Hordeum vulgare* (Hv; HORVU4Hr1G066170_HvLysMRLK10 (SEQ ID NO: 19), AK357612 HvLysMRLK2 (SEQ ID NO: 17), AK370300_HvLysmRLK1 (SEQ ID NO: 16), AK372128_HvLysMRLK3 (SEQ ID NO: 18), HvLysMRLK4_AK369594.1 (SEQ ID NO: 35)), *Oryza sativa* (Os; XP_015611967_OsCERK1 (SEQ ID NO: 36)), *Medicago truncatula* (Mt; XP 003613904.2 MtNFP (SEQ ID NO: 45), Mt_LYK3_XP_003616958 (SEQ ID NO: 33), Mt_LYK9 XP 003601376 (SEQ ID NO: 31)), and *Lotus japonicus* (Lj; CAE02590.1 NFR1 (SEQ ID NO: 32), CAE02597.1_NFR5 (SEQ ID NO: 40), BAI79273.1_CERK6 (SEQ ID NO: 30),). LjNFR1, LjNFR5, MtLYK3 and MtNFP are functional Nod factor receptors, AtCERK1, OsCERK1, LjCERK6 are functional chitin receptors. C(x)XXXC and CxC motifs flanking the three LysM domains are shown. LysM1 (black line), LysM2 (green line) and LysM3 (brown line) are shown. The number of “X” residues in the C(x)XXXC motif located before LysM1 varies between receptors and therefore the location of LysM1 (black line) changes accordingly in the alignments in this figure and in successive figures.
Figure 9B:
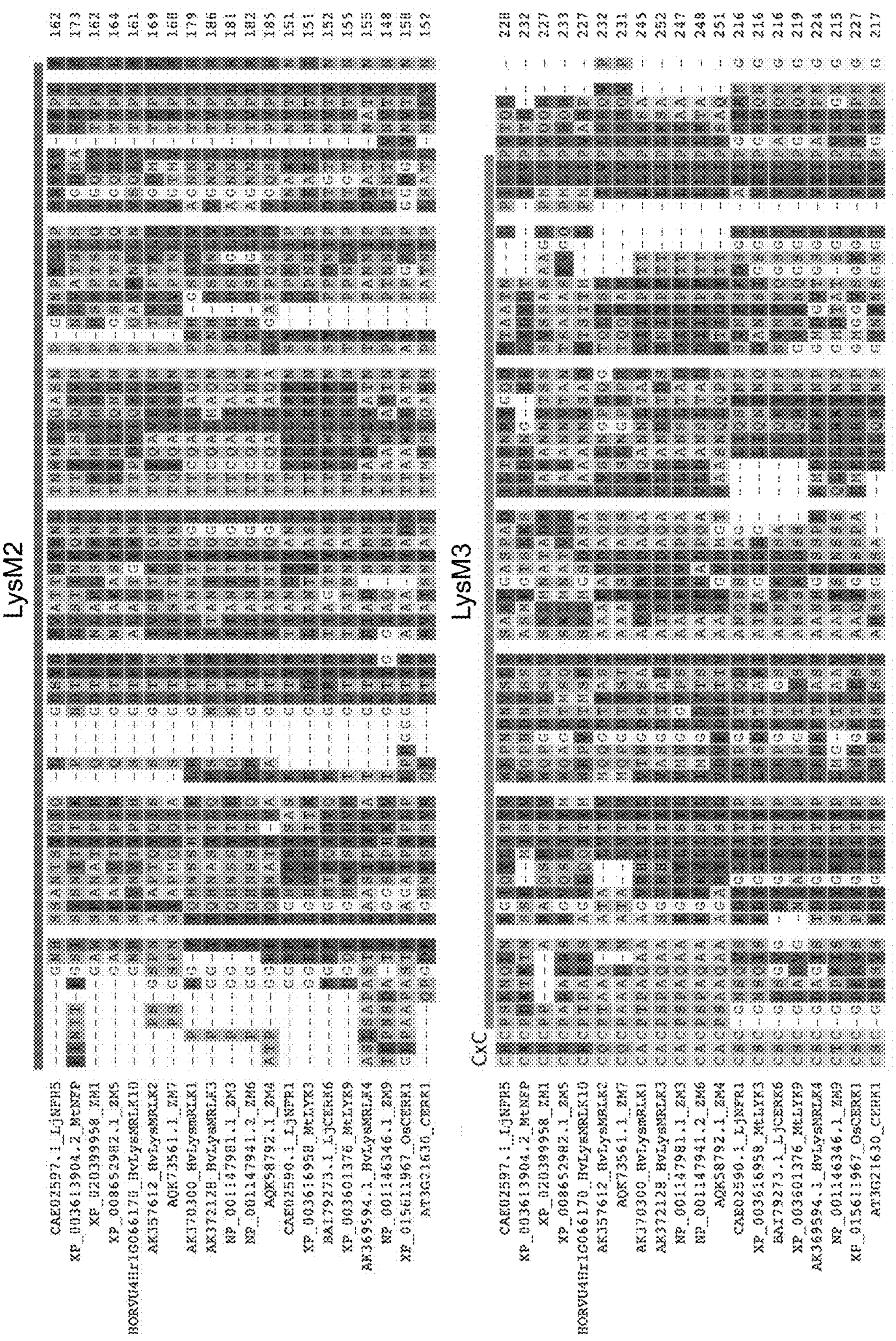
Figure 10A:
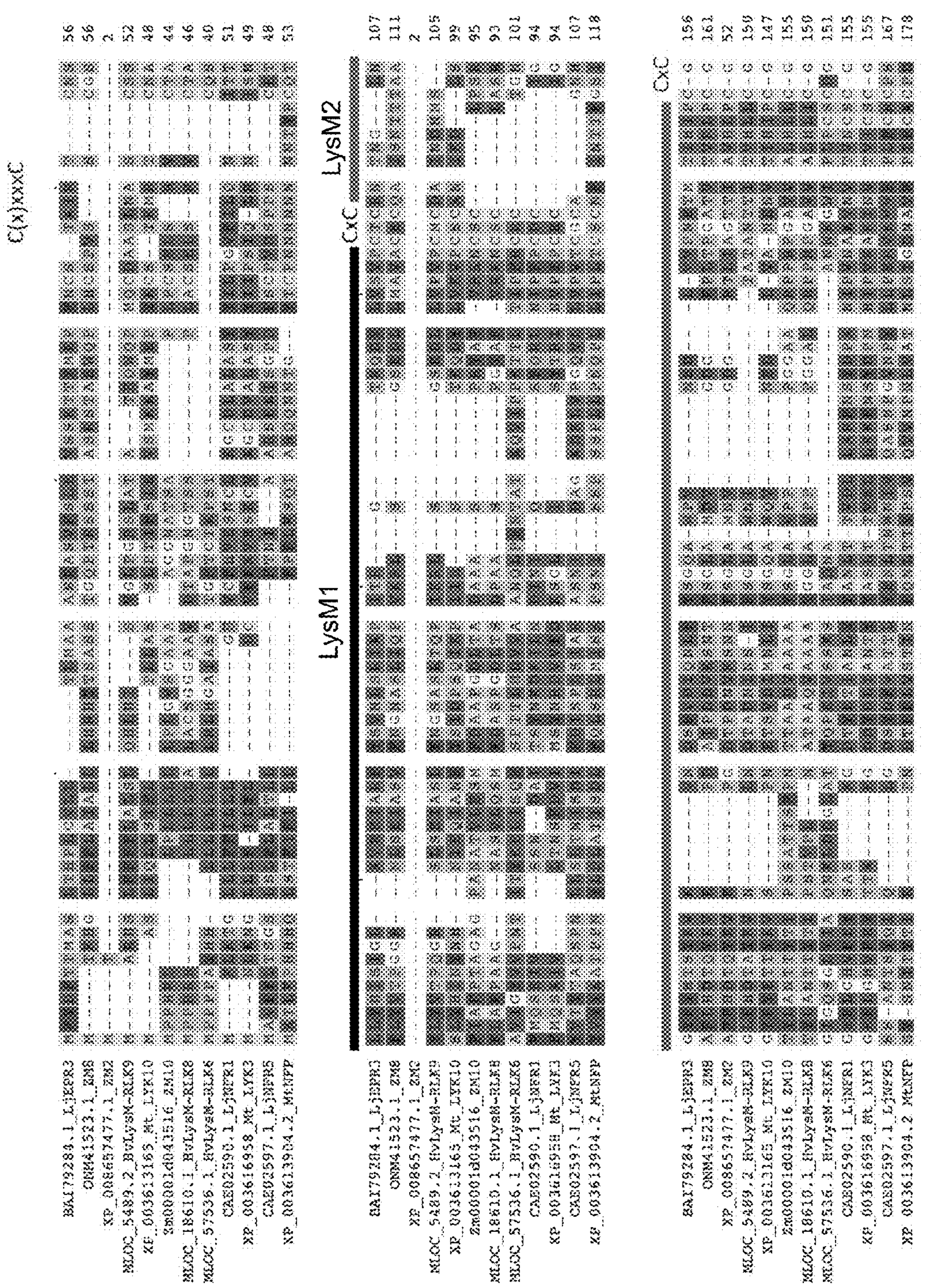
FIGS. 10A-10B show an alignment of selected LysM receptors from *Zea mays* (Zm; ONM41523.1_ZM8 (SEQ ID NO: 50), XP_008657477.1_ZM2 (SEQ ID NO: 51), Zm00001d043516 ZM10 (SEQ ID NO: 53)), *Hordeum vulgare* (Hv; MLOC_5489.2_HvLysM-RLK9 (SEQ ID NO: 52), MLOC_18610.1_HvLysM-RLK8 (SEQ ID NO: 54), MLOC_57536.1_HvLysM-RLK6 (SEQ ID NO: 55)), *Medicago truncatula* (Mt; Mt_LYK10 XP_003613165 (SEQ ID NO: 39), Mt_LYK3_XP_003616958 (SEQ ID NO: 33), XP_003613904.2 MtNFP (SEQ ID NO: 45)), and *Lotus japonicus* (Lj; BAI79284.1 EPR3 (SEQ ID NO: 38), CAE02590.1_NFR1 (SEQ ID NO: 32), CAE02597.1_NFR5 (SEQ ID NO: 40)). LjNFR1, LjNFR5, MtLYK3 and MtNFP are functional Nod factor receptors, LjEPR3 is functional EPS receptor. C(x)XXXC and CxC motifs flanking the three LysM domains are shown. LysM1 (black line), LysM2 (green line) and LysM3 (brown line) are shown.
Figure 10B:
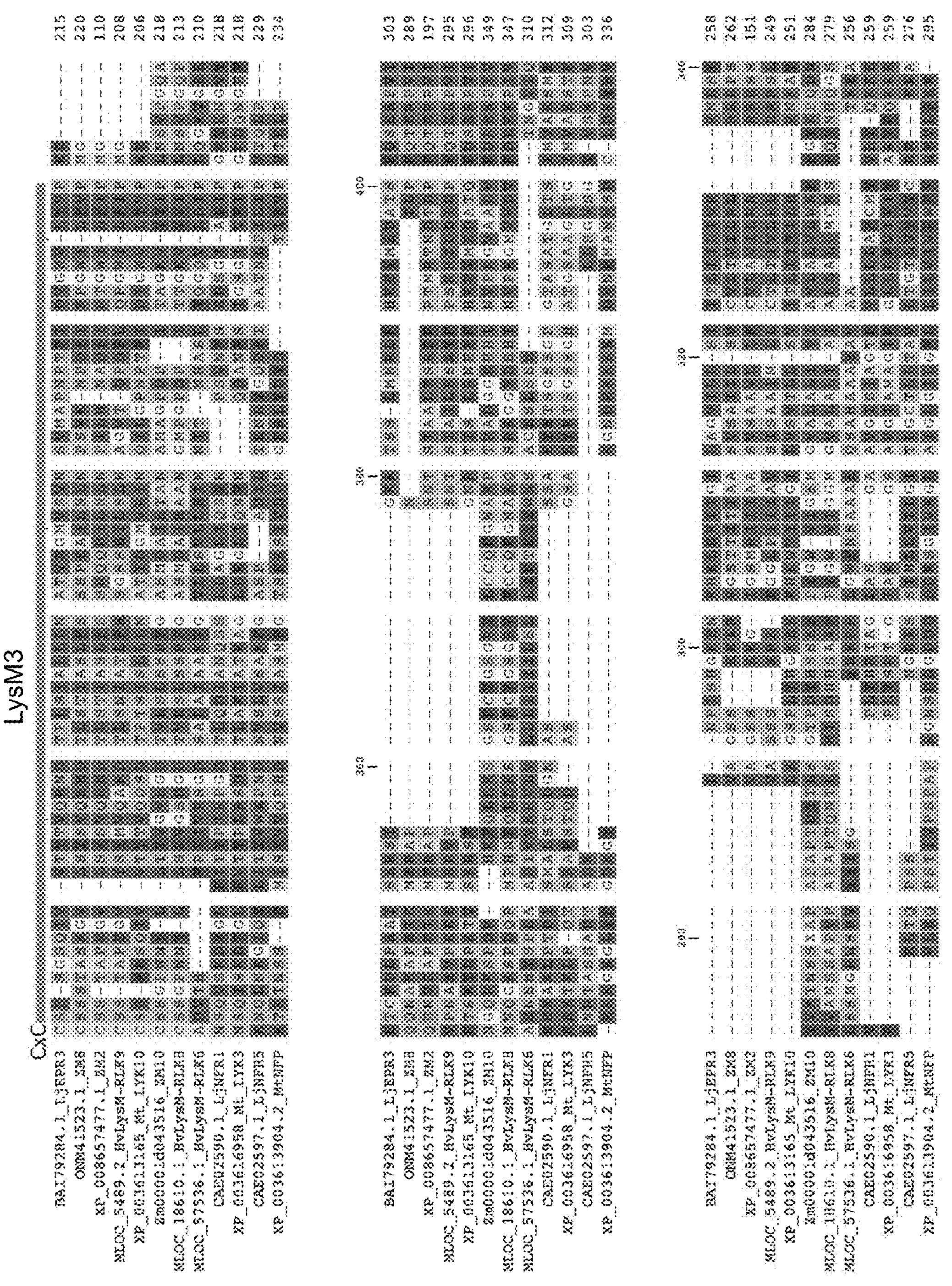
Figure 11A:
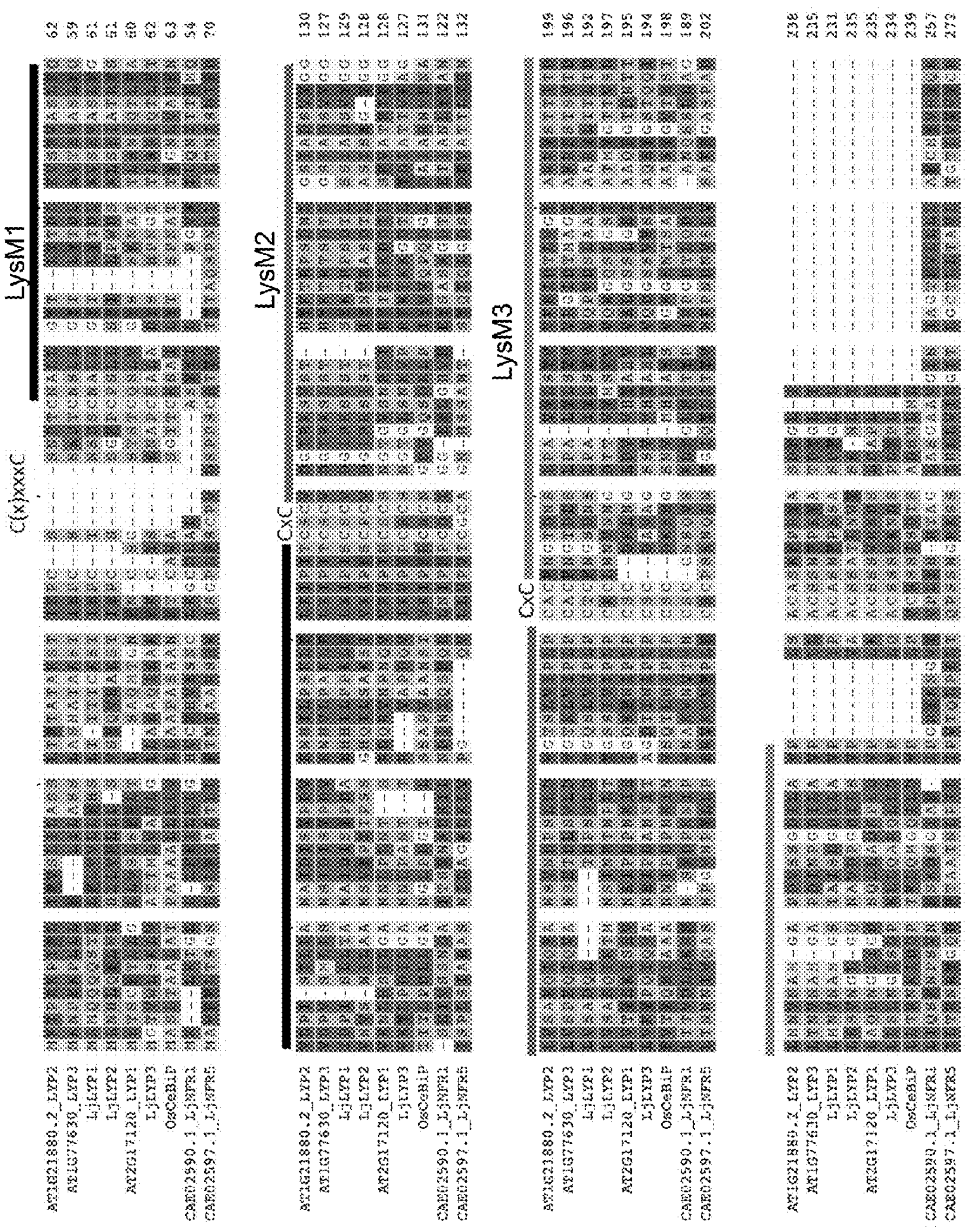
FIGS. 11A-11B show an alignment of selected LysM receptors from *Arabidopsis thaliana* (At; AT1G21880.2_LYP2 (SEQ ID NO: 56), AT1G77630_LYP3 (SEQ ID NO: 42), AT2G17120 LYP1 (SEQ ID NO: 44)), *Oryza sativa* (Os; OsCeBiP (SEQ ID NO: 43)), and *Lotus japonicus* (Lj; LjLYP1 (SEQ ID NO: 57), LjLYP2 (SEQ ID NO: 58), LjLYP3 (SEQ ID NO: 58), CAE02590.1_NFR1 (SEQ ID NO: 32), CAE02597.1_NFR5 (SEQ ID NO: 40)). LjNFR1, LjNFR5, are functional Nod factor receptors, AtLYP2 and AtLYP3, are PGN receptors, OsCeBiP is a functional chitin receptor. C(x)XXXC and CxC motifs flanking the three LysM domains are shown. LysM1 (black line), LysM2 (green line) and LysM3 (brown line) are shown.
Figure 11B:
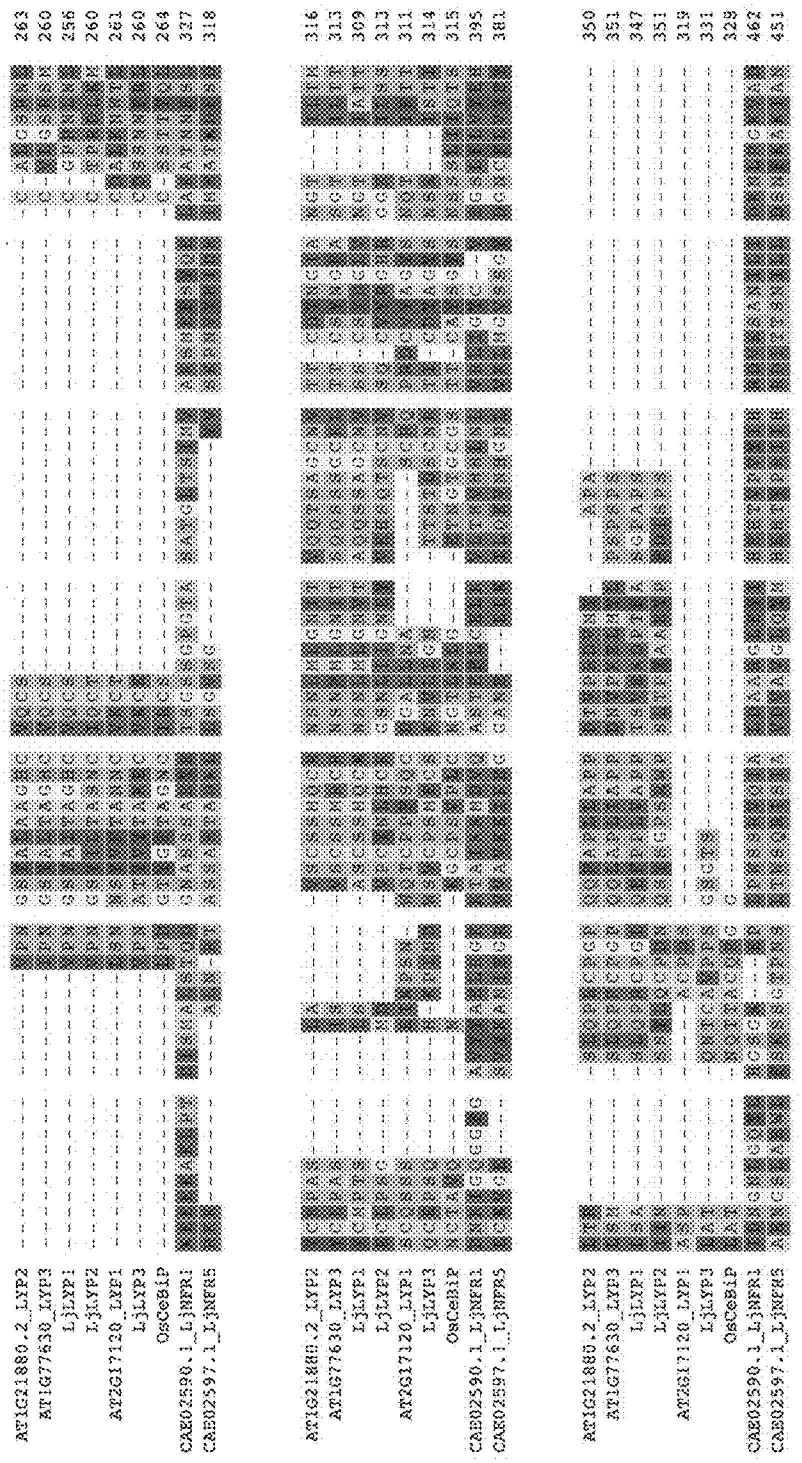

LysM receptors are a well known and well understood type of receptor. LysM receptors have three characteristic domains located in the ectodomain of the protein: LysM1, LysM2, and LysM3, which are present in this order on the protein sequence. The LysM1 domain is located toward the N-terminal end of the protein sequence, and is preceded by an N-terminal signal peptide as well as a C(x)xxxC motif. The LysM1 domain is separated from the LysM2 domain by a CxC motif, and the LysM2 domain is separated from the LysM3 domain by a CxC motif as well. The three LysM motifs, as well as the C(x)xxxC and CxC motif are clearly shown in FIGS. 8A-8C. FIGS. 9A-9B, FIGS. 10A-10B, and FIGS. 11A-11B show individual alignments of Nod factor (e.g., LCO) LysM receptors, EPS LysM receptors, and chitin (CO) as well as PGN LysM receptors, again clearly depicting the three LysM motifs as well as the C(x)xxxC and CxC motifs. The category of LysM receptors is therefore known by one of skill in the art.

As used in the present disclosure, the term "selectivity" refers to the differentiation between different polysaccharide ligands, specifically between lipo-chitooligosaccharides (LCOs) as a class and other polysaccharide ligands, preferably chitooligosaccharides (COs). The LysM receptors of the present disclosure contain a hydrophobic patch in their LysM2 domain. This hydrophobic patch confers selective recognition of LCOs over COs, and therefore LysM receptors with the hydrophobic patch have high selectivity as compared to LysM receptors without the hydrophobic patch.

As used in the present disclosure, the term "affinity" refers to affinity for LCOs generally. Again, the hydrophobic patch present in the LysM2 domain of LysM receptors of the present disclosure confers higher affinity for LCOs. Therefore, LysM receptors with the hydrophobic patch have high affinity as compared to LysM receptors without the hydrophobic patch. Affinity can be measured using the methods described in the Examples below, and using other methods known in the art that measure binding kinetics, association, dissociation, and $K_D$. For at least these reasons, the high affinity and high selectivity LysM receptors of the present disclosure will be readily understood by one of skill in the art.

Methods of Producing and Cultivating Genetically Altered Plants

Certain aspects of the present disclosure relate to a method of producing the genetically altered plant of any of the above embodiments, comprising introducing a genetic alteration to the plant comprising the nucleic acid sequence. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the nucleic acid sequence is inserted into the genome of the plant so that the nucleic acid sequence is operably linked to an endogenous promoter. In some embodiments, the endogenous promoter is a root specific promoter.

Certain aspects of the present disclosure relate to a method of producing a genetically altered plant able to recognize LCOs, comprising the steps of: introducing a genetic alteration to the plant comprising the provision of an ability for LCOs produced by nitrogen-fixing bacteria and/or mycorrhizal fungi to be recognized, thereby enabling the plant to recognize LCOs.

In some aspects, the present disclosure relates to a method of producing a genetically altered plant able to recognize LCOs, comprises the steps of: introducing a genetic alteration to the plant comprising the provision of an ability for LCOs produced by nitrogen-fixing bacteria and/or mycorrhizal fungi to be recognized with high affinity and/or high selectivity, thereby enabling the plant to recognize LCOs with high affinity and/or high selectivity.

In some aspects, the present disclosure relates to a method of cultivating a plant with the ability to recognize LCOs, comprising the steps of: providing a seed with one or more genetic alterations that provide an ability for LCOs produced by nitrogen-fixing bacteria and/or mycorrhizal fungi to be recognized, wherein the seed produces a plant with the ability to recognize LCOs produced by nitrogen-fixing bacteria and/or mycorrhizal fungi; cultivating the plant under conditions where the ability to recognize LCOs produced by nitrogen-fixing bacteria and/or mycorrhizal fungi results in increased growth, yield, and/or biomass, as compared to a plant grown under the same conditions that lacks the one or more genetic alterations. In some embodiments, the plant is cultivated in nutrient-poor soil.

In some aspects, the present disclosure relates to a method of cultivating a plant with the ability to recognize LCOs with high affinity and/or high selectivity, comprising the steps of: providing a seed with one or more genetic alterations that provide an ability for LCOs produced by nitrogen-fixing bacteria and/or mycorrhizal fungi to be recognized with high affinity and/or high selectivity, wherein the seed produces a plant with the ability to recognize LCOs produced by nitrogen-fixing bacteria and/or mycorrhizal fungi with high affinity and/or high selectivity; cultivating the plant under conditions where the ability to recognize LCOs produced by nitrogen-fixing bacteria and/or mycorrhizal fungi with high affinity and/or high selectivity results in increased growth, yield, and/or biomass, as compared to a plant grown under the same conditions that lacks the one or more genetic alterations. In some embodiments, the plant is cultivated in nutrient-poor soil.

In some aspects, the present disclosure relates to a method of cultivating a plant with the ability to recognize LCOs, comprising the steps of: providing a tissue culture or protoplast with one or more genetic alterations that provide an ability for LCOs produced by nitrogen-fixing bacteria and/or mycorrhizal fungi to be recognized; regenerating the tissue culture or protoplast into a plantlet; growing the plantlet into a plant, wherein the plant has the ability to recognize LCOs produced by nitrogen-fixing bacteria and/or mycorrhizal fungi; transplanting the plant into conditions where the ability to recognize LCOs produced by nitrogen-fixing bacteria and/or mycorrhizal fungi results in increased growth, yield, and/or biomass, as compared to a plant grown under the same conditions that lacks the one or more genetic alterations. In some embodiments, the plant is cultivated in nutrient-poor soil.

In some aspects, the present disclosure relates to a method of cultivating a plant with the ability to recognize LCOs with high affinity and/or high selectivity, comprising the steps of: providing a tissue culture or protoplast with one or more genetic alterations that provide an ability for LCOs produced by nitrogen-fixing bacteria and/or mycorrhizal fungi to be recognized with high affinity and/or high selectivity, regenerating the tissue culture or protoplast into a plantlet; growing the plantlet into a plant, wherein the plant has the ability to recognize LCOs produced by produced by nitrogen-fixing bacteria and/or mycorrhizal fungi with high affinity and/or high selectivity; transplanting the plant into conditions where the ability to recognize LCOs produced by nitrogen-fixing bacteria and/or mycorrhizal fungi with high affinity and/or high selectivity results in increased growth, yield, and/or biomass, as compared to a plant grown under the same conditions that lacks the one or more genetic alterations. In some embodiments, the plant is cultivated in nutrient-poor soil.

In some embodiments of any of the above methods, the ability to recognize LCOs is conferred by a nucleic acid sequence encoding a heterologous receptor polypeptide, wherein the heterologous receptor polypeptide is selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:5 (i.e., chickpea, *Cicer arietinum* NFR5), a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:7 (i.e., bean, *Phaseolus vulgaris* NFR5), a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:9 (i.e., peanut, *Arachis* NFR5), a fourth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:11 (i.e., *Lotus* LYS11), a fifth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:12 (i.e., *Medicago* LYR1), a sixth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:13 (i.e., *Parasponia* NFP1), a seventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:16 (i.e., barley HvLysM-RLK1 (AK370300)), an eighth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:17 (i.e., barley HvLysM-RLK2 (AK357612)), a ninth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:18 (i.e., barley HvLysM-RLK3 AK372128), a tenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:19 (i.e., barley HvLysM-RLK10 (HORVU4Hr1 G066170)), an eleventh polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:20 (i.e., maize ZM1 (XP_020399958)), a twelfth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:21 (i.e., maize ZM5 (XP_008652982.1)), a thirteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:22 (i.e., apple NFP5 XP_008338966.1), or a fourteenth polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% sequence identity to SEQ ID NO:23 (i.e., strawberry NFR5 XP_004300586.2). In some embodiments, the heterologous receptor polypeptide is selected from the group of SEQ ID NO:5 (i.e., chickpea, *Cicer arietinum* NFR5), SEQ ID NO:7 (i.e., bean, *Phaseolus vulgaris* NFR5), SEQ ID NO:9 (i.e., peanut, *Arachis* NFR5), SEQ ID NO:11 (i.e., *Lotus* LYS11), SEQ ID NO:12 (i.e., *Medicago* LYR1), SEQ ID NO:13 (i.e., *Parasponia* NFP1), SEQ ID NO:16 (i.e., barley HvLysM-RLK1 (AK370300)), SEQ ID NO:17 (i.e., barley HvLysM-RLK2 (AK357612)), SEQ ID NO:18 (i.e., barley HvLysM-RLK3 AK372128), SEQ ID NO:19 (i.e., barley HvLysM-RLK10 (HORVU4Hr1 G066170)), SEQ ID NO:20 (i.e., maize ZM1 (XP_020399958)), SEQ ID NO:21 (i.e., maize ZM5 (XP_008652982.1)), SEQ ID NO:22 (i.e., apple NFP5 XP_008338966.1), and SEQ ID NO:23 (i.e., strawberry NFR5 XP_004300586.2). In some embodiments, the expression of the heterologous receptor polypeptide allows the plant or part thereof to recognize lipo-chitooligosaccharides (LCOs) through the heterologous receptor polypeptide. In some embodiments, the LCOs are produced by nitrogen-fixing bacteria or by mycorrhizal fungi. In some embodiments, the LCOs are produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli, Burkholderiales* optionally symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizobium* spp., *Azorhizobium* spp. *Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division *Glomeromycota*, or any combination thereof. In some embodiments, the heterologous polypeptide is localized to a plant cell plasma membrane. In some embodiments, the plant cell is a root cell. In some embodiments, the root cell is a root epidermal cell or a root cortex cell. In some embodiments, the heterologous polypeptide is expressed in a developing plant root system. In some embodiments, the nucleic acid sequence is operably linked to a promoter. In some embodiments, the promoter is a root specific promoter. In some embodiments, the promoter is selected from the group of a NFR1 or NFR5/NFP promoter, the *Lotus* NFR5 promoter (SEQ ID NO: 24) and the *Lotus* NFR1 promoters (SEQ ID NO:25) the maize allothioneine promoter, the chitinase promoter, the maize ZRP2 promoter, the tomato LeExtl promoter, the glutamine synthetase soybean root promoter, the RCC3 promoter, the rice antiquitine promoter, the LRR receptor kinase promoter, or the *Arabidopsis* pCO2 promoter. In some embodiments, the promoter is a constitutive promoter optionally selected from the group of the CaMV35S promoter, a derivative of the CaMV35S promoter, the maize ubiquitin promoter, the trefoil promoter, a vein mosaic cassava virus promoter, or the *Arabidopsis* UBQ10 promoter. In some embodiments, the plant is selected from the group of corn (e.g., maize, *Zea mays*), rice (e.g., *Oryza sativa, Oryza glaberrima, Zizania* spp.), barley (e.g., *Hordeum vulgare*), wheat (e.g., common wheat, spelt, durum, *Triticum aestivum, Triticum spelta, Triticum durum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa*), apple (e.g., *Malus pumila*), pear (e.g., *Pyrus communis, Pyrus xbretschneideri, Pyrus pyrifolia, Pyrus sinkiangensis, Pyrus pashia, Pyrus* spp.), plum (e.g., prune, damson, bullaces, *Prunus domestica, Prunus salicina*), apricot (e.g., *Prunus armeniaca, Prunus brigantina, Prunus mandshurica, Prunus mume, Prunus sibirica*), peach (e.g., nectarine, *Prunus persica*), almond (e.g., *Prunus dulcis, Prunus amygdalus*), walnut (e.g., Persian walnut, English walnut, black walnut, *Juglans regia, Juglans nigra, Juglans cinerea, Juglans californica*), strawberry (e.g., *Fragaria× ananassa, Fragaria chiloensis, Fragaria virginiana, Fragaria vesca*), raspberry (e.g., European red raspberry, black raspberry, *Rubus idaeus, Rubus occidentalis, Rubus strigosus*), blackberry (e.g., evergreen blackberry, Himalayan blackberry, *Rubus fruticosus, Rubus ursinus, Rubus laciniatus, Rubus argutus, Rubus armeniacus, Rubus plicatus, Rubus ulmifolius, Rubus allegheniensis*), red currant (e.g., *Ribes rubrum, Ribes spicatum, Ribesbes alpinum, Ribes schlechtendalii, Ribes multiflorum, Ribes petraeum, Ribes triste*), black currant (e.g., *Ribes nigrum*), melon (e.g., watermelon, winter melon, casabas, cantaloupe, honeydew, muskmelon, *Citrullus lanatus, Benincasa hispida, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vinifera, Vitis amurensis, Vitis labrusca, Vitis mustangensis, Vitis riparia, Vitis rotundifolia*), or hemp (e.g., *cannabis, Cannabis sativa*).

Molecular Biological Methods to Produce Genetically Altered Plants and Plant Cells One embodiment of the present invention provides a genetically altered plant or plant cell comprising one or more modified plant genes and/or introduced genes. For example, the present disclosure provides genetically altered plants with a nucleic acid sequence encoding a heterologous receptor polypeptide. The heterologous receptor allows the plants to recognize lipo-chitooligosaccharides (LCOs) through the heterologous receptor polypeptide.

Transformation and generation of genetically altered monocotyledonous and dicotyledonous plant cells is well known in the art. See, e.g., Weising, et al., Ann. Rev. Genet. 22:421-477 (1988); U.S. Pat. No. 5,679,558; *Agrobacterium* Protocols, ed: Gartland, Humana Press Inc. (1995); and Wang, et al. Acta Hort. 461:401-408 (1998). The choice of method varies with the type of plant to be transformed, the particular application and/or the desired result. The appropriate transformation technique is readily chosen by the skilled practitioner.

Any methodology known in the art to delete, insert or otherwise modify the cellular DNA (e.g., genomic DNA and organelle DNA) can be used in practicing the inventions disclosed herein. As an example, the CRISPR/Cas-9 and related systems may be used to insert a heterologous gene to a targeted site in the genomic DNA or substantially edit an endogenous gene to express the heterologous gene. For example, a disarmed Ti plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833 839); Gordon-Kamm et al., The Plant Cell, (1990) 2, 603 618) and rice (Shimamoto et al., Nature, (1989) 338, 274 276; Datta et al., Bio/Technology, (1990) 8, 736 740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

Genetically altered plants of the present invention can be used in a conventional plant breeding scheme to produce more genetically altered plants with the same characteristics, or to introduce the genetic alteration(s) in other varieties of the same or related plant species. Seeds, which are obtained from the altered plants, preferably contain the genetic alteration(s) as a stable insert in chromosomal or organelle DNA or as modifications to an endogenous gene or promoter. Plants comprising the genetic alteration(s) in accordance with the invention include plants comprising, or derived from, root stocks of plants comprising the genetic alteration (s) of the invention, e.g., fruit trees or ornamental plants. Hence, any non-transgenic grafted plant parts inserted on a transformed plant or plant part are included in the invention.

Introduced genetic elements, whether in an expression vector or expression cassette, which result in the expression of an introduced gene will typically utilize a plant-expressible promoter. A 'plant-expressible promoter' as used herein refers to a promoter that ensures expression of the genetic alteration(s) of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871 2887), CabbB S (Franck et al., Cell (1980) 21, 285 294) and CabbB JI (Hull and Howell, Virology, (1987) 86, 482 493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T DNA (Velten et al., EMBO J, (1984) 3, 2723 2730).

Alternatively, a plant-expressible promoter can be a tissue-specific promoter, e.g., a promoter directing a higher level of expression in some cells or tissues of the plant, e.g., in root epidermal cells. Examples of constitutive promoters that are often used in plant cells are the cauliflower mosaic (CaMV) 35S promoter (KAY et al. Science, 236, 4805, 1987), and various derivatives of the promoter, the maize ubiquitin promoter (CHRISTENSEN & QUAIL, Transgenic Res, 5, 213-8, 1996), the trefoil promoter (Ljubql, MAEKAWA et al. Mol Plant Microbe Interact. 21, 375-82, 2008), the vein mosaic cassava virus promoter (International Application WO 97/48819), and the *Arabidopsis* UBQ10 promoter, Norris et al. Plant Mol. Biol. 21, 895-906, 1993).

In preferred embodiments, root specific promoters will be used. Non-limiting examples include a NFR1 or NFR5/NFP promoter, particularly the *Lotus* NFR5 promoter (SEQ ID NO: 24) and the *Lotus* NFR1 promoters (SEQ ID NO: 25) the maize allothioneine promoter (DE FRAMOND et al, FEBS 290, 103-106, 1991 Application EP 452269), the chitinase promoter (SAMAC et al. Plant Physiol 93, 907-914, 1990), the maize ZRP2 promoter (U.S. Pat. No. 5,633,363), the tomato LeExtlpromoter (Bucher et al. Plant Physiol. 128, 911-923, 2002), the glutamine synthetase soybean root promoter (HIREL et al. Plant Mol. Biol. 20, 207-218, 1992), the RCC3 promoter (PCT Application WO 2009/016104), the rice antiquitine promoter (PCT Application WO 2007/076115), the LRR receptor kinase promoter (PCT application WO 02/46439), and the *Arabidopsis* pCO2 promoter (HEIDSTRA et al, Genes Dev. 18, 1964-1969, 2004). These plant promoters can be combined with enhancer elements, they can be combined with minimal promoter elements, or can comprise repeated elements to ensure the expression profile desired.

In some embodiments, genetic elements to increase expression in plant cells can be utilized. For example, an intron at the 5' end or 3' end of an introduced gene, or in the coding sequence of the introduced gene, e.g., the hsp70 intron. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

An introduced gene of the present invention can be inserted in host cell DNA so that the inserted gene part is upstream (i.e., 5') of suitable 3' end transcription regulation signals (e.g., transcript formation and polyadenylation signals). This is preferably accomplished by inserting the gene in the plant cell genome (nuclear or chloroplast). Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835 845), the SCSV or the Malic enzyme terminators (Schunmann et al., Plant Funct Biol, (2003) 30:453-460), and the T DNA gene 7 (Velten and Schell, Nucleic Acids Res, (1985) 13, 6981 6998), which act as 3' untranslated DNA sequences in transformed plant cells. In some embodiments, one or more of the introduced genes are stably integrated into the nuclear genome. Stable integration is present when the nucleic acid sequence remains integrated into the nuclear genome and continues to be expressed (e.g., detectable mRNA transcript or protein is produced) throughout subsequent plant generations. Stable integration into and/or editing of the nuclear genome can be accomplished by any known method in the art (e.g., microparticle bombardment, *Agrobacterium*-mediated transformation, CRISPR/Cas9, electroporation of protoplasts, microinjection, etc.).

The term recombinant or modified nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As used herein, the terms "overexpression" and "upregulation" refer to increased expression (e.g., of mRNA, polypeptides, etc.) relative to expression in a wild type organism (e.g., plant) as a result of genetic modification. In some embodiments, the increase in expression is a slight increase of about 10% more than expression in wild type. In some embodiments, the increase in expression is an increase of 50% or more (e.g., 60%, 70%, 80%, 100%, etc.) relative to expression in wild type. In some embodiments, an endogenous gene is overexpressed. In some embodiments, an exogenous gene is overexpressed by virtue of being expressed. Overexpression of a gene in plants can be achieved through any known method in the art, including but not limited to, the use of constitutive promoters, inducible promoters, high expression promoters (e.g., PsaD promoter), enhancers, transcriptional and/or translational regulatory sequences, codon optimization, modified transcription factors, and/or mutant or modified genes that control expression of the gene to be overexpressed.

Where a recombinant nucleic acid is intended for expression, cloning, or replication of a particular sequence, DNA constructs prepared for introduction into a host cell will typically comprise a replication system (e.g. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., plasma membrane localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology (e.g., sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Preferred host cells are plant cells. Recombinant host cells, in the present context, are those which have been genetically modified to contain an isolated nucleic molecule, contain one or more deleted or otherwise non-functional genes normally present and functional in the host cell, or contain one or more genes to produce at least one recombinant protein. The nucleic acid(s) encoding the protein(s) of the present invention can be introduced by any means known to the art which is appropriate for the particular type of cell, including without limitation, transformation, lipofection, electroporation or any other methodology known by those skilled in the art.

Having generally described this invention, the same will be better understood by reference to certain specific examples, which are included herein to further illustrate the invention and are not intended to limit the scope of the invention as defined by the claims.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

Example 1: Expression and Purification of *Medicago* NFP Ectodomain

The following example describes the protein expression and purification materials and methods that were used to prepare protein for all of the following examples.

Materials and Methods

Expression and purification of *Medicago* NFP ectodomain: The *Medicago truncatula* NFP ectodomain (residues 28-246) was codon-optimized for insect cell expression (Genscript, Piscataway, USA) and cloned into the pOET4 baculovirus transfer vector (Oxford Expression Technologies). The native NFP signal peptide (residues 1-27, predicted by SignalP 4.1) was replaced with the AcMNPV gp67 signal peptide to facilitate secretion and a hexa-histidine tag was added to the C-terminus. Point mutants of NFP were engineered using site-directed mutagenesis. Recombinant baculoviruses were produced in Sf9 cells (*Spodoptera frugiperda*) using the FlashBac Gold kit (Oxford Expression technologies) according to the manufacturer's instructions with Lipofectin (ThermoFisher Scientific) as a transfection reagent. Protein expression was performed as follows. Suspension-cultured Sf9 cells were maintained with shaking at 299 K in serum-free MAX-XP (BD-Biosciences, discontinued) or HyClone SFX (GE Healthcare) medium supplemented with 1% Pen-Strep (10000 U/ml, Life technologies) and 1% CD lipid concentrate (Gibco). Protein expression was induced by adding recombinant passage 3 virus once the Sf9 cells reached a cell density of 1.0*$10^{7}$^6 cells/ml. After 5-7 days of expression, medium supernatant containing NFP ectodomains was harvested by centrifugation. This was followed by an overnight dialysis step against 50 mM Tris-HCl pH 8, 200 mM NaCl at 277 K. The NFP ectodomain was enriched by two subsequent steps of Ni-IMAC purification (HisTrap excel/HisTrap HP, both GE Healthcare). For crystallography experiments, N-glycans were removed using the endoglycosidase PNGase F (1:15 (w/w), room temperature, overnight). As a final purification step, NFP ectodomain was purified by SEC on a Superdex 200 10/300 or HiLoad Superdex 200 16/600 (both GE Healthcare) in phosphate buffered saline at pH 7.2 supplemented to a total of 500 mM NaCl (for binding assays) or 50 mM Tris-HCl, 200 mM NaCl (for crystallography). NFP ectodomain elutes as a single, homogeneous peak corresponding to a monomer. Point mutated versions of NFP were expressed and purified following the same protocol.

Example 2: Structural Characterization of *Medicago* NFP Ectodomain

The following example describes the structural characterization of the *Medicago* NFP protein ectodomain.

Materials and Methods

Crystallization and structure determination: Crystals of deglycosylated NFP ectodomain (see Example 1) were obtained using a vapour diffusion setup at 3-5 mg/ml in 0.2 M Na-acetate, 0.1 M Na-cacodylate pH 6.5, and 30% (w/v) PEG-8000. Crystals were cryoprotected in their crystallization condition by supplementing with 5% (w/v) PEG-400 before being snap-frozen in liquid nitrogen. Complete diffraction data to 2.85 Å resolution was obtained at the MaxLab 1911-3 beamline. The phase problem was solved by molecular replacement using Phaser from the PHENIX suite with a homology model based on the AtCERK1 ectodomain structure (PDB coordinates 4EBZ) as a search model. Model building and refinement was done using COOT and the PHENIX suite, respectively. The output pdb filled structural model was generated and its electrostatic surface potential was calculated using the PDB2PQR and APBS webservers (PMID: 21425296). The results were visualized in PyMol using APBS tools 2.1 (DeLano, W. L. (2002). PyMOL. DeLano Scientific, San Carlos, CA, 700.).

Small-angle X-ray scattering (SAXS): Small-angle X-ray scattering of NFP-ECD was measured in batch at different concentrations (1, 2, 4 and 6 mg/ml for glycosylated NFP-ECD; and 1, 2 and 3 mg/ml for deglycosylated NFP-ECD and 1, 2, 4) in phosphate buffered saline, pH 7.4, 500 mM NaCl, at the EMBL β12 beamline PETRA III in a temperature-controlled cell at 20° C. at a wavelength of 1.24 Å. Data analysis and modelling was done using BioXTAS RAW, GNOM and the ATSAS program suite (Hopkins, J. B., Gillilan, R. E. & Skou, S. BioXTAS RAW: Improvements to a free open-source program for small-angle X-ray scattering data reduction and analysis. *Journal of Applied Crystallography* 50, 1545-1553 (2017); Svergun, D. I. Determination of the regularization parameter in indirect-transform methods using perceptual criteria. *Journal of Applied Crystallography* 25, 495-503 (1992); Konarev, P. V., Volkov, V. V., Sokolova, A. V., Koch, M. H. J. & Svergun, D. I. PRIMUS: a Windows PC-based system for small-angle scattering data analysis. *Journal of Applied Crystallography* 36, 1277-1282 (2003)). The ab initio low resolution structure was modelled in DAMMIF using 15 individual reconstructions. Envelopes were aligned and averaged with DAMAVER (Franke, D. & Svergun, D. I. DAMMIF, a program for rapid ab-initio shape determination in small-angle scattering. *Journal of Applied Crystallography* 42, 342-346 (2009)). The average was finally refined in DAMMIN (Svergun, D. I. Restoring Low Resolution Structure of Biological Macromolecules from Solution Scattering Using Simulated Annealing. *Biophysical Journal* 76, 2879-2886 (1999)). NFP-ECD models with added N- and C-terminal tails were rigid-body fitted into envelopes with colors (Wriggers, W. & Chacon, P. Using Situs for the registration of protein structures with low resolution bead models from x-ray solution scattering. *Journal of Applied Crystallography* 914 34, 773-776 (2001)). Theoretical scattering curves were calculated in CRYSOL online (Svergun, D., Barberato, C. & Koch, M. H. J. CRYSOL—a Program to Evaluate X-ray Solution Scattering of Biological Macromolecules from Atomic Coordinates. *Journal of Applied Crystallography* 28, 768-773 (1995)). Dimensionless Kratky plots were prepared in BioXTAS RAW (Hopkins, J. B., Gillilan, R. E. & Skou, S. BioXTAS RAW: Improvements to a free open-source program for small-angle X-ray scattering data reduction and analysis. *Journal of Applied Crystallography* 50, 1545-1553 (2017)). The molecular weight derived from the forward scattering was determined using an internal BSA standard. Mixtures were analysed with OLIGOMER (Konarev, P. V., Volkov, V. V., Sokolova, A. V., Koch, M. H. J. & Svergun, D. I. PRIMUS: a Windows PC-based system for small-angle scattering data analysis. *Journal of Applied Crystallography* 36, 1277-1282 (2003)).

Results

Figure 1A:
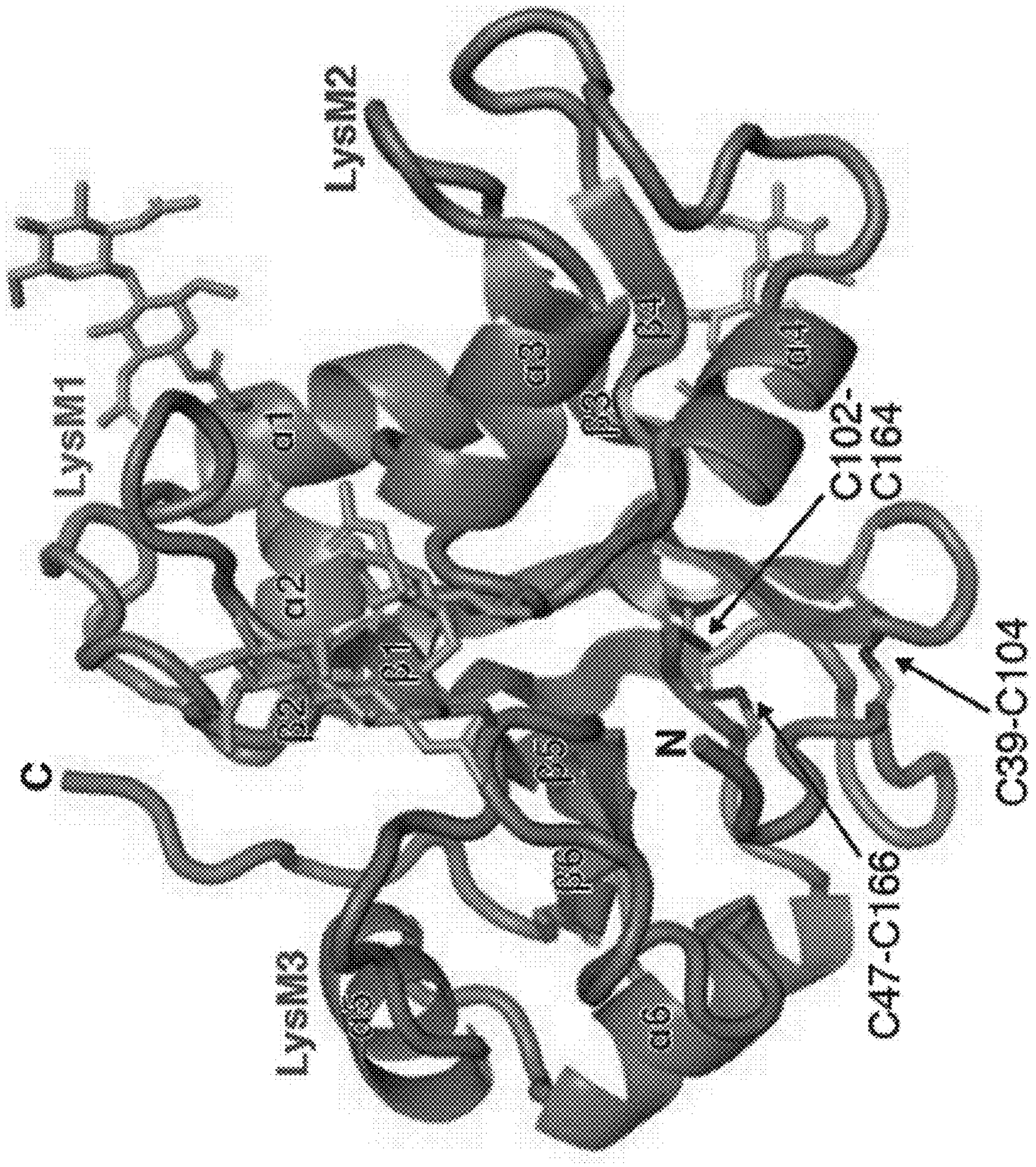
FIGS. 1A-1B show the structure of the NFP receptor ectodomain (NFP-ECD).

The structure of *Medicago* NFP-ECD was determined by molecular replacement using a homology model based on the inner low B-factor scaffold of AtCERK1. The complete structure of the NFP-ECD (residues 33-233) was built this way, including four N-glycosylations that were clearly resolved in the 2.8 Å electron density map. NFP forms a compact structure where three classical βααβ LysM domains are tightly interconnected and stabilized by 3 conserved disulfide bridges (C3-C104, C47-C166 and C102-C164) (FIG. 1A). The disulfide connectivity pattern and the overall scaffold arrangement is shared with other LysM-RLK proteins involved in chitin defense signaling, supporting a common evolutionary origin of these class of receptors (Zhang 2007).

Figure 1B:
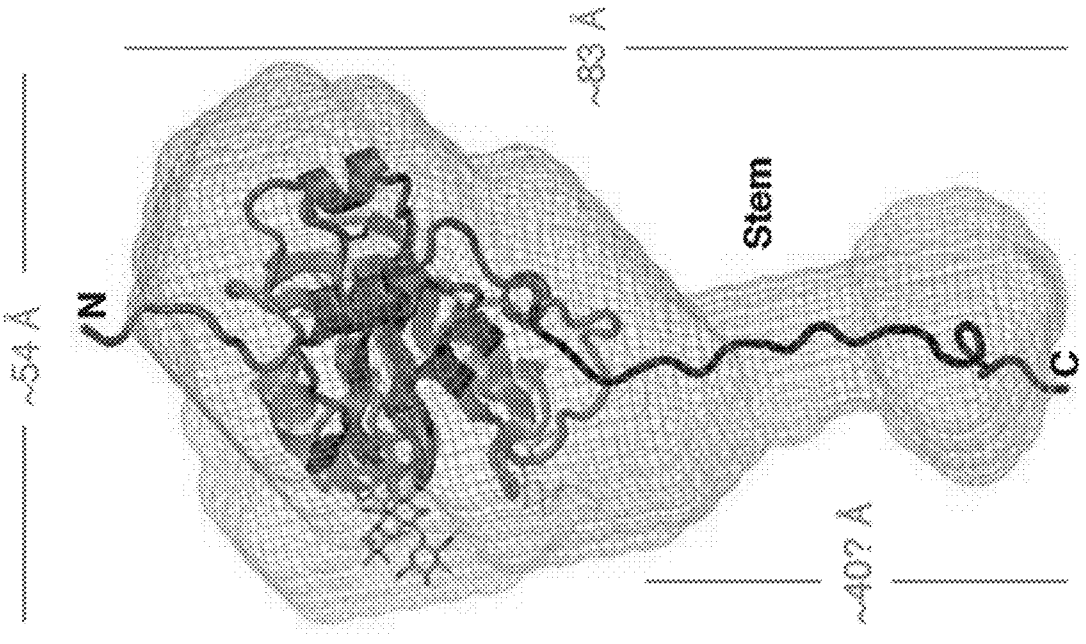

To confirm the determined structure, small-angle X-ray scattering (SAXS) measurements were performed on the NFP-ECD. FIG. 1B shows the SAXS reconstructed envelope, which has the same overall dimensions as the determined structure and otherwise fits well with the crystal structure. In addition, an elongated ridged structure most likely originating from the C-terminal stalk region of the receptor was seen in the SAXS reconstructed envelope. This stalk region is conserved in length and to some degree in sequence amongst LCO LysM receptor homologues, suggesting that the ectodomain in these receptors needs a certain distance from the membrane for correct function.

SAXS measurements were also performed to compare deglycosylated and glycosylated NFP-ECD. FIG. 14A shows the SAXS analysis of deglycosylated NFP-ECD, while FIG. 14B shows the SAXS analysis of glycosylated NFP-ECD. The SAXS data and the reconstructed ab initio model are in agreement with the crystal structure, however in addition an elongated stem like structure is present (FIG. 1B). This stem region is most likely comprised of the C-terminal part of NFP which was not visible in the crystal structure and might serve to position the ectodomain of NFP at the correct distance from the plasma membrane. FIG. 14C compares the dimensionless Kratky plots for deglycosylated and glycosylated NFP-ECD, and this comparison showed that glycans have an effect on the globularity of NFP-ECD. Glycosylated NFP-ECD had a more globular shape, where the peak lay close to the Guinier-Kratky point (dotted line, left graph of FIG. 14C) and closer to the surface/volume ratio of an ideal sphere (0.82, dotted line, right graph of FIG. 14C). This more globular shape was likely due to the presence of 15-20 kDa of glycans. The loss of globularity and elongated shape became more pronounced and visible upon glycan removal (deglycosylated NFP-ECD in both graphs of FIG. 14C).

Example 3: NFP Binding Ability and Affinity for Different Chitooligosaccharide (CO), Lipochitooligosaccharide (LCO), and Carbohydrate Ligands The following example describes experiments measuring NFP binding ability and affinity. These experiments were designed to investigate whether NFP has differential binding ability and affinity for different ligands.

Materials and Methods

Microscale thermophoresis (MST): NFP were fluorescently labelled (Protein Labeling Kit Blue NHS, NanoTemper Technologies). A constant concentration of NFP was used to measure binding to dilution series of ligands. The ligands used were CO4 chitin oligomer (corresponding to the backbone of *S. meliloti* LCO-IV), CO5 chitin oligomer (corresponding to the backbone of *S. meliloti* LCO-V), maltohexaose (carbohydrate from *S. meliloti*), and octosaccharide exopolysaccharide (EPS). Data analysis was performed in GraphPad Prism7 software (GraphPad Software, Inc.) using the sigmoidal dose-response model to obtain equilibrium dissociation constants values.

Biolayer interferometry (BLI): Binding of NFP and mutated versions of NFP to ligands was measured on an Octet RED 96 system (Pall ForteBio). The ligands used were LCO-IV (from *S. meliloti*), LCO-V (from *S. meliloti*), LCO-V (from *M. loti*), and C06 (from *M. loti*). *S. meliloti* LCO consists of a tetrameric/pentameric N-acetylglucosamine backbone that is 0-sulfated on the reducing terminal residue, 0-acetylated on the non-reducing terminal residue, and mono-N-acylated by unsaturated C16 acyl groups. *M. loti* LCO is a pentameric N-acetylglucosamine with a cis-vaccenic acid and a carbamoyl group at the non-reducing terminal residue together with a 2,4-O-acetylfucose at the reducing terminal residue. Biotinylated ligand conjugates were immobilized on streptavidin biosensors (kinetic quality, Pall ForteBio) at a concentration of 125-250 nM for 5 minutes. The binding assays using the *S. meliloti* ligands (LCO-IV and LCO-V) were replicated seven times, while the binding assays using the *M. loti* ligands (LCO-V and C06) were replicated six times. Data analysis was performed in GraphPad Prism 6 software (GraphPad Software, Inc.). Equilibrium dissociation constants derived from the steady-state were determined by applying a non-linear regression (one site, specific binding) to the response at equilibrium plotted against the protein concentration. Kinetic parameters were determined by non-linear regression (association followed by dissociation) on the subtracted data.

Results

Since LCOs consist of a N-acetylglucosamine (chitin) backbone, the first tests measured whether NFP has affinity for CO4 and CO5 chitin oligomers that correspond to the backbone of *S. meliloti* LCO-IV and LCO-V, respectively. In microscale thermophoresis (MST) experiments, NFP was found to bind CO4 and CO5 with a dissociation constant of (Kd), 150 μM and 93 μM respectively. NFP is, however, not able to bind the unrelated carbohydrate ligands maltohexaose or octasaccharide exopolysaccharide purified from *S. meliloti*. This shows that NFP selectively binds chitinous ligands.

Figure 2A:
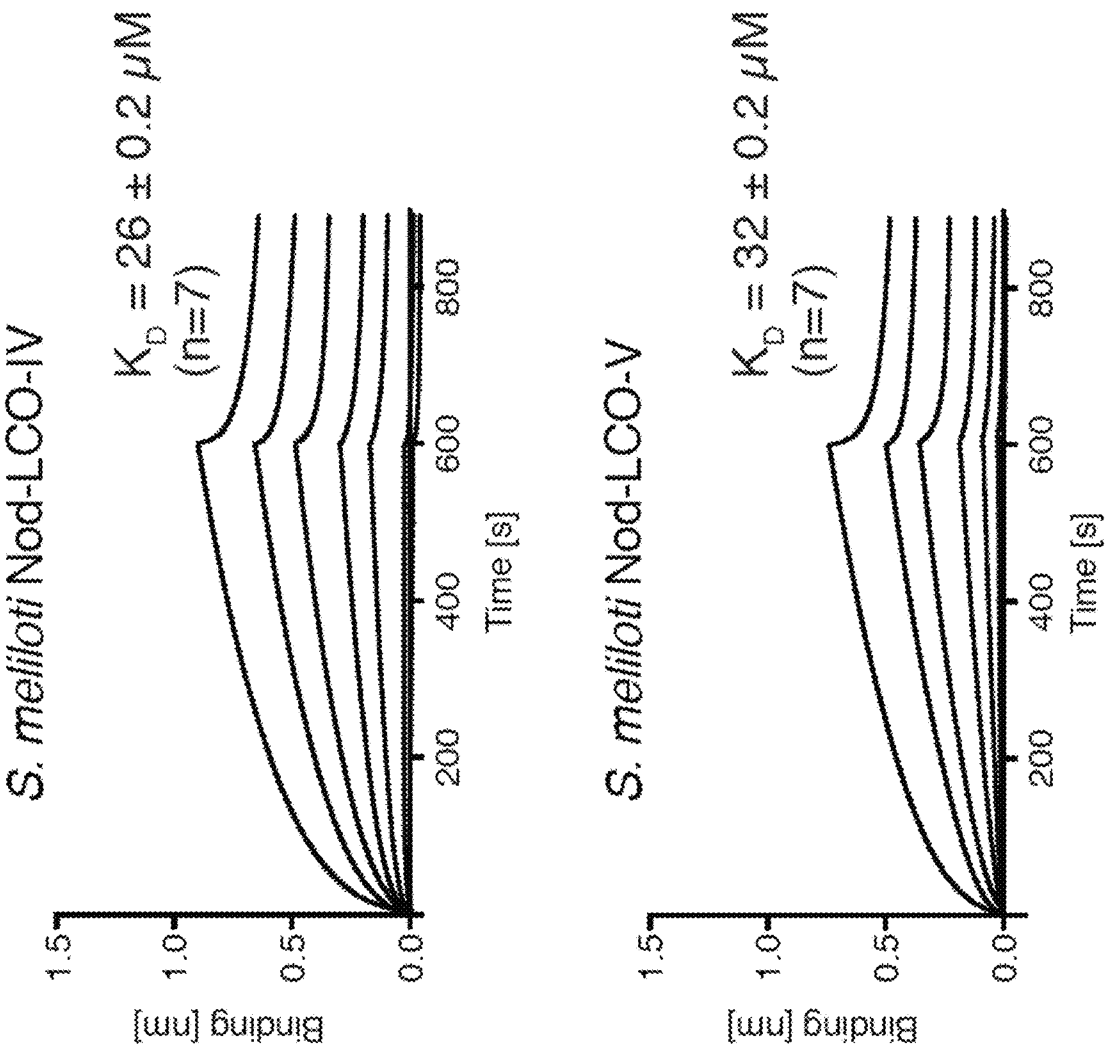
FIGS. 2A-2B show biolayer interferometry (BLI) binding curves using *S. meliloti* LCO-IV and LCO-V, and *M. loti* LCO-V and C06.
Figure 2B:
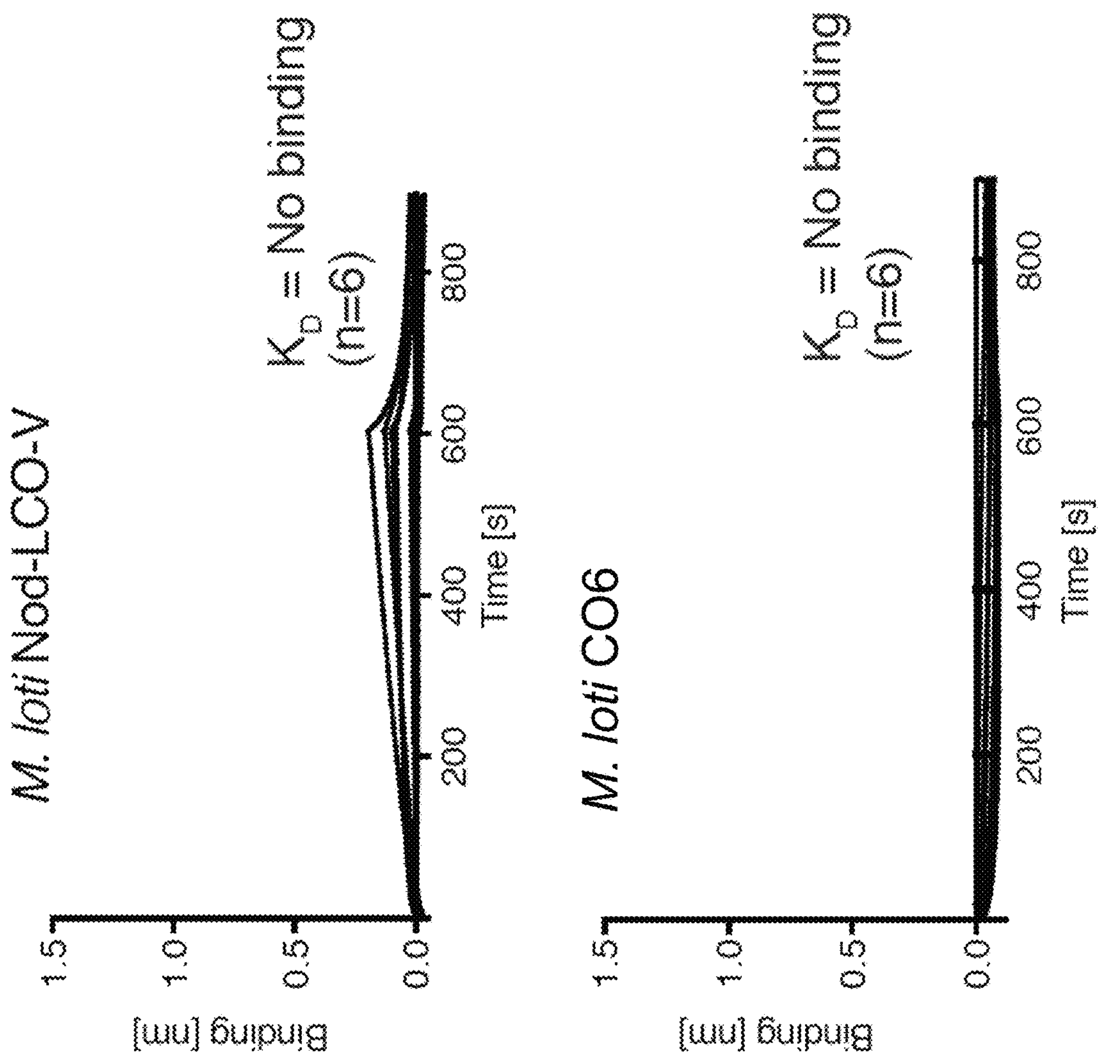

LCO ligands are difficult to handle in solution due to the hydrophobic sticky nature and micelle phase, which hinder accurate concentration determination. To overcome this problem, previously developed chemistry to site-specifically label the reducing end of LCOs with a biotinylated linker was used. Using biolayer interferometry (BLI), it was found that NFP binds immobilized *S. meliloti* LCO-IV with a Kd of 26±0.2 μM and *S. meliloti* LCO-V with a Kd of 32±0.2 μM (FIG. 2A). Interestingly, NFP binding of *M. loti* LCO-V was not detected, and neither was NFP binding of *M. loti* C06 (FIG. 2B).

Further BLI assays showed that NFP-ECD bound *S. meliloti* LCO-V with an average $K_d$ of 22.3±0.1 μM (FIG. 15A). NFP-ECD bound *M. loti* LCO-V weakly (Kd could not be fitted; FIG. 15B), and did not bind chitin (FIG. 15C). As shown in FIGS. 15D-15E, elimination of the O-acetyl group on the non-reducing end in nodL-LCO-IV reduced binding to NFP-ECD by more than 10-fold (Kd of 133.2±0.3 μM) compared to wild type *S. meliloti* LCO-IV. Lack of the reducing end sulfate in nodH-LCO-IV drastically lowered binding to NFP-ECD by more than 21-fold (Kd of 275.3±1.3 μM), which could explain the reduced calcium spiking observed with this nonsulfated LCO in *Medicago* (Oldroyd, G. E. D., Mitra, R. M., Wais, R. J. & Long, S. R. Evidence for structurally specific negative feedback in the Nod factor signal transduction pathway. *The Plant Journal* 28, 191-284 199 (2001)). Similarly, both nodFE-LCO-IV containing vaccenic acid C18:1 instead of the C16:2 fatty acid and nodFL-LCO-IV lacking the acetyl group and displaying a C20:1 fatty acid showed no significant binding, reflecting the inability to induce both nodule development and infection thread formation after inoculation of the respective *S. meliloti* mutants (Ardourel, M. et al. *Rhizobium meliloti* lipooligosaccharide nodulation factors: different structural requirements for bacterial entry into target root hair cells and induction of plant symbiotic developmental responses. *Plant Cell* 6, 1357-1374 (1994)). The data support the conclusion that NFP directly recognises all individual decorations present on its cognate LCO ligand, making NFP a highly specific receptor.

These results show that NFP has differential binding ability and affinity depending on the ligand. Moreover, these results show that NFP can differentiate between the same ligand produced by different symbiont species (compare results from *S. meliloti* LCO-V and *M. loti* LCO-V). This indicates that NFP can discriminate symbionts based on direct LCO binding.

Example 4: NFP Binding Ability and Affinity for Mutated Lipochitooligosaccharide (LCO) Ligands Studies using bacterial mutants and measuring calcium transients in root hairs after LCO application have shown that side-chain decorations on the terminal N-acetylglucosamine residues are functionally important (Oldroyd GE1, Murray J D, Poole P S, and Downie J A. *Annu Rev Genet.* 2011; 45:119-44). The following example describes experiments performed to understand how LCO side-chain decoration contributes to this apparent selectivity using NFP and its cognate LCO ligand from *S. meliloti.*

Materials and Methods

Figure 3A:
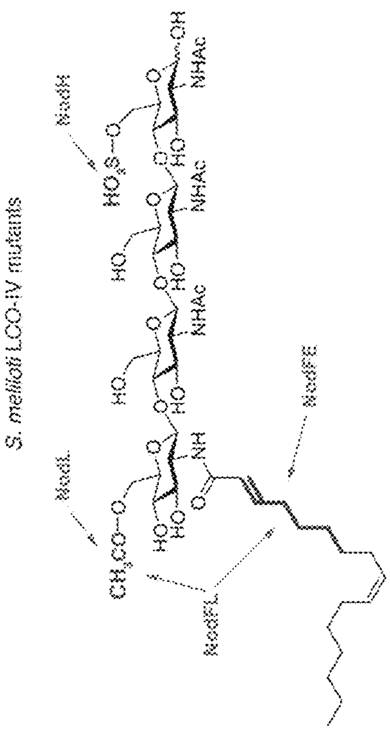
FIGS. 3A-3B show *S. meliloti* LCO-IV mutants, and the results of binding assays using these variants.

Mutated lipochitooligosaccharide (LCO) ligands: *S. meliloti* LCO consists of a tetrameric/pentameric N-acetylglucosamine backbone that is O-sulfated on the reducing terminal residue, O-acetylated on the non-reducing terminal residue, and mono-N-acylated by unsaturated C16 acyl groups. The LCO ligands used here were purified from *S. meliloti* nodH, nodL, nodFE, and nodFL mutants. Each of these mutants lacks one or more of the side-chain decorations on the terminal moieties of LCO. FIG. 3A depicts *S. meliloti* LCO-IV, and indicates which side-chain decorations are altered in each mutant.

Ligand binding tests: Ligand binding tests were done as in Example 3.

Results

Figure 3B:
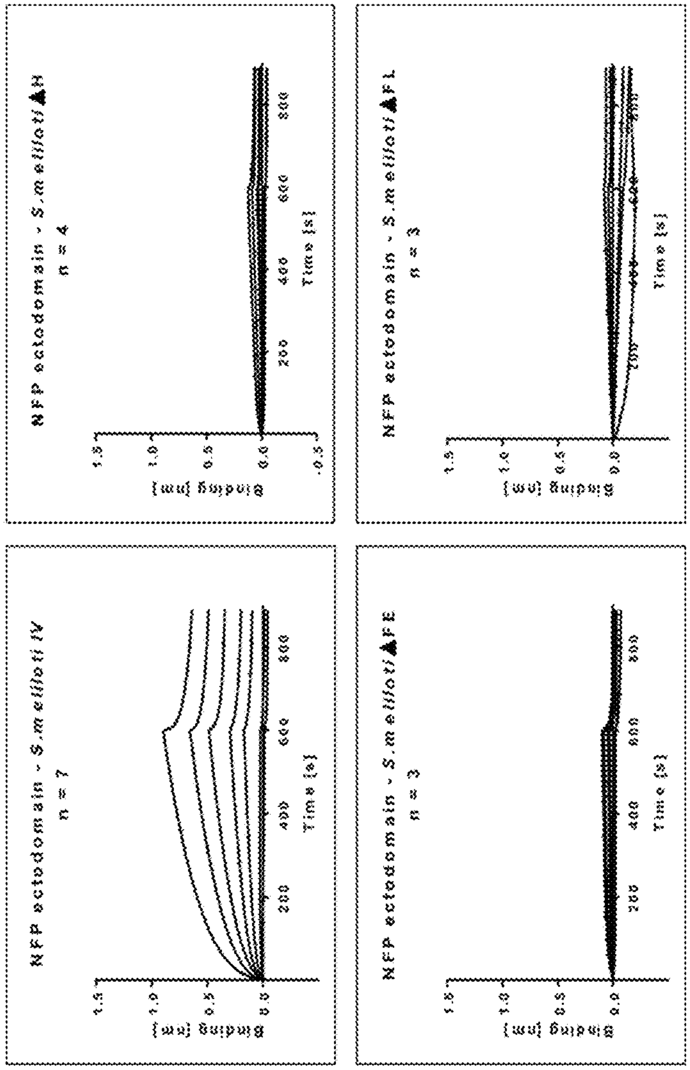

FIG. 3B shows the results of ligand binding tests using mutated LCOs. Dramatically reduced binding to NFP was seen in tests with nodH-LCO, which has a missing sulfate modification, and in tests with nodL-LCO, which lacks an O-acetyl group. This is consistent with the perturbed nodulation and infection observed after plant inoculation with these *S. meliloti* mutants, as well as the decreased calcium transients found after applying these mutated LCOs. Similarly, tests using nodFE-LCO, which contains vaccenic acid C18:1 instead of the C16:2 fatty acid, reduced NFP binding. Further, the nodFL double mutant, which lacks an O-acetyl group and containing vaccenic acid C18:1, shows no binding to NFP. This reflects the perturbed nodulation, inability to induce nodule development, and lack of infection thread formation observed after plant inoculation with the respective *S. meliloti* mutants (Ardourel M, et al. *Plant Cell.* 1994 October; 6(10):1357-74.). Taken together, this data shows that the NFP receptor can recognize individual modifications of its cognate LCO ligand.

Example 5: Identification of Important Residues for Lipochitooligosaccharide (LCO) Perception The following example describes the use of a structurally-guided approach to identify important residues in NFP for LCO perception. After identifying important residues, NFP point mutations were created, and tested using the ligand-binding assays described above (see Example 3 and Example 4).

Materials and Methods

Figure 4A:
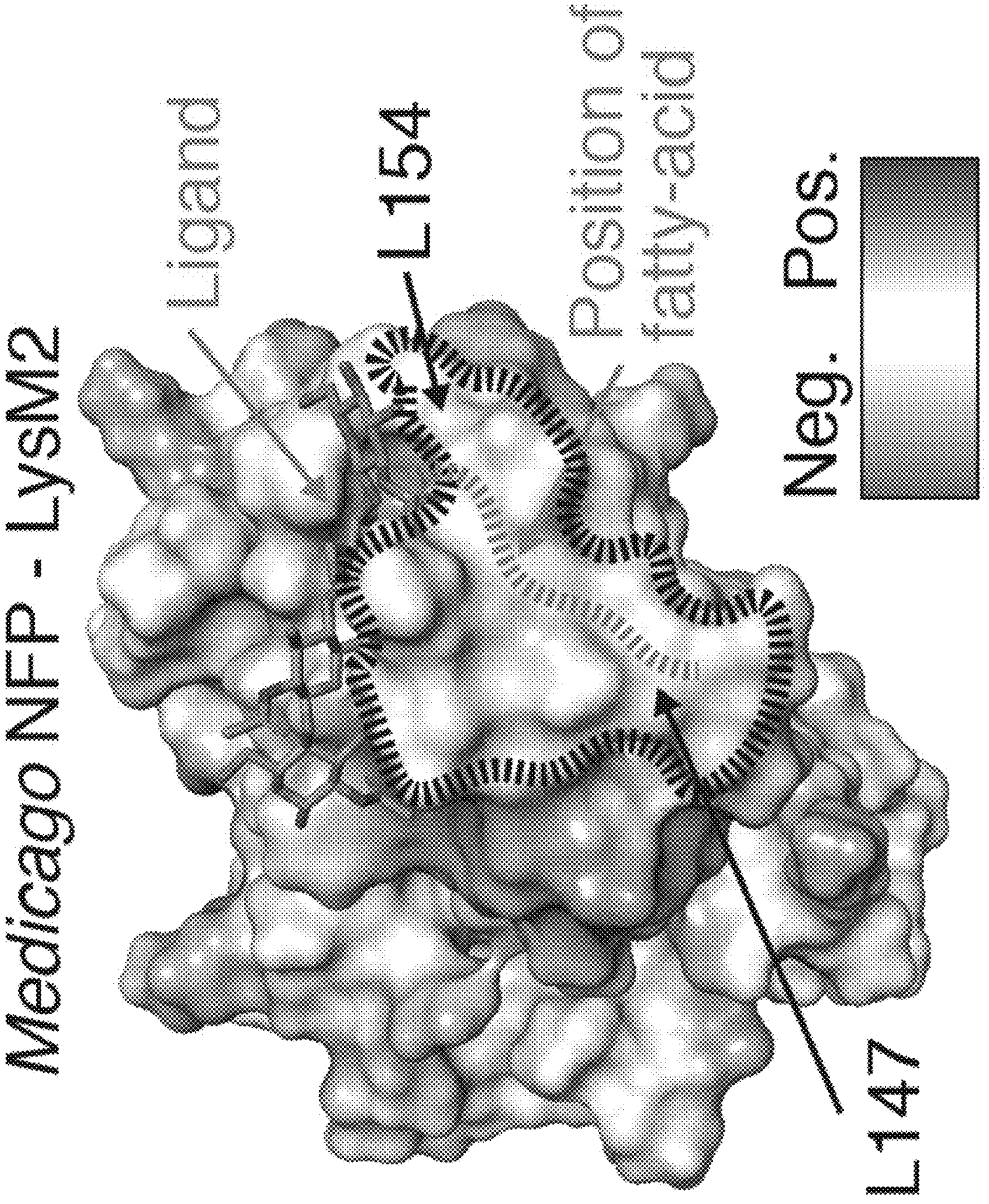

Structurally-guided residue identification: The NFP ectodomain was structurally aligned to ligand-bound CERK1. Then, the electrostatic surface potential was mapped to the previously-developed structure of the NFP ectodomain. The predicted ligand-binding location and electrostatic surface potential are depicted in FIG. 4A.

Creation of NFP point mutations: The NFP leucine residues L147 and L154 were replaced with aspartate residues. Aspartate is similar in size to leucine, but negatively charged where leucine is hydrophobic. Point mutants of NFP were engineered using site-directed mutagenesis. In particular, a double-mutated NFP was engineered where the leucine residues L147 and L154 were replaced with aspartate residues to create the mutant NFP L147D L154D. Point mutated versions of NFP were expressed and purified as described in Example 1.

NFP mutant binding assays: The binding assay using NFP wild type (WT) protein was replicated seven times, while the binding assay using the NFP mutant NFP L147D L154D was replicated four times.

Biolayer interferometry (BLI): Binding of NFP WT and NFP L147D/L154D mutant to *S. meliloti* LCO-IV was measured on an Octet RED 96 system (Pall ForteBio). *S. meliloti* LCO consists of a tetrameric/pentameric N-acetylglucosamine backbone that is O-sulfated on the reducing terminal residue, 0-acetylated on the non-reducing terminal residue, and mono-N-acylated by unsaturated C16 acyl groups. Biotinylated ligand conjugates were immobilized on streptavidin biosensors (kinetic quality, Pall ForteBio) at a concentration of 125-250 nM for 5 minutes. The binding assays were replicated 7 times for the NFP WT, and 4 times for the NFP L147D/L154D mutant. Data analysis was performed in GraphPad Prism 6 software (GraphPad Software, Inc.). Equilibrium dissociation constants derived from the steady-state were determined by applying a non-linear regression (one site, specific binding) to the response at equilibrium plotted against the protein concentration. Kinetic parameters were determined by non-linear regression (association followed by dissociation) on the subtracted data. Results are shown in FIGS. 16A-16C. Binding ofA. *thaliana* CERK1 (AtCERK1) to chitopentaose (C05) and chitooctaose (C08) was measured in the same way. Results are shown in FIGS. 17A-17B.

Results

FIG. 4A shows modelling of the NFP ectodomain bound to a ligand with predicted chitin and LCO fatty acid chain locations. Structural alignment of the NFP ectodomain with ligand-bound CERK1 positions chitin in the LysM2 binding groove of NFP without any obvious clashes. Strikingly, the electrostatic surface potential revealed a hydrophobic patch on the NFP ectodomain that is located near the non-reducing moiety of the docked chitin molecule, which potentially could accommodate the fatty acid chain of the LCO ligand. Two leucine residues (L147 and L154) were identified as the residues that give this patch its hydrophobic character.

To test the contribution of these two residues to LCO binding, both residues were replaced with similarly sized but negatively charged aspartate residues to produce NFP L147D L154D. Interestingly, the double mutated NFP L147D L154D ectodomain bound *S. meliloti* LCO-IV with approximately two times lower affinity; Kd of 48.0±1.0 μM (FIG. 4B). Closer inspection of the binding kinetics revealed that the association ($K_{on}$) was almost unaffected whereas the dissociation ($K_{off}$) was approximately 15 times faster in the double mutant. These results show that the hydrophobic patch of the NFP ectodomain is stabilizing the LCO bound state, and that this stabilization is most likely occurring via the fatty acid chain. Docking the LCO fatty acid in this hydrophobic patch and the chitin backbone in the LysM2 binding site (derived from CERK1) would place the sulphate and acetyl side groups facing K141.

Biochemical analysis of LCO binding to the hydrophobic patch mutant reveals that purified L147D/L154D NFP-ECD bound *S. meliloti* LCO-IV with 13-fold lower affinity (Kd of 166.7±4.2 μM) compared to WT NFP-ECD (FIGS. 16A-16C). The association rate ($k_{on}$) was 4.5-fold faster and the dissociation rate ($k_{off}$) was dramatically increased with 59-fold in the double mutant compared to the WT NFP-ECD, suggesting that the hydrophobic patch had a strong stabilizing effect on LCO binding mediated by the acyl chain.

The binding kinetics of AtCERK1 binding to chitin fragments were measured as a comparison. As shown in FIGS. 17A-17B, fast association and dissociation rates were seen. These kinetics were reminiscent of the kinetics observed for the mutant L147D/L154D NFP-ECD (FIG. 16B). The binding kinetics of AtCERK1 to chitin fragments were clearly different than the binding kinetics of NFP to LCO (FIG. 16A).

Together, the data provided evidence that the hydrophobic patch in NFP (shown in FIG. 16D) was a conserved structural imprint critical for LCO perception and symbiotic signaling.

Example 6: Complementation Test in *Medicago* Nfp Mutants

To confirm the biochemical observations described in the previous examples, next a complementation test was performed in *Medicago* nfp mutants using hairy root transformation.

Materials and Methods

Figure 5:
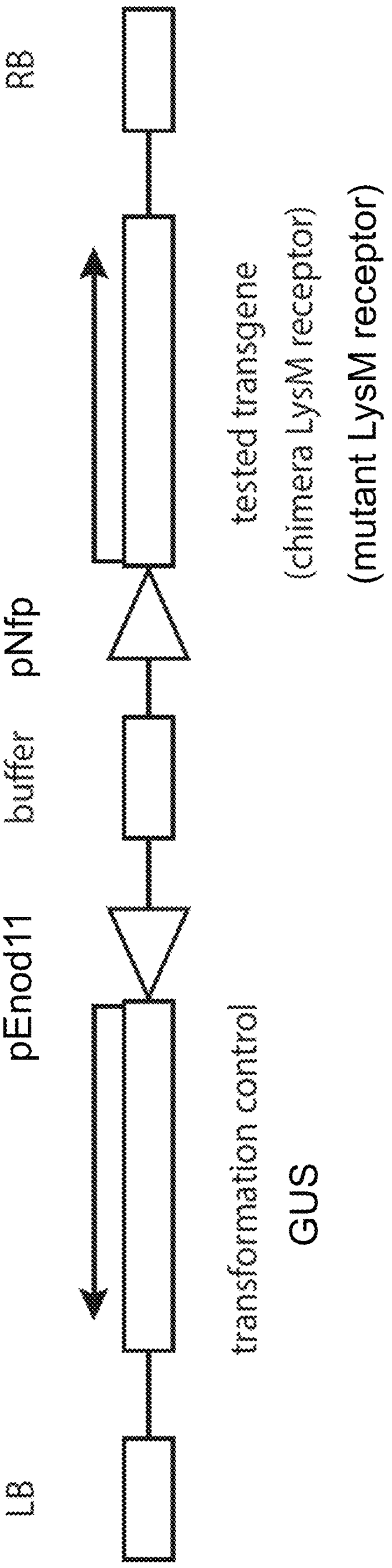
FIG. 5 shows the general schematic of the construct used for mutant complementation experiments. Designations are as follows: T-DNA left border sequence=LB, T-DNA right border sequence=RB, β-glucuronidase gene=GUS, buffer sequence=buffer, early nodulin-11 precursor promoter=pEnod11, NFP promoter=pNfp. The arrows indicate the directions of gene transcription.

Complementation assay: Construct assembly, plant growth conditions, hairy root transformations, nodulation and ROS assays were generally conducted as described in Bozsoki et al. (2017) (Bozsoki Z, Cheng J, Feng F, Gysel K, Vinther M, Andersen K R, Oldroyd G, Blaise M, Radutoiu S, Stougaard J (2017) Receptor-mediated chitin perception in legume roots is functionally separable from Nod factor perception. Proc Natl Acad Sci 114: E8118-E8127). A general schematic of the construct is provided in FIG. 5. The tested transgenes were the mutated LysM receptors described in Example 5. In addition, NFP substitution variants replacing residues outside the hydrophobic patch in LysM2 (Q119F, K141E and T150H) or in LysM3 (T216F) were tested.

Results

Figure 6B:
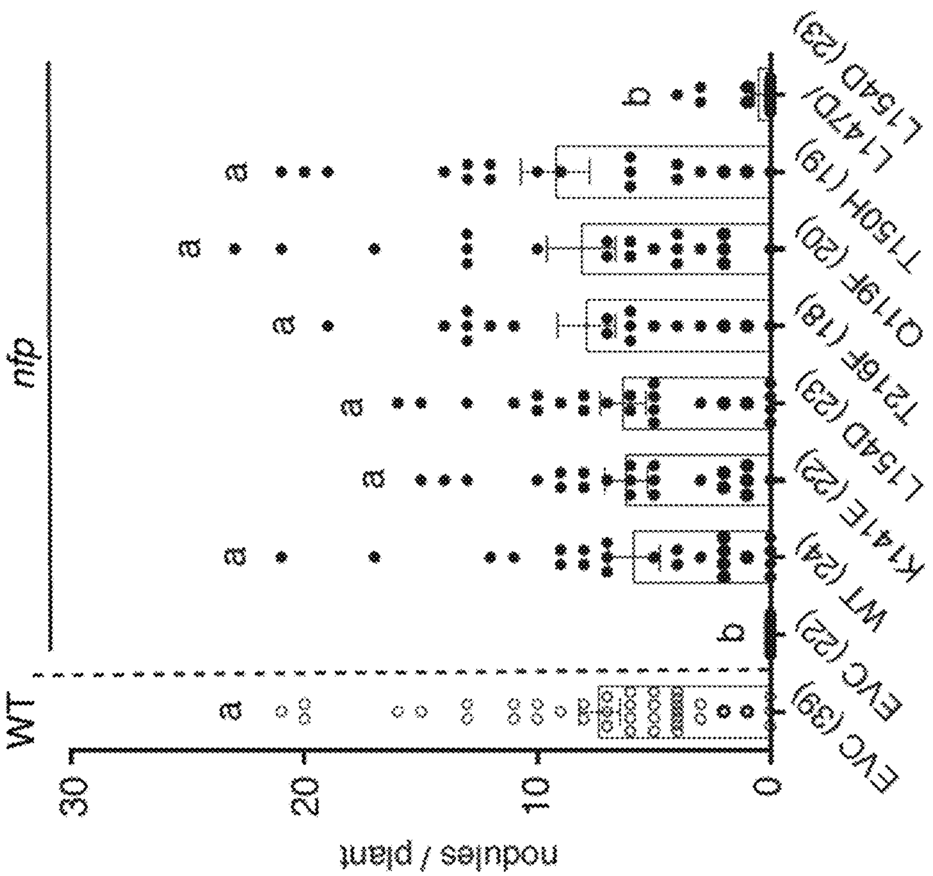
FIGS. 6A-6B show complementation assays of *Medicago* nfp mutants.
Figure 6A:
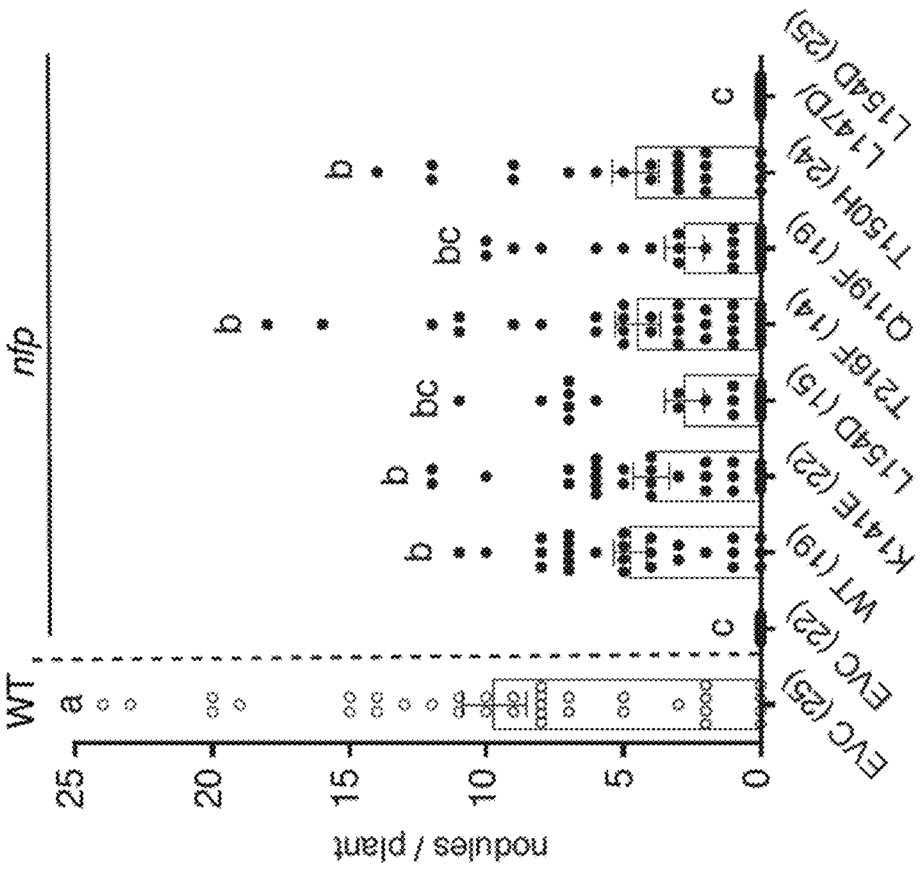

FIG. 6A-6B shows the results of the complementation test. The results shown in FIG. 6A are complementation tests where the plants were inoculated with *S. meliloti* strain 1021. When *Medicago* nfp mutants are transformed with the wild type Nfp gene, complementation is seen, which is defined as an average of 5 nodules per plant 49 days after inoculation with *S. meliloti* strain 1021. In contrast, roots transformed with the construct containing the double-mutated NFP L147D L154D (the surface residues that five NFP its hydrophobic character in LysM2) did not develop any nodules per plant after inoculation with *S. meliloti* strain 1021. Corresponding experiments with NFP substitution variants replacing residues outside the hydrophobic patch in LysM2 (Q119F, K141E and T150H) or in LysM3 (T216F) did not affect nodulation.

These complementation experiments were repeated using *S. medicae* inoculation, which has been reported to nodulate *Medicago* with higher efficiency. The results shown in FIG. 6B are complementation tests where the plants were inoculated with *S. medicae*. The *S. medicae* results confirm that the construct containing the double-mutated NFP L147D L154D complements poorly. Taken together, these results show that the hydrophobic patch in NFP is required for LCO recognition, and for functional symbiotic signaling.

Example 7: Conservation of the Hydrophobic Patch

Previously, SYM10 in pea, NFR5 in *Lotus*, and NFR5A in soybean had been shown to be crucial for LCO perception (see, e.g., Plant Cell Physiol. 2010 February; 51(2):201-14 and Madsen, E B et al. Nature. 2003 Oct. 9; 425(6958):637-40.). Therefore, homology modelling was used to determine whether the hydrophobic patch adjacent to LysM2 identified in *Medicago* NFP was a conserved feature across these proteins. In addition, homology modelling for *Lotus* LYS11 was done, and a crystal structure for *Lotus* LYS11 was obtained to verify the homology modelling results.

Materials and Methods

Modelling: Homology modelling was performed with SWISS-MODEL (Biasini 2014). The crystal structure of *Medicago* NFP served as the template model onto which the amino acid sequence of the target receptor was mapped. The output pdb filled structural model was generated and its electrostatic surface potential was calculated using the PDB2PQR and APBS webservers (PMID: 21425296). The results were visualized in PyMol using APBS tools 2.1 (DeLano, W. L. (2002). PyMOL. DeLano Scientific, San Carlos, CA, 700.).

Crystal structure: Crystals of LYS11 were obtained using a vapour diffusion setup at 6.8 mg/mL in 0.1 M sodium malonate pH 6.0 and 12% PEG3350. Complete diffraction data was obtained and the phase problem was solved by molecular replacement using Phaser from the PHENIX suite with a homology model based on the AtCERK1 ectodomain structure (PDB coordinates 4EBZ) as a search model. Model building and refinement was done using COOT and the PHENIX suite, respectively. The output pdb filled structural model was generated and its electrostatic surface potential was calculated using the PDB2PQR and APBS webservers (PMID: 21425296). The results were visualized in PyMol using APBS tools 2.1 (DeLano, W. L. (2002). PyMOL. DeLano Scientific, San Carlos, CA, 700.).

Results

Figure 7A:
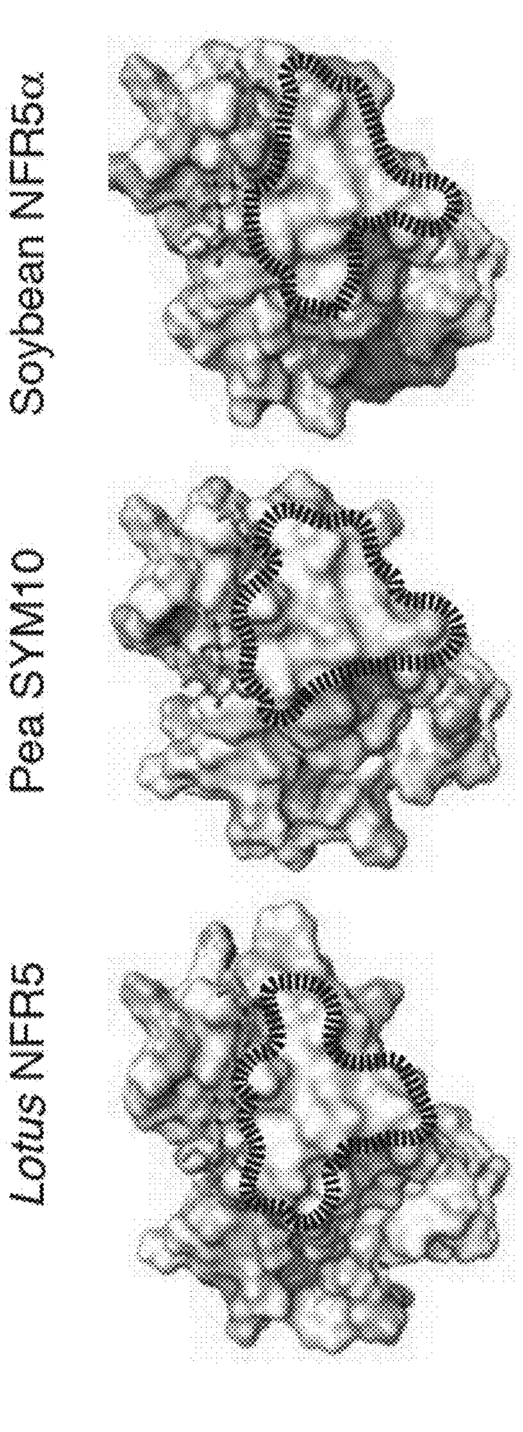
FIGS. 7A-7G show homology modelling of other LCO receptor ectodomains with surface representations of different LCO receptors shaded according to their electrostatic potential (negative=red; hydrophobic=white; positive=blue). When present, the hydrophobic patch is circled by a dashed black line, and a negative patch is circled by a dashed red line. The docked ligand (chitin) is shown as guidance.

FIG. 7A shows homology modelling results for SYM10 in pea, NFR5 in *Lotus*, and NFR5a in soybean. Homology modelling reveals that the hydrophobic patch is indeed present in the equivalent positions immediately below the LysM2 domain of these receptors.

Figure 7B:
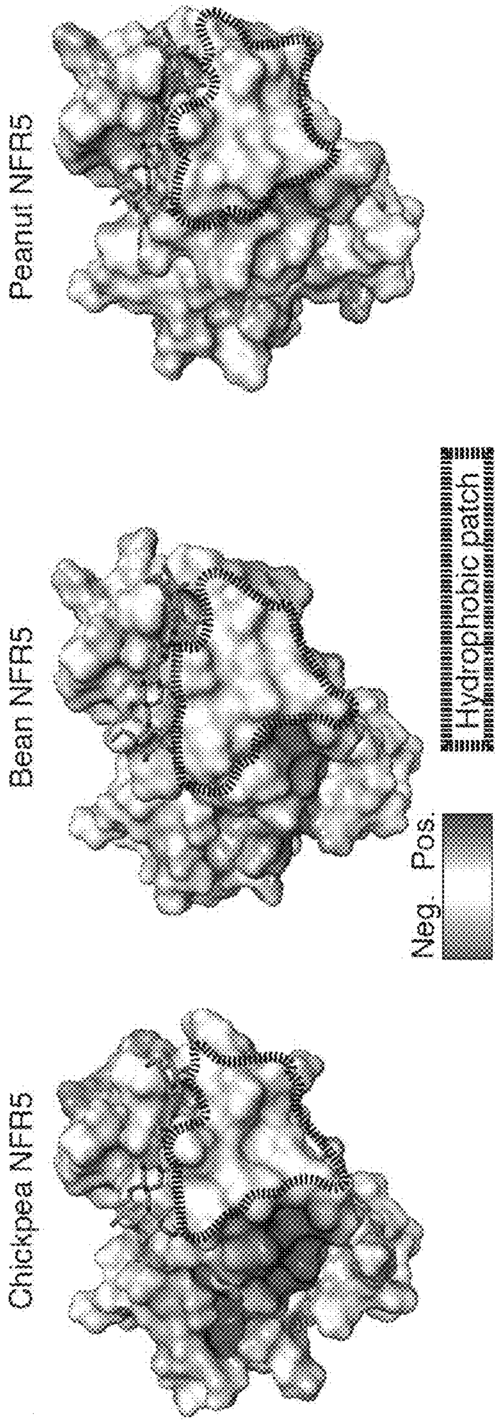

To investigate the predictive power of this approach, the closest receptor homologs derived from the genomes of chickpea, bean, and peanut were also modelled (FIG. 7B). None of these receptor homologs has previously been functionally characterized. The hydrophobic patch in LysM2 is found to be conserved here as well, which predicts that these proteins are NFP/NFR5 type of LCO receptors.

Figure 7C:
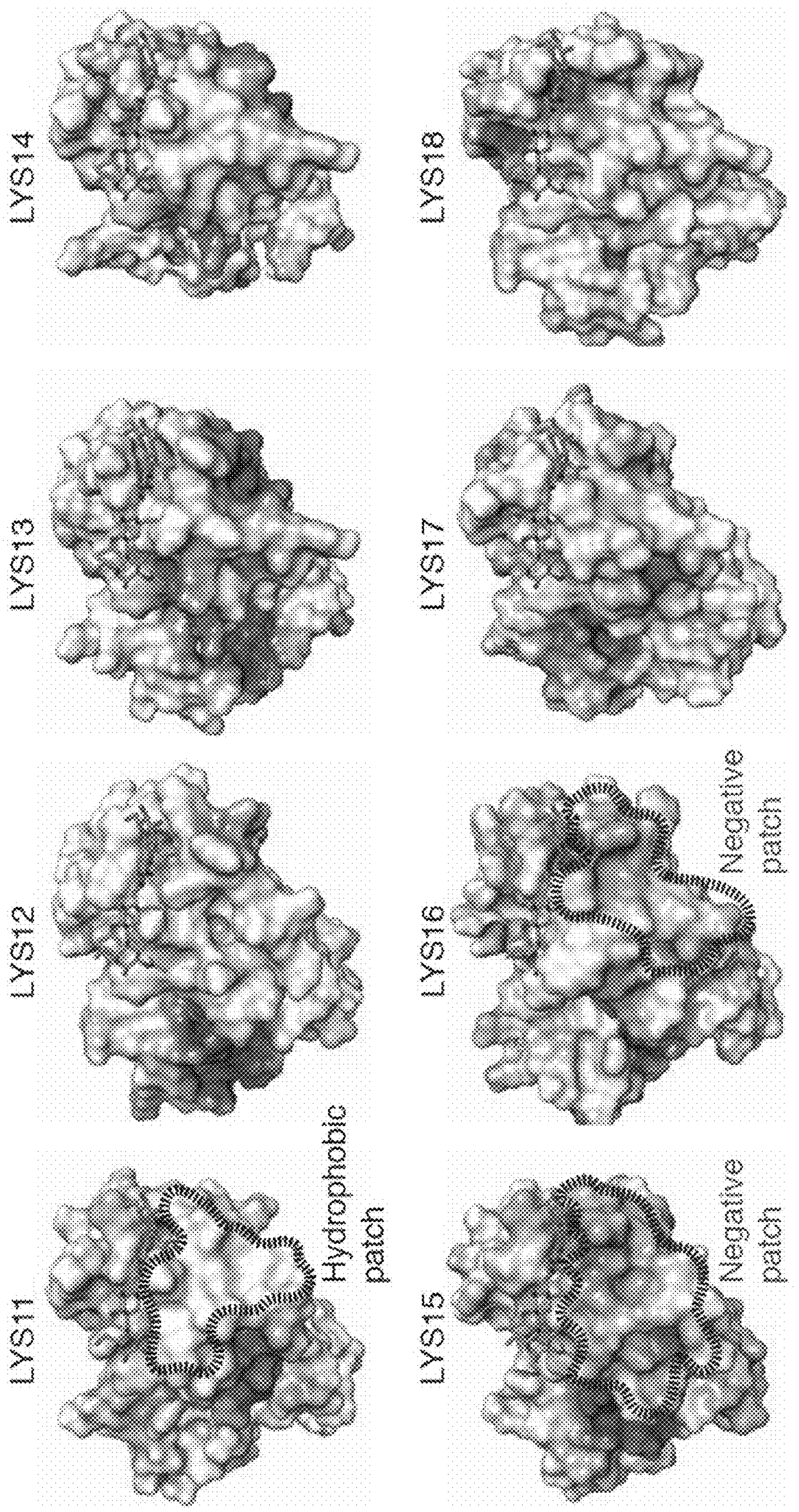
Figure 7D:
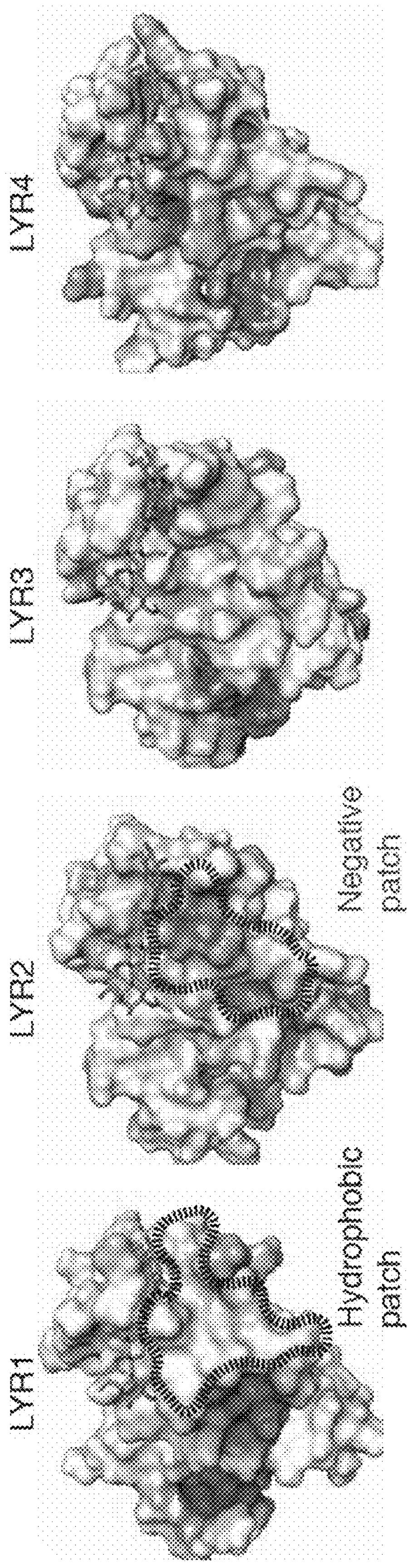
Figure 7E:
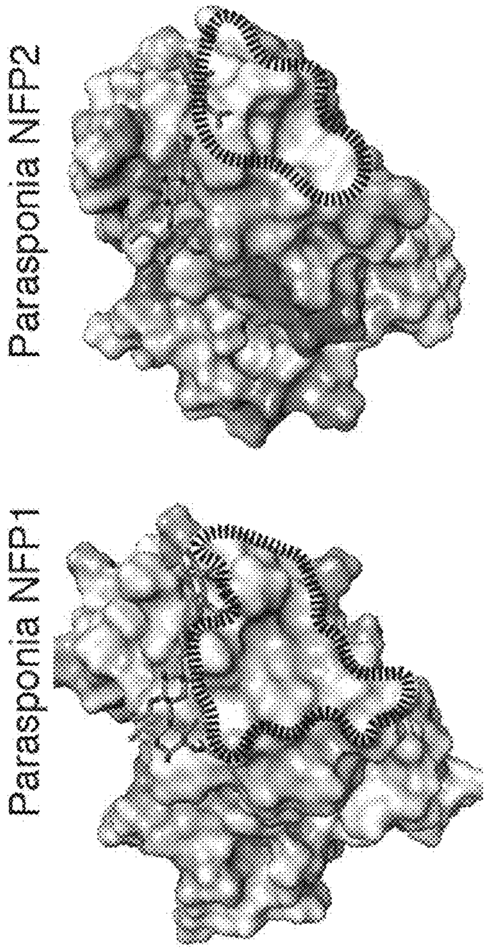
Figure 7F:
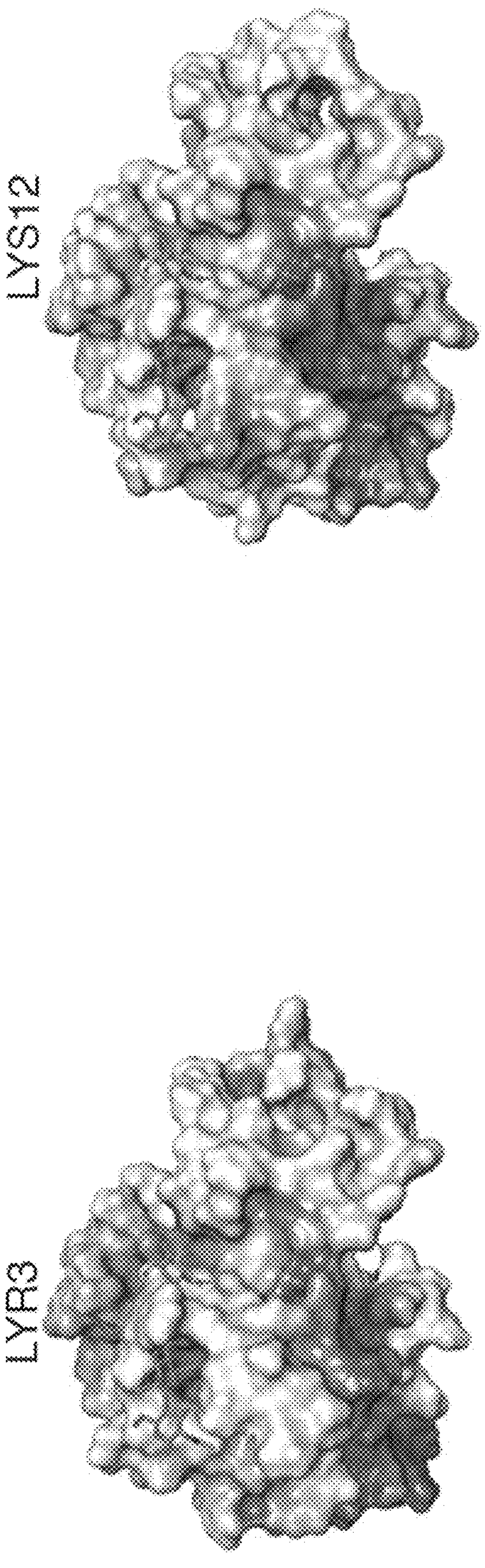

Further, the diagnostic ability of modelling was tested in the *Medicago* NFP and *Lotus* NFR5 families of pseudokinases. FIGS. 7C-7D shows that *Medicago* LYR1 and *Lotus* LYS11 both contain the hydrophobic patch indicative of LCO receptor function, which is interesting in light of their putative role in AM symbiosis (See, e.g., Rasmussen, S R et al. *Sci Rep.* 2016 Jul. 20; 6:29733 and Gomez, S K et al. *BMC Plant Biol.* 2009 Jan. 22; 9:10.). FIG. 7E shows the predicted modeled of three LCO receptors: *Lotus* NFR5, Pea SYM10 and Soybean NFR5A. The models are shown as surfaces and colored in accordance with their electrostatic surface potential. The predicted hydrophobic patch is marked with a black dotted line and the C04 chitin molecule is show in the LysM2 ligand binding groove. FIG. 7F shows a comparison of two receptors lacking the hydrophobic patch, *Medicago* LYR3 and *Lotus* LYS12.

Figure 7G:
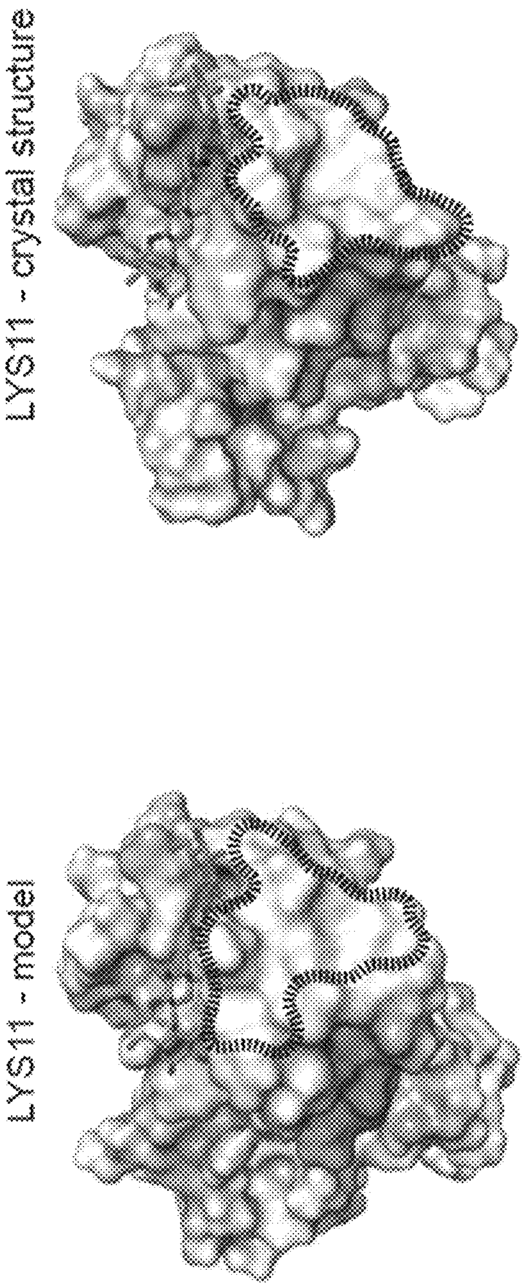

In order to experimentally validate the prediction that *Lotus* LYS11 had a hydrophobic patch comparable to NFP, the crystal structure of *Lotus* LYS11 was determined. FIG. 7G shows a comparison of the *Lotus* LYS11 model (left; also in FIG. 7C) with the crystal structure of *Lotus* LYS11 (right). From the electrostatic surface potential of the crystal structure, it was clear that LYS11 indeed contained a hydrophobic patch in LysM2 that was similar to the hydrophobic path in LysM2 of NFP. The presence of the hydrophobic domain, which had been predicted by modelling, in the actual structure of LYS11 determined by crystallography demonstrated the power of NFP-based modelling for identification of the hydrophobic patch in previously uncharacterized LCO receptor homologues.

Taken together, these results show that the hydrophobic patch is a conserved structural fingerprint found across NFP/NFR5 receptors (e.g., LCO receptors). The hydrophobic patch can therefore be used to predictively identify the class of NFP/NFR5 receptors in other legumes, which was not previously possible.

Example 8: Modelling of Non-Legume LCO Receptors of the NFP/NFR5 Class

Next, homology modelling was used to determine whether the hydrophobic patch adjacent to LysM2 identified in *Medicago* NFP was present in barley LysM receptor kinases.

Materials and Methods

Modelling: Homology modelling was performed with SWISS-MODEL (Biasini, M. et al. SWISS-MODEL: modelling protein tertiary and quaternary structure using evolutionary information. *Nucleic Acids Res.* 42, W252-W258 (2014)). The crystal structure of *Medicago* NFP served as the template model onto which the amino acid sequence of the target receptor was mapped. The output pdb filled structural model was generated and its electrostatic surface potential was calculated using the PDB2PQR and APBS webservers (PMID: 21425296). The results were visualized in PyMol using APBS tools 2.1 (DeLano, W. L. (2002). PyMOL. DeLano Scientific, San Carlos, CA, 700.).

Expression and purification of Barley RLK10 ectodomain: The *H. vulgare* RLK10 (HvRLK10; HvLysM-RLK10) ectodomain (residues 25-231; SEQ ID NO: 29) was codon-optimized for insect cell expression (Genscript, Piscataway, USA) and cloned into the pOET4 baculovirus transfer vector (Oxford Expression Technologies). The native RLK10 signal peptide was replaced with the gp64 signal peptide to facilitate secretion and a hexa-histidine (6×HIS) tag was added to the C-terminus to make the sequence HvRLK10-ecto (25-231), N-term gp64, C-term 6His (SEQ ID NO: 28). Recombinant baculoviruses were produced in Sf9 cells (*Spodoptera frugiperda*) using the FlashBac Gold kit (Oxford Expression technologies) according to the manufacturer's instructions with Lipofectin (ThermoFisher Scientific) as a transfection reagent. Protein expression was performed as follows. Suspension-cultured Sf9 cells were maintained with shaking at 299 K in serum-free MAX-XP (BD-Biosciences, discontinued) or HyClone SFX (GE Healthcare) medium supplemented with 1% Pen-Strep (10000 U/ml, Life technologies) and 1% CD lipid concentrate (Gibco). Protein expression was induced by adding recombinant passage 3 virus once the Sf9 cells reached a cell density of $1.0*10^{7}$^6 cells/ml. After 5-7 days of expression, medium supernatant containing RLK10 ectodomains was harvested by centrifugation. This was followed by an overnight dialysis step against 50 mM Tris-HCl pH 8, 200 mM NaCl at 277 K. The RLK10 ectodomain was enriched by two subsequent steps of Ni-IMAC purification (HisTrap excel/HisTrap HP, both GE Healthcare).

Ligand binding tests: Ligand binding tests were performed using BLI as in Example 3.

Results

Homology modelling of all ten barley LysM receptor-like kinases (RLKs) was done using the *Medicago* NFP structure as a template. Of the barley LysM RLKs, HvRLK10 was the receptor that was closest to *Medicago* NFP and modelled the best using this approach. FIG. 13B shows homology modelling results for HvRLK10, which revealed that the hydrophobic patch was indeed present in the equivalent positions immediately below the LysM2 domain of this receptor. This clear hydrophobic patch indicated that HvRLK10 was a NFP/NFR5 type of LCO receptor.

Figure 13A:
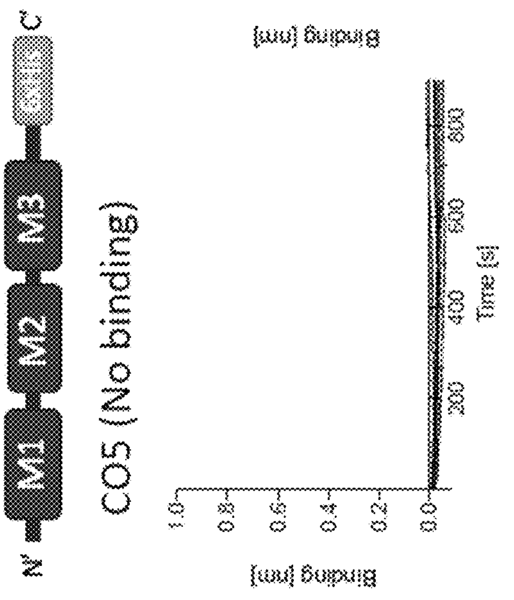
FIGS. 13A-13D show homology modelling of the barley RLK10 receptor (HvRLK10) ectodomain and results of binding experiments using the HvRLK10 ectodomain.
Figure 13B:
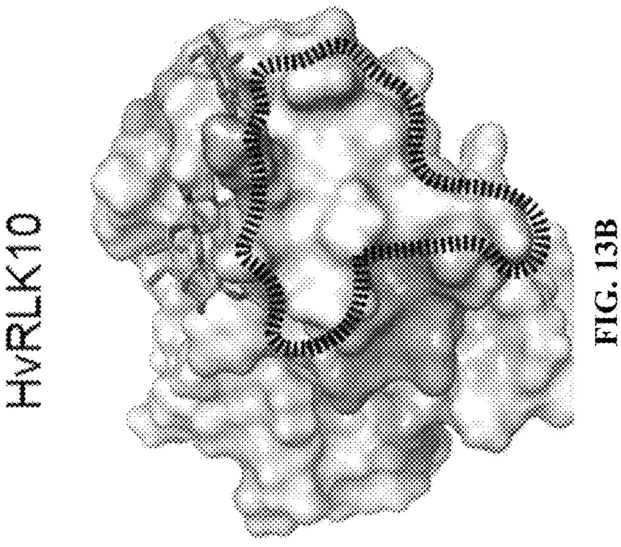
Figure 13C:
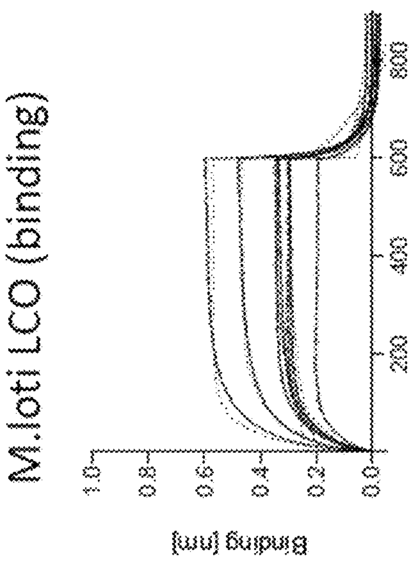
Figure 13D:
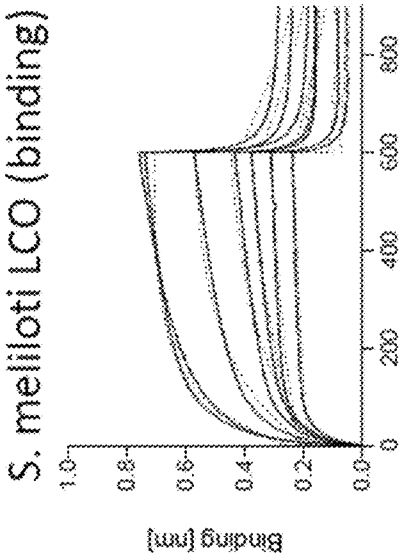

To experimentally validate this prediction, the HvRLK10 ectodomain was expressed and purified for use in binding experiments (ectodomain schematic shown at top of FIG. 13A). The HvRLK10 ectodomain was shown to bind both *M. loti* LCO (FIG. 13C) and *S. meliloti* LCO (FIG. 13D). In contrast, the HvRLK10 ectodomain did not bind C05 (FIG. 13A). These binding studies showed that the HvRLK10 predicted to have a hydrophobic patch bound LCOs but not COs.

Taken together, these results show that the hydrophobic patch is a conserved structural fingerprint found across NFP/NFR5 receptors (e.g., LCO receptors). This conservation extends beyond the legume family into non-legume plants, such as barley. The hydrophobic patch can therefore be used to predictively identify the class of NFP/NFR5 receptors in non-legume plants, which was not previously possible.

The invention claimed is:

1. A genetically altered plant or part thereof, comprising a heterologous receptor polypeptide that has at least 95% sequence identity to SEQ ID NO: 19 and comprises a hydrophobic patch in a LysM2 domain that is bound to a lipo-chitooligosaccharide (LCO).

2. The genetically altered plant or part thereof of claim 1, wherein the heterologous receptor polypeptide comprises the sequence of SEQ ID NO: 19.

3. The genetically altered plant or part thereof of claim 1, wherein the LCO is produced by nitrogen-fixing bacteria or by mycorrhizal fungi.

4. The genetically altered plant or part thereof of claim 3, wherein the nitrogen-fixing bacteria or mycorrhizal fungi is selected from the group consisting of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum, Rhizobium leguminosarum trifolii, Rhizobium leguminosarum viciae, Rhizobium leguminosarum phaseoli*, Burkholderiales, Burkholderiales symbionts of *Mimosa, Sinorhizobium meliloti, Sinorhizobium medicae, Sinorhizobium fredii, Sinorhizobium fredii* NGR234, *Azorhizobium caulinodans, Bradyrhizobium japonicum, Bradyrhizobium elkanii, Bradyrhizobium liaonginense, Rhizobium* spp., *Mesorhizobium* spp., *Sinorhizobium* spp., *Azorhizobium* spp., *Frankia* spp., *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., *Glomeromycota* spp., and any combination thereof.

5. The genetically altered plant or part thereof of claim 1, wherein the heterologous receptor polypeptide is localized to a plant cell plasma membrane.

6. The genetically altered plant or part thereof of claim 5, wherein the plant cell is a root cell, and wherein the root cell is a root epidermal cell or a root cortex cell.

7. The genetically altered plant or part thereof of claim 1, wherein the heterologous receptor polypeptide is expressed in a developing plant root system.

8. The genetically altered plant or part thereof of claim 1, wherein the heterologous receptor polypeptide is encoded by a nucleic acid sequence that is operably linked to a promoter.

9. The genetically altered plant or part thereof of claim 8, wherein the promoter is a root specific promoter, and wherein the promoter is selected from the group consisting of a *Lotus* NFR5 promoter comprising the nucleotide sequence set forth in SEQ ID NO: 24, a *Lotus* NFR1 promoter comprising the nucleotide sequence set forth in SEQ ID NO:25, a maize metallothionein promoter, a chitinase promoter, a maize ZRP2 promoter, a tomato LeExtl promoter, a glutamine synthetase soybean root promoter, an RCC3 promoter, a rice antiquitin promoter, an LRR receptor kinase promoter, and an *Arabidopsis* pCO2 promoter.

10. The genetically altered plant or part thereof of claim 8, wherein the promoter is a constitutive promoter optionally selected from the group consisting of a CaMV35S promoter, a maize ubiquitin promoter, a polyubiquitin promoter, a vein mosaic cassava virus promoter, and an *Arabidopsis* UBQ10 promoter.

11. The genetically altered plant or part thereof of claim 1, wherein the plant is selected from the group consisting of corn, rice, barley, wheat, *Trema* spp., apple, pear, plum, apricot, peach, almond, walnut, strawberry, raspberry, blackberry, red currant, black currant, melon, cucumber, pumpkin, squash, grape, and hemp.

12. The genetically altered plant part of claim 1, wherein the plant part is a leaf, a stem, a root, a root primordia, a flower, a seed, a fruit, a kernel, a grain, a cell, or a portion thereof.

13. A pollen grain or an ovule of the genetically altered plant of claim 1.

14. A protoplast produced from the genetically altered plant of claim 1.

15. A tissue culture produced from protoplasts or cells from the genetically altered plant of claim 1, wherein the cells or protoplasts are produced from a plant part selected from the group consisting of leaf, anther, pistil, stem, petiole, root, root primordia, root tip, fruit, seed, flower, cotyledon, hypocotyl, embryo, and meristematic cell.

16. A method of producing the genetically altered plant of claim 1, comprising introducing a genetic alteration to the plant comprising a nucleic acid sequence encoding the heterologous receptor polypeptide.

17. The method of claim 16, wherein the nucleic acid sequence is operably linked to a promoter.

18. The method of claim 17, wherein the promoter is a root specific promoter, and wherein the promoter is selected from the group consisting of a *Lotus* NFR5 promoter comprising the nucleotide sequence set forth in SEQ ID NO: 24, a *Lotus* NFR1 promoter comprising the nucleotide sequence set forth in SEQ ID NO: 25, a maize metallothionein promoter, a chitinase promoter, a maize ZRP2 promoter, a tomato LeExtl promoter, a glutamine synthetase soybean root promoter, a RCC3 promoter, a rice antiquitin promoter, an LRR receptor kinase promoter, and an *Arabidopsis* pCO2 promoter.

19. The method of claim 17, wherein the promoter is a constitutive promoter optionally selected from the group consisting of a CaMV35S promoter, a maize ubiquitin promoter, a polyubiquitin promoter, a vein mosaic cassava virus promoter, and an *Arabidopsis* UBQ10 promoter.

20. The method of claim 17, wherein the nucleic acid sequence is inserted into the genome of the plant so that the nucleic acid sequence is operably linked to an endogenous promoter.

21. The method of claim 20, wherein the endogenous promoter is a root specific promoter.

22. An isolated DNA construct comprising a nucleic acid sequence encoding a receptor polypeptide that has at least 98% sequence identity to SEQ ID NO: 19 and comprises a hydrophobic patch in a LysM2 domain that allows a plant or part thereof comprising the receptor polypeptide to bind LCOs, wherein the nucleic acid sequence is operably linked to a heterologous promoter.

* * * * *